(12) United States Patent
Le Page et al.

(10) Patent No.: US 7,098,182 B2
(45) Date of Patent: Aug. 29, 2006

(54) NUCLEIC ACIDS AND PROTEINS FROM GROUP B STREPTOCOCCUS

(75) Inventors: Richard William Falla Le Page, London (GB); Jeremy Mark Wells, Norwich (GB); Sean Bosco Hanniffy, Cambridge (GB)

(73) Assignee: Microbial Technics Limited, Cambridge (GB)

( * ) Notice: Subject to any disclaimer, the term of this patent is extended or adjusted under 35 U.S.C. 154(b) by 248 days.

(21) Appl. No.: 09/769,736

(22) Filed: Jan. 26, 2001

(65) Prior Publication Data

US 2003/0138775 A1 Jul. 24, 2003

Related U.S. Application Data

(63) Continuation of application No. PCT/GB99/02444, filed on Jul. 27, 1999.
(60) Provisional application No. 60/125,163, filed on Mar. 19, 1999.

(30) Foreign Application Priority Data

Jul. 27, 1998 (GB) .......................................... 9816335.5

(51) Int. Cl.
 *C07K 14/00* (2006.01)
(52) U.S. Cl. ............................ 514/2; 530/300; 530/350
(58) Field of Classification Search ................. 530/300, 530/350; 514/2
 See application file for complete search history.

(56) References Cited

FOREIGN PATENT DOCUMENTS

| WO | WO9410317 | 5/1994 |
|---|---|---|
| WO | WO9506732 | 3/1995 |
| WO | WO9818930 | 5/1998 |
| WO | WO9818931 | 5/1998 |
| WO | WO9823631 | 6/1998 |
| WO | WO9916882 | 4/1999 |
| WO | WO9942588 | 8/1999 |

OTHER PUBLICATIONS

Larsson, Charlotte; et al., "Experimental Vaccination Against Group B Streptococcus, an Encapsulated Bacterium, with Highly Purified Preparations of Cell Surface Proteins Rib and α," *Infection and Immunity*, 64:3518–3523 (1996).

Michel, James L., et al., "Cloned Alpha and Beta C–Protein Antigens of Group B Streptococci Elicit Protective Immunity," *Infection and Immunity*, 59:2023–2028 (1991).

Lachenauer, Catherine S., et al., "Cloning and Expression in *Escherichia coli* of a Protective Surface Protein from Type V Group B Streptococci," *Advances in Experimental Medicine and Biology*, 418:615–618 (1997).

Yoshida, K., et al., "Hypothetical Sensor–Like Histidine Kinase in IDH 3' Region," (1995) SWISS–PROT Sequence.

Tognomi, A., et al., "Peptide Synthetase 1", (1995), SWISS–PROT Sequence.

Yoshida, K., et al., "Homologous to Many ATP–Binding Transport Proteins," (1997), SWISS–PROT Sequence.

Puyet, A., et al., "Maltose/Maltodextrin–Binding Protein Precursor," (1993), SWISS–PROT Sequence.

*Primary Examiner*—Karen Cochrane Carlson
(74) *Attorney, Agent, or Firm*—Hunton & Williams LLP

(57) ABSTRACT

Novel protein antigens from Group B *Streptococcus* are described, together with nucleic acid sequences encoding them. Their use in vaccines and screening methods is also described.

6 Claims, 60 Drawing Sheets

FIG. 1

ID-1

Clone 4

Figure 4A:
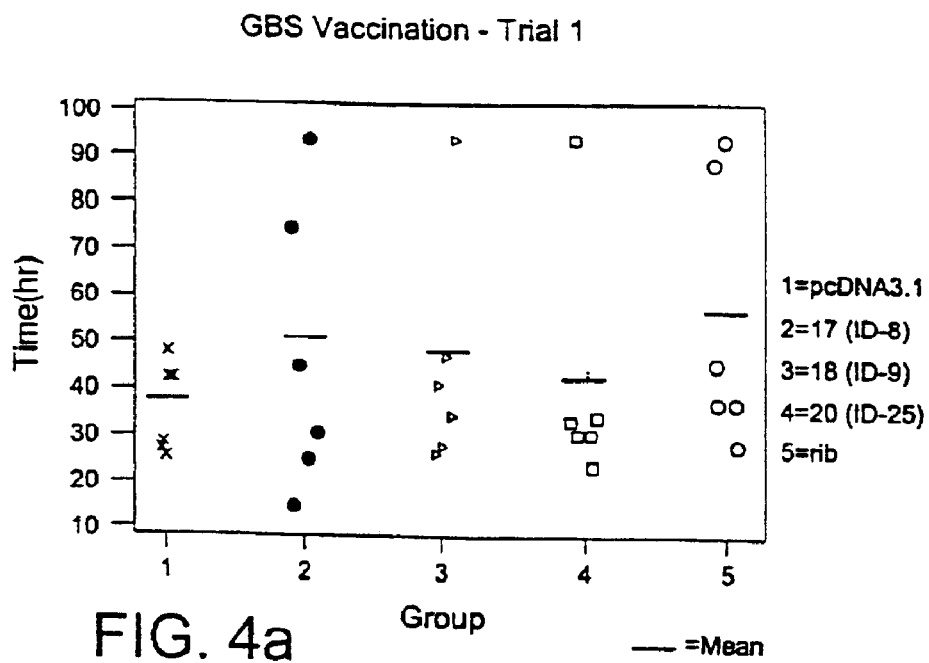

ATGGAAAAAAATACTTGGAAAAAATTACTTGTTAGTACTGCTGCTCTTTCAGTAGT
TGCAGGAGGAGCAATTGCTGCTACTCACTCTAACTCAGTTGATGCTGCTTCAAAAA
AAACTATCAAACTTTGGGTCCCAACAGATTCAAAAGCGTCTTATAAAGCAATTGTT
AAAAAATTCGAGAAGGAAAACAAAGGCGTTACTGTAAAAATGATTGAGTCTAATG
ACTCCAAAGCTCAAGAAAACGTAAAAAAAGACCCAAGCAAGGCAGCCGATGTATT
CTCACTTCCACATGACCAACTTGGTCAATTAGTAGAATCTGGTGTTATCCAAGAAA
TTCCAGAGCAATACTCAAAAGAAATTGCTAAAAACGACACTAAACAATCACTTAC
TGGTGCACAATATAAAGGGAAAACTTATGCATTCCCATTTGGTATTGAATCTCAAG
TTCTTTATTATAATAAAACAAAGTTAACTGCTGACGACGTTAAATCATACGAAACA
ATTACAAGCAAAGGGAAATTCGGTCAACAGCTTAAAGCAGCTAACTCATATGTAA
CAGGTCCTCTTTTCCTTTCTGTAGGCGACACTTTATTTGGTAAATCTGGTGAAGATG
CTAAAGGCACTAACTGGGGTAATGAAGCAGGTGTTTCTGTCCTTAAATGGATTGCA
GATCAAAAGAAAAATGATGGTTTTGTCAACTTGACAGCTGAAAATACAATGTCTAA
ATTTGGCGATGGTTCTGTTCATGCTTTTGAAAGTGGACCATGGGATTACGACGCTG
CTAAAAAAGCTGTCGGTGAAGATAAAATCGGTGTTGCTGTTTACCCAACAATGAAA
ATCGGTGACAAAGAAGTTCAACAAAAGCATTCTTGGGCGTTAAACTTTATGCCGT
TAACCAAGCACCTGCTGGTTCAAACACTAAACGAATCTCAGCTAGCTACAAACTCG
CTGCATATCTAACTAATGCTGAAAGTCAAAAAATTCAATTCGAAAAACGTCATATC
GTTCCTGCTAACTCATCAATTCAATCTTCTGATAGCGTCCAAAAAGATGAACTTGC
AAAAGCAGTTATCGAAATGGGTAGCTCAGATAAATATACAACGGTTATGCCTAAG
TTGAGTCAAATGTCAACATTCTGGACAGAAAGTGCTGCTATTCTTAGCGATACTTA
CAGTGGTAAAATCAAATCTAGCGATTACCTTAAACGTCTAAAACAATTCGATAAAG
ACATCGCTAAAACAAAATAG

MEKNTWKKLLVSTAALSVVAGGAIAATHSNSVDAASKKTIKLWVPTDSKASYKAIVK
KFEKENKGVTVKMIESNDSKAQENVKKDPSKAADVFSLPHDQLGQLVESGVIQEIPEQ
YSKEIAKNDTKQSLTGAQYKGKTYAFPFGIESQVLYYNKTKLTADDVKSYETITSKGK
FGQQLKAANSYVTGPLFLSVGDTLFGKSGEDAKGTNWGNEAGVSVLKWIADQKKND
GFVNLTAENTMSKFGDGSVHAFESGPWDYDAAKKAVGEDKIGVAVYPTMKIGDKEV
QQKAFLGVKLYAVNQAPAGSNTKRISASYKLAAYLTNAESQKIQFEKRHIVPANSSIQS
SDSVQKDELAKAVIEMGSSDKYTTVMPKLSQMSTFWTESAAILSDTYSGKIKSSDY
LKRLKQFDKDIAKTKZ

ID-2

Clone 5

```
ATGTCAAAACAAAAAGTAACGGCAACTTTGTTGTTATCCACTTTAGTCTTATCGCT
ATCATCACCTTTAGTGACCTTAGCAGAAACTATTAATCCAGAAACAAGCCTGACAA
TGGCAACAGCATCAACAGAAAGTTCTTCTGAAGCAGAGAAACAGGAAAAAACACA
ACCTACAGATTCAGAAACTGCTTCACCTTCAGCCGAAGGAAGTATCTCAACAGAA
AAAACAGAGATTGGTACGACAGAGACATCATCAAGCAATGAATCATCATCAAGTT
CATCACATCAATCTTCTTCCAACGAAGATGCTAAAACATCTGATTCTGCTTCAACA
GCATCTACTCCTAGCACTAATACTACAAACAGTAGTCAAGCAGACAGTAAGCCAG
GTCAATCAACAAAGACTGAATTAAAACCTGAGCCTACCTTACCATTAGTAGAGCCT
AAAATAACTCCCGCTCCGTCTCAGATAGAAAGTGTTCAGACAAATCAGAATGCTTC
TGTTCCTGCTTTATCCTTTGATGATAACTTATTATCAACACCGATTTCACCAGTGAC
AGCAACGCCATTCTACGTAGAACACTGGTCTGGTCAGGATGCCTACTCTCACTATT
TATTGTCACATCGTTACGGTATCAAAGCTGAACAATTAGATGGGTACTTAAAATCT
TTAGGGATTCAATATGATTCTAATCGTATCAATGGTGCTAAGTTATTACAATGGGA
AAAAGATAGTGGTTTAGATGTCCGTGCTATTGTAGCTATTGCTGTCCTTGAAAGTTC
ATTGGGAACTCAAGGAGTGGCTAAAATGCCAGGTGCTAATATGTTTGGTTATGGTG
CCTTTGATCATGACTCTAGCCATGCTAGTGCTTATAATGATGAAGAAGCAATTATG
TTGTTGACAAAAAATACAATTATTAAAAACAACAACTCTAGCTTTGAAATCCAAGA
TTTGAAAGCACAGAAATTATCTTCTGGACAACTTAATACAGTTACTGAGGGTGGTG
TTTATTATACAGATAACTCTGGAACTGGTAAACGTCGTGCCCAGATTATGGAAGAT
TTAGACCGCTGGATTGATCAACATGGAGGGACACCAGAAATTCCTGCTGCCTTGAA
AGCTTTATCGACAGCAAGTTTAGCAGATTTACCAAGTGGTTTTAGCTTATCAACAG
CGGTTAACACAGCTAGCTATATTGCATCAACTTATCCATGGGGTGAATGTACATGG
TATGTCTTTAACCGCGCTAAAGAGTTAGGTTATACATTTGATCCATTTATGGGTAAT
GGTGGAGATTGGCAACATAAGGCTGGCTTTGAAACAACACATTCACCAAAAGTAG
GCTATGCTGTATCATTTTCACCAGGACAAGCTGGTGCTGATGGCACTTACGGTCAC
GTAGCTATTGTTGAAGAAGTTAAAAAAGATGGTTCAGTTCTCATTTCAGAATCTAA
TGCAATGGGACGTGGTATTGTCTCTTACCGTACTTTTAGTTCAGCACAAGCTGCAC
AATTAACTTATGGTATTGGCCATAAATAA
```

```
MSKQKVTATLLLSTLVLSLSSPLVTLAETINPETSLTMATASTESSSEAEKQEKTQPTDS
ETASPSAEGSISTEKTEIGTTETSSSNESSSSSSHQSSSNEDAKTSDSASTASTPSTNTTNS
SQADSKPGQSTKTELKPEPTLPLVEPKITPAPSQIESVQTNQNASVPALSFDDNLLSTPIS
PVTATPFYVEHWSGQDAYSHYLLSHRYGIKAEQLDGYLKSLGIQYDSNRINGAKLLQ
WEKDSGLDVRAIVAIAVLESSLGTQGVAKMPGANMFGYGAFDHDSSHASAYNDEEAI
MLLTKNTIIKNNNSSFEIQDLKAQKLSSGQLNTVTEGGVYYTDNSGTGKRRAQIMEDL
DRWIDQHGGTPEIPAALKALSTASLADLPSGFSLSTAVNTASYIASTYPWGECTWYVF
NRAKELGYTFDPFMGNGGDWQHKAGFETTHSPKVGYAVSFSPGQAGADGTYGHVAI
VEEVKKDGSVLISESNAMGRGIVSYRTFSSAQAAQLTYGIGHKZ
```

FIG. 1 CONT'D

ID-3

Clone 6

GTGCATATGTTACAAAACATTGGACAAACAGGCATTCAAGCAACTCGAATTGCTTT
AGGTTGTATGAGAATGAGTGACTTGAAAGGAAAACAAGCTGAAGAAGTAGTTGGA
ACAGCATTAGATTTGGGTATTATAAATAATAAAGTGCAAGAAAGTGTCTCTGGCGT
CAAAGTGACTAAATCATTGTGTTATCAAGAACAAGAAATTGCTTCTTTTCAAGAGA
TTAATCAGATGACTTTCGTGAAGAACATGCGGACCATGACTTATGATGTCATGTTT
GATCCTTTAGTTCTTCTTTTTATAGGTGCCTCCTACGTATTAACATTGGCTATGGGA
GCTTTTATGATTTCAAAAGGTCAAGTTACTGTTGGTGACTTGGTAACATTTGTGACG
TATTTAGATATGTTGGTATGGCCCTTGATGGCGATTGGTTTCTTGTTCAATATGGTA
CAGCGTGGTAGTGTTTCTTATAACCGTATTAATAGTCTACTTGAGCAAGAATCGGA
TATAACTGATCCTTTAAATCCTATCAAACCTGTTGTCAATGGAACATTAAGATA
TGATATTGATTTCTTTAGATACGACAATGAGGAAACCTTAGCCGATATTCATTTCAC
CTTAGAAAAAGGTCAAACCTTAGGTTTGGTAGGTCAAACGGGATCAGGGAAGACA
AGTCTTATTAAGTTATTGCTACGTGAACATGATGTGACTCAGGGGAAAATTACTTT
AAATAAACATGATATACGTGATTATCGATTGTCTGAGTTACGTCAACTAATCGGTT
ATGTTCCTCAAGATCAGTTTTTATTTGCTACCAGTATTTTAGAAAATGTTCGCTTTG
GAAATCCAACTCTATCTATCAATGCTGTCAAAGAAGCAACTAAATTGGCACATGTT
TACGATGACATTGAACAGATGCCAGCAGGATTTGAGACTCTAATTGGAGAAAAAG
GAGTCTCATTATCTGGTGGACAAAAACAAAGGATTGCGATGAGTCGTGCCATGATT
TTAGATCCAGATATTCTTATTTTGGATGATTCTCTATCAGCAGTGGACGCTAAAACG
GAACATGCTATTGTTGAGAATCTTAAAACGAATCGTCAAGGGAAATCGACTATTA
TTTCAGCACATCGTTTATCAGCTGTTGTGCACGCAGACCTTATCTTAGTTATGCGAG
ACGGCAGAGTCATTGAGCGAGGTCAACATCAAGAGTTGCTAAATAAAGGTGGTTG
GTATGCTGAAACGTATGCCTCACAGCAATTAGAAATGGAGGAAGCATTTGATGAA
GTCTAA

MHMLQNIGQTGIQATRIALGCMRMSDLKGKQAEEVVGTALDLGIINNKVQESVSGVK
VTKSLCYQEQEIASFQEINQMTFVKNMRTMTYDVMFDPLVLLFIGASYVLTLAMGAF
MISKGQVTVGDLVTFVTYLDMLVWPLMAIGFLFNMVQRGSVSYNRINSLLEQESDITD
PLNPIKPVVNGTLRYDIDFFRYDNEETLADIHFTLEKGQTLGLVGQTGSGKTSLIKLLLR
EHDVTQGKITLNKHDIRDYRLSELRQLIGYVPQDQFLFATSILENVRFGNPTLSINAVKE
ATKLAHVYDDIEQMPAGFETLIGEKGVSLSGGQKQRIAMSRAMILDPDILILDDSLSAV
DAKTEHAIVENLKTNRQGKSTIISAHRLSAVVHADLILVMRDGRVIERGQHQELLNKG
GWYAETYASQQLEMEEAFDEVZ

ID-4

Clone 6b

TTGATGAAGTCTAATCAATGGCAAGTCTTTAAGAGATTAATCTCCTATTTACGCCCT
TATAAATGGTTTACAGTATTAGCTCTATCTCTCTTATTGTTGACGACTGTTGTTAAA

FIG. 1 CONT'D

AATATTATTCCTTTAATTGCTTCACATTTTATTGATCACTATCTGACAAATGTTAAT
CAAACAGCAGTTCTTATTTTAGTGGGATATTATTCAATGTATGTCTTGCAGACCTTA
ATTCAATATTTTGGGAATCTCTTTTTTGCGCGTGTTTCTTATAGTATTGTTAGAGAT
ATTCGTAGAGATGCTTTTGCTAATATGGAAAGGCTAGGCATGTCTTATTTTGATAG
GACACCGGCAGGATCTATTGTGTCACGTATTACTAATGATACTGAAGCAATATCTG
ATATGTTTTCGGGTATTTTATCAAGTTTTATCTCGGCGATATTTATTTTACAGTTAC
TCTGTACACTATGTTGATGCTAGACATTAAACTAACAGGACTCGTCGCTCTTTTGTT
ACCTGTTATCTTTATATTAGTGAATGTCTATCGGAAAAAATCAGTCACTGTCATTGC
TAAAACGAGAAGTTTACTTAGTGATATCAACAGTAAATTATCAGGAAGTATTGAAG
GAATTCGCATTGTACAGGCTTTTGGTCAAGAAGAGCGCTTGAAGACTGAATTTGAG
GAAATTAACAAAGAGCATGTTGTGTATGCCAATCGTTCTATGGCTCTTGATAGTCT
CTTCTTAAGACCGGCGATGTCTCTTTTAAAACTCCTAGCATATGCTGTTCTTATGTC
TTATTTTGGATTTACAGGAGTTAAAGGAGGTCTTACGGCAGGATTAATGTATGCTT
TTATTCAGTACGTTAATCGTCTATTTGACCCTTTAATTGAAGTAACGCAAAATTTTT
CAACCTTACAAACATCAATGGTATCAGCAGGGCGTGTGTTTGATCTGATTGAT
GAAACAGGTTTTGAACCAAGCCAAAAAAATACAGAAGCT

MKSNQWQVFKRLISYLRPYKWFTVLALSLLLLTTVVKNIIPLIASHFIDHYLTNVNQTA
VLILVGYYSMYVLQTLIQYFGNLFFARVSYSIVRDIRRDAFANMERLGMSYFDRTPAG
SIVSRITNDTEAISDMFSGILSSFISAIFIFTVTLYTMLMLDIKLTGLVALLLPVIFILVNVY
RKKSVTVIAKTRSLLSDINSKLSGSIEGIRIVQAFGQEERLKTEFEEINKEHVVYANRSM
ALDSLFLRPAMSLLKLLAYAVLMSYFGFTGVKGGLTAGLMYAFIQYVNRLFDPLIEVT
QNFSTLQTSMVSAGRVFDLIDETGFEPSQKNTEA

ID-5

Clone 7

ATGAAAAGAAAAGACTTATTTGGTGATAAACAAACTCAATACACGAT
TAGAAAGTTAAGTGTTGGAGTAGCTTCAGTTGCAACAGGGGTATGTA
TTTTTCTTCATAGTCCACAGGTATTTGCTGAAGAAGTAAGTGTTTCTC
CTGCAACTACAGCGATTGCAAAGTCGAATATTAATCAGGTTGACAAC
CGGCAATCTACTAATTTAAAAGATGACATAAACTCAAACTCTGAGAC
GGTTGTGACACCCTCAGATATGCCGGATACCAAGCAATTAGTATCAG
ATGAAACTGACACTCAAAAAGGAGTGACAGAGCCGGATAAGGCGAC
AAGCCTGCTTGAAGAAATAAAGGTCCTGTTTCAGATAAAAATACCT
TAGATTTAAAAGTGGCACCATCTACATTGCAAAATACTCCCGACAAA
ACTTCTCAAGCTATAGGTGCTCCAAGTCCGACCTTGAAAGTTGCTAAT
CAAGCTCCACAGATTGAAAATGGTTACTTTAGGTTACATCTTAAAGA
ATTGCCTCAAGGTCATCCTGTAGAAAGCACTGGGCTTTGGATATGGG
GAGATGTTGATCAACCGTCTAGTAATTGGCCAAATGGTGCTATCCCT
ATGACTAATGCTAAGAAAGATGATTACGGTTATTATGTTGATTTTAA
ATTATCTGAAAAACAACGAAAACAAATATCTTTTTTAATTAATAACA
AAGCAGGAACAAATTTAAGCGGCGATCATCATATTCCATTATTACGA

```
CCTGAGATGAACCAAGTTTGGATTGATGAAAAGTACGGTATACATAC
TTATCAGCCCCTCAAAGAAGGGTATGTCCGTATTAACTATTTGAGTTC
ATCTGGTAACTATGACCACTTATCAGCATGGCTCTTTAAAGATGTTGC
AACCCCCTCAACAACTTGGCCAGATGGTAGTAATTTTGTGAATCAAG
GACTATATGGAAGGTATATTGATGTACCACTGAAAACTAATGCCAAA
GAGATTGGTTTTCTAATCTTAGATGAAAGTAAGACAGGAGATGCAGT
GAAAGTTCAACCCAACGACTATGTTTTTAGAGATTTAGCTAACCATA
ACCAAATTTTTGTAAAAGATAAGGATCCAAAGGTTTATAATAATCCT
TATTACATTGATCAAGTGCAGCTAAAGGATGCTCAACAAACTGATTT
AACAAGTATTCAAGCAAGTTTTACAACTCTAGATGGGGTAGATAAAA
CTGAAATTTTAAAAGAATTGAAAGTGACAGATAAAAATCAAAATGCT
ATACAAATTTCTGATATCACTCTCGATACTAGTAAATCTCTTTTAATA
ATCAAAGGCGACTTTAATCCTAAACAAGGTCATTTCAATATATCTTAT
AATGGTAACAATGTCACGACAAGGCAATCTTGGGAATTTAAAGACCA
ACTTTATGCTTATAGTGGAAATTTAGGTGCAGTTCTCAATCAAGATGG
TTCAAAAGTTGAAGCCAGCCTCTGGTCACCGAGTGCTGATAGTGTCA
CTATGATTATTTATGACAAAGATAATCAAAACAGGGTTGTAGCGACT
ACCCCCCTTGTGAAAAATAATAAAGGTGTTTGGCAGACGATACTTGA
TACTAAATTAGGTATTAAAAACTATACTGGTTACTATTATCTTTACGA
AATAAAAAGAGGTAAGGATAAGGTTAAGATTTTAGATCCTTATGCAA
AGTCATTAGCAGAGTGGGATAGTAATACTGTTAATGACGATATAAAA
ACGGCTAAAGCAGCTTTTGTAAATCCAAGTCAACTTGGACCTAAAAA
TTTAAGTTTTGCTAAAATTGCTAATTTTAAAGGAAAACAAGATGCTGT
TATATACGAAGCACATGTAAGAGACTTCACTTCTGATCAATCTTTGG
ACGGAAAATTAAAAAATCAACTTGGTACCTTTGCAGCCTTTTCAGAG
AAACTAGATTATTTACAGAAATTAGGAGTTACACACATTCAGCTTTT
ACCGGTATTGAGTTATTTTTATGTTAATGAAATGGATAAGTCACGCTC
AACAGCTTACACTTCCTCAGACAATAATTACAATTGGGGCTATGACC
CACAGAGCTATTTTGCTCTTTCTGGAATGTATTCAGAGAAACCAAAA
GATCCATCAGCACGTATCGCCGAATTAAAACAATTAATACATGATAT
TCATAAACGTGGCATGGGGGTTATACTTGATGTCGTCTATAATCACA
CTGCAAAAACTTATCTCTTTGAGGATATAGAACCTAATTATTATCACT
TTATGAATGAAGATGGTTCACCAAGAGAAAGTTTTGGAGGGGGACGT
TTAGGAACCACTCATGCAATGAGTCGTCGTGTTTTGGTTGATTCCATT
AAATATCTTACAAGTGAATTTAAAGTTGATGGTTTCCGTTTTGATATG
ATGGGAGATCATGATGCGGCTGCGATTGAATTAGCTTATAAAGAAGC
TAAAGCTATTAATCCTAATATGATTATGATTGGTGAGGGCTGGAGAA
CATTCCAAGGCGATCAAGGTAAGCCGGTTAAACCAGCTGACCAAGAT
TGGATGAAGTCAACCGATACAGTTGGCGTCTTTTCAGATGATATTCGT
AATAGCTTGAAATCTGGTTTTCCAAATGAAGGTACTCCAGCTTTCATC
ACAGGTGGCCCACAATCTTTACAAGGTATTTTTAAAAATATCAAAGC
ACAACCTGGGAATTTTGAAGCAGATTCGCCAGGAGATGTGGTGCAGT
ATATTGCTGCACATGATAACCTTACCTTGCATGATGTGATTGCAAAAT
CAATTAATAAAGACCCTAAGGTAGCTGAAGAAGATATTCATAGACGT
```

FIG. 1 CONT'D

```
CTGCGTTTAGGAAATGTAATGATTTTAACATCTCAAGGGACAGCATT
CATTCATTCTGGTCAAGAGTATGGTCGTACGAAGCGTTTACTTAACCC
TGATTACATGACAAAAGTTTCAGATGACAAATTGCCTAATAAAGCAA
CACTTATTGAAGCTGTTAAAGAATACCCATATTTTATTCATGATTCAT
ATGATTCTTCAGATGCCATTAATCATTTTGATTGGGCAGCAGCCACAG
ATAATAACAAACACCCAATTTCAACGAAAACACAGGCCTATACAGCA
GGTTTAATCACATTAAGGCGTTCAACAGATGCTTTCCGGAAATTGAG
CAAAGCAGAAATTGATCGTGAGGTTAGCTTGATTACAGAGGTAGGTC
AAGGTGATATTAAAGAAAAGATTTGGTTATTGCTTACCAAACAATA
GATTCTAAAGGCGATATTTACGCAGTATTTGTTAATGCTGATAGTAA
AGCTAGAAACGTTTTACTAGGTGAAAAATATAAACACCTTTTAAAAG
GGCAAGTAATTGTTGATGCTGATCAAGCGGGGATTAAACCAATCTCA
ACTCCTAGAGGTGTTCATTTGAAAAAGATAGTTTGCTGATTGATCCA
TTAACAGCAATTGTGATTAAAGTTGGCAAAGTTGCTCCTAGCCCTAA
GGAGGAATTGCAAGCAGATTATCCCAAAACACAATCTTTCAAGGGAT
CTAAAACGGTAGAAAAAGTAAATAGAATAGCTAATAAGACCTCAAT
AACTCCTGTAGTTTCTAATAAGACCGATTCATATCTGACAAATGAAG
CTAATTTGCCAAAAACTGGAGATAAGTCATCAAAAATACTAAGTGTA
GTAGGAATAAGCATTCTAGCAAGTCTACTTGCTCTACTAGGTCTCTCT
TTAAAGAGGAATCGCACTTAA
```

```
MKRKDLFGDKQTQYTIRKLSVGVASVATGVCIFLHSPQVFAEEVSVSPA
TTAIAKSNINQVDNRQSTNLKDDINSNSETVVTPSDMPDTKQLVSDETDT
QKGVTEPDKATSLLEENKGPVSDKNTLDLKVAPSTLQNTPDKTSQAIGA
PSPTLKVANQAPQIENGYFRLHLKELPQGHPVESTGLWIWGDVDQPSSN
WPNGAIPMTNAKKDDYGYYVDFKLSEKQRKQISFLINNKAGTNLSGDH
HIPLLRPEMNQVWIDEKYGIHTYQPLKEGYVRINYLSSSGNYDHLSAWL
FKDVATPSTTWPDGSNFVNQGLYGRYIDVPLKTNAKEIGFLILDESKTGD
AVKVQPNDYVFRDLANHNQIFVKDKDPKVYNNPYYIDQVQLKDAQQT
DLTSIQASFTTLDGVDKTEILKELKVTDKNQNAIQISDITLDTSKSLLIIKG
DFNPKQGHFNISYNGNNVTTRQSWEFKDQLYAYSGNLGAVLNQDGSKV
EASLWSPSADSVTMIIYDKDNQNRVVATTPLVKNNKGVWQTILDTKLGI
KNYTGYYYLYEIKRGKDKVKILDPYAKSLAEWDSNTVNDDIKTAKAAF
VNPSQLGPKNLSFAKIANFKGKQDAVIYEAHVRDFTSDQSLDGKLKNQL
GTFAAFSEKLDYLQKLGVTHIQLLPVLSYFYVNEMDKSRSTAYTSSDNN
YNWGYDPQSYFALSGMYSEKPKDPSARIAELKQLIHDIHKRGMGVILDV
VYNHTAKTYLFEDIEPNYYHFMNEDGSPRESFGGGRLGTTHAMSRRVL
VDSIKYLTSEFKVDGFRFDMMGDHDAAAIELAYKEAKAINPNMIMIGEG
WRTFQGDQGKPVKPADQDWMKSTDTVGVFSDDIRNSLKSGFPNEGTPA
FITGGPQSLQGIFKNIKAQPGNFEADSPGDVVQYIAAHDNLTLHDVIAKSI
NKDPKVAEEDIHRRLRLGNVMILTSQGTAFIHSGQEYGRTKRLLNPDYM
TKVSDDKLPNKATLIEAVKEYPYFIHDSYDSSDAINHFDWAAATDNNKH
PISTKTQAYTAGLITLRRSTDAFRKLSKAEIDREVSLITEVGQGDIKEKDL
```

FIG. 1 CONT'D

VIAYQTIDSKGDIYAVFVNADSKARNVLLGEKYKHLLKGQVIVDADQA
GIKPISTPRGVHFEKDSLLIDPLTAIVIKVGKVAPSPKEELQADYPKTQSFK
GSKTVEKVNRIANKTSITPVVSNKTDSYLTNEANLPKTGDKSSKILSVVG
ISILASLLALLGLSLKRNRT*

ID-6

Clone 9

ATGAAAAAAGTTTTTTTTCTCATGGCTATGGTTGTGAGTTTAGTAATGATAGCAGG
GTGTGATAAGTCAGCAAACCCCAAACAGCCTACGCAAGGCATGTCAGTTGTAACC
AGCTTTTACCCAATGTATGCGATGACAAAAGAAGTATCTGGAGACCTAAATGATGT
GAGGATGATCCAATCAGGTGCAGGCATTCATTCCTTTGAACCGTCTGTAAATGATG
TGGCAGCTATTTATGACGCGGATTTGTTTGTTTACCAATCACATACCTTAGAAGCTT
GGGCAAGGGATCTAGACCCTAATTTAAAAAAATCAAAGGTTAATGTGTTTGAAGC
GTCAAAACCTCTGACACTAGATAGAGTCAAAGGGCTAGAAGATATGGAAGTCACA
CAAGGCATTGACCCTGCGACACTTTATGACCCACATACCTGGACGGATCCCGTTTT
AGCTGGTGAGGAAGCTGTTAATATCGCTAAAGAGCTAGGACATTTGGATCCTAAAC
ACAAAGACAGTTACACTAAAAAGGCTAAGGCTTTCAAAAAAGAAGCAGAGCAACT
AACTGAAGAATACACTCAAAAATTTAAAAAGGTGCGCTCAAAAACATTTGTGACG
CAACACACGGCATTTTCTTATCTGGCTAAACGATTCGGCTTGAAACAACTTGGTAT
CTCGGGTATTTCTCCAGAGCAAGAGCCCTCTCCTCGCCAATTGAAAGAAATTCAAG
ACTTTGTTAAAGAATACAACGTCAAGACTATTTTTGCAGAAGACAACGTCAACCCC
AAAATTGCTCATGCTATTGCGAAATCAACAGGAGCTAAAGTAAAGACATTAAGTC
CACTTGAAGCTGCTCCAAGCGGAAACAAGACATATCTAGAAAATCTTAGAGCAAA
TTTGGAAGTGCTCTATCAACAGTTGAAGTAA

MKKVFFLMAMVVSLVMIAGCDKSANPKQPTQGMSVVTSFYPMYAMTKEVSGDLND
VRMIQSGAGIHSFEPSVNDVAAIYDADLFVYQSHTLEAWARDLDPNLKKSKVNVFEAS
KPLTLDRVKGLEDMEVTQGIDPATLYDPHTWTDPVLAGEEAVNIAKELGHLDPKHKD
SYTKKAKAFKKEAEQLTEEYTQKFKKVRSKTFVTQHTAFSYLAKRFGLKQLGISGISPE
QEPSPRQLKEIQDFVKEYNVKTIFAEDNVNPKIAHAIAKSTGAKVKTLSPLEAAPSGNK
TYLENLRANLEVLYQQLK*

ID-7

Clone 15

TTGTTCAATAAAATAGGTTTTAGAACTTGGAAATCAGGAAAGCTTTG
GCTTTATATGGGAGTGCTAGGATCAACTATTATTTTAGGATCAAGTCC
TGTATCTGCTATGGATAGTGTTGGAAATCAAAGTCAAGGTAATGTTTT
AGAGCGTCGCCAACGTGATGCGGAAAACAAAAGTCAGGGTAATGTT
TTAGAGCGTCGCCAACGTGATGCGGAAAACAAGAGCCAAGGCAATG
TTTTAGAGCGTCGTCAACGCGATGTTGAGAATAAGAGCCAAGGCAAT

FIG. 1 CONT'D

```
GTTTTAGAGCGTCGTCAACGTGATGCGGAAAACAAAAGTCAGGGCA
ATGTTCTAGAGCGCCGCCAACGTGATGCGGATAACAAGAGCCAAGTA
GGTCAACTTATAGGGAAAAATCCACTTTTTTCAAAGCCAACTGTATCT
AGAGAAAATAATCACTCTAGTCAAGGTGACTCTAACAAACAGTCATT
CTCTAAAAAAGTATCTCAGGTTACTAATGTAGCTAATAGACCGATGT
TAACTAATAATTCTAGAACAATTTCAGTGATAAATAAATTACCTAAA
ACAGGTGGTGATCAAAATGTCATTTTTAAACTTGTAGGTTTTGGTTTA
ATTTGTTAACAAGTCGCTGCGGTTTGAGACGCAATGAAAATTAA

MFNKIGFRTWKSGKLWLYMGVLGSTIILGSSPVSAMDSVGNQSQGNVL
ERRQRDAENKSQGNVLERRQRDAENKSQGNVLERRQRDVENKSQGNV
LERRQRDAENKSQGNVLERRQRDADNKSQVGQLIGKNPLFSKPTVSREN
NHSSQGDSNKQSFSKKVSQVTNVANRPMLTNNSRTISVINKLPKTGGDQ
NVIFKLVGFGLILLTSRCGLRRNEN*
```

ID-8

Clone 17

```
ATGACAAAAAAACTTATTATTGCTATATTAGCACTATGCACTATCTTAACCACTTCT
CAAGCTGTTTTAGCTAAAGAAAAATCACAAACTGTTACCATAAAAAACAACTATTC
GGTCTATATTAAAAAAGAAAAAGAGACAAGCCGGATAATAAAAAGCAAATCAG
CGAGACACTTAAAGTTCCTTTAAAACCCAAAAAAGTAGTTGTTTTTGATATGGGAG
CTTTGGATACTATCACAGCTTTAGGAGCTGAAAAATCTGTTATTGGTATCCCGAAG
GCTAAAAATGCTCTAAGTTTATTGCCCAATAACGTCAAATCTGTTTATAAAGCTAA
GAGATACCAAGACGTAGGAAGTCTCTTCGAACCAAACTTTGAAGCTATTGCTCGTA
TGCAACCTGATGTGGTTTTCCTAGGAGCACGTATGGCTTCTGTTGATAATATTGAA
AAATTAAAGGAGGCTGCACCTAAAGCAGCATTAGTATATGCTGGAGTCGACTCAA
AAAAAGTATTTGACAAAGGAGTTGCTGAGCGTGTCACAATGTTAGGGAAAATCTTC
GACCAAAATAAAAAGGCAAAAACCTTTAATAAAGATATCGCACAAGCTGTTCTTA
AATTGCAGAAAACTATTGAGAAAAAAGGTAAACCTACAGCTCTATTTGTAATGGC
AAACAGCGGTGAACTTTTAACTCAATCACCTTCTGGTCGTTTTGGTTGGATTTTCTC
TGTAGGTGGATTTAAAGCAGTCAATGAAAATGAAAAACTAAGTTCACATGGTACTC
CCGTATCTTATGAATACATCGCTGAAAAAAATCCTAACTATCTCTTTGTTTTAGATC
GTGGAGCGACTATTGGACAAGGAGCTTCATCAAAAGAACTTTTTAATAACGATGTT
ATTAAAGCAACTGATGCTGTCAAAAACAAACGTGTTCATGAGGTAGATGGAAAAG
ATTGGTATATCAATTCAGGCGGAAGCCGAGTAACACTCCGTATGATTAAAGATGTA
CAGAACTTTGTTGATAATCGTTAA
```

```
MTKKLIIAILALCTILTTSQAVLAKEKSQTVTIKNNYSVYIKKEKRDKPDN
KKQISETLKVPLKPKKVVVFDMGALDTITALGAEKSVIGIPKAKNALSLL
PNNVKSVYKAKRYQDVGSLFEPNFEAIARMQPDVVFLGARMASVDNIE
KLKEAAPKAALVYAGVDSKKVFDKGVAERVTMLGKIFDQNKKAKTFN
KDIAQAVLKLQKTIEKKGKPTALFVMANSGELLTQSPSGRFGWIFSVGG
```

FKAVNENEKLSSHGTPVSYEYIAEKNPNYLFVLDRGATIGQGASSKELFN
NDVIKATDAVKNKRVHEVDGKDWYINSGGSRVTLRMIKDVQNFVDNR
*

ID-9

Clone 18

GTGAAGAAAACATATGGTTATATCGGCTCAGTTGCTGCTATTTTACTAGCTACTCAT
ATTGGAAGTTACCAGCTTGGTAAGCATCATATGGGTCTAGCAACAAAGGACAATC
AGATTGCCTATATTGATGATAGCAAAGGTAAGGTAAAAGCCCCTAAAACAAACAA
AACGATGGATCAAATCAGTGCTGAAGAAGGCATCTCTGCTGAACAGATCGTAGTC
AAAATTACTGACCAAGGTTATGTTACCTCACACGGTGACCATTATCATTTTTACAAT
GGGAAAGTTCCTTATGATGCGATTATTAGTGAAGAGTTGTTGATGACGGATCCTAA
TTACCATTTTAAACAATCAGACGTTATCAATGAAATCTTAGACGGTTACGTTATTA
AAGTCAATGGCAACTATTATGTTTACCTCAAGCCAGGTAGTAAGCGCAAAAACATT
CGAACCAAACAACAAATTGCTGAGCAAGTAGCCAAAGGAACTAAAGAAGCTAAA
GAAAAAGGTTTAGCTCAAGTGGCCCATCTCAGTAAAGAAGAAGTTGCGGCAGTCA
ATGAAGCAAAAAGACAAGGACGCTATACTACAGACGATGGCTATATTTTAGTCC
GACAGATATCATTGATGATTTAGGAGATGCTTATTTAGTACCTCATGGTAATCACT
ATCATTATATTCCTAAAAAAGATTTGTCTCCAAGTGAGCTAGCTGCTGCACAAGCC
TACTGGAGTCAAAAACAAGGTCGAGGTGCTAGACCGTCTGATTACCGCCCGACAC
CAGCCCCAGGTCGTAGGAAAGCCCCAATTCCTGATGTGACGCCTAACCCTGGACA
AGGTCATCAGCCAGATAACGGTGGTTATCATCCAGCGCCTCCTAGGCCAAATGATG
CGTCACAAAACAAACACCAAAGAGATGAGTTTAAAGGAAAAACCTTTAAGGAACT
TTTAGATCATCTACACCGTCTTGATTTGAAATACCGTCATGTGGAAGAAGATGGGT
TGATTTTTGAACCGACTCAAGTGATCAAATCAAACGCTTTTGGGTATGTGGTGCCT
CATGGAGATCATTATCATATTATCCCAAGAAGTCAGTTATCACCTCTTGAAATGGA
ATTAGCAGATCGATACTTAGCCGGCCAAACTGATGACAACGACTCAGGTTCAGATC
ACTCAAAACCATCAGATAAAGAAGTGACACATACCTTTCTTGGTCATCGCATCAAA
GCTTACGGAAAAGGCTTAGATGGTAAACCATATGATACGAGTGATGCTTATGTTTT
TAGTAAAGAATCCATTCATTCAGTGGATAAATCAGGAGTTACAGCTAAACACGGA
GATCATTTCCACTATATAGGATTTGGAGAACTTGAACAATATGAGTTGGATGAGGT
CGCTAACTGGGTGAAAGCAAAAGGTCAAGCTGATGAGCTTGTTGCTGCTTTGGATC
AGGAACAAGGCAAAGAAAAACCACTCTTTGACACTAAAAAAGTGAGTCGCAAAGT
AACAAAAGATGGTAAAGTGGGCTATATTATGCCAAAAGATGGCAAGGACTATTTC
TATGCTCGTTATCAACTTGATTTGACTCAGATTGCCTTTGCCGAACAAGAACTAATG
CTTAAAGATAAGAAGCATTACCGTTATGACATTGTTGATACAGGCATTGAGCCACG
ACTTGCTGTAGATGTGTCAAGTCTGCCGATGCATGCTGGTAATGCTACTTACGATA
CTGGAAGTTCGTTTGTTATCCCACATATTGATCATATCCATGTCGTTCCGTATTCAT
GGTTGACGCGCAATCAGATTGCAACAATCAAGTATGTGATGCAACACCCCGAAGT
TCGTCCGGATGTATGGTCTAAGCCAGGGCATGAAGAGTCAGGTTCGGTCATTCCAA
ATGTTACGCCTCTTGATAAACGTGCT

FIG. 1 CONT'D

```
GGTATGCCAAACTGGCAAATTATCCATTCTGCTGAAGAAGTTCAAAAAGCCCTAGC
AGAAGGTCGTTTTGCAGCACCAGACGGCTATATTTTCGATCCACGAGATGTTTTGG
CAAAAGAAACTTTTGTATGGAAAGATGGCTCCTTTAGCATCCCAAGAGCAGATGGC
AGTTCATTGAGAACCATTAATAAATCCGATCTATCCCAAGCTGAGTGGCAACAAGC
TCAAGAGTTATTGGCAAAGAAAAATGCTGGTGATGCTACTGATACGGATAAACCT
GAAGAAAAGCAACAGGCAGATAAGAGCAATGAAAACCAACAGCCAAGTGAAGCC
AGTAAAGAAGAAAAAGAATCAGATGACTTTATAGACAGTTTACCAGACTATGGTC
TAGATAGAGCAACCCTAGAAGATCATATCAATCAATTAGCACAAAAAGCTAATAT
CGATCCTAAGTATCTCATTTTCCAACCAGAAGGTGTCCAATTTTATAATAAAAATG
GTGAATTGGTAACTTATGATATCAAGACACTTCAACAAATAAACCCTTAA
```

MKKTYGYIGSVAAILLATHIGSYQLGKHHMGLATKDNQIAYIDDSKGKVKAPKTNKT
MDQISAEEGISAEQIVVKITDQGYVTSHGDHYHFYNGKVPYDAIISEELLMTDPNYHFK
QSDVINEILDGYVIKVNGNYYVYLKPGSKRKNIRTKQQIAEQVAKGTKEAKEKGLAQV
AHLSKEEVAAVNEAKRQGRYTTDDGYIFSPTDIIDDLGDAYLVPHGNHYHYIPKKDLS
PSELAAAQAYWSQKQGRGARPSDYRPTPAPGRRKAPIPDVTPNPGQGHQPDNGGYHP
APPRPNDASQNKHQRDEFKGKTFKELLDHLHRLDLKYRHVEEDGLIFEPTQVIKSNAF
GYVVPHGDHYHIIPRSQLSPLEMELADRYLAGQTDDNDSGSDHSKPSDKEVTHTFLGH
RIKAYGKGLDGKPYDTSDAYVFSKESIHSVDKSGVTAKHGDHFHYIGFGELEQYELDE
VANWVKAKGQADELVAALDQEQGKEKPLFDTKKVSRKVTKDGKVGYIMPKDGKDY
FYARYQLDLTQIAFAEQELMLKDKKHYRYDIVDTGIEPRLAVDVSSLPMHAGNATYD
TGSSFVIPHIDHIHVVPYSWLTRNQIATIKYVMQHPEVRPDVWSKPGHEESGSVIPNVTP
LDKRAGMPNWQIIHSAEEVQKALAEGRFAAPDGYIFDPRDVLAKETFVWKDGSFSIPR
ADGSSLRTINKSDLSQAEWQQAQELLAKKNAGDATDTDKPEEKQQADKSNENQQPSE
ASKEEKESDDFIDSLPDYGLDRATLEDHINQLAQKANIDPKYLIFQPEGVQFYNKNGEL
VTYDIKTLQQINP*

ID-10

Clone 22

```
ATGATACGCCAGTTTTTAAGAGAACACTTGATTTGGTATATTTTATATATCATGATG
TTTGTCCTATTTTTTATTAGTTTCTATCTATATCATTTACCAATGCCCTATTTGTTTA
ATTCCTTAGGTTTAAATGTTATTGTTTTACTAGGAATTAGTATTTGGCAATACAGTC
GTTACAGGAAAAAAATGTTACATCTCAAATATTTTAATAGTAGTCAGGACCCCTCT
TTCGAACTTCAACCGAGTGATTACGCTTATTTTAATATTATTACACAATTAGAAGCT
AGAGAAGCGCAAAAAGTTTCTGAAACAATTGAACAAACCAATCATGTTGCACTTA
TGATAAAGATGTGGTCGCACCAAATGAAAGTTCCATTGGCAGCTATTTCATTAATG
GCCCAGACAAATCATCTCGATCCTAAGGAAGTTGAACAACAATTATTGAAATTGCA
ACATTATCTTGAAACGTTGTTAGCATTTTTGAAATTTAGACAATATCGTGACGATTT
TCGTTTTGAAGCTGTTAGCCTTAGAGAAGTAGTAGTAGAAATTATAAAATCGTATA
AGGTTATTTGTCTATCCAAAAGCTTATCTATCATAATTGAAGGCGATAATATCTGG
AAAACAGACAAAAAGTGGTTAACTTTTGCTCTTTCACAGGTGCTAGATAATGCCAT
```

AAAATATTCTAATCCTGAGTCAAAGATAATAATAAGCATAGGAGAAGAGAGTATT
AGAATACAAGACTACGGTATCGGCATACTCGAAGAGGATATCCCTAGACTTTTTGA
AGATGGCTTTACGGGTTACAACGGTCATGAGCACCAAAAGGCAACAGGCATGGGG
TTATATATGACAAAAGAAGTCTTATCTAGTCTGAATTTGTCCATTTCGGTGGATAGC
AAAATTAATTATGGGACTGCTGTTTCTATACATAAATAA

MIRQFLREHLIWYILYIMMFVLFFISFYLYHLPMPYLFNSLGLNVTVLLGISIWQYSRYR
KKMLHLKYFNSSQDPSFELQPSDYAYFNIITQLEAREAQKVSETIEQTNHVALMIKMW
SHQMKVPLAAISLMAQTNHLDPKEVEQQLLKLQHYLETLLAFLKFRQYRDDFRFEAV
SLREVVVEIIKSYKVICLSKSLSIIIEGDNIWKTDKKWLTFALSQVLDNAIKYSNPESKIIIS
IGEESIRIQDYGIGILEEDIPRLFEDGFTGYNGHEHQKATGMGLYMTKEVLSSLNLSISV
DSKINYGTAVSIHKZ

ID-11

Clone 23

ATGACTTATCAAAAAACAGTTGTTTTGGCTGGTGATTATTCCTACATTAGACAAATT
GAAACCACATTAAAATCTCTCTGTGTCTATCATGAGAATCTCTCAATTTTTATTTTT
AATCAAGATATTCCTCAAGAATGGTTTTTAGCTATGAAAGATAGGGTTGGACAAAC
TGGAAATCAAATTCAGGATGTAAAGCTCTTCCATGATCACTTATCCCCAAAATGGG
AAAATAAAAAGCTTAATCATATTAATTATATGACCTATGCTCGTTATTTCATACCTC
AGTACATCTCAGCTGATACAGTTTTATATCTTGACTCTGACTTAGTTGTTACTACTA
ATTTAGATAACCTCTTTCAAATTTCACTAGACAATGCATATTTAGCTGCAGTTCCAG
CTCTTTTTGGGCTTGGATATGGGTTTAATGCTGGAGTAATGGTAATTAACAACCAA
CGTTGGCGACAAGAAAATATGACTATTAAATTAATTGAAAAAAATCAAAAGGAAA
TTGAGAATGCCAACGAAGGGGATCAAACAATTCTTAATCGCATGTTTGAAAATCAG
GTAATTTATTTAGATGATACCTACAATTTTCAAATTGGTTTTGATATGGGAGCTGCT
ATCGATGGGCATAAATTTATTTTTGACATCCCAATTACCCCACTCCCAAAAATTATT
CACTACATTTCGGGAATCAAACCTTGGCAAACATTATCAAATATGAGACTCCGTGA
GGTATGGTGGCACTATAATTTACTTGAATGGTCAAGTATCATATCTAGTAAAAAAG
TATTTGGTTTAGACCACCCAATTAAAACACAAAATTATCGTCTCAATTTCCTTATTG
CTACAACTTCTGATTGTATACCATCTATCTCAGAATTAGTCACTGCCCTTCCAGATT
GTCTATTTCACATTGCATGCACCAACAGTTATGTCTGA

MTYQKTVVLAGDYSYIRQIETTLKSLCVYHENLSIFIFNQDIPQEWFLAMKDRVGQTG
NQIQDVKLFHDHLSPKWENKKLNHINYMTYARYFIPQYISADTVLYLDSDLVVTTNLD
NLFQISLDNAYLAAVPALFGLGYGFNAGVMVINNQRWRQENMTIKLIEKNQKEIENAN
EGDQTILNRMFENQVIYLDDTYNFQIGFDMGAAIDGHKFIFDIPITPLPKIIHYISGIKPW
QTLSNMRLREVWWHYNLLEWSSIISSKKVFGLDHPIKTQNYRLNFLIATTSDCIPSISEL
VTALPDCLFHIACTNSYV*

ID-12

FIG. 1 CONT'D

Clone 27

GTGAAGAAAACATATTGTTATATCGGCTCAGTTGCTGCTATTTTACTAGCTACTCAT
ATTGGAAGTTACCAGCTTGGTAAGCATCATATGGGTCTAGCAACAAAGGACAATC
AGATTGCCTATATTGATGATAGCAAAGGTAAGGTAAAAGCCCCTAAAACAAACAA
AACGATGGATCAAATCAGTGCTGAAGAAGGCATCTCTGCTGAACAGATCGTAGTC
AAAATTACTGACCAAGGTTATGTTACCTCACACGGTGACCATTATCATTTTTACAAT
GGGAAAGTTCCTTATGATGCGATTATTAGTGAAGAGTTGTTGATGACGGATCCTAA
TTACCATTTTAAACAATCAGACGTTATCAATGAAATCTTAGACGGTTACGTTATTA
AAGTCAATGGCAACTATTATGTTTACCTCAAGCCAGGTAGTAAGCGCAAAAACATT
CGAACCAAACAACAAATTGCTGAGCAAGTAGCCAAAGGAACTAAAGAAGCTAAA
GAAAAGGTTTAGCTCAAGTGGCCCATCTCAGTAAAGAAGAAGTTGCGGCAGTCA
ATGAAGCAAAAAGACAAGGACGCTATACTACAGACGATGGCTATATTTTTAGTCC
GACAGATATCATTGATGATTTAGGAGATGCTTATTTAGTACCTCATGGTAATCACT
ATCATTATATTCCTAAAAAAGATTTGTCTCCAAGTGAGCTAGCTGCTGCACAAGCC
TACTGGAGTCAAAAACAAGGTCGAGGTGCTAGACCGTCTGATTACCGCCCGACAC
CAGCCCCAGGTCGTAGGAAAGCCCCACTTCCTGATGTGACGCCTAACCCTGGACAA
GGTCATCAGCCAGATAACGGTGGTTATCATCCAGCGCCTCCTAGGCCAAATGATGC
GTCACAAAACAAACACCAAAGAGATGAGTTTAAAGGAAAAACCTTTAAGGAACTT
TTAGATCAACTACACCGTCTTGATTTGAAATACCGTCATGTGGAAGAAGATGGGTT
GATTTTTGAACCGACTCAAGTGATCAAATCAAACGCTTTTGGGTATGTGGTGCCTC
ATGGAGATCATTATCATATTATCCCAAGAAGTCAGTTATCACCTCTTGAAATGGAA
TTAGCAGATCGATACTTAACCCGGCCAAACTGA

MKKTYCYIGSVAAILLATHIGSYQLGKHHMGLATKDNQIAYIDDSKGKVKAPKTNKT
MDQISAEEGISAEQIVVKITDQGYVTSHGDHYHFYNGKVPYDAIISEELLMTDPNYHFK
QSDVINEILDGYVIKVNGNYYVYLKPGSKRKNIRTKQQIAEQVAKGTKEAKEKGLAQV
AHLSKEEVAAVNEAKRQGRYTTDDGYIFSPTDIIDDLGDAYLVPHGNHYHYIPKKDLS
PSELAAAQAYWSQKQGRGARPSDYRPTPAPGRRKAPLPDVTPNPGQGHQPDNGGYHP
APPRPNDASQNKHQRDEFKGKTFKELLDQLHRLDLKYRHVEEDGLIFEPTQVIKSNAF
GYVVPHGDHYHIIPRSQLSPLEMELADRYLTRPN*

ID-13

Clone 28

ATGGTAAATGATATATTAGAAAGAATGTATAAAGAGAATATTCCAAAATCTTACCT
TACATCCGTCCCATTAGTTATTTCTCAAAAAGGAAGAACAACCTATTCGTTTAGTAT
GACTGGTGGTCAACAAATAGATGGAGTGAAATTCACACAGATATATGAGGACTAT
ATGAAATTACTCAGTCAAGGTAAGGATATCGCAGAGTTATATCAAAAATATTCTAA
AGAAGAGTTGGCAAATCTAGGCATTAATATTTATCAATCCAATGATATAGAAAGG
ACTGAGGAAAGAACTTTTGATGAAATTATCAGTTGGGTTTCCAACCCTTATGCAAC
AAGACCAATTCAAGAAAGGCACACTATTCAATTAGAGCCAACAAGATTTTCACTA

```
GAGGATAAGAAAAGAATTGAAGAAGCTGCAGCTCAAGGACTAAGCGAAATCGAC
CTTATTGATTTAGTTGACCTATATGATATTAATTTAGACAATACAAGCGTCAATCGC
CATATTGTGGGGTTATTGACTAATAACACCCAAGTAACATACTATTTCCAAGAACA
ATTAAATAAGGAGTTGCTGTCAATGGCTCACGCTTTAGATAACGTACAACAGGCCT
TTATTAAATTATTAAGTGAAGAGGAGATACGAAAATTTGCTCTTTAA
```

MVNDILERMYKENIPKSYLTSVPLVISQKGRTTYSFSMTGGQQIDGVKFTQIYEDYMK
LLSQGKDIAELYQKYSKEELANLGINIYQSNDIERTEERTFDEIISWVSNPYATRPIQERH
TIQLEPTRFSLEDKKRIEEAAAQGLSEIDLIDLVDLYDINLDNTSVNRHIVGLLTNNTQV
TYYFQEQLNKELLSMAHALDNVQQAFIKLLSEEEIRKFAL*

ID-14

Clone 31

```
ATGAATAAAAGAAGAAAATTATCAAAATTGAATGTAAAAAAACAACATTTAGCTT
ATGGAGCTATCACTTTAGTAGCCCTTTTTTCATGTATTTTGGCTGTAACGGTCATCT
TTAAAAGTTCACAAGTTACTACTGAATCTTTGTCAAAAGCAGATAAAGTTCGCGTA
GCCAAAAAATCAAAAATGACTAAGGCGACATCTAAATCAAAAGTAGAAGATGTAA
AACAGGCTCCAAAACCTTCTCAGGCATCTAATGAAGCCCCAAAATCAAGTTCTCAA
TCTACAGAAGCTAATTCTCAGCAACAAGTTACTGCGAGTGAAGAGGCGGCTGTAG
AACAAGCAGTTGTAACAGAAAATACCCCTGCTACCAGTCAGGCACAACAAACTTA
TGCTGTTACTGAGACAACTTACAAACCTGCTCAACACCAGACAAGTGGCCAAGTAT
TGAGCAATGGAAATACTGCAGGGGCGGTCGGATCTGCTGCTGCAGCACAAATGGC
TGCTGCAACAGGAGTCCCTCAGTCTACTTGGGAACATATTATTGCCCGTGAATCAA
ATGGTAATCCTAATGTTGCTAATGCCTCAGGGAGCTTCAGGACTTTTCCAAACGAT
GCCAGGTTGGGGTTCAACAGCTACAGTTCAGGATCAAGTTAA
```

MNKRRKLSKLNVKKQHLAYGAITLVALFSCILAVTVIFKSSQVTTESLSKADKVRVAK
KSKMTKATSKSKVEDVKQAPKPSQASNEAPKSSSQSTEANSQQQVTASEEAAVEQAV
VTENTPATSQAQQTYAVTETTYKPAQHQTSGQVLSNGNTAGAVGSAAAAQMAAATG
VPQSTWEHIIARESNGNPNVANASGASGLFQTMPGWGSTATVQDQVNSAIKAYRAQG
LSAWGY*

ID-15

Clone 32

```
ATGATTGTTGGACACGGAATTGATTTACAAGAGATAGAGGCGATTACTAAAGCAT
ATGAGCGTAATCAACGTTTTGCAGAACGCGTTTTGACCGAACAAGAATTGCTTCTT
TTTAAAGGAATTTCCAATCCCAAGCGTCAGATGTCTTTTTTAACAGGGCGATGGGC
AGCAAAAGAGGCTTATAGCAAAGCACTTGGAACAGGAATTGGGAAAGTTAATTTT
CATGATATCGAAATTTTATCGGATGATAAAGGAGCGCCTTTGATTACAAAAGAACC
```

GTTTAATGGAAAATCTTTTGTTTCAATATCTCATAGTGGTAATTATGCACAAGCTAG
TGTTATTTTGGAGGAAGAAAAATGA

MIVGHGIDLQEIEAITKAYERNQRFAERVLTEQELLLFKGISNPKRQMSFLTGRWAAKE
AYSKALGTGIGKVNFHDIEILSDDKGAPLITKEPFNGKSFVSISHSGNYAQASVILEEEK*

ID-16

Clone 35

ATGATTTTTGTCACAGTGGGGACACATGAACAGCAGTTCAACCGTCTTATTAAAGA
AGTTGATAGATTAAAAGGGACAGGTGCTATTGATCAAGAAGTGTTCATTCAAACG
GGTTACTCAGACTTCGAACCTCAGAATTGTCAGTGGTCAAAATTTCTCTCATATGAT
GATATGAACTCTTACATGAAAGAAGCTGAGATTGTTATCACACATGGCGGCCCAGC
GACGTTTATGTCAGTTATTTCTTTAGGGAAATTACCAGTTGTTGTTCCTAGGAGAAA
GCAGTTTGGTGAACATATCAATGATCATCAAATACAATTTTTAAAAAAAATTGCCC
ACCTGTATCCCTTGGCTTGGATTGAAGATGTAGATGGACTTGCGGAAGCGTTGAAA
AGGAATATAGCTACAGAAAAATATCAGGGAAATAATGATATGTTTTGTCATAAATT
AGAAAAAATTATAGGTGAAATATGA

MIFVTVGTHEQQFNRLIKEVDRLKGTGAIDQEVFIQTGYSDFEPQNCQWSKFLSYDDM
NSYMKEAEIVITHGGPATFMSVISLGKLPVVVPRRKQFGEHINDHQIQFLKKIAHLYPL
AWIEDVDGLAEALKRNIATEKYQGNNDMFCHKLEKIIGEI*

ID-17

Clone39

TTGGAAGACAAATTATTCAACAAACATTTTATAGGCATTACTATTTTAAACTTTATT
GTTTATATGGTCTATTATTTGTTCACCGTTATCATAGCTTTTATTGCGACTAAAGAG
TTAGGTGTTAGCACTAGCCAAGCAGGATTAGCAACGGGGATTTATATTGTAGGGAC
TTTGATTGCTCGTCTTATATTTGGTAAGCAATTAGAAGTTCTAGGACGTAAGTTAGT
TTTACGTGGAGGGGCTATTTTTTACTTACTAACAACTTTAGCTTATTTTTATATGCC
AAGTATCGGAGTAATGTATTTAGTTCGTTTCCTAAATGGTTTTGGTTATGGCGTCGT
GTCAACAGCAACTAATACTATTGTAACAGCCTATATACCAGCTGATAAAAGAGGTG
AGGGGATTAACTTTTACGGTCTATCAACAAGTTTAGCCGCAGCTATTGGTCCTTTTG
TAGGAACATTTATGCTAGACAACCTTCATATTAACTTTAAAATGGTTATTGTATTAT
GTAGTATTTTAATTGCGATTGTAGTGTTGGGAGCATTTGTTTTCCCAGTCAAAAATA
TTACTTTAAATCCAGAACAGTTAGCTAAATCAAAATCATGGACTATTGATAGTTTC
ATTGAGAAAAAAGCAATTTTTATCACAATTATTGCATTTTTGATGGGTATCTCCTAT
GCTTCCGTGTTAGGTTTCCAAAAATTATATACAACAGAAATTAATTTGATGACAGT
AGGAGCTTATTTCTTTATTGTTTATGCACTTGTCATCACTTTAACCAGACCATCTAT
GGGAAGATTAATGGACGCTAAGGGAGATAAGTGGGTGCTTTATCCAAGTTATCTGT
TCTTAACTTTGGGACTTGCTTTATTAGGGAGTGCTATGGGAAGTGTTACCTACCTTC

```
TATCAGGTGCTTTGATTGGTTTTGGTTATGGCACCTTTATGTCTTGTGGCCAAGCAG
CATCAATCAAAGGTGTTGAGGAACATCGTTTCAATACAGCCATGTCAACTTACATG
ATAGGTCTTGATTTAGGGTTAGGTGCTGGACCTTACATTTTGGGACTTGTTAAAGAT
GGTTTTCTTGGAGCTGGTGTGCAATCCTTTAGAGAATTATTCTGGATAGCAGCGATT
ATTCCTGTTGTTTGTGGTATTCTATATTTCTTAAAATCATCTAGACAAGTTGAAACT
AAAACTATA
TAA

MEDKLFNKHFIGITILNFIVYMVYYLFTVIIAFIATKELGVSTSQAGLATGIYIVGTLIARL
IFGKQLEVLGRKLVLRGGAIFYLLTTLAYFYMPSIGVMYLVRFLNGFGYGVVSTATNTI
VTAYIPADKRGEGINFYGLSTSLAAAIGPFVGTFMLDNLHINFKMVIVLCSILIAIVVLG
AFVFPVKNITLNPEQLAKSKSWTIDSFIEKKAIFITIIAFLMGISYASVLGFQKLYTTEINL
MTVGAYFFIVYALVITLTRPSMGRLMDAKGDKWVLYPSYLFLTLGLALLGSAMGSVT
YLLSGALIGFGYGTFMSCGQAASIKGVEEHRFNTAMSTYMIGLDLGLGAGPYILGLVK
DGFLGAGVQSFRELFWIAAIIPVVCGILYFLKSSRQVETKTIZ
```

ID-18

Clone 47

```
ATGAATAGTGAACCTAAAAGTCAGTCAAACGAAGTAAAAAATAGCAAGCAATCAG
AAGTGAAGAAAGATAAAAAAATGACAAAAAAAGAACAATTAGCCTATCTCAAAG
AGCATGAGCAAGAAATCATAGATTATGTAAAATTACATAACAACCAAATTGAGTC
CGTTCAATTCGATTGGTCAAGTGTAAAAGTAGAACAAAGCGGGAATGGAACTCCA
CAAGGGGGTGATTATAATCTTTCACTGAGAGGAAAGTTTAATCATCTACAAAATTC
AAAATTAATAGTTGATTTTTATTTAGCTCATAAAAATGATATCCCAAATATCAAAT
CAATGGGAATGCTAAATAAGCCATATATACATAAAAATGGTATTTGGCACATTTAT
GAATAG
```

```
MILGGCQMNSEPKSQSNEVKNSKQSEVKKDKKMTKKEQLAYLKEHEQEIIDYVKLHN
NQIESVQFDWSSVKVEQSGNGTPQGGDYNLSLRGKFNHLQNSKLIVDFYLAHKNDIPN
IKSMGMLNKPYIHKNGIWHIYEZ
```

ID-19

Clone 102

```
ATGAAAAAGATTCGATTATCAAAGTTTATTAAAATGATTGTTGTTATTTTGTTTTTA
ATTAGTGTAGCAGCTAGTTTTTATTTTTTCCACGTTGCCCAAGTTCGAGATGATAAA
TCCTTTATTTCAAATGGTCAACGTAAGCCTGGAAACTCTTTATATGCTTATGATAAA
TCCTTTGATAAGCTATTAAAGCAAAAAATAGAAATGACAAACCAAATATAAAGC
AAGTTGCTTGGTATGTTCCTGCTGCTAAGAAAACTCATAAGACAGTTGTTGTCGTTC
ATGGTTTTGCGAATAGCAAAGAGAATATGAAGGCATATGGTTGGCTGTTTCATAAG
TTAGGATACAATGTTCTTATGCCTGACAACATTGCACATGGTGAAAGTCATGGGCA
```

FIG. 1 CONT'D

```
GTTGATAGGCTATGGCTGGAACGACCGCGAGAACATTATCAAATGGACAGAAATG
ATAGTGGATAAGAATCCATCAAGCCAAATTACTTTATTTGGTGTTTCAATGGGTGG
AGCAACAGTCATGATGGCTAGTGGTGAAAAATTACCTAGTCAGGTTGTTAATAT
CATTGAAGATTGTGGTTATTCTAGTGTTTGGGATGAATTAAAATTTCAGGCTAAAG
AGATGTATGGTTTACCAGCCTTCCCACTCTTATATGAAGTTTCAACAATTTCTAAAA
TCAGAGCAGGTTTTTCGTATGGACAAGCAAGTAGTGTCGAACAATTGAAAAAGAA
TAATTTACCAGCCCTCTTTATTCATGGTGATAAGGATAATTTTGTTCCAACAAGTAT
GGTTTATGACAACTATAAAGCTACAGCAGGTAAGAAAGAGCTTTATATTGTAAAA
GGGGCAAAACATGCGAAATCTTTTGAAACAGAGCCAGAAAAATATGAGAAACGTA
TCTCTAGTTTTTTGAAAAAATATGAAAAATAA

MKKIRLSKFIKMIVVILFLISVAASFYFFHVAQVRDDKSFISNGQRKPGNSLYAYDKSFD
KLLKQKIEMTNQNIKQVAWYVPAAKKTHKTVVVVHGFANSKENMKAYGWLFHKLG
YNVLMPDNIAHGESHGQLIGYGWNDRENIIKWTEMIVDKNPSSQITLFGVSMGGATV
MMASGEKLPSQVVNIIEDCGYSSVWDELKFQAKEMYGLPAFPLLYEVSTISKIRAGFSY
GQASSVEQLKKNNLPALFIHGDKDNFVPTSMVYDNYKATAGKKELYIVKGAKHAKSF
ETEPEKYEKRISSFLKKYEK*
```

ID-20

Clone 120

```
TTGAGGAGTAATATGGTAAAGACAGCAGTTTTAATGGCGACATACAATGGCGAAA
AATTTATATCTGAACAACTTGATTCAATTCGCCAACAGACATTAAAACCAGATTAT
GTATTATTGAGGGATGATTGTTCAACGGATGAAACAGTCAATGTCGTCAATAACTA
TATCGCAAAACATGAGTTAGAAGGCTGGAAAATTGTTAAAAACGACAAAAACTTA
GGCTGGCGTTTAAATTTTCGTCAATTACTTATTGATGTGTTAGCCTATGAGGTTGAC
TATGTCTTTTTTAGTGATCAAGATGATATTTGGTATCTTGATAAAAACGAACGACA
GTTTGCCATTATGTCAGATAACCCTCAAATTGAGGTTTTGAGTGCAGACGTTGATA
TCAAAACGATGTCTACAGAAGCCAGTGTTCCACATTTTCTAACTTTTTCTTCTAGTG
ATAGAATCAGTCAGTATCCTAAAGTATATGATTATCAAACATTCCGTCCCGGATGG
ACCATTGCTATGAAGAGAGATTTTGCGCAAGCTATCGCTTGA
```

MRSNMVKTAVLMATYNGEKFISEQLDSIRQQTLKPDYVLLRDDCSTDETVNVVNNYI
AKHELEGWKIVKNDKNLGWRLNFRQLLIDVLAYEVDYVFFSDQDDIWYLDKNERQF
AIMSDNPQIEVLSADVDIKTMSTEASVPHFLTFSSSDRISQYPKVYDYQTFRPGWTIAM
KRDFAQAIAZ

ID-21

Clone 143

```
ATGATTCATGAGATTCACGATTGTCAATTTATTGAAAAAGGAAGTTACGTTTATTT
GAATTATATTAATGCTGAGGGCGAGAGAGTAGTTATTATAATCATAGATTTTGTCC
```

GTAGTGTTAGTCCTATTTTATATCGTCTATTTATGATTTTACTTGCACAAGAAGTAC
CTCACTTGCATGATTACATCTATAATGCAAGAGATGATCACTACGATACTTGGAAG
TTTAAAGAATTAAAGGAGTCAAACCATCCAGTCCTTTTGGCATTCTCTGAAAGGTG
GCACGATAGTCGCTTGACTTCTAAAAGCCTTGCAGAATGTTTACAATTAACCGACC
TTGATGAAGAAGTGAAATCGACCATCATTCAATTAAGACAGTTCGAAAAATCAGTC
AGAAATCCTTTGGCTCACCTGATTAAACCTTTTGATGAGCAAGAACTATATCGTAC
AACTCAATTTTCTTCTCAAGCATTTTTAGACCAGATTATCTTCTTGGCAAAGGTAAT
TGGTGTTGAGTATGATACTGTTAATTTTCACTACGATACGGTTAACAAGCTTATTAT
AAAGATACTTGAGTAA

MIHEIHDCQFIEKGSYVVYLNYINAEGERVVIIIIDFVRSVSPILYRLFMILLAQEVPHLHD
YIYNARDDHYDTWKFKELKESNHPVLLAFSERWHDSRLTSKSLAECLQLTDLDEEVKS
TIIQLRQFEKSVRNPLAHLIKPFDEQELYRTTQFSSQAFLDQIIFLAKVIGVEYDTVNFHY
DTVNKLIIKILE*

ID-22

Clone 1

ATGGTAAAAGTTTCAAATTTAGGGTATCCACGTCTTGGTGAACAGCGCGAATGGAA
GCAAGCGATCGAAGCTTTCTGGGCAGGGAATCTTGAACAAAAAGATTTAGAAAAA
CAACTAAAACAATTACGTATCAATCATTTAAAGAAACAAAAAGAGGCAGGTATTG
ACCTTATTCCAGTGGGGGATTTTTCTTGTTATGATCATGTTTTGGATTTGTCATTTCA
ATTCAATGTAATCCCAAAGCGTTTCGATGAGTATGAGAGGAATTTAGACCTTTATT
TTGCTATTGCAAGAGGTGACAAAGATAATGTCGCATCATCTATGAAAAAGTGGTTT
AATACCAACTACCACTACATAGTCCCAGAATGGGAGGTTGAGACTAAACCTCACTT
GCAGAATAATTACTTACTTGATCTTTATCTAGAAGCTAGGGAAGTAGTTGGTGATA
AAGCAAAGCCGGTTATC

MEEIMVKVSNLGYPRLGEQREWKQAIEAFWAGNLEQKDLEKQLKQLRINHLKKQKE
AGIDLIPVGDFSCYDHVLDLSFQFNVIPKRFDEYERNLDLYFAIARGDKDNVASSMKK
WFNTNYHYIVPEWEVETKPHLQNNYLLDLYLEAREVVGDKAKPVI

ID-23

Clone 2

ATGGTGTTACTTTTATTGCTAATGGTAGCCAAGTCAAGTTTGATGGTTACATGGCTG
TTTATAACGATACTGACAAAAATAAAATGTTACCAGATATGGAGGAAGGAGAAAG
TTATCAAGTTAA

MVLLLLLMVAKSSLMVTWLFITILTKIKCYQIWRKEKVIKL

ID-24

FIG. 1CONT'D

Clone 14

ATGAACAAAAAAATTTCCGGGATCGGCTTGGCTTCGATTGCAGTACT
TAGTTTAGCTGCATGTGGACATCGTGGTGCTTCTAAATCTGGTGGTAA
ATCAGATAGCTTGAAGGTTGCAATGGTAACAGATACCGGTGGTGTTG
ATGATAAATCATTTAACCAATCTGGTTGGGAAGGTATGCAAGCTTGG
GGCAAGAAGAATGGCCTTAAAAAAGGAGCTGGTTTTGACTATTTCCA
ATCGGCAAGTGAATCTGATTATGCAACTAACTTAGATACAGCTGTGT
CTAGTGGTTATAAATTGATTTTCGGTATTGGATTTTCTCTTCATGATG
CTATTGATAAAGCAGCAGACAATAACAAAGATGTTAATTACGTCATC
GTTGATGATGTTATTAAAGGGAAAGATAATGTTGCAAGTGTTGTCTTT
GCGGATAATGAATCAGCTTACTTAGCAGGTATTGCAGCCGCTAAAAC
TACCAAAACAAAAACAGTTGGCTTTGTAGGTGGTATGGAATCTGAGG
TTATTACCCGTTTTGAAAAAGGTTTTGAAGCAGGTGTCAAATCAGTTG
ATAAATCAATTAAAATTAAAGTTGACTATGCTGGTTCATTCGGTGAT
GCTGCTAAGGGTAAGACAATTGCAGCCGCACAATATGCTTCTGGCGC
AGATATT

MNKKISGIGLASIAVLSLAACGHRGASKSGGKSDSLKVAMVTDTGGVD
DKSFNQSGWEGMQAWGKKNGLKKGAGFDYFQSASESDYATNLDTAVS
SGYKLIFGIGFSLHDAIDKAADNNKDVNYVIVDDVIKGKDNVASVVFAD
NESAYLAGIAAAKTTKTKTVGFVGGMESEVITRFEKGFEAGVKSVDKSI
KIKVDYAGSFGDAAKGKTIAAAQYASGADI

ID-25

Clone 20

ATGTTACATTCTAAAAAAATACATTCCTTATCGCTTATTGCCGTTCTC
TCTTTAGCAACATATACGAGTTTACAACCAAATCATGTAGCGGCTGA
ACAATCACAAAAAACATCAACTGTTCTTATGAGTCAAAAACTATTG
AACATAAGTTAAAAGTTGCAGATAAAGAAGCTGCTCCTCTCTACGCT
AAAATCGACCATATCCAACGACATATTGAAGTCAAAAAAGCAAAAG
ATTTAAAAGTTATTGAATTGTATATTAACAAAGATATCAACCAACTA
GAGAAGCAAAATAAACGTCTACTAACTAAATTCTATACTTCTATTGA
TAATCAAACATGGGATAGCACAAGTGAAGTCAAAAAATTGATTGATA
AGACAACCCTATCCACTAACGAAAAGATAGATTAAAATTATATTTT
GAACAACGTGCTTACCTTGAGACAAGGTTGAACGACCGCTATCAAAA
ATTTGATAACTCTATTGAAACCAAAATAAAGAACTAAAAATATTAA
CGTCAAAAATAGAAAAAATCTATCAAAAACATGGTATTACAAAAGA
GGTATTAAAAACTTACTATGCTAAAAAAACAGTACGAGCTGACTGA

MLHSKKIHSLSLIAVLSLATYTSLQPNHVAAEQSQKTSTVLMSQKTIEHK
LKVADKEAAPLYAKIDHIQRHIEVKKAKDLKVIELYINKDINQLEKQNK
RLLTKFYTSIDNQTWDSTSEVKKLIDKTTLSTNEKDRLKLYFEQRAYLET
RLNDRYQKFDNSIENQNKELKILTSKIEKIYQKHGITKEVLKTYYAKKTV
RAD*

ID-26

Clone 25

Clone 25 (partial sequence)

CTGAATTCCCAAAAACGCTACAATCAAACTTGGTATCCTACTTATGGTTTTTCTGAT
ACTTATGCATTCATGGTTACTAAAGAGTTTGCCAGACAGAATAAAATCACCAAGAT
CTCTGATCTCAAAAAGTTATCAACAACTATGAAGGCAGGGGTTGATAGTTCATGGA
TGAATCGCGAGGGAGATGGATACACTGATTTCGCTAAAACATACGGTTTTGAATTT
TCACATATTTACCCTATGCAAATTGGCTTAGTCTATGATGCGGTTGAAAGTAACAA
AATGCAATCTGTATTAGGCTACTCCACTGACGGTCGTATTTCGAGCTATGATTTAG
AAATTTTAAGGGATGATAAAAAATTCTTTCCTCCTTATGAAGCCTCTATGGTTGTCA
ACAATTCTATCATCAAAAAGATCCTAAACTAAAAAAATTACTCCATCGACTCGAT
GGTAAAATCAATTTAAAAACGATGCAAAACCTTAATTATATGGTAGATGATAAACT
TTTAGAAGCTTGGCGTAATCATGGTCATAGCTGTTTCCTGTGTGAAATTGTTATCCG
CTCACAATTCCACACAACATACGAGCCGGAAGCATAA

LNSQKRYNQTWYPTYGFSDTYAFMVTKEFARQNKITKISDLKKLSTTMKAGVDSSWM
NREGDGYTDFAKTYGFEFSHIYPMQIGLVYDAVESNKMQSVLGYSTDGRISSYDLEILR
DDKKFFPPYEASMVVNNSIIKKDPKLKKLLHRLDGKINLKTMQNLNYMVDDKLLEAW
RNHGHSCFLCEIVIRSQFHTTYEPEA*

ID-29

Clone 37

ATGAAAAAATTACTTTCCCTAACATGTCTAATCATGATGTCTTTATGT
TTAGTGGCATGTACTAAGCAAGCAATGTCGTCTAAGCAAGCAATGTC
GTCTAAGCAAATTAAAGATAAGAATAGTAAAGAAAAGGTGATTACT
GTTGCAACTTACAGCAAACCTACATCTACCTTTTTAGATTTGATTAAA
GATAATGTAAAAGAAAAGGATATACTTTAAAGGTTGTCATGGTCTC
TGACTATATTCAGGCTAACATTGCTTTAGAAAACAAAGAACATGATG
CTAACCTTTTACAACATGAATTTTTCATGAGTATCTTTAATAAGGAAA

```
ATGATGGTCATCTAGTGTCAATTACACCAATTTATCATTCATTGGCTG
GTTTTTATGGTCAACATTTGAAAAATATTGCCGAGCTTAAAGACGGT
GCTAAGGTAGCGATTCCGTCTGATCCTGCCAATATGACTAGAGCTCT
GCTATTATTGCAAGAAAAGAAACTTATCACCTTAAAGAATACGTCCA
AAAAGACCAAGGCTATCGAAGATATTATTACTAACCCTAAAAAATTA
CGAATTGAACCTGTAGCATTACTTAACCTCAATCAGGCCTATTTTGAA
TATGACCTTGTCTTTAATTTCCCTGGATATGTGACAAAAATCAATCTA
GTTCCTAAAAGGGATAGATTATTATATGAGAAAAAACCAGATATCCG
TTTTGCAGGTGCCTTGGTAGCTCGTGAAGATAATAAAAATAGTGATA
AAATAAAAGTACTTAAAGAAGTACTAACAAGTAAAGAGATTCGTCA
CTATATCACTAAGGAGATTCCAAGTGAAGCAGACGTTGCGTTCTAG
```

MKKLLSLTCLIMMSLCLVACTKQAMSSKQAMSSKQIKDKNSKEKVITV
ATYSKPTSTFLDLIKDNVKEKGYTLKVVMVSDYIQANIALENKEHDANL
LQHEFFMSIFNKENDGHLVSITPIYHSLAGFYGQHLKNIAELKDGAKVAI
PSDPANMTRALLLLQEKKLITLKNTSKKTKAIEDIITNPKKLRIEPVALLN
LNQAYFEYDLVFNFPGYVTKINLVPKRDRLLYEKKPDIRFAGALVARED
NKNSDKIKVLKEVLTSKEIRHYTTKEIPSEADVAF*

ID-30

Clone 38

```
CTGTTGGCTAAGGAAACCACTATGTCTGTCCTTTGGTATCAAAATTCTGCAGAAGC
CAAGGCTTTATATTTACAAGGTTATAATGTTGCTAAAATGAAGTTAGATGATTGGT
TACAAAAGCCCAGTGAAAAACCATATTCAATTATCTTAGATTTAGATGAAACAGTT
TTAGATAATAGCCCATATCAAGCAAAGAATATTAAAGATGGCTCTAGTTTCACGCC
AGAGAGTTGGGATAAATGGGTGCAAAAGAAATCAGCTAAGGCTGTTGCGGGTGCC
AAAGAATTTTTGAAGTATGCTAATGAAAAGGGAATAAAAATTTATTATGTCTCAGA
TCGTACAGATGCTCAAGTTGATGCGACTAAAGAAAATTTAGAGAAGGAAGGTATA
CCTGTTCAAGGGAAAGACCACTTGCTTTTCCTTAAAAAAGGAATGAAATCTAAAGA
GAGTCGCCGTCAGGCAGTTCAAAAAGATACCAATTTAATTATGCTTTTTGGAGATA
ATTTAGTTGATTTTGCTGATTTTTCTAAATCATCTAGTACAGATAGAGAACAACTAC
TAACTAAACTTCAAAGTGAGTTTGGTAGTAAATTTATTGTTTTCCCAAATCCTATGT
ACGGTTCTTGGGAAAGTGCTATTTATCAAGGAAAACATCTGGATGTTCAAAAACAA
TTGAAAGAACGACAAAAAATGTTGCATTCGTATGATTAA
```

MAKLTVKDVDLKGKKVLVRVDFNVPLKDGVITNDNRRITAALPTIKYIIEQGGRAILFSH
LGRVKEEADKEGKSLAPVAADLAAKLGQDVVFPGVTRGAKLEEAINALEDGQVLLVE
NTRFEDVDGKKESKNDEELGKYWASLGDGIFVNDAFGTAHRAHASNVGISSNVEKAV
AGFLLENEIAYIQEAVETPERPFVAILGGSKVSDKIGVIENLLEKADKVLIGGGMTYTFY
KAQGIEIGTYLEKEDKLDVAKDSZ

ID-31

Clone 41

ATGGATAATAAAGGTAATAACGCCAATGTGATTGATGCAATCGCTGAGGGTGCAA
GCACAGGTGCACAAATGGCTTTCTCAATTGGTGCTAGTTTGATTGCCTTTGTTGGTT
TAGTTTCTTTGATTAA

MDNKGNNANVIDAIAEGASTGAQMAFSIGASLIAFVGLVSLI

ID-32

Clone 42

ATGAAAAAGAAAAACAAATCCTCTAACATTGCTATAATTGCAATCTT
TTTTGCTATTATGCTTGTCATTCATTTTTTGTCATCATTTATTTTTAGTT
TTTGGTTAGTCCCTATTAAACCTACTTTGATGCATATCCCAGTTATTA
TTGCATCTATAGCCTATGGACCTCGTATTGGTGCAACTCTAGGCGCCT
TAATGGGGGGGATCAGCGTAGCTAACAGCAGCATTGTTCTATTACCA
ACGAGTTACCTCTTCTCACCTTTTGTTGAAAATGGTAATTTTTATTCG
CTAATTATTGCACTTGTACCACGTATTCTAATCGGGATTATTCCTTAT
TTCGTTTACAAATTACTACACAACCGCTTTGGTTTGGCTATCTCAGGT
GCTATAGGCTCTCTAACAAACACAGTATTTGTTTTATCTGGAATTTTT
ATCTTTTTTTCAAGTACTTATAATGGGAATATCAAGCTAATGCTCGCT
GGGATTATTTCATCTAATTCATTAGCTGAGATGGTCATTGCAGCTATC
ATTGTATATCTAACTGATCCTCGTATTCTCAATATTAAACATTAA

MKKKNKSSNIAILAIFFAIMLVIHFLSSFIFSFWLVPIKPTLMHIPVIIASIAY
GPRIGATLGALMGGISVANSSIVLLPTSYLFSPFVENGNFYSLIIALVPRILI'
GIIPYFVYKLLHNRFGLAISGAIGSLTNTVFVLSGIFIFFSSTYNGNIKLML
AGIISSNSLAEMVIAAIIVYLTDPRILNIKH*

ID-33

Clone 43

TTGAATATGACATTACAAGACGAAATCAAAAAACGCCGTACTTTTGCCATCATCTC
TCACCCGGATGCTGGTAAGACGACTATTACTGAGCAATTATTATATTTTGGTGGTG
AAATTAGAGAAGCAGGGACAGTAAAAGGGAAAAAATCAGGTACTTTTGCAAAGTC
CGACTGGATGGATATTGAAAAGCAACGGGGTATCTCTGTTACTTCATCTGTTATGC
AATTTGATTACGCGGGTAAACGTGTTAA

MNMTLQDEIKKRRTFAIISHPDAGKTTITEQLLYFGGEIREAGTVKGKKSGTFAKSDW
MDIEKQRGISVTSSVMQFDYAG

KRV

ID-34

Clone 44

ATGGCAGATAAAAACAGAACATTTAAACTTGTAGGTGCAGGATCTTC
TAGCACACAAGAAAAAATTGAAAAGCCTGCTCTTTCGTTTATGCAAG
ATGCGTGGCGTCGCTTGAAAAAAAACAAATTAGCAGTAGTTTCACTC
TATTTATTAGCTCTTTTACTTACTTTTTCGTTAGCCTCAAATTTATTTG
TAACTCAGAAGGATGCTAATGGGTTTGATTCGAAAAAAGTAACGACA
TATCGCAACTTACCACCTAAATTGAGTTCAAACCTTCCTTTTTGGAAT
GGTAGCATTAATCCATCA

MADKNRTFKLVGAGSSSTQEKIEKPALSFMQDAWRRLKKNKLAVVSLY
LLALLLTFSLASNLFVTQKDANGFDSKKVTTYRNLPPKLSSNLPFWNGSI
NPS

ID-35

Clone 46

ATGAAAAGAAAACAGTTTATAAAATTAGGAATTGCAACCTTACTAACGGTTATTTC
GCTTTACACACCAATAAACCTAGCTACAAATCATACCACAGAAAATATTGTTACTG
CTCAAGAGTATAAAACAAAGAGAATGGTACTTTACCTTTTAA

MKRKQFIKLGIATLLTVISLYTPINLATNHTTENIVTAQEYKTKENILFLL

ID-36

Clone 50

ATGTTTTATAATCCTTTACTTTTTATTGTACTAATTACAATTGCTGTATTTTTCTTAG
CTAAGAAAAAATGGCAATTACCGACATTTACTTTCATTGGTTTGCTATTTATCTATA
ACCAAGGGCTGTGGGAACAGTTGATTAAT

MFYNPLLFIVLITIAVFFLAKKKWQLPTFTFIGLLFIYNQGLWEQLIN

FIG. 1 CONT'D

ID-37

Clone 51/52

GTGGTGCAAATAATGAAAAAACATATAAAAAGTATCATACCAATAGT
TCTTATTGGTATGATACTAGGAGGCTGTCAAATGAATAGTGAACATA
AAAGTCAGTATAATGAAACAAAAAGTAGCAAGCAATCAGAAGTGAA
GAAAGATAAAAAAATGACAAAAAAAGAACAATTAGCTTATCTCAAA
GAGCATGAACAAGAAATAATTGATTTTGTAAAATCTCAGAATAAAAA
GATAGAATCTGTACAAATTGATTGGAATGATGTTCGATGGAGTAAAG
GGGGAAATGGTACACCTCAAGGAGGAGGAGAGGGGATTTTACTTTTT
GGGGAGATTAATAATGATTCTGAATCAAGTTGGAGAGTTGATATTGA
TATAGAAAAAGGACGGCTAGACCTAAAAAATATGTATTTAGGACAA
CCTATACGAATTGGAGGTAAATTATTTGAGTAA

MVQIMKKHIKSIIPIVLIGMILGGCQMNSEHKSQYNETKSSKQSEVKKDK
KMTKKEQLAYLKEHEQEIIDFVKSQNKKIESVQIDWNDVRWSKGGNGT
PQGGGEGILLFGEINNDSESSWRVDIDIEKGRLDLKNMYLGQPIRIGGKLF
E*

ID-38

Clone 53

ATGGAATTTTTGGCTTATAATGCTTTCACAGCAATCGGTGTTTCTATT
CCGCACGGTAATCATTTCCACTTTATTCACTATAAGGATATGTCTCCA
TTAGAGTTAGAAGCAACAAGGATGGTGGCAGAGCATAGAGGACATC
ATATTGATGCATTAGGGAAAAAGATTCTACAGAGAAACCAAAGCA
TATTTCTCATGAACCTAATAAGGAACCTCACACAGAGGAAGAACACC
ATGCAGTAACACCGAAAGACCAACGTAAAGGCAAACCAAATAGCCA
GATTGTCTACAGTGCTCAAGAAATTGAAGAGGCAAAAAAGCTGGT
AAATACACAACATCTGATGGTTACATTTTGATGCTAAAGATATTAA
AAAAGATACAGGTACAGGTTATGTCATTCCACATATGACACATGAGC
ATTGGGTACCAAAGAAAGATTTATCAGAGTCGGAATTAAAAGCAGCT
CAAGAATTTCTTTCAGGAAAATCTGAAGCAAATCAAGACAAACCAAA
AACAGGTAAAACAGCTCAAGAAATCTATGAGGCAATTGAACCAAAA
GCAATTGTTAAACCTGAAGATTTATTATTTGGAATTGCACAAGCGAC
AGACTATAAGAATGGTACATTTGTAATTCCTCATAAAGATCATACC
ATTATGTGGAATTAAAATGGTTTGATGAAGAAAAGATCTTTTAGCT
GATTCAGATAAGACATATTCTTTAGAAGACTATTTAGCTACGGCTAA
ATATTACATGATGCACCCAGAAAAACGTCCTAAAGTTGAAGGATGGG
GTAAAGATGCTGAAATTTATAAGGAAAAGGACTCTAATAAAGCAGA
TAAACCAAGTCCTGCACCAACTGATAATAAATCAACATCAAATTCTA

GTGACAAAAACTTAAGTGCTGCAGAAGTATTCAAACAAGCAAAACC
AGAAAAAATTGTACCGCTTGATAAAATTGCTGCTCACATGGCATATG
CAGTTGGATTTGAAGATGATCAATTGATTGTTCCTCATCATGATCATT
ATCATAATGTTCCTATGGCATGGTTTGACAAGGGTGGTTTATGGAAA
GCACCAGAAGGCTATACATTACAACAACTCTTCTAACAATTAAATA
CTACATGGAACATCCTAATGAATTACCAAAAGAAAAGGGTTGGGGA
CACGACAGTGATCATAACAAAGGCTCAAATAAAGACAATAAAGCCA
AAAATTATGCTCCAGATGAAGAACCTGAAGATTCAGGGAAAGTAACT
CACAACTATGGTTTTTATGATGTTAATAAAGGTTCAGACGAAGAAGA
ACCAGAAAAACAAGAAGATGAATCAGAGCTAGATGAATATGAACTA
GGAATGGCACAAAACGCTAAGAAATATGGTATGGATAGACAATCTTT
TGAAAAGCAACTCATCCAATTATCAAATAAATAGTGTAAGTTTTG
AAAGC

MEFLAYNAFTAIGVSIPHGNHFHFIHYKDMSPLELEATRMVAEHRGHHI
DALGKKDSTEKPKHISHEPNKEPHTEEEHHAVTPKDQRKGKPNSQIVYS
AQEIEEAKKAGKYTTSDGYIFDAKDIKKDTGTGYVIPHMTHEHWVPKK
DLSESELKAAQEFLSGKSEANQDKPKTGKTAQEIYEAIEPKAIVKPEDLL
FGIAQATDYKNGTFVIPHKDHYHYVELKWFDEEKDLLADSDKTYSLED
YLATAKYYMMHPEKRPKVEGWGKDAEIYKEKDSNKADKPSPAPTDNK
STSNSSDKNLSAAEVFKQAKPEKIVPLDKIAAHMAYAVGFEDDQLIVPH
HDHYHNVPMAWFDKGGLWKAPEGYTLQQLFSTIKYYMEHPNELPKEK
GWGHDSDHNKGSNKDNKAKNYAPDEEPEDSGKVTHNYGFYDVNKGS
DEEEPEKQEDESELDEYELGMAQNAKKYGMDRQSFEKQLIQLSNKYSV
SFES

ID-39 (Same as ID-76)

Clone 56

ATGAGGAAACGTTTTTCCTTGCTAAATTTTATTGTTGTTACTTTTATTT
TCTTTTTCTTTATTCTTTTTCCGCTTTTTAAGGCCAAAGATTGTCAGGT
TGTTTATGCAAGTTTTCAAGGAGATCATTGGGACATTTGTAACGCATT
TGATTTTCCGTATTTACATCGCTTTGATCTCATTAAAGGTAAAGAAAA
TCAACTTTACTTTATAGGTTGTACAATTGCTAACAGTAAAGCCTACAC
TGAGGATTGGAGTGATAAAGGCCGAATTTTGTTGCTCGTTTTAATAC
TCAAACCATACATTGGAAGGATTGCAACAATTGCCTCAAACTTTAT
TAAAAAATCATGGATACTATGCCATTCAGGATGAAGGATATTCATTG
ATTACTTCAGTAGAAGGGGTACTCAAACTCACTTATCCAGAATTTTCT
ACTACAGGCGACTGGCAATTAGAACGGCTTTTCGATGAGGAGACAAG
CGATGTGGTGAAAGTGGATATTAATCAGGATGGTAAGGATGAGTATG
TGATCATCCAAGGTTTTCATGGAGATCGTTTACGTATCTTCACTGAAG
ATTTCGGTCGAGAATTATTCCATTATCCTGAAAAAACCCCATTTGGTC
ACGCTATTTGGAGTGGTCGTTTACTTAATCAGACTTGTTTCGTATTCG

FIG. 1 CONT'D

```
GGTGGCGATCAGAAAAAGCAGAATTAAGGCTTTTTCACTTTGTAGAT
GGGCACTTGGTTTCAGAATTAGTAGATGCAAAAGCAGCTTCTAGTAA
TGTCTTAGCTTTTGAAAAGATGGAAAAGCTTATCTTTTCTCAGCCAA
TAACGGACGTGGCGAAGTTGCTCTTTATCAATTAGTAAAATAA
```

```
MRKRFSLLNFIVVTFIFFFFILFPLFKAKDCQVVYASFQGDHWDICNAFDF
PYLHRFDLIKGKENQLYFIGCTIANSKAYTEDWSDKGRIFVARFNTQNHT
LEGLQQLPQTLLKNHGYYAIQDEGYSLITSVEGVLKLTYPEFSTTGDWQ
LERLFDEETSDVVKVDINQDGKDEYVIIQGFHGDRLRIFTEDFGRELFHY
PEKTPFGHAIWSGRLLNQTCFVFGWRSEKAELRLFHFVDGHLVSELVDA
KAASSNVLAFEKDGKAYLFSANNGRGEVALYQLVK*
ID-40
```

Clone 57

```
ATGAAGCACAAGTTAAAAGCTTTTACGCTTGCTTTACTCTCAATATTC
TTTGTGTTTGGTGGAAAGGTCAGTGCAGAGACTGTGAATATTGTTTCT
GATACAGCATACGCTCCATTCGAATTTAAAGATTCTGATCAAACTTAT
AAAGGAATCGATGTTGACATCGTTAACGAAGTCGCTAAGCGTGCTGG
CTGGAATGTTAACATGACGTATCCAGGTTTTGATGCCGCAGTTAACG
CTGTTCAATCTGGACAGGCAGATGCGCTAATGGCCGGAACTACTGTT
ACTGAAGCACGTAAAAAGTCTTTAATTTCTCAGATACTTATTACGAT
ACTTCCGTTATTCTTTATACTAAAAATAATAATAAAGTCACAAACTAC
AAACAACTAAAAGGAAAAGTAGTCGGTGTAAAAAATGGAACAGCTG
CTCAAAGCTTCTTAGAAGAAAATAAATCTAAATACGGCTATAAAGTT
AAAACATTTGATACAAGCGACCTAATGAATAACAGCCTTGATTCTGG
TTCTATTTACGCCGCTATGGACGATCAACCAGTTGTGCAATTTGCGAT
AAATCAAGGAAAAGCTTACGCCATTAACATGGAAGGCGAAGCAGTT
GGTAGCTTTGCATTTGCTGTCAAAAAAGGTAGTGGACACGATAATCT
AATTAAAGAATTTAACACAGCTTTTGCACAAATGAAATCAGATGGCA
CTTATAATGACATCATGGATAAATGGCTTGGAAAAGACGCTACAAAA
ACAAGCGGCAAAGCAACAGGTAATGCCAATGAAAAAGCAACTCCTG
TAAAGCCAAGTTATAAAATTGTTTCTGATTCTTCATTCGCACCATTCG
AATATCAAAACGGTAAAGGGAAATATACTGGTTTTGATATGGAATTA
ATCACGAAAATTGCTAAACAGCAAGGTTTTAAACTTGATATCTCAAA
TCCAGGTTTTGATGCCGCTTTAAATGCTGTCCAATCTGGGCAAGCTGA
CGGTGTTATTGCAGGAGCCACAATCACAGAAGCACGCCAAAAAATCT
TTGATTTTTCTGATCCTTATTACACATCTAGCGTTATCTTAGCGGTTAA
AAAAGGAAGCAATGTCAAATCATACCAAGATTTAAAAGGAAAAACA
GTTGGTGCTAAAAATGGTACTGCCTCATATACTTGGTTATCAGACCAC
GCAGATAAGTACAACTATCATGTTAAAGCATTTGATGAAGCATCTAC
AATGTATGATAGTATGAACTCAGGTTCAATTGATGCTCTAATGGATG
ACGAAGCCGTTCTTGCTTACGCTATTAATCAAGGTCGTAAATTTGAA
ACACCTATCAAAGGTGAAAAATCAGGCGATATCGGATTTGCAGTGAA
```

```
AAAAGGGGCAAATCCAGAATTAATTAAAATGTTTAACAACGGTCTTG
CTTCACTCAAAAAATCGGGTGAGTACGATAAACTTGTTAAAAAATAC
CTTTCCACAGCCAGCACTTCTTCAAACGATAAAGCTGCTAAACCTGT
AGATGAATCAACTATTTTAGGGTTAATTTCTAATAACTACAAACAATT
GCTATCTGGTATTGGAACTACTTTAAGTTTAACTCTTATCTCGTTTGC
GATTGCTATGGTTATTGGTATTATCTTTGGTATGATGAGCGTATCACC
AAGTAATACTCTCCGCACAATTTCAATGATTTTTGTTGATATTGTCCG
TGGTATTCCACTCATGATTGTGGCCGCTTTTATTTTCTGGGGTATTCCT
AATTTAATCGAAAGCATCACAGGTCACCAAAGTCCAATTAATGACTT
CGTTGCTGCTACTATCGCTCTTTCTTTAAATGGTGGTGCGTACATTGC
TGAAATTGTACGTGGTGGTATTGAAGCTGTTCCTTCTGGTCAAATGGA
AGCAAGTCGCAGCTTAGGTATTTCTTACGGCAAAACTATGCAAAAGG
TTATCTTACCTCAAGCAGTACGCCTTATGTTACCAAACTTTATCAACC
AATTTGTCATCTCATTAAAGGATACAACAATTGTATCAGCAATCGGA
CTTGTGGAACTCTTCCAAACTGGTAAATCATAA
```

```
MKHKLKAFTLALLSIFFVFGGKVSAETVNTVSDTAYAPFEFKDSDQTYK
GIDVDIVNEVAKRAGWNVNMTYPGFDAAVNAVQSGQADALMAGTTV
TEARKKVFNFSDTYYDTSVILYTKNNNKVTNYQLKGKVVGVKNGTA
AQSFLEENKSKYGYKVKTFDTSDLMNNSLDSGSIYAAMDDQPVVQFAI
NQGKAYAINMEGEAVGSFAFAVKKGSGHDNLIKEFNTAFAQMKSDGTY
NDIMDKWLGKDATKTSGKATGNANEKATPVKPSYKIVSDSSFAPFEYQ
NGKGKYTGFDMELITKIAKQQGFKLDISNPGFDAALNAVQSGQADGVIA
GATITEARQKIFDFSDPYYTSSVILAVKKGSNVKSYQDLKGKTVGAKNG
TASYTWLSDHADKYNYHVKAFDEASTMYDSMNSGSIDALMDDEAVLA
YAINQGRKFETPIKGEKSGDIGFAVKKGANPELIKMFNNGLASLKKSGEY
DKLVKKYLSTASTSSNDKAAKPVDESTILGLISNNYKQLLSGIGTTLSLTL'
ISFAIAMVIGIIFGMMSVSPSNTLRTISMIFVDIVRGIPLMIVAAFIFWGIPN
LIESITGHQSPINDFVAATIALSLNGGAYIAEIVRGGIEAVPSGQMEASRSL
GISYGKTMQKVILPQAVRLMLPNFINQFVISLKDTTTVSAIGLVELFQTGK
S*
```

ID-41

Clone 58

```
TTGGAAGGTTTACTTATTGCATTGATTCCCATGTTTGCGTGGGGAAGTATTGGATTT
GTTAGTAATAAAATTGGAGGGCGTCCAAATCAACAAACATTTGGAATGACTTTAGG
AGCATTGCTATTTGCGATTATCGTATGTTTATTTAA
```

MEGLLIALIPMFAWGSIGFVSNKIGGRPNQQTFGMTLGALLFAIIVCLF

FIG. 1 CONT'D

ID-42

Clone 70

ATGAATACTATTTATAATACATTGAGAACAGATAAAGGTTATAAAGT
TTATGAGGGGTATTTATATGAAATTACTGGTGAAGAATGTGAAGAAG
CCTTAGACCTTGTGATTCCTAAGAATATTGTATTTGCAGATACAGATA
CTTGTGGCTACACTTTTTTACTCAATGAAGATGGAACAGTTTATGATG
ATGTGACTTTCTACAAATTTGATGATAAATATTGGTTGGCTAGTCATA
AAGCTTTGGATTCTTATTTAGACAACATCAATTTTGACTATACCGTAA
CAGATATTTCTGACGAGTATAAAATGCTGCAAATTGAAGGAAGATAT
TCGGGAGAAATTGCTCAGTCATTTTATGAATATGATATTTCAACACTT
AATTTTCGTACTCTTCGCATAGAGATGGACTTCATCAAAGGTGAGGA
AAGGTTATCTTGGCGTAGATTTGGTTTTTCTGGAGAATTTGGCTATCA
ATTTTTCCTACCATCTTCTATTTTTGCTACTTTTGTTTCGGATGTCTGT
GAAGGTATAGCAGAGTGTGGGGATGAACTTGATAGATATTTAAGGTT
TGAAGTGGGACAACCCATTACTGATATTTATCAACAAGAAGAATATT
CTTTATATGAAATAGGTTATTCTTGGAATCTAGATTTCACAAAGGAA
GAATTTAGAGGTCGCGATAGCTTGTTAGAGCACATCAGATCAGCAAC
AGTTAAAAGTGTTGGATTCTAACGAAGGAAAAACTCGCTTCAGGAA
CACCAGTGCTATTTGATGACCAAATTGTTGGAAAGATTTTTTGGATAG
CAGACGAGAAACACTCTTCGGAAAATTACCTAGGTTTGATGATTGTT
AACCAAACATATGCTCATTCAGGAGTTACTTTTGTAACAGAAGATGG
CCAAATTTTGAAAACACAATCAAGCCCTTATTGTATCCCAGAAAGTT
GGAACAAAGAATGA

MNTIYNTLRTDKGYKVYEGYLYEITGEECEEALDLVIPKNIVFADTDTCG
YTFLLNEDGTVYDDVTFYKFDDKYWLASHKALDSYLDNINFDYTVTDIS
DEYKMLQIEGRYSGEIAQSFYEYDISTLNFRTLRIEMDFIKGEERLSWRRF
GFSGEFGYQFFLPSSIFATFVSDVCEGIAECGDELDRYLRFEVGQPITDIY
QQEEYSLYEIGYSWNLDFTKEEFRGRDSLLEHIRSATVKSVGFSTKEKLA
SGTPVLFDDQIVGKIFWIADEKHSSENYLGLMIVNQTYAHSGVTFVTED
GQILKTQSSPYCIPESWNKE*

ID-43

Clone 78/94

ATGGAGTTAGTAATTAGAGATATTCGTAAGCGGTTTCAGGAAACAGA
GGTCTTGAGAGGAGCAAGTTACCGATTTTATTCAGGTAAAATAACAG
GGGTCTTAGGTAGGAATGGTGCTGGGAAAACAACTTTATTTAATATA
CTTTATGGGGATCTTGCAGCTGACAACGGGACCATTTGTTTATTGAAG
ATAATCACGAGTATCCTCTTACCGATAAGGATATTGGTATTGTTTAT

```
TCCGAAAACTACCTTCCAGAATTTTTAACAGGGTATGAATTTGTAAA
ATTTTACATGGATTTACATCCTTCAGATGATTTAATGACAATAGATGA
TTATTTAGATTTTATGGAAATAGGACAAACAGAGCGTCATAGAATTA
TCAAAGGATATTCTGATGGAATGAAGAGTAAGCTCTCATTAATTTGC
CTGATGATTTCTAAGCCAAAAGTAATTTTACTAGATGAGCCACTGAC
TGCAGTTGATGTTGTATCAAGTATTGCAATAAAACGCCTTTTGTTGGA
ATTAAGTGAGGATCATATTATTATATTATCAACTCATATAATGGCCTT
AGCAGAAGATCTATGTGATATTGTGGCTGTATTAGACAAAGGAAAAC
TCCAAACATTAGATATTGATCGTAAACATGAACAATTCGAAGAGCGT
CTTCTTCAAGTGTTGAAGGGAGATGAATATGACAAGTAA
```

MELVIRDIRKRFQETEVLRGASYRFYSGKITGVLGRNGAGKTTLFNILYG
DLAADNGTICLLKDNHEYPLTDKDIGIVYSENYLPEFLTGYEFVKFYMD
LHPSDDLMTIDDYLDFMEIGQTERHRIIKGYSDGMKSKLSLICLMISKPK
VILLDEPLTAVDVVSSIAIKRLLLELSEDHIIILSTHIMALAEDLCDIVAVL
DKGKLQTLDIDRKHEQFEERLLQVLKGDEYDK*

ID-44

Clone 80

```
TTGTTTATGAGATATACAAATGGAAATTTTGAAGCCTTTGCAAGACCT
CGAAAACCTGAAGGTGTGGATAAAAAATCCGCTTATATTGTTGGTTC
TGGTTTAGCAGGATTAGCTGCCGCTGTCTTTTTAATACGTGACGGTCA
AATGGATGGTCAACGTATTCATATTTTTGAAGAACTACCTCTTTCTGG
AGGATCACTTGACGGTGTCAAACGACCTGATATCGGTTTTGTAACGC
GTGGTGGTCGTGAAATGGAAAATCACTTCGAATGTATGTGGGATATG
TACCGTTCCATCCCCTCTCTCGAAGTTCCAGATGCTTCTTATCTAGAT
GAATTTTATTGGCTTGACAAGGATGATCCCAATTCATCTAACTGTCGC
CTCATTCATAAACAGGGGAATCGCTTAGAATCTGATGGTGATTTTAC
ACTCGGAACACATTCCAAAGAGTTAGTTAAGCTAGTCATGGAGACTG
AAGAGTCTTTAGGTGCTAAGACGATTGAAGAAGTTTTTTCAAAAGAA
TTTTTTGAAAGTAATTTTTGGACTTATTGGGCTACTATGTTTGCCTTTG
AGAAATGGCATTCAGCGATTGAAATGCGTCGATATGCTATGCGCTTT
ATCCATCATATTGGTGGTCTGCCTGATTTCACTTCATTAAAATTTAAT
AAATATAATCAATATGATTCTATGGTGAAACCAATCATCAGTTATTTA
GAGTCTCATAATGTAGATGTTCAATTTGATAGCAAGGTAACTAATAT
CTCCGTAGACTTT
```

MFMRYTNGNFEAFARPRKPEGVDKKSAYIVGSGLAGLAAAVFLIRDGQ
MDGQRIHIFEELPLSGGSLDGVKRPDIGFVTRGGREMENHFECMWDMY
RSIPSLEVPDASYLDEFYWLDKDDPNSSNCRLIHKQGNRLESDGDFTLGT
HSKELVKLVMETEESLGAKTIEEVFSKEFFESNFWTYWATMFAFEKWHS

AIEMRRYAMRFIHHIGGLPDFTSLKFNKYNQYDSMVKPIISYLESHNVDV
QFDSKVTNISVDF

ID-45

Clone 81

TTGTTGGCTTCTTTATTTATCGTCCGTTTGTCAAAATCGCTTTCGCTAA
GGAGGAGCAATATGAAAAAATTACTTAGATGGCTTCCTCCTGTACTT
TTCATTATTATCCTTATAGGAATGACTATCTTAGGTAAGTCCTATATC
AATAAAGTAACAGCTCACAAAATAAAACTCTATAACTCTCGAATGAC
TCCTACTATTTTAATTTCAGGATCCAGTGCTACTCAAGAACGATTTAA
CAGCATGTTAGCACAGCTCAACCAAATGGGAGAAAAACATAGCGTTT
TAAAGTTAACTGTCAAAAAGACAATAGCATTATCTACAATGGACAA
ATTAGCGGCAATGACCACAAACCCTACATTGTCATTGGATTTGAAAA
TAATGAAGATGGTTATAGTAACATCAAAAAACAAACAAAATGGCTA
CAGATTGCTATGAATGATCTTCAGAAGAAATATAAATTTAAACGTTT
TAACGCTATCGGTCATTCAAATGGTGGCTTATCATGGACTATTTTCCT
AGAAGATTATTACGACTCTGATGAATTTGATATGAAATCATTGTTAA
CAATGGGAACACCTTTTAACTTTGAAGAAAGTAACACCTCAAATCAT
ACTCAAATGCTTAAAGATTTAATCAGTAATAAAGGAAATATTCCATC
AAGTCTCATGGTATACAATTTGGCAGGAACTAATTCATATGATGGTG
ATAAAATTGTTCCATTTGCTAGTGTGGAGACTGGTAAATATATTTTCC
AAGAAACCGCTAAACACTATACCCAACTAACAGTAACTGGTAATAAT
GCTACACATTCTGACTTGCCTGATAATCCTGAAGTTATCCAATATGTC
GCAGAAAAAATTCTTAAAAATGAGAAAGGTAAATTACCAAAACCTC
ACTAA

MLASLFIVRLSKSLSLRRSNMKKLLRWLPPVLFIILIGMTILGKSYINKVT
AHKIKLYNSRMTPTILISGSSATQERFNSMLAQLNQMGEKHSVLKLTVK
KDNSIIYNGQISGNDHKPYIVIGFENNEDGYSNIKKQTKWLQIAMNDLQK
KYKFKRFNAIGHSNGGLSWTIFLEDYYDSDEFDMKSLLTMGTPFNFEES
NTSNHTQMLKDLISNKGNIPSSLMVYNLAGTNSYDGDKIVPFASVETGK
YIFQETAKHYTQLTVTGNNATHSDLPDNPEVIQYVAEKILKNEKGKLPK
PH
*

ID-46

Clone 83

TTGAAATTAGGTATTACAACATTCGGAGAGACAACAATCCTTGAAGAAACAAACC
AAAGCTATTCACATCCTGAGAGGATTCGCCAATTAGTTGCTGAGATTGAACTAGCT
GATCAAGTTGGTTTAGATGTATATGGTATTGGAGAGCACCATCGTGAAGATTTTGC

FIG. 1CONT'D

```
GGTCTCTGCACCCGAAATTATCCTAGCAGCAGGAGCGGTTAGAACTAATAATATCC
GTTTATCTAGTGCAGTAACGATTCTCTCTTCCAATGATCCTATTCGCGTCTATCAGC
AATTTTCAACGATTGACGCACTTTCAAATGGTAGAGCAGAAATTATGGCAGGGCGT
GGTTCCTTTATTGAGTCTTTTCCATTGTTTGGATACGATTTAGCGGATTATGATGAT
TTATTTAATGAAAAATGGATATGTTGTTAGCAATTAACTCAGCGACAAATCTCGA
TTGGAAAGGTCATTTGACACAAACAGTTAATGAGCGACCAATTTATCCAAGAGCAT
TACAAAGACAGTTATCAATATGGGTGGCAACAGGAGGAAATGTTGATTCTACAATT
CGTATTGCAGAACAAGGTTTGCCAATTGTTTATGCAACTATTGGTGGGAATCCCAA
AGCCTTTCGTCAATTGGTCCATATTTATAAAGAAGTTGGTAAGTCCGTAATGGACA
CAAACCAGGAACAACTAAAAGTTGCTGCTCACTCTTGGGGATGGATTGAAGAGGA
TAATCAAACCGCTATTGACCGTTATTTTTTCCCTACGAAACAGACCGTCGATAATAT
TGCTAAGGGACGCCCTCATTGGTCTGAAATGACTAAAGAGCAGTATTTACGTTCAA
TAGGTCCAGAAGGTGCTATTTTTGTAGGAAATCCTGAAGTGGTTGCACATAAAATT
ATAGGACTTTGGTGA
```

MKLGITTFGETTILEETNQSYSHPERIRQLVAEIELADQVGLDVYGIGEHHREDFAVSAP
EIILAAGAVRTNNIRLSSAVTILSSNDPIRVYQQFSTIDALSNGRAEIMAGRGSFIESFPLF
GYDLADYDDLFNEKMDMLLAINSATNLDWKGHLTQTVNERPIYPRALQRQLSIWVAT
GGNVDSTIRIAEQGLPIVYATIGGNPKAFRQLVHIYKEVGKSVMDTNQEQLKVAAHSW
GWIEEDNQTAIDRYFFPTKQTVDNIAKGRPHWSEMTKEQYLRSIGPEGAIFVGNPEVV
AHKIIGLW

ID-47

Clone 86

```
ATGATAGAGTGGATTCAAACACATTTACCAAATGTATATCAAATGGG,
TTGGGAAGGTGCTTACGGCTGGCAGACAGCTATTGTACAAACCCTTT
ATATGACTTTTTGGTCGTTCCTTATTGGAGGTTTAATGGGATTGTTAG
GAGGTTTATTCCTTGTTTTAACTAGTCCTAGAGGAGTTATTGCTAATA
AATTAGTATTTGGAGTTTTAGATAAAGTTGTTTCTGTTTTTAGAGCTC
TGCCCTTCATTATTCTTCTTGCTTTGATTGCGCCAGTAACTCGCGTAAT
TGTAGGAACAACACTTGGTTCACCAGCAGCTTTGGTACCTCTTTCTTT
GGCAGTTTTCCCATTTTTTGCTCGTCAAGTTCAAGTTGTTTTAGCTGA
ACTTGATGGTGGAGTTATTGAGGCTGCACAAGCCTCAGGTGGAACAC
TTTGGGATATTATTGTAGTTTATCTTCGTGAAGGTCTACCAGATTTAA
TTCGAGTATCAACGGTTACTTTGATTTCTTTAGTAGGTGAAACAGCTA
TGGCTGGCGCTATTGGTGCAGGAGGATTGGGTTCTGTTGCTATTACTA
AAGGATATAACTATTCTCGTGATGATATTACTTTAGTAGCGACTATTC
TGATTTTATTATTAATTTTCTTTATCCAATTTTTAGGTGATTTTTTAAC
ACGTCGCTTGAGTCATAAATAA
```

MIEWIQTHLPNVYQMGWEGAYGWQTAIVQTLYMTFWSFLIGGLMGLL
GGLFLVLTSPRGVIANKLVFGVLDKVVSVFRALPFIILLALIAPVTRVIVG

TTLGSPAALVPLSLAVFPFFARQVQVVLAELDGGVIEAAQASGGTLWDII
VVYLREGLPDLIRVSTVTLISLVGETAMAGAIGAGGLGSVAITKGYNYSR
DDITLVATILILLLIFFIQFLGDFLTRRLSHK*

ID-48 (same as ID-43)

ID-49

Clone 96

TTGGCAGTTAGTTTTCATGAAGTATTTGGTTGGGATTCTGCTTTTTTTA
TTATGATTATCAATATTCCATTGCTCCTTCTTTGCTACTTTGGCTTAGG
TAAACAAACCTTTTTAAAAACTGTCTATGGTTCTTGGATTTTTCCTGT
TTTTATTAAGTTAACACAAAGTGTACCAACTTTGACCCACAACTCACT
CCTCGCAGCACTTTTTGGAGGTGTTATTGTAGGATGTGGTTTGGGGAT
TGTTTTTTGGAGCGACTCTTCAACTGGTGGAACGGGGATTATCATTCA
ATTCTTAGGAAAATATACTCCTATAAGCCTTGGACAAGGGGTTATAT
TGATTGATGGACTTGTTACAATTGTTGGTTTCCTAGCTTTTGACAGTG
ATACGGTTATGTTTTCTATTATTGGTTGATAACTATTAGTTATATTAT
TAATGCTATCCAAACTGGATTTACAACCTTAAGCACTGTCTTAATCGT
TTCTCAAGAGCACCAAAAAATTAAGACATATATCAATACTGTCGCAG
ATAGAGGAGTAACAGAAATTCCCGTTAAAGGGGGATATTCTGGAACT
AATCAAATCATGCTTATGACAACTATTGCTGGTTATGAGTTTGCTAAA
TTACAAGAGGCAATAGCAGAAATTGACGAAACAGCCTTCATAACAGT
AACTCCAACATCACAAGCTTCTGGACGTGGATTTAGTCTTCAAAAAA
ATCATGGACGTCTTGATGAAGACATTCTTATGCCAATGTAA

MAVSFHEVFGWDSAFFIMIINIPLLLLCYFGLGKQTFLKTVYGSWIFPVFI
KLTQSVPTLTHNSLLAALFGGVIVGCGLGIVFWSDSSTGGTGIIQFLGKY
TPISLGQGVILIDGLVTIVGFLAFDSDTVMFSIIGLITISYIINAIQTGFTTLST
VLIVSQEHQKIKTYINTVADRGVTEIPVKGGYSGTNQIMLMTTIAGYEFA
KLQEAIAEIDETAFITVTPTSQASGRGFSLQKNHGRLDEDILMPM*

ID-50

Clone 99

ATGAAAGAAAAACAGTCGAAAAGGCTTATTTATATACTACTGATTGTTCCCATTAT
CTTTATAAGTGTTTTTACATACAGTATTAGCCAGCCTTCTAAACTACTTCCACCAAA
AGAATTAGTTATTCTAAGTCCAAATAGTCAAGCCATTTTAACAGGAACGATTCCAG
CTTTTGAGGAAAAATACGGTATAAAAGTTAAGCTTATTCAAGGTGGGACAGGGCA
ACTAATAGATAGATTAAGTAAGGAGGGTAAGCAGTTGAAGGCGGATATTTTCTTTG
GAGGAAATTATACGCAATTTGAAAGTCATAAGGCATTGTTTGAGTCTTACGTATCA

FIG. 1 CONT'D

```
AAGAATGTTCATACTGTTATTCCAGACTATATCCATCCGAGTGATACGGCGACACC
TTATACTATAAATGGGAGTGTCTTGATTGTAAATAACGAATTAGCTAAGGGACTTA
CCATCAAGAGTTATGAAGATTTATTACAGCCTTCCTTAAAAGGTAAAATTGCCTTT
GCAGATCCTCTAGAGTCGACCTGCAAGCATGCAAGCTTGGCGTAA
```

MKEKQSKRLIYILLIVPIIFISVFTYSISQPSKLLPPKELVILSPNSQAILTGTIPAFEEKYGI
KVKLIQGGTGQLIDRLSKEGKQLKADIFFGGNYTQFESHKALFESYVSKNVHTVIPDYI
HPSDTATPYTINGSVLIVNNELAKGLTIKSYEDLLQPSLKGKIAFADPLESTCKHASLA

ID-51

Clone 103

```
CCTCCTATCAAATGATGACAAACGTGAGAGGTACATGGAACAAATGCTCTTTAAAA
TTGAAAATGCAACCTGGCAGCGTGTGGTAAGAGCACTTTATCGTAAATACAATAAG
GAATTTTTTACATATCCAGCCGCCAAAACAAACCACCACGCTTTTGAATCAGGATT
GGCATATCACACGGCAACAATGGTTCGTTTGGCAGATAGTATCGGAGATATCTATC
CAGAACTTAATAAAAGTTTGATGTTTGCTGGTATTATGCTACATGATTTAGCCAAG
GTCATAGAGTTATCGGGTCCTGATAATACAGAATATACTATTCGAGGTAATCTTAT
CGGTCATATTTCACTTATTGATGAGGAATTAA
```

LLSNDDKRERYMEQMLFKIENATWQRVVRALYRKYNKEFFTYPAAKTNHHAFESGL
AYHTATMVRLADSIGDIYPELNKSLMFAGIMLHDLAKVIELSGPDNTEYTIRGNLIGHIS
LIDEEL

ID-52

Clone 104

```
ATGAAAAAAAATAAAATTATCCGATTCAGTTTAGTTGGTGTTCTACTT
GCGATACTATGCTTTAGTCTTTTTGCTTTATTGAAGCCTAACAGTCAA
CAATCATCATCTCAAAAGTTGAGGAATGAGGATATAAAAAAGACATC
CTCTCAAAAAAGAAATAAGAAATTACGATTACCAGCTGTATCATCAA
AAGATTGGAACTTGATTTTGGTCAATCGTGACCATAAACATGAAGAA
TTAAGTCCAGATGTGGTGCCTGTTGAAAATATTTATTTGGATAAACGT
ATTACGAAGCAAGCTACTCAGTTTTTAGAGGCTGCTAGAGCAATTGA
TTCACGAGAACATTTAATTTCGGGTTATCGTAGTGTTGCCTATCAGGA
GAAGTTGTTCAATTCTTATGTTACTCAAGAGATGACTAGTAACCCTAA
TTTGACGAGGGGACAAGCAGAAAAGTTGGTAAAAACTTACTCTCAGC
CTGCAGGTGCTAGTGAACACCAGACTGGATTAGCGATGGATATGAGT
ACTGTAGATTCTTTGAATGAGAGCGATCCTAGAGTAGTCAGTCAGTT
GAAAAAGATAGCTCCACAATATGGTTTTGTCTTACGGTTTCCGGATG
GTAAAACAGCAGAAACAGGGGTAGGTTATGAAGATTGGCATTACCG
```

CTATGTTGGGGTAGAGTCTGCAAAATATATGGTCAAACATCATTTAA
CATTAGAAGAATACATAACTTTATTAAAGGAGAATAACCAATGA

MKKNKIIRFSLVGVLLAILCFSLFALLKPNSQQSSSQKLRNEDIKKTSSQK
RNKKLRLPAVSSKDWNLILVNRDHKHEELSPDVVPVENIYLDKRITKQA
TQFLEAARAIDSREHLISGYRSVAYQEKLFNSYVTQEMTSNPNLTRGQA
EKLVKTYSQPAGASEHQTGLAMDMSTVDSLNESDPRVVSQLKKIAPQY
GFVLRFPDGKTAETGVGYEDWHYRYVGVESAKYMVKHHLTLEEYITLL
KENNQ*

ID- 53

Clone 106

CTGTTATGTGGATTTCTTCCATCAATTCCTGTGTCTAATTCCGGGGGG
TATGGTATAATAACAGTTATGAAAAATAAAAAAATCTTATTTGGGAC
TGGCCTTGCTGGTGTGGGTTTACTGGCAGCTGCTGGTTATACCCTAAC
TAAAAAAGTAACAGATTATAAACGTCAGCAAATCACTCAGACCTTAA
GAGAACTTTTTAGTCAGATGGGTGATATTCAGGTATTTATTTTAATG
AATTTGAATCTGATATTAAAATGACCAGTGGTGGTCTTGTCTTGGAA
GATGGCAGAATTTTCGAATTCATTTATCGTCAAGGTGTTCTTGATTAT
GTGGAGGTGAGCAAATGA

LLCGFLPSIPVSNSGGYGIITVMKNKKILFGTGLAGVGLLAAAGYTLTKK
VTDYKRQQITQTLRELFSQMGDIQVFYFNEFESDIKMTSGGLVLEDGRIF
EFIYRQGVLDYVEVSK*

ID-54

Clone 108

ATGTATCAAACTCAGACAAATAAGGAAAAATTTGTTTTATTTTTGAAATTATTTATC
CCAGTATTGATTTATCAATTTGCTAATTTTTCAGCTACTTTTATTGATTCGGTTATGA
CTGGACAGTATAGTCAGCTACATTTGGCAGGTGTGTCAACTGCTAGTAATTTATGG
ACTCCGTTTTTCGCTTTATTAGTAGGTATGATTTCAGCATTAGTACCAGTAGTTGGT
CAACATTTGGGTAGAGGAAATAAAGAACAAATTCGCACAGAATTTCATCAATTTCT
ATATTTAGGTTTGATACTGTCCTTAA

MYQTQTNKEKFVLFLKLFIPVLIYQFANFSATFIDSVMTGQYSQLHLAGVSTASNLWTP
FFALLVGMISALVPVVGQHLGRGNKEQIRTEFHQFLYLGLILSL

ID-55

FIG. 1 CONT'D

Clone 112

CTGCTCTTTTTAGCTAACTTTTCTAATTTATGGTATAATTGTATGGATT
GTTTAGCTAGAATGGAGAAGATGATGCAAGATGTTTTCATTATAGGA
AGTAGAGGGTTGCCAGCTCGTTACGGTGGTTTTGAAACTTTTGTTTCA
GAATTGATTAATCATCAAAAAAGTTCCGACATAAAATACCATGTTGC
ATGCCTTAGTGATAAAGAACATCATACTCATTTTAACTTTGCTGACGC
TGATTGTTTTACTATAAATCCTCCCCAATTAGGGCCAGCACGTGTGAT
TGCTTATGATATTATGGCCATTAATTATGCCCTTGACTTGGTTAAGAC
ACATGATTTAAAAGAGCCTATTTTTTATATTTTAGGAAATACAATTGG
TGCCTTTATTTGGCATTTTGCCAATAAAATACATAAAGTCGGTGGCTT
ATTGTATGTTAATCCGGATGGTTTAGAGTGGAAGCGATCAAAGTGGT
CTCGTCCCACACAGCGTTATTTAAAATACGCCGAAAAATGTATGACT
AAAAATGCAGACCTAATTATTTCTGATAATATTGGTATTGAAAATTA
CATTCAATCTACCTACTCTAATGTGAAGACAAGGTTCATTGCTTACGG
TACAGAGATTAATTCTAGGAAATTATCGTCAGATGATCCACGTGTCA
AACAGTTGTTTAAAAAATGGAATATTAAGTCTAAGGGTTACTATCTA
ATCGTTGGTCGATTTGTCCCTGAAAACAATTATGAAACGGCTATTAG
GGAGTTCATGGCTTCAGATACTAAGCGTGATTTAGTTATTATCTGTAA
CCATCAAAATAACCCCTACTTTGAAAAGTTGTCCTTAAAGACAAACC
TTCAACAAGATAAAAGAGTTAAGTTTGTAGGTACGCTCTATGAAAAA
GATCTGCTGGATTATGTTCGTCAACAAGCCTTTGCTTATATTCATGGG
CATGAAGTTGGCGGTACTAATCCAGGACTGCTTGAGGCTTTAGCTAA
TACTGATTTGAATCTTGTTCTAGATGTTGATTTCAACAAATCAGTAGC
AGGTCTCTCAAGTTTTTACTGGACTAAAAAAGAGGGGGATTTAGCTA
AGCTT

MLFLANFSNLWYNCMDCLARMEKMMQDVFIIGSRGLPARYGGFETFVS
ELINHQKSSDIKYHVACLSDKEHHTHFNFADADCFTINPPQLGPARVIAY
DIMAINYALDLVKTHDLKEPIFYILGNTIGAFIWHFANKIHKVGGLLYVN
PDGLEWKRSKWSRPTQRYLKYAEKCMTKNADLIISDNIGIENYIQSTYSN
VKTRFIAYGTEINSRKLSSDDPRVKQLFKKWNIKSKGYYLIVGRFVPENN
YETAIREFMASDTKRDLVIICNHQNNPYFEKLSLKTNLQQDKRVKFVGT
LYEKDLLDYVRQQAFAYIHGHEVGGTNPGLLEALANTDLNLVLDVDFN
KSVAGLSSFYWTKKEGDLAKL

ID-56

Clone 120

TTGAGGAGTAATATGGTAAAGACAGCAGTTTTAATGGCGACATACAA
TGGCGAAAAATTTATATCTGAACAACTTGATTCAATTCGCCAACAGA
CATTAAAACCAGATTATGTATTATTGAGGGATGATTGTTCAACGGAT
GAAACAGTCAATGTCGTCAATAACTATATCGCAAAACATGAGTTAGA

```
AGGCTGGAAAATTGTTAAAAACGACAAAAACTTAGGCTGGCGTTTAA
ATTTTCGTCAATTACTTATTGATGTGTTAGCCTATGAGGTTGACTATG
TCTTTTTTAGTGATCAAGATGATATTTGGTATCTTGATAAAAACGAAC
GACAGTTTGCCATTATGTCAGATAACCCTCAAATTGAGGTTTTGAGTG
CAGACGTTGATATCAAAACGATGTCTACAGAAGCCAGTGTTCCACAT
TTTCTAACTTTTTCTTCTAGTGATAGAATCAGTCAGTATCCTAAAGTA
TATGATTATCAAACATTCCGTCCCGGATGGACCATTGCTATGAAGAG
AGATTTTGCGCAAGCTATCGCTTGA

MRSNMVKTAVLMATYNGEKFISEQLDSIRQQTLKPDYVLLRDDCSTDET
VNVVNNYIAKHELEGWKIVKNDKNLGWRLNFRQLLIDVLAYEVDYVFF
SDQDDIWYLDKNERQFAIMSDNPQIEVLSADVDIKTMSTEASVPHFLTFS
SSDRISQYPKVYDYQTFRPGWTIAMKRDFAQAIA*
```

ID-57

Clone 123

```
GTGATTATGGATAAGTCTATTCCTAAAGCAACTGCTAAACGTTTATCA
CTGTACTACCGTATTTTTAAACGTTTTAATACTGATGGCATCGAAAAA
GCTAGTTCCAAACAAATTGCAGATGCCCTAGGTATCGATTCTGCTACT
GTTCGACGTGATTTTTCTTATTTTGGTGAACTAGGACGCCGTGGTTTT
GGTTATGATGTCAAAAAACTTATGAACTTCTTTGCAGAAATATTGAA
CGATCATTCTACAACAAATGTTATGCTGGTGGGGTGTGGAAATATCG
GTAGAGCTCTCTTGCATTATCGTTTCCACGATCGCAATAAAATGCAA
ATTTCAATGGCTTTTGATTTAGATAGCAATGATTTAGTTGGTAAAACA
ACCGAGGATGGAATTCCTGTCTACGGTATTTCGACTATCAATGACCA
TTTAATAGATAGTGATATTGAAACTGCTATCCTAACAGTACCTAGTAC
AGAAGCCCAAGAAGTTGCTGACATCTTAGTCAAAGCAGGTATAAAA
GGCATCTTGAGTTTTTCTCCAGTTCATTTAACATTACCAAAAGATATC
ATTGTCAGTATGTAGATTTAACAAGCGAATTACAAACTTTACTTTAT
TTCATGAACCAGCAGCGATAA

MIMDKSIPKATAKRLSLYYRIFKRFNTDGIEKASSKQIADALGIDSATVRR
DFSYFGELGRRGFGYDVKKLMNFFAEILNDHSTTNVMLVGCGNIGRALL
HYRFHDRNKMQISMAFDLDSNDLVGKTTEDGIPVYGISTINDHLIDSDIE
TAILTVPSTEAQEVADILVKAGIKGILSFSPVHLTLPKDIIVQYVDLTSELQ
TLLYFMNQQR*
```

ID-58

Clone 125

FIG. 1 CONT'D

ATGGGTGCTAAAGGAGCAGATGTCATTCTCGTTTTATCACACTCTGGCATTGGAGA
TGATCGATATGAAGAAGGTGAAGAAAACGTTGGCTATCAAATTGCCAGCATCAAG
GGAGTGGATGCCGTTGTTACGGGACACTCACACGCTGAATTTCCATCAGGTAACGG
TACTGGCTTCTATGAAAAATACACTGGAGTTGATGGTATCAATGGAAAAATAAATG
GAACACCTGTTACAATGGCAGGCAAGTACGGGGATCACCTTGGTATTATTGATTTA
GGACTTAGTTATACTAATGGAAAATGGCAAGTCTCCGAAAGCAGTGCTAAAATCC
GTAAAATTGATATGAACTCAACAACTGCTGACGAGCGTATCATTGCATTGGCTAAG
GAAGCACACGATGGCACTATCAACTATGTTCGCCAACAAGTAGGTACAACAACTG
CGCCAATTACAAGTTACTTTGCACTAGTTAA

MGAKGADVILVLSHSGIGDDRYEEGEENVGYQIASIKGVDAVVTGHSHAEFPSGNGTG
FYEKYTGVDGINGKINGTPVTMAGKYGDHLGIIDLGLSYTNGKWQVSESSAKIRKIDM
NSTTADERIIALAKEAHDGTINYVRQQVGTTTAPITSYFALV

ID-59

Clone 135

TTGTCAATAAGGTTTCAAATCAGCTTGAAATATGATAAAATAAAACAGATTGTAAG
TGACTGTTTAAGCTTGTTTTTCAGAGAGGTTTTTATGAATACAAACACAATAAAAA
AGGTTGTAGCGACTGGAATTGGAGCTGCACTTTTTATCATTATAGGTATGCTAGTT
AA

MSIRFQISLKYDKIKQIVSDCLSLFFREVFMNTNTIKKVVATGIGAALFIIIGMLV

ID-60

Clone 145

ATGAAACATTTAAAATTTCAATCGGTCTTCGACATTATTGGTCCTGTTATGATTGGA
CCATCAAGTAGTCATACTGCAGGAGCTGTCCGCATTGGTAAAGTTGTCCATTCTAT
TTTTGGTGAACCTAGTGAAGTAACCTTTCATTTATACAATTCTTTTGCTAAAACTTA
CCAAGGACACGGTACTGATAAAGCATTGGTTGCAGGGATTCTAGGAATGGATACA
GATAATCCAGATATTAA

MKHLKFQSVFDIIGPVMIGPSSSHTAGAVRIGKVVHSIFGEPSEVTFHLYNSFAKTYQG
HGTDKALVAGILGMDTDNPDI

ID-61

Clone 147

FIG. 1 CONT'D

GTGTCAGAAGGTGTTTTAATGTTTCTAAAAGAAGATGACGTAGAGACTTTTCTTCA
TATCCTGACAAATTCATTTAGCCAATTTATGGCACAATTTGATTTGTGTCATAAGGA
AATGATTAA

ID-62

Clone 150

ATGACCTACAAAGATTACACAGGTTTAGATCGGACTGAACTTTTGAGTAAAGTGCG
TCATATGATGTCCGACAAACGTTTTAA

MTYKDYTGLDRTELLSKVRHMMSDKRF

ID-63

Clone S2

CTGAGTTGGGTCTTGGAAACGGTCCTGTCAATCATACTAGCTATCAAGGAGACTAA
AATGTATTTAGAACAACTAAAAGAGGTAAATCCTTTAA

MSWVLETVLSIILAIKETKMYLEQLKEVNPL

ID-67

Clone 3-40

GTGAAAAAAAAATTAGTCTCATCACTTCTAAAGTGTTCTCTAATCATT
ATTGTTAGCTTTGCTGGTGGAGCATTTGCTAGTTTTGTCATGAATCAT
AATGACAATATTCCAAATGGTGGTGTCACTAAAACTAGTAAAGTAAA
TTATAATAACATAACGCCTACAACAAAAGCTGTTAAAAAGGTACAAA
ATAGTGTTGTTTCTGTTATCAATTATAAACAACAAGAGAGTCGTTCTG
ACCTATCAGACTTCTATAGTCATTTTTTTTGGTAATCAGGGGGGCAACA
CTGATAAGGGCTTACAAGTTTACGGTGAAGGCTCTGGAGTCATCTAT
AAAAAAGATGGTAAAAATGCCTATGTTGTCACTAATAACCACGTCAT
TGATGGGGCTAAACAAATTGAAATTCAACTAGCTGATGGCTCAAAAG
CAGTTGGGAAACTTGTTGGGTCAGATACCTACTCTGATTTAGCCGTCG
TCAAAATTCCATCAGATAAAGTTTCAAATATTGCAGAATTTGCTGATT
CATCAAAACTCAACATTGGTGAAACTGCTATAGCGATCGGAAGCCCT
CTTGGAACTGAGTATGCAAATTCTGTAACTCAAGGTATTGTATCTAGT
TTAAAAAGAACTGTAACAATGACTAATGAAGAAGGACAAACAGTTT
CTACAAATGCTATCCAGACGGATGCTGCTATCAATCCTGGTAATTCA
GGTGGAGCACTTATCAATATTGAAGGACAGGTTATTGGAATTAATTC
TAGTAAAATTTCTTCTACATCAAATCAAACCTCAGGACAATCGTCAG

FIG. 1 CONT'D

GAAATAGCGTTGAAGGTATGGGATTTGCCATTCCTTCAAATGATGTT
GTTAAGATTATCAATCAACTTGAGAGTAACGGACAAGTAGAGAGACC
TGCTCTAGGTATTTCTATGGCTGGATTAAGTAATTTACCATCCGATGT
TATTAGTAAACTGAAAATCCCAAGTAATGTTACTAATGGTATTGTAG
TAGCATCTATCCAATCTGGCATGCCAGCTCAAGGCAAACTAAAGAAA
TACGATGTCATTACTAAAGTTGACGATAAAGAAGTAGCATCTCCAAG
TGATTTACAAAGTTTACTCTATGGCCACCAGGTAGGGGATTCCATAA
CAGTAACCTTTTATCGTGGTGAAAATAAACAAACAGTCACTATAAAA
CTTACTAAAACTAGTAAAGATTTAGCTAAACAACGAGCAAATAACTA
A

MKKKLVSSLLKCSLIIIVSFAGGAFASFVMNHNDNIPNGGVTKTSKVNY
NNITPTTKAVKKVQNSVVSVINYKQQESRSDLSDFYSHFFGNQGGNTDK
GLQVYGEGSGVIYKKDGKNAYVVTNNHVIDGAKQIEIQLADGSKAVGK
LVGSDTYSDLAVVKIPSDKVSNIAEFADSSKLNIGETAIAIGSPLGTEYAN
SVTQGIVSSLKRTVTMTNEEGQTVSTNAIQTDAAINPGNSGGALINIEGQ
VIGINSSKISSTSNQTSGQSSGNSVEGMGFAIPSNDVVKIINQLESNGQVE
RPALGISMAGLSNLPSDVISKLKIPSNVTNGIVVASIQSGMPAQGKLKKY
DVITKVDDKEVASPSDLQSLLYGHQVGDSITVTFYRGENKQTVTIKLTKT
SKDLAKQRANN*

ID-68

Clone 3-30

ATGTTAAAATGGTATACAAACAAAGGAGGGAGGATGATAATGAAGA
AATGTTTTTTGGCTATTTGTTTAGCTCTTAGTTTTTTATGGTTTCAGT
TCAAGCAGATGAGGTGGACTATAACATTCCTCATTATGAGGGTAATC
TAACTATTCACAATGATAATAGTGCTGATTTTACAGAGAAGGTTACTT
ACCAATTTGATTCGTCCTATAATGGACAGTATGTCACGTTAGGTACG
GCGGGTAAGTTATCTGACAATTTTGATATTAATAATAAGCCACAGGT
TGAAGTTTCAATTAATGGTAAAGTAAGGAAAGTTAGTTACCAGATAG
AAGATTTGGAGGATGGCTACCGTTTGAAAGTGTTTAATGGTGGTGAA
GCAGGTGATACTGTTAAAGTCAATGTTCAGTGGAAACTAAAAAATGT
TCTATTTATGCATAAGGATGTTGGTGAACTTACTGGATTCCTATTAG
CGACTGGGATAAAACGTTAGAGAAAGTAGATTTTGGATATCAACTG
ACAAAAAGGTTGCTCTTTCTCGTCTTTGGGGGCACTTGGGTTATCTTA
AAACTCCTCCTAAAATAAGACAAAATAATAATCGTTACCATTTGACA
GCTTTTAATGTAAACAAACGATTAGAATTTCATGGTTATTGGGATAG
ATCTTATTTTAATCTACCTACAAACAGTAAAAATAATTACAAGAAAA
AAATTGAACATCAAGAGAAGATAATAGAGCGTCATGGTTTTATCCTA
AGTTTCTTGTTAAGGATATTATTACCTTCATTCTTTATTATTGTGACAC
TATTCATCTCAATTAGGGTGTTCCTGTTTAGAAAAAAAGTTAATAAAT

FIG. 1 CONT'D

ACGGGCAATTCCCTAAGGATCATCATTTATATGAAGCACCTGAGGAC
CTTTCACCATTAGAGTTAACTCAAAGCATTTATAGTATGAGCTTTAAA
AATTTTCAAGATGAGGAGAAGAAAACTCACCTTATCAGTCAAGAACA
ACTCATACAGTCAATTCTATTAGACTTGATTGATAGAAAAGTATTGA
ATTATGATGATAACTTGTTATCTCTAGCTAACTTAGATAGAGCTTCTG
ATGCAGAAATAGATTTTATAGAGTTTGCTTTTGCGGATTCTACGAGTT
TGAAGCCAGATCAACTCTTTTCTAATTACCAATTTAGTTATAAAGAAA
CACTACGTGAACTGAAAAAGCAGCACAAGGCTTCAGATCTGCAAAAT
CAAATGAGACGCCGAGGAAGTAATGCCTTATCAAGAATTACGCGTCT
CACAAGGTTGATTTCTAAAGACAATATAAACTCTCTTAGAAGAAAGG
GAATTTCATCCCCTTATCGTAAAATGTCTTCAGAAGAGTCTAAAGAA
TTATCTAGGTTAAAAAGATTCAGTTACCTATCACCTCTTATTTCTTTTG
TTGTTATAATTTATCGCTTTTTTTAAATTATTTTACCTATTTCTGTAT
CTATCTCTTATTGTTTGGTGTTATCCTGTTGTTGAATAAAATCATTTTT
ATGATGACAAGAAAAATAAGTAACGGTTATATTGTAACTGAAGATGG
AGCAAGTCGTGTCTACCAATGGACTAGTTTTAGGAACATGCTAAGGG
ATATCAAATCGTTTGATCGTTCAGAGTTAGAAAGTATCGTATTATGG
AATCGAATATTGGTTTACGCTACTTTATTCGGCTACGCTGACCGTGTT
GAGAAAGTACTCAGAGTGAACCAAATAGATATTCCAGAAAGATTTGC
AAACATTGATAGTCATCGATTTGCGATTTCAGTCAATCAATCTAGTAA
TCATTTTTCAACGATAACTGAAGATGTTAGTCACGCTTCTAATTTTAG
TGTTAATTCAGGCGGTTCTTCAGGTGGTTTCTCAGGCGGCGGAGGCG
GCGGAGGTGGCGGTGCCTTCTAA

MLKWYTNKGGRMIMKKCFLAICLALSFFMVSVQADEVDYNIPHYEGNL
TIHNDNSADFTEKVTYQFDSSYNGQYVTLGTAGKLSDNFDINNKPQVEV
SINGKVRKVSYQIEDLEDGYRLKVFNGGEAGDTVKVNVQWKLKNVLF
MHKDVGELNWIPISDWDKTLEKVDFWISTDKKVALSRLWGHLGYLKTP
PKIRQNNNRYHLTAFNVNKRLEFHGYWDRSYFNLPTNSKNNYKKKIEH
QEKIIERHGFILSFLLRILLPSFFIIVTLFISIRVFLFRKKVNKYGQFPKDHHL
YEAPEDLSPLELTQSIYSMSFKNFQDEEKKTHLISQEQLIQSILLDLIDRKV
LNYDDNLLSLANLDRASDAEIDFIEFAFADSTSLKPDQLFSNYQFSYKET
LRELKKQHKASDLQNQMRRRGSNALSRITRLTRLISKDNINSLRRKGISS
PYRKMSSEESKELSRLKRFSYLSPLISFVVIIYTLFLNYFTYFCIYLLLFGVI
LLLNKIIFMMTRKISNGYIVTEDGASRVYQWTSFRNMLRDIKSFDRSELE
SIVLWNRILVYATLFGYADRVEKVLRVNQIDIPERFANIDSHRFAISVNQS
SNHFSTITEDVSHASNFSVNSGGSSGGFSGGGGGGGGAF*

ID-69

Clone 3-38
ATGATGATTGTGAATAATGGTTATCTAGAAGGGAGAAAAATGAAAA
AGAGACAAAAAATATGGAGAGGGTTATCAGTTACTTTACTAATCCTG

FIG. 1 CONT'D

```
TCCCAAATTCCATTTGGTATATTGGTACAAGGTGAAACCCAAGATAC
CAATCAAGCACTTGGAAAAGTAATTGTTAAAAAAACGGGAGACAAT
GCTACACCATTAGGCAAAGCGACTTTTGTGTTAAAAAATGACAATGA
TAAGTCAGAAACAAGTCACGAAACGGTAGAGGGTTCTGGAGAAGCA
ACCTTTGAAAACATAAAACCTGGAGACTACACATTAAGAGAAGAAA
CAGCACCAATTGGTTATAAAAAAACTGATAAAACCTGGAAAGTTAAA
GTTGCAGATAACGGAGCAACAATAATCGAGGGTATGGATGCAGATA
AAGCAGAGAAACGAAAGAAGTTTTGAATGCCCAATATCCAAAATC
AGCTATTTATGAGGATACAAAAGAAAATTACCCATTAGTTAATGTAG
AGGGTTCCAAAGTTGGTGAACAATACAAAGCATTGAATCCAATAAAT
GGAAAAGATGGTCGAAGAGAGATTGCTGAAGGTTGGTTATCAAAAA
AAAATCCAGGGGTCAATGATCTCGATAAGAATAAATATAAAATTGAA
TTAACTGTTGAGGGTAAAACCACTGTTGAAACGAAAGAACTTAATCA
ACCACTAGATGTCGTTGTGCTATTAGATAATTCAAATAGTATGAATA
ATGAAAGAGCCAATAATTCTCAAAGAGCATTAAAAGCTGGGGAAGC
AGTTGAAAAGCTGATTGATAAAATTACATCAAATAAAGACAATAGA
GTAGCTCTTGTGACATATGCCTCAACCATTTTTGATGGTACTGAAGCG
ACCGTATCAAAGGGAGTTGCCGATCAAAATGGTAAAGCGCTGAATG
ATAGTGTATCATGGATTATCATAAAACTACTTTTACAGCAACTACA
CATAATTACAGTTATTTAAATTTAACAAATGATGCTAACGAAGTTAA
TATTCTAAAGTCAAGAATTCCAAAGGAAGCGGAGCATATAAATGGG
GATCGCACGCTCTATCAATTTGGTGCGACATTTACTCAAAAAGCTCTA
ATGAAAGCAAATGAAATTTTAGAGACACAAAGTTCTAATGCTAGAAA
AAAACTTATTTTTCACGTAACTGATGGTGTCCCTACGATGTCTTATGC
CATAAATTTTAATCCTTATATATCAACATCTTACCAAAACCAGTTTAA
TTCTTTTTTAAATAAAATACCAGATAGAAGTGGTATTCTCCAAGAGG
ATTTTATAATCAATGGTGATGATTATCAAATAGTAAAAGGAGATGGA
GAGAGTTTTAAACTGTTTCGGATAGAAAAGTTCCTGTTACTGGAGG
AACGACACAAGCAGCTTATCGAGTACCGCAAAATCAACTCTCTGTAA
TGAGTAATGAGGGATATGCAATTAATAGTGGATATATTTATCTCTATT
GGAGAGATTACAACTGGGTCTATCCATTTGATCCTAAGACAAAGAAA
GTTTCTGCAACGAAACAAATCAAAACTCATGGTGAGCCAACAACATT
ATACTTTAATGGAAATATAAGACCTAAAGGTTATGACATTTTTACTGT
TGGGATTGGTGTAAACGGAGATCCTGGTGCAACTCCTCTTGAAGCTG
AGAAATTTATGCAATCAATATCAAGTAAAACAGAAAATTATACTAAT
GTTGATGATACAAATAAATTTATGATGAGCTAAATAAATACTTTAA
AACAATTGTTGAGGAAAAACATTCTATTGTTGATGGAAATGTGACTG
ATCCTATGGGAGAGATGATTGAATTCCAATTAAAAAATGGTCAAAGT
TTTACACATGATGATTACGTTTTGGTTGGAAATGATGGCAGTCAATTA
AAAAATGGTGTGGCTCTTGGTGGACCAAACAGTGATGGGGGAATTTT
AAAAGATGTTACAGTGACTTATGATAAGACATCTCAAACCATCAAAA
TCAATCATTTGAACTTAGGAAGTGGACAAAAAGTAGTTCTTACCTAT
GATGTACGTTTAAAAGATAACTATATAAGTAACAAATTTTACAATAC
AAATAATCGTACAACGCTAAGTCCGAAGAGTGAAAAAGAACCAAAT
```

FIG. 1CONT'D

ACTATTCGTGATTTCCCAATTCCCAAAATTCGTGATGTTCGTGAGTTT
CCGGTACTAACCATCAGTAATCAGAAGAAAATGGGTGAGGTTGAATT
TATTAAAGTTAATAAAGACAAACATTCAGAATCGCTTTTGGGAGCTA
AGTTTCAACTTCAGATAGAAAAAGATTTTTCTGGGTATAAGCAATTT
GTTCCAGAGGGAAGTGATGTTACAACAAAGAATGATGGTAAAATTTA
TTTTAAAGCACTTCAAGATGGTAACTATAAATTATATGAAATTTCAA
GTCCAGATGGCTATATAGAGGTTAAAACGAAACCTGTTGTGACATTT
ACAATTCAAAATGGAGAAGTTACGAACCTGAAAGCAGATCCAAATG
CTAATAAAAATCAAATCGGGTATCTTGAAGGAAATGGTAAACATCTT
ATTACCAACACTCCCAAACGCCCACCAGGTGTTTTTCCTAAAACAGG
GGGAATTGGTACAATTGTCTATATATTAGTTGGTTCTACTTTTATGAT
ACTTACCATTTGTTCTTTCCGTCGTAAACAATTGTAA

MMIVNNGYLEGRKMKKRQKIWRGLSVTLLILSQIPFGILVQGETQDTNQ
ALGKVIVKKTGDNATPLGKATFVLKNDNDKSETSHETVEGSGEATFENI
KPGDYTLREETAPIGYKKTDKTWKVKVADNGATIIEGMDADKAEKRKE
VLNAQYPKSAIYEDTKENYPLVNVEGSKVGEQYKALNPINGKDGRREIA
EGWLSKKNPGVNDLDKNKYKIELTVEGKTTVETKELNQPLDVVVLLDN
SNSMNNERANNSQRALKAGEAVEKLIDKITSNKDNRVALVTYASTIFDG
TEATVSKGVADQNGKALNDSVSWDYHKTTFTATTHNYSYLNLTNDAN
EVNILKSRIPKEAEHINGDRTLYQFGATFTQKALMKANEILETQSSNARK
KLIFHVTDGVPTMSYAINFNPYISTSYQNQFNSFLNKIPDRSGILQEDFIIN
GDDYQIVKGDGESFKLFSDRKVPVTGGTTQAAYRVPQNQLSVMSNEGY
AINSGYTYLYWRDYNWVYPFDPKTKKVSATKQIKTHGEPTTLYFNGNIR
PKGYDIFTVGIGVNGDPGATPLEAEKFMQSISSKTENYTNVDDTNKIYDE
LNKYFKTIVEEKHSIVDGNVTDPMGEMIEFQLKNGQSFTHDDYVLVGND
GSQLKNGVALGGPNSDGGILKDVTVTYDKTSQTIKINHLNLGSGQKVVL
TYDVRLKDNYISNKFYNTNNRTTLSPKSEKEPNTIRDFPIPKIRDVREFPV
LTISNQKKMGEVEFIKVNKDKHSESLLGAKFQLQIEKDFSGYKQFVPEGS
DVTTKNDGKIYFKALQDGNYKLYEISSPDGYIEVKTKPVVTFTIQNGEVT
NLKADPNANKNQIGYLEGNGKHLITNTPKRPPGVFPKTGGIGTIVYILVG
STFMILTICSFRRKQL*

ID-70

Clone 141

ATGAATAGAAAAGTTGAGGAAAAAATGGCTGGGAATCGTAATAACG
ATATGAATGTCTATTGTTCATTTTGTGGCAAAAGCCAAGATGAAGTA
AAAAAAATTATTGCAGGTAATGGTGTTTTCATTTGTAATGAATGTGTG
GCCTTATCACAAGAAATTATTAAGGAAGAATTAGCTGAGGAAGTACT

FIG. 1CONT'D

GGCTCATTTAGCAGAAGTACCAAAACCTAAGGAACTATTAGAAATAT
TAAATCAATATGTTGTAGGGCAAGATCGTGCTAAACGTGCTTTAGCA
GTTGCTGTCTACAATCATTACAAGCGTGTTAGTTATACCGAGAGTAGT
GACGATGATGTAGATTTGCAAAAATCCAACATTTTGATGATTGGTCC
AACTGGCTCAGGAAAAACCTTCTTAGCACAAACACTGGCTAAAAGCC
TTAATGTACCGTTTGCTATTGCAGATGCGACTTCATTGACCGAAGCAG
GATACGTTGGAGAAGATGTTGAGAATATTCTTCTTAAATTGATTCAA
GCTGCTGATTATAATGTCGAACGTGCTGAGCGTGGTATTATCTACGTT
GATGAAATAGATAAAATTGCTAAGAAAGGCGAAAATGTTTCTATCAC
ACGTGATGTGTCTGGTGAAGGTGTACAGCAAGCCCTTCTTAAAATTA
TTGAGGGTACGGTAGCAAGTGTTCCCCCACAGGGTGGGCGTAAACAT
CCTAACCAAGAAATGATTCAAATTAATACCAAGAACATCCTTTTTATT
GTCGGTGGTGCTTTTGATGGTATTGAAGACCTTGTGAAGCAACGTTTA
GGCGAAAAGTTATTGGTTTTGGACAGACAAGCCGTAAAATTGATGA
CAACGCTTCTTATATGCAAGAGATAATTTCTGAGGATATTCAAAAGT
TTGGACTGATTCCAGAGTTTATTGGCCGTTTACCAGTAGTTGCAGCGT
TAGAACTTCTTACTGCAGAAGATCTGGTTCGTATTCTGACAGAACCA
CGCAATGCTTTGGTTAAACAATACCAAACCTTATTATCTTATGATGGT
GTAGAATTGGAATTTGACCAGGATGCTCTATTGGCTATCGCTGATAA
GGCTATCGAGCGCAAGACTGGTGCACGTGGTTTACGTTCTATTATTG
AAGAAACGATGCTTGATATCATGTTTGAAATTCCAAGCCAAGAAGAT
GTAACAAAAGTTCGTATCACAAAGGCTGCTGTTGAGGGTACTGACAA
GCCTGTTTTAGAGACGGCTTAG

MNRKVEEKMAGNRNNDMNVYCSFCGKSQDEVKKIIAGNGVFICNECV
ALSQEIIKEELAEEVLAHLAEVPKPKELLEILNQYVVGQDRAKRALAVA
VYNHYKRVSYTESSDDDVDLQKSNILMIGPTGSGKTFLAQTLAKSLNVP
FAIADATSLTEAGYVGEDVENILLKLIQAADYNVERAERGIYVDEIDKIA
KKGENVSITRDVSGEGVQQALLKIIEGTVASVPPQGGRKHPNQEMIQINT
KNILFIVGGAFDGIEDLVKQRLGEKVIGFGQTSRKIDDNASYMQEIISEDI
QKFGLIPEFIGRLPVVAALELLTAEDLVRILTEPRNALVKQYQTLLSYDG
VELEFDQDALLAIADKAIERKTGARGLRSIIEETMLDIMFEIPSQEDVTKV
RITKAAVEGTDKPVLETA*

ID-71

Clone 3-20

ATGAAAAGATTACATAAACTGTTTATAACCGTAATTGCTACATTAGG
TATGTTGGGGGTAATGACCTTTGGTCTTCCAACGCAGCCGCAAAACG
TAACGCCGATAGTACATGCTGATGTCAATTCATCTGTTGATACGAGC
CAGGAATTTCAAAATAATTTAAAAAATGCTATTGGTAACCTACCATT
TCAATATGTTAATGGTATTTATGAATTAAATAATAATCAGACAAATTT
AAATGCTGATGTCAATGTTAAAGCGTATGTTCAAAATACAATTGACA

```
ATCAACAAAGACTATCAACTGCTAATGCAATGCTTGATAGAACCATT
CGTCAATATCAAAATCGCAGAGATACCACTCTTCCCGATGCAAATTG
GAAACCATTAGGTTGGCATCAAGTAGCTACTAATGACCATTATGGGC
ATGCAGTCGACAAGGGGCATTTAATTGCCTATGCTTTAGCTGGAAAT
TTCAAAGGTTGGGATGCTTCCGTGTCAAATCCTCAAAATGTTGTCACA
CAAACAGCTCATTCCAACCAATCAAATCAAAAAATCAATCGTGGACA
AAATTATTATGAAAGCTTAGTTCGTAAGGCGGTTGACCAAAACAAAC
GTGTTCGTTACCGTGTAACTCCATTGTACCGTAATGATACTGATTTAG
TTCCATTTGCAATGCACCTAGAAGCTAAATCACAAGATGGCACATTA
GAATTTAATGTTGCTATTCCAAACACACAAGCATCATACACTATGGA
TTATGCAACAGGAGAAATAACACTAAATTAA

MKRLHKLFITVIATLGMLGVMTFGLPTQPQNVTPIVHADVNSSVDTSQE
FQNNLKNAIGNLPFQYVNGIYELNNNQTNLNADVNVKAYVQNTIDNQQ
RLSTANAMLDRTIRQYQNRRDTTLPDANWKPLGWHQVATNDHYGHAV
DKGHLIAYALAGNFKGWDASVSNPQNVVTQTAHSNQSNQKINRGQNY
YESLVRKAVDQNKRVRYRVTPLYRNDTDLVPFAMHLEAKSQDGTLEFN
VAIPNTQASYTMDYATGEITLN*

ID-72

Clone 13

ATGAAAAACTATCGAAAACTTATTGTACTACTACTTCTAATCTTTTTT
GCCATTTTTATGGGAGCATATGCTTACACGCATATTGTTGAAAAAAG
ATCCCTAACTAGCAATACTATTGAAAAAACTCTACCTGTGGTAAATC
AGATTAAGCCTCAAACCATTAAAGAATACCAAAATTACTTAACTAAG
GTAGCTAAACGTAATGTTCTTCCTGTAGACATTCCTCAGGCATTAAAT
AATGAAAAGGTAGAAATTACTGCTACTGATGGCATGCAAACATTCAC
TTGGAATGATAAAAATAATCCTAAGCAAAAGGTTATCTTCTATGTTC
ATGGAGGATCATATATCCATCAAGCTTCCGAATTACAATATATTTTTG
TCAATAAACTAGCTAAAAAATTAGATGCAAAAGTTGTCTTTCCTATTT
ACCCTAAAGCTCCTACATATAATTATAGTGATGCTATCCCCAAAATTA
AAAAATTATACCAAAATACATTAGCTAGCGTCACATCTCACAAACAG
ATTATCCTAGTAGGTGAAAGTGCAGGCGGAGGCCTTGCTTTAGGTAT
TGCTGATAACCTTGCACGGAGCATATCAAACAACCAAAAGAAATTAT
TTAA

MKNYRKLIVLLLLIFFAIFMGAYAYTHIVEKRSLTSNTIEKTLPVVNQIKP
QTIKEYQNYLTKVAKRNVLPVDIPQALNNEKVEITATDGMQTFTWNDK
NNPKQKVIFYVHGGSYIHQASELQYIFVNKLAKKLDAKVVFPIYPKAPT
YNYSDAIPKIKKLYQNTLASVTSHKQIILVGESAGGGLALGIADNLARSIS
NNQKKLF*
```

FIG. 1 CONT'D

ID-73

Clone 2-19

TTGATTCTAATAACTTCCTATGGGATAATATCTTTATCACAAAAATTG
AGGGAATTTATTATGAAGTTAAAACATATTGTCTTAGGATTAGCCTTA
ACAACACTTTTAGGAGTCACATTTAGTAATCAAGAAGTTTCAGCAAG
CTCAACTTCAAGTAAAGTTGTTAAAGTTGGTGTTATGACCTTTTCTGA
CACTGAAAAAGCACGTTGGGATAAAATTGAAAAGCTAGTAGGTGAT
AAAGCTAAAATCAAATTTACAGAATTTACAGATTATACACAACCAAA
TCAAGCGACAGCCAATAAGGATGTGGATATTAATGCCTTTCAACATT
ACAATTTCTTAGAAAACTGGAATAAGGAAAATAAGAAAACTTAATT
CCACTTGAAAAGACTTACTTAGCTCCAATTCGTATCTATTCTGAGAAG
GTAAAATCTCTTAAAAAATTGAAAAAAGGAGCCACTATTGCAATTCC
AAATGATGCAACAAATGGTAGCCGTGCATTGTATGTCCTTCAGTCAG
CAGGTTTAATCAAATTGAATGTTTCTGGTAAGAAGGTTGCAACAGTT
GCTAATATCACATCTAATAAAAAGGATATTAATATTCAGGAGTTAGA
TGCGAGTCAAACACCACGTGCACTCAAAGATGTAGATGCAGCTATTA
TTAATAATACATACATTGAGCAAGCTAATTTAAAACCTTCAGATGCT
ATCTTTGTTGAGAAATCAGATAAAAATTCAAAACAATGGATTAATAT
CATTGCGGGACGTAAAAATTGGAAAAAGCAAAGAACGCTAAAGCT
ATCCAAGCTATCTTGGATGCTTATCACACAGATGAAGTGAAAAAAGT
TATCAAAGATACTTCAGCTGATATTCCACAATGGTAA

MILITSYGIISLSQKLREFIMKLKHIVLGLALTTLLGVTFSNQEVSASSTSS
KVVKVGVMTFSDTEKARWDKIEKLVGDKAKIKFTEFTDYTQPNQATAN
KDVDINAFQHYNFLENWNKENKKNLIPLEKTYLAPIRIYSEKVKSLKKL
KKGATIAIPNDATNGSRALYVLQSAGLIKLNVSGKKVATVANITSNKKDI
NIQELDASQTPRALKDVDAAIINNTYIEQANLKPSDAIFVEKSDKNSKQW
INIIAGRKNWKKQKNAKAIQAILDAYHTDEVKKVIKDTSADIPQW*

ID-74

Clone 3-6

ATGTCAAATCAATATGATTATATCGTTATTGGTGGAGGTAGTGCAGG
CAGTGGTACCGCTAATAGGGCAGCCATGTATGGAGCAAAAGTCCTGT
TAATTGAAGGTGGACAAGTAGGTGGAACTTGTGTTAACTTAGGTTGT
GTACCTAAGAAAATCATGTGGTATGGTGCACAAGTTTCTGAGACACT
CCATAAGTATAGTTCAGGTTATGGTTTTGAAGCCAATAATCTTAGTTT
TGATTTTACTACTCTAAAAGCTAATCGCGATGCTTACGTGCAGCGGTC
TAGACAGTCGTATGCCGCTAATTTTGAGCGTAATGGGGTCGAAAAGA

```
TTGATGGATTTGCTCGTTTTATTGATAACCATACTATTGAAGTGAATG
GTCAGCAATATAAAGCTCCTCACATTACTATTGCAACAGGTGGACAC
CCTCTTTACCCTGATATTATTGGAAGTGAACTTGGTGAGACTTCTGAT
GATTTTTTTGGATGGGAGACCTTACCAAATTCTATATTGATTGTTGGG
GCGGGCTATATCGCGGCAGAACTTGCTGGAGTGGTTAATGAATTAGG
CGTTGAAACCCATCTTGCATTTAGAAAAGACCATATTCTACGCGGAT
TTGATGACATGGTAACAAGTGAGGTTATGGCTGAAATGGAGAAATCA
GGTATCTCTTTACATGCTAACCATGTACCTAAATCTCTTAAACGCGAT
GAAGGTGGCAAGTTGATTTTTGAAGCTGAAAATGGGAAAACGCTTGT
CGTTGATCGTGTAATATGGGCTATCGGCCGTGGACCAAATGTAGACA
TGGGACTTGAAAATACCGATATTGTTTTAAATGATAAAGATTATATC
AAAACAGATGAATTTGAGAATACTTCTGTAGATGGCGTGTATGCTAT
TGGAGATGTTAATGGGAAAATTGCCTTGACACCGGTAGCAATTGCAG
CAGGTCGTCGCTTATCAGAAAGACTTTTTAATCATAAAGATAACGAA
AAATTAGATTACCATAATGTACCTTCAGTTATTTTTACTCACCCTGTA
ATTGGGACGGTAGGACTTTCAGAAGCAGCAGCTATCGAGCAATTTGG
AAAAGATAATATCAAAGTCTATACATCAACTTTTACCTCTATGTATAC
GGCTGTTACCAGTAATCGCCAAGCAGTTAAGATGAAGCTCATAACCC
TAGGAAAAGAGGAAAAAGTTATTGGGCTTCATGGTGTTGGTTATGGT
ATTGATGAAATGATTCAAGGTTTTTCAGTTGCTATCAAAATGGGGGC
TACTAAAGCAGACTTTGATGATACTGTTGCTATTCACCCAACTGGATC
TGAGGAATTTGTTACAATGCGCTAA
```

MSNQYDYIVIGGGSAGSGTANRAAMYGAKVLLIEGGQVGGTCVNLGC
VPKKIMWYGAQVSETLHKYSSGYGFEANNLSFDFTTLKANRDAYVQRS
RQSYAANFERNGVEKIDGFARFIDNHTIEVNGQQYKAPHITIATGGHPLY
PDIIGSELGETSDDFFGWETLPNSILIVGAGYIAAELAGVVNELGVETHLA
FRKDHILRGFDDMVTSEVMAEMEKSGISLHANHVPKSLKRDEGGKLIFE
AENGKTLVVDRVIWAIGRGPNVDMGLENTDIVLNDKDYIKTDEFENTSV
DGVYAIGDVNGKIALTPVAIAAGRRLSERLFNHKDNEKLDYHNVPSVIF
THPVIGTVGLSEAAAIEQFGKDNIKVYTSTFTSMYTAVTSNRQAVKMKLI
TLGKEEKVIGLHGVGYGIDEMIQGFSVAIKMGATKADFDDTVAIHPTGS
EEFVTMR*

ID-75

Clone 3-51

```
ATGAGTATCAAAAAAGTGTGATTGGTTTTTGCCTCGAAGCTGCAGC
ATTATCAATGTTTGCTTGTAGACAGTAGTCAATCTGTTATGGCTGC
```

```
CGAGAAGGATAAAGTCGAAATTACGTGGTGGGCTTTTCCAACCTTTA
CTCAAGAAAAGGCTAAGGATGGAGTAGGTACTTATGAGAAAAAGT
CATCAAGGCTTTTGAAAAGAAAAATCCTAATATAAAAGTAAAACTAG
AGACAATTGATTTCACATCTGGACCTGAAAAAATCACTACAGCAATT
GAAGCAGGGACAGCACCTGATGTGCTTTTTGATGCACCAGGGCGAAT
TATTCAATATGGTAAAAATGGTAAATTAGCAGATTTGAATGATTTATT
TACAGACCAATTTATTAAGGATGTCAATAATAAGAACATCATTCAAG
CTTCTAAGTCTGGCGATAAAGCCTACATGTATCCAATAAGTTCTGCCC
CATTTTATATGGCGTTCAATAAAAAAATGCTTAAAGATGCAGGAGTT
TTGAAACTTGTAAAAGAAGGTTGGACTACTAGTGATTTTGAAAAAGT
ACTAAAAGCACTAAAAAATAAAGGCTATACACCAGGTTCATTCTTTG
CAAACGGGCAAGGAGGAGATCAAGGACCACGTGCATTTTTTGCTAAT
CTTTATAGTGCTCCAATAACAGATAAGAAGTAACAAAATATACCAC
TGACACTAAAAATTCTGTAAAATCAATGAAAAAAATAGTTGAATGGA
TTAAGAAAGGCTACTTGATGAATGGGTCTCAGTATGATGGCTCAGCT
GACATTCAAAACTTCGCCAATGGACAAACTGCTTTCACTATCCTATG
GGCTCCAGCTCAACCAAAAACTCAAGCAAAATTATTAGAGTCAAGTA
AAGTGGATTACCTTGAAGTGCCATTCCCATCAGAAGATGGAAAACCA
GATTTAGAATACCTTGTTAATGGTTTTGCGGTCTTTAATAATAAAGAT
GAAAACAAAGTAAAAGCCTCTAAGAAATTTATCACTTTTATTGCTGA
TGATAAAAAATGGGGACCAAAAGATGTTATACGTACAGGTGCTTTCC
CAGTTAGAACATCATTTGGGGATCTTTATAAAGGTGATAAACGTATG
ATGAAGATTTCAAAATGGACTCAATATTATTCACCATATTACAACAC
TATCGATGGATTTTCTGAAATGAGAACCTTATGGTTCCCAATGGTTCA
ATCTGTATCCAATGGTGATGAAAAACCAGCAGATGCTTTGAAAGACT
TTACTCAAAAAGCAAATGATACCATTAAAAAAGCAGCTAAATAA
```

MSIKKSVIGFCLEAAALSMFACVDSSQSVMAAEKDKVEITWWAFPTFTQ
EKAKDGVGTYEKKVIKAFEKKNPNIKVKLETIDFTSGPEKITTAIEAGTAP
DVLFDAPGRIIQYGKNGKLADLNDLFTDQFIKDVNNKNIIQASKSGDKA
YMYPISSAPFYMAFNKKMLKDAGVLKLVKEGWTTSDFEKVLKALKNK
GYTPGSFFANGQGGDQGPRAFFANLYSAPITDKEVTKYTTDTKNSVKSM
KKIVEWIKKGYLMNGSQYDGSADIQNFANGQTAFTILWAPAQPKTQAK
LLESSKVDYLEVPFPSEDGKPDLEYLVNGFAVFNNKDENKVKASKKFIT
FIADDKKWGPKDVIRTGAFPVRTSFGDLYKGDKRMMKISKWTQYYSPY
YNTIDGFSEMRTLWFPMVQSVSNGDEKPADALKDFTQKANDTIKKAAK
*

ID-76 (Same as ID-39)

Clone 3-56
```
ATGAGGAAACGTTTTTCCTTGCTAAATTTTATTGTTGTTACTTTTATTT
TCTTTTTCTTTATTCTTTTTCCGCTTTTTAAGGCCAAAGATTGTCAGGT
```

```
TGTTTATGCAAGTTTTCAAGGAGATCATTGGGACATTTGTAACGCATT
TGATTTTCCGTATTTACATCGCTTTGATCTCATTAAAGGTAAAGAAAA
TCAACTTTACTTTATAGGTTGTACAATTGCTAACAGTAAAGCCTACAC
TGAGGATTGGAGTGATAAAGGCCGAATTTTTGTTGCTCGTTTTAATAC
TCAAAACCATACATTGGAAGGATTGCAACAATTGCCTCAAACTTTAT
TAAAAAATCATGGATACTATGCCATTCAGGATGAAGGATATTCATTG
ATTACTTCAGTAGAAGGGGTACTCAAACTCACTTATCCAGAATTTTCT
ACTACAGGCGACTGGCAATTAGAACGGCTTTTCGATGAGGAGACAAG
CGATGTGGTGAAAGTGGATATTAATCAGGATGGTAAGGATGAGTATG
TGATCATCCAAGGTTTTCATGGAGATCGTTTACGTATCTTCACTGAAG
ATTTCGGTCGAGAATTATTCCATTATCCTGAAAAAACCCCATTTGGTC
ACGCTATTTGGAGTGGTCGTTTACTTAATCAGACTTGTTTCGTATTCG
GGTGGCGATCAGAAAAAGCAGAATTAAGGCTTTTTCACTTTGTAGAT
GGGCACTTGGTTTCAGAATTAGTAGATGCAAAAGCAGCTTCTAGTAA
TGTCTTAGCTTTTGAAAAAGATGGAAAAGCTTATCTTTCTCAGCCAA
TAACGGACGTGGCGAAGTTGCTCTTTATCAATTAGTAAAATAA
```

MRKRFSLLNFIVVTFIFFFFILFPLFKAKDCQVVYASFQGDHWDICNAFDF
PYLHRFDLIKGKENQLYFIGCTIANSKAYTEDWSDKGRIFVARFNTQNHT
LEGLQQLPQTLLKNHGYYAIQDEGYSLITSVEGVLKLTYPEFSTTGDWQ
LERLFDEETSDVVKVDINQDGKDEYVIIQGFHGDRLRIFTEDFGRELFHY
PEKTPFGHAIWSGRLLNQTCFVFGWRSEKAELRLFHFVDGHLVSELVDA
KAASSNVLAFEKDGKAYLFSANNGRGEVALYQLVK*

FIG. 1 CONT'D nucS1
    Bgl II  Eco RV
5'-cgagatctgatatctcacaaacagataacggcgtaaatag -3' nucS2
    Bgl II     Sma I
5'-gaagatcttccccgggatcacaaacagataacggcgtaaatag -3' nucS3
    Bgl II  Eco RV
5'-cgagatctgatatccatcacaaacagataacggcgtaaatag -3' nucR
    Bam HI
5'-cgggatccttatggacctgaatcagcgttgtc -3'

NucSeq
5'-ggatgctttgtttcaggtgtatc -3' pTREP$_F$
5'-catgatatcggtacctcaagctcatatcattgtccggcaatggtgtgggcttttttgttttagcggataa
caatttcacac -3' pTREP$_R$
5'-gcggatccccgggcttaattaatgttttaaacactagtcgaagatctcgcgaattctcctgtgtgaaatt
gttatccgcta -3' pUC$_F$
5'-cgccagggttttcccagtcacgac -3'

V$_R$
5'-tcaggggggcggagcctatg -3'

V$_1$
5'-tcgtatgttgtgtggaattgtg -3'

V$_2$
5'-tccggctcgtatgttgtgtggaattg -3'

FIG. 2 pTREP-Nuc vectors allow cloning of genomic DNA into each frame with respect to the nuclease gene (i)
```
pTREP1-nuc1 (EcoRV)   AAGTATCAGATCT--GATATC--TCACAAACAGATAACGGCGTAAAT  Frame=+1
                      ::::::::::::::        ::::::::::::::::::::::::::
                                    ▲
                      :::::::::::::         ::::::::::::::::::::::::::
pTREP1-nuc2 (Sma 1)   AAGTATCAGATCTTCCCCGGGA-TCACAAACAGATAACGGCGTAAAT  Frame=+2
                      :::::::::::::         ::::::::::::::::::::::::::
                                    ▲
                      :::::::::::::         ::::::::::::::::::::::::::
pTREP1-nuc3 (EcoRV)   AAGTATCAGATCT--GATATCCATCACAAACAGATAACGGCGTAAAT  Frame=+3
                                    ▲
                                          ::::::::::::::::::::::::::
Nuclease Gene                             TCACAAACAGATAACGGCGTAAAT Cloning site is indicated bt an arrow
```

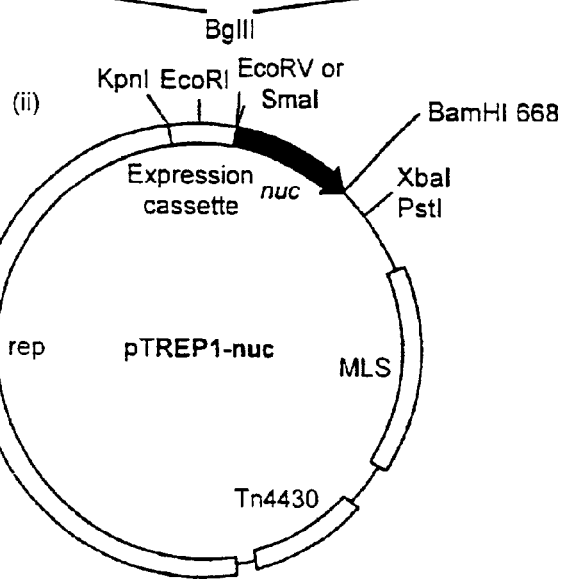

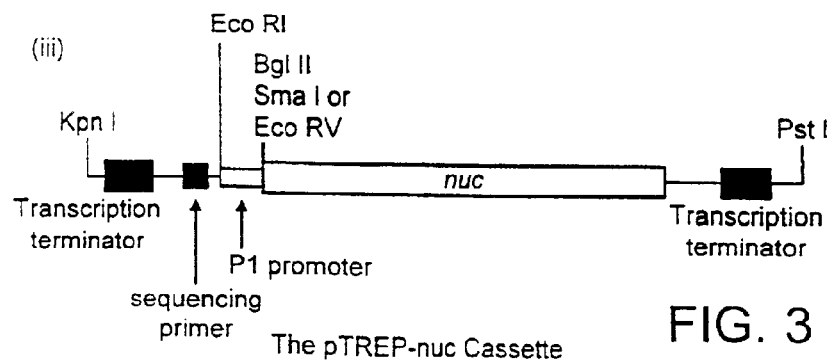

The pTREP-nuc Cassette

FIG. 3

NUCLEIC ACIDS AND PROTEINS FROM GROUP B STREPTOCOCCUS

This application is a continuation of PCT/GB99/02444, filed Jul. 27, 1999, which claims priority to provisional application 60/125,163, filed Mar. 19, 1999, and GB 9816335.5, filed Jul. 27, 1998.

The present invention relates to proteins derived from *Streptococcus agalactiae*, nucleic acid molecules encoding such proteins, and the use of the proteins as antigens and/or immunogens and in detection/diagnosis. It also relates to a method for the rapid screening of bacterial genomes to isolate and characterise bacterial cell envelope associated or secreted proteins.

The Group B *Streptococcus* (GBS) (*Streptococcus agalactiae*) is an encapsulated bacterium which emerged in the 1970s as a major pathogen of humans causing sepsis and meningitis in neonates as well as adults. The incidence of early onset neonatal infection during the first 5 days of life varies from 0.7 to 3.7 per 1000 live births and causes mortality in about 20% of cases. Between 25–50% of neonates surviving early onset infections frequently suffer neurological sequalae. Late onset neonatal infections occur from 6 days to three months of age at a rate of about 0.5–1.0 per 1000 live births.

There is an established association between the colonisation of the maternal genetic tract by GBS at the time of birth and the risk of neonatal sepsis. In humans it has been established that the rectum may act as a reservoir for GBS. Susceptibility in the neonate is correlated with the a low concentration or absence of IgG antibodies to the capsular polysaccharides found on GBS causing human disease. In the USA strains isolated from clinical cases usually belong to capsular serotypes Ia, Ib, II, III although serotype V may be of increasing significance. Type VIII GBS is the major cause of neonatal sepsis in Japan.

A possible means of prevention involves intra or postpartum administration of antibiotics to the mother but there are concerns that this might lead to the emergence of resistant organisms and in some cases allergic reactions. Vaccination of the adolescent females to induce long lasting maternally derived immunity is one of the most promising approaches to prevent GBS infections in neonates. The capsular polysaccharide antigens of these organisms have attracted most attention as with regard to vaccine development. Studies in healthy adult volunteers have shown that serotype Ia, II and III polysaccharides are non-toxic and immunogenic in approximately 65%, 95% and 70% of non-immune adults respectively. One of the problems with using capsule antigens as vaccines is that the response rates vary according to pre-immunisation status and the polysaccharide antigen and not all vaccinees produce adequate levels of IgG antibody as indicated in vaccination studies with GBS polysaccharides in human volunteers.

Some people do not respond despite repeated stimuli. These properties are due to the T-independent nature of polysaccharide antigens. One strategy to enhance the immunogenicity of these vaccines is to enhance the T cell dependent properties of polysaccharides by conjugating them to a protein. The use of polysaccharide conjugates looks promising but there are still unresolved questions concerning the nature of the carrier protein. A conjugate vaccine against GBS would require at least 4 different conjugates to be prepared adding to the cost of a vaccine.

Recent evidence also suggests that bacterial surface proteins may be useful to confer immunity. A protein called Rib which is found on most serotype III strains but rarely on serotypes Ia, Ib or II confers immunity to challenge with Rib expressing GBS in animal models (Stalhammar-Carlemalm et al., *Journal of Experimental Medicine* 177:1593–1603 (1993)). Another surface protein of interest as a component of a vaccine is the alpha antigen of the C proteins which protected vaccinated mice against lethal infection with strains expressing alpha protein. The amount of antigen expressed by GBS strains varies markedly.

Approaches to vaccination against GBS infections which rely on the use of capsular polysaccharides have the disadvantage that response rates are likely to vary considerably according to pre-immunisation status and the particular type of polysaccharide antigen used. Results of trials in human volunteers have indicated that response rates may only be around 65% for some of the key capsule antigens (Larsson et al., *Infection and Immunity* 64:3518–3523 (1996)). It is also not clear whether all individuals responding to the vaccine would have adequate levels of polysaccharide specific IgG which can cross the placenta and afford immunity to neonates. By conjugating a protein carrier to the polysaccharide antigen it may be possible to convert them to T-cell dependent antigens and enhance their immunogenicity.

Preliminary studies with GBS type III polysaccharide-tetanus toxoid conjugate have been encouraging (Baker et al., *Reviews of Infectious Diseases* 7:458–467 (1985), Baker et al., *The New England Journal of Medicine* 319:1180–1185 (1988), Paoletti et al., *Infection and Immunity* 64:677–679 (1996), Paoletti et al., *Infection and Immunity* 62:3236–3243 (1994)) but in developed countries the use of tetanus may be disadvantageous since most adults will have been immunised against tetanus within the past five years. Additional boosters with tetanus toxoid may cause adverse reactions (Boyer., *Current Opinions in Pediatrics* 7:13–18 (1995)). The polysaccharide conjugate vaccines have the disadvantage of being costly to produce and manufacture in comparison with many other kinds of vaccines. There is also the possible risk of problems caused by the cross reactivity between GBS polysaccharides and sialic acid-containing human glycoproteins.

An alternative to polysaccharides as antigens is the use of protein antigens derived from GBS. Recent evidence suggest that the GBS surface associated proteins Rib and alpha C protein may be used to confer immunity to GBS infections in experimental model systems (Stalhammar-Carlemalm et al., (1993) [supra], Larsson et al., (1996) [supra]). However these two proteins are not conserved in all serotypes of GBS which cause disease in humans. Assuming that these antigens would be immunogenic and elicit protective level responses in humans they would not confer protection against all infections as 10% of infectious Group B *streptococci* do not express Rib or C protein alpha.

This invention seeks to overcome the problem of vaccination against GBS by using a novel screening method specifically designed to identify those Group B *Streptococcus* genes encoding bacterial cell surface associated or secreted proteins (antigens). The proteins expressed by these genes may be immunogenic, and therefore may be useful in the prevention and treatment of Group B *Streptococcus* infection. For the purposes of this application, the term immunogenic means that these proteins will elicit a protective immune response within a subject. Using this novel screening method a number of genes encoding novel Group B *Streptococcus* proteins have been identified.

Thus in a first aspect, the present invention provides a Group B *Streptococcus* protein, having a sequence selected from those shown in FIG. 1, or fragments or derivatives thereof.

It will be apparent to the skilled person that proteins and polypeptides included within this group may be cell surface receptors, adhesion molecules, transport proteins, membrane structural proteins, and/or signalling molecules.

Alterations in the amino acid sequence of a protein can occur which do not affect the function of a protein. These include amino acid deletions, insertions and substitutions and can result from alternative splicing and/or the presence of multiple translation start sites and stop sites. Polymorphisms may arise as a result of the infidelity of the translation process. Thus changes in amino acid sequence may be tolerated which do not affect the proteins function.

Thus, the present invention includes derivatives or variants of the proteins, polypeptides, and peptides of the present invention which show at least 50% identity to the proteins, polypeptides and peptides described herein. Preferably the degree of sequence identity is at least 60% and preferably it is above 75%. More preferably still is it above 80%, 90% or even 95%.

The term identity can be used to describe the similarity between two polypeptide sequences. A software package well known in the art for carrying out this procedure is the CLUSTAL program. It compares the amino acid sequences of two polypeptides and finds the optimal alignment by inserting spaces in either sequence as appropriate. The amino acid identity or similarity (identity plus conservation of amino acid type) for an optimal alignment can also be calculated using a software package such as BLASTx. This program aligns the largest stretch of similar sequence and assigns a value to the fit. For any one pattern comparison several regions of similarity may be found, each having a different score. One skilled in the art will appreciate that two polypeptides of different lengths may be compared over the entire length of the longer fragment. Alternatively small regions may be compared. Normally sequences of the same length are compared for a useful comparison to be made.

Manipulation of the DNA encoding the protein is a particularly powerful technique for both modifying proteins and for generating large quantities of protein for purification purposes. This may involve the use of PCR techniques to amplify a desired nucleic acid sequence. Thus the sequence data provided herein can be used to design primers for use in PCR so that a desired sequence can be targeted and then amplified to a high degree.

Typically primers will be at least five nucleotides long and will generally be at least ten nucleotides long (e.g. fifteen to twenty-five nucleotides long). In some cases primers of at least thirty or at least thirty-five nucleotides in length may be used.

As a further alternative chemical synthesis may be used. This may be automated. Relatively short sequences may be chemically synthesised and ligated together to provide a longer sequence.

Thus in a further aspect, the present invention provides, a nucleic acid molecule comprising or consisting of a sequence which is:

(i) any of the DNA sequences set out in FIG. 1 herein or their RNA equivalents;

(ii) a sequence which is complementary to any of the sequences of (i);

(iii) a sequence which codes for the same protein or polypeptide, as those sequences of (i) or (ii);

(iv) a sequence which is shows substantial identity with any of those of (i), (ii) and (iii); or (v) a sequence which codes for a derivative or fragment of a nucleic acid molecule shown in FIG. 1.

The term identity can also be used to describe the similarity between two individual DNA sequences. The 'bestfit' program (Smith and Waterman, Advances in applied Mathematics, 482–489 (1981)) is one example of a type of computer software used to find the best segment of similarity between two nucleic acid sequences, whilst the GAP program enables sequences to be aligned along their whole length and finds the optimal alignment by inserting spaces in either sequence as appropriate.

The term 'RNA equivalent' when used above indicates that a given RNA molecule has a sequence which is complementary to that of a given DNA molecule, allowing for the fact that in RNA 'U' replaces 'T' in the genetic code. The nucleic acid molecule may be in isolated or recombinant form.

The nucleic acid molecule may be in an isolated or recombinant form. DNA constructs can readily be generated using methods well known in the art. These techniques are disclosed, for example in J. Sambrook et al, *Molecular Cloning 2$^{nd}$ Edition*; Cold Spring Harbour Laboratory Press (1989). Modifications of DNA constructs and the proteins expressed such as the addition of promoters, enhancers, signal sequences, leader sequences, translation start and stop signals and DNA stability controlling regions, or the addition of fusion partners may then be facilitated.

Normally the DNA construct will be inserted into a vector which may be of phage or plasmid origin. Expression of the protein is achieved by the transformation or transfection of the vector into a host cell which may be of eukaryotic or prokaryotic origin. Such vectors and suitable host cells form yet further aspects of the present invention.

The Group B *Streptococcus* proteins (antigens) described herein can additionally be used to raise antibodies, or to generate affibodies. These can be used to detect Group B *Streptococcus*.

Thus in a further aspect the present invention provides, an antibody, affibody, or a derivative thereof which binds to any one or more of the proteins, polypeptides, peptides, fragments or derivatives thereof, as described herein.

Antibodies within the scope of the present invention may be monoclonal or polyclonal. Polyclonal antibodies can be raised by stimulating their production in a suitable animal host (e.g. a mouse, rat, guinea pig, rabbit, sheep, goat or monkey) when a protein as described herein, or a homologue, derivative or fragment thereof, is injected into the animal. If desired, an adjuvant may be administered together with the protein. Well-known adjuvants include Freund's adjuvant (complete and incomplete) and aluminium hydroxide. The antibodies can then be purified by virtue of their binding to a protein as described herein.

Monoclonal antibodies can be produced from hybridomas. These can be formed by fusing myeloma cells and spleen cells which produce the desired antibody in order to form an immortal cell line. Thus the well-known Kohler & Milstein technique (*Nature* 256 (1975)) or subsequent variations upon this technique can be used.

Techniques for producing monoclonal and polyclonal antibodies that bind to a particular polypeptide/protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to proteins etc as described herein. Thus the present invention includes antibody fragments and synthetic constructs. Examples of antibody fragments and synthetic constructs are given by Dougall et al in *Tibtech* 12 372–379 (September 1994).

Antibody fragments include, for example, Fab, F(ab')$_2$ and Fv fragments. Fab fragments (These are discussed in Roitt et al [supra]). Fv fragments can be modified to produce a synthetic construct known as a single chain Fv (scFv) molecule. This includes a peptide linker covalently joining $V_h$ and $V_l$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions. Ways of producing chimaeric antibodies are discussed for example by Morrison et al in *PNAS*, 81, 6851–6855 (1984) and by Takeda et al in *Nature*, 314, 452–454 (1985).

Synthetic constructs also include molecules comprising an additional moiety that provides the molecule with some desirable property in addition to antigen binding. For example the moiety may be a label (e.g. a fluorescent or radioactive label). Alternatively, it may be a pharmaceutically active agent.

Affibodies are proteins which are found to bind to target proteins with a low dissociation constant. They are selected from phage display libraries expressing a segment of the target protein of interest (Nord K, Gunneriusson E, Rigdahl J, Stahl S, Uhlen M, Nygren P A, Department of Biochemistry and Biotechnology, Royal Institute of Technology (KTH), Stockholm, Sweden).

In a further aspect the invention provides an immunogenic composition comprising one or more proteins, polypeptides, peptides, fragments or derivatives thereof, or nucleotide sequences described herein. A composition of this sort may be useful in the treatment or prevention of Group B *Streptococcus* infection in subject. In a preferred aspect of the invention the immunogenic composition is a vaccine.

In other aspects the invention provides:

i) Use of an immunogenic composition as described herein in the preparation of a medicament for the treatment or prophylaxis of Group B *Streptococcus* infection. Preferably the medicament is a vaccine.
ii) A method of detection of Group B *Streptococcus* which comprises the step of bringing into contact a sample to be tested with at least one antibody, affibody, or a derivative thereof, as described herein.
iii) A method of detection of Group B *Streptococcus* which comprises the step of bringing into contact a sample to be tested with at least one protein, polypeptide, peptide, fragments or derivatives as described herein.
iv) A method of detection of Group B *Streptococcus* which comprises the step of bringing into contact a sample to be tested with at least one nucleic acid molecule as described herein.
v) A kit for the detection of Group B *Streptococcus* comprising at least one antibody, affibody, or derivatives thereof, described herein.
vi) A kit for the detection of Group B *Streptococcus* comprising at least one Group B *Streptococcus* protein, polypeptide, peptide, fragment or derivative thereof, as described herein.
vii) A kit for the detection of Group B *Streptococcus* comprising at least one nucleic acid of the invention.

As described previously, the novel proteins described herein are identified and isolated using a novel screening method which specifically identifies those Group B *Streptococcus* genes encoding bacterial cell envelope associated or secreted proteins.

The information necessary for the secretion/export of proteins has been extensively studied in bacteria. In the majority of cases, export requires a signal pep tide positioned at the N-terminus of the precursor protein to target the precursor to translocation sites on the membrane. During or after translocation, the signal peptide is removed by a signal peptidase. The ultimate destination/localisation of the protein, (whether it be secreted extracellularly or anchored to the bacterium's surface, etc) is determined by sequences other than the leader peptide sequence.

Recently, Poquet et al. (*J. Bacteriol.* 180:1904–1912 (1998)) have described a screening vector incorporating the nuc gene lacking its own signal leader as a reporter to identify exported proteins in Gram positive bacteria, and have applied it to *L. lactis*. Staphylococcal nuclease is a naturally secreted heat-stable, monomeric enzyme which has been efficiently expressed and secreted in a range of Gram positive bacteria (Shortle., *Gene* 22:181–189 (1983), Kovacevic et al., *J. Bacteriol.* 162:521–528 (1985), Miller et al., *J. Bacteriol.* 169:3508–3514 (1987), Liebl et al., *J. Bacteriol.* 174:1854–1861(1992), Le Loir et al., *J Bacteriol.* 176:5135–5139 (1994), Poquet et al., 1998 [supra]). The screening vector (pFUN) contains the pAMβ1 replicon which functions in a broad host range of Gram-positive bacteria in addition to the ColE1replicon that promotes replication in *Escherichia coli* and certain other Gram negative bacteria Unique cloning sites present in the vector can be used to generate transcriptional and translational fusions between cloned genomic DNA fragments and the open reading frame of the truncated nuc gene devoid of its own signal secretion leader. The nuc gene makes an ideal reporter gene because the secretion of nuclease can readily be detected using a simple and sensitive plate test: Recombinant colonies secreting the nuclease develop a pink halo whereas control colonies remain white (Shortle, 1983 [supra], Le Loir et al., 1994 [supra]).

A direct screen to identify and isolate DNA encoding bacterial cell envelope associated or secreted proteins (antigens).in pathogenic bacteria has been developed by the present inventors which utilises a vector-system (PTREP1 expression vector) in *Lactococcus lactis* that specifically detects DNA sequences which are adjacent to, and associated with DNA encoding surface proteins from Group B *Streptococcus*. The screening vector also incorporates the nuc gene encoding the Staphylococcal nuclease as a reporter gene.

Only the part of the nuc gene encoding the mature nuclease protein (minus its signal peptide sequence) is cloned into the pTREP1 expression vector in *L. lactis*. In this form, the nuc-encoded nuclease cannot be secreted even when expressed intracellularly. The reporter vector is then randomly combined with appropriately digested genomic DNA from Group B *Streptococcus,* cloned into *L. lactis* and used as a screening system for sequences permitting the export of nuclease. In this way gene/partial gene sequences encoding exported proteins from Group B *Streptococcus* are isolated. Once a partial gene sequence is obtained, full length sequences encoding exported proteins can readily be obtained using techniques well known in the art.

In possessing a promoter, the pTREP1-nuc vectors differ from the pFIN vector described by Poquet et al. (1998) [supra], which was used to identify *L. lactis* exported proteins by screening directly for Nuc activity directly in *L. lactis*. As the pFUN vector does not contain a promoter upstream of the nuc open reading frame the cloned genomic DNA fragment must also provide the signals for transcription in addition to those elements required for translation initiation and secretion of Nuc. This limitation may prevent the isolation of genes that are distant from a promoter for example genes which are within polycistronic operons. Additionally there can be no guarantee that promoters derived from other species of bacteria will be recognised and functional in *L. lactis*. Certain promoters may be under stringent regulation in the natural host but not in *L. lactis*. In contrast, the presence of the P1 promoter in the pTREP1-nuc series of vectors ensures that promoterless DNA fragments (or DNA fragments containing promoter sequences not active in *L. lactis*) may still be transcribed. Thus yet another advantage of this invention is that genes missed in other screening methods may be identified.

Hence in a further aspect the present invention provides a method of screening for DNA encoding bacterial cell wall associated or surface antigens in gram positive bacteria comprising the steps of:

combining a reporter vector including the nucleotide sequence encoding the mature from of the staphylcoccus nuclease gene and an upstream promoter region with DNA from a gram positive bacteria.

transforming the resultant vector into *Lactococcus lactis* cells.

assaying for the secretion of *staphlycoccus* nuclease protein in the transformed cells.

Preferably, the reporter vector is one of the pTREP1-nuc vectors shown in FIG. 4.

In another aspect, the present invention provides a vector as shown in FIG. 4 for use in screening for DNA encoding exported or surface antigens in gram positive bacteria. Examples of gram positive bacteria which may be screened include Group B *Streptococcus, Streptococcus pneumoniae, Staphylcoccus aureus* or pathogenic Group A *Streptococci*.

Given that the inventors have identified a group of important proteins, such proteins are potential targets for antimicrobial therapy. It is necessary, however, to determine whether each individual protein is essential for the organism's viability. Thus, the present invention also provides a method of determining whether a protein or polypeptide as described herein represents a potential anti-microbial target which comprises inactivating said protein and determining whether Group B *Streptococcus* is still viable.

A suitable method for inactivating the protein is to effect selected gene knockouts, ie prevent expression of the protein and determine whether this results in a lethal change. Suitable methods for carrying out such gene knockouts are described in Li et al, *P.N.A.S.*, 94:13251–13256 (1997) and Kolkman et al.

In a final aspect the present invention provides the use of an agent capable of antagonising, inhibiting or otherwise interfering with the function or expression of a protein or polypeptide of the invention in the manufacture of a medicament for use in the treatment or prophylaxis of Group B *Streptococcus* infection.

The invention will now be described by means of the following example which should not in any way be construed as limiting. The examples refer to the figures in which FIG. 1: shows a number of full length nucleotide sequences encoding Group B *Streptococcus* proteins and the corresponding amino acid sequences.

FIG. 2: Shows a number of oligonucleotide primers used in the screening process nucS1 primer designed to amplify a mature form of the nuc A gene nucS2-primer designed to amplify a mature form of the nuc A gene.

nucS3 primer designed to amplify a mature form of the nuc A gene nucR primer designed to amplify a mature form of the nuc A gene nucseq primer designed to sequence DNA cloned into the pTREP-Nuc vector pTREPF nucleic acid sequence containing recognition site for ECORV. Used for cloning fragments into pTREX7.

pTREPR nucleic acid sequence containing recognition site for BAMH1. Used for cloning fragments into pTREX7.

PUCF forward sequencing primer, enables direct sequencing of cloned DNA fragments.

VR example of gene specific primer used to obtain further antigen DNA sequence by the method of DNA walking.

$V_1$ example of gene specific primer used to obtain further antigen DNA sequence by the method of DNA walking.

$V_2$ example of gene specific primer used to obtain further antigen DNA sequence by the method of DNA walking.

FIGS. 3(i)–(iii): Schematic presentation of the nucleotide sequence of the unique gene cloning site immediately upstream of the mature nuc gene in pTREP1-nuc1, pTREP1-nuc2 and pTREP1-nuc3. Each of the pTREP-nuc vectors contain an EcoRV (a SmaI site in pTREP1-nuc2) cleavage site which allows cloning of genomic DNA fragments in 3 different frames with respect to the mature nuc gene.

(ii) A physical and genetic summary map of the pTREP1-nuc vectors. The expression cassette incorporating nuc, the macrolides, lincosamides and streptogramin B (MLS) resistance determinant, and the replicon (rep) Ori-pAMβ1 are depicted (not drawn to scale).

(iii) Schematic presentation of the expression cassette showing the various sequence elements involved in gene expression and location of unique restriction endonuclease sites (not drawn to scale).

FIGS. 4a to 4e: Shows the results of various DNA vaccine trials;

FIGS. 5a to 5e: Shows the results of a second group of DNA vaccine trials;

FIGS. 6–11: Show various Southern Blot analyses of different Group B *streptococcus* strains.

EXAMPLE 1

Thus far more than 100 gene/partial gene sequences putatively encoding exported proteins in *S. agalactiae* have been identified using the nuclease screening system of the invention. These have been further analysed to remove artifacts. The nucleotide sequences of genes identified using the screening system has been characterised using a number of parameters described below. All of these sequences are novel in that they have not been described previously.

1. All putative surface proteins are analysed for leader/signal peptide sequences. Bacterial signal peptide sequences share a common design. They are characterised by a short positively charged N-terminus (N region) immediately preceding a stretch of hydrophobic residues (central portion-h region) followed by a more polar C-terminal portion which contains the cleavage site (c-region). Computer software is used to perform hydropathy profiling of putative proteins (Marcks, *Nuc. Acid Res.*, 16:1829–1836 (1988)) which is used to identify the distinctive hydrophobic portion (h-region) typical of leader peptide sequences. In addition, the presence/absence of a potential ribosomal binding site (Shine-Dalgarno sequence required for translation) is also noted.

2. All putative surface protein sequences are used to search the OWL sequence database which includes a translation of the GENBANK and SWISSPROT database. This allows identification of similar sequences which may have been previously characterised not only at the sequence level but at a functional level. It may also provide information indicating that these proteins are indeed surface related and not artifacts.

3. Putative *S. agalactiae* surface proteins are also be assessed for their novelty. Some of the identified proteins may or may not possess a typical leader peptide sequence and may not show homology with any DNA/protein sequences in the database. Indeed these proteins may indicate the primary advantage of our screening method, i.e. isolating a typical surface-related proteins, which would have been missed in all previously described screening protocols.

The construction of three reporter vectors and their use in *L. lactis* to identify and isolate genomic DNA fragments from pathogenic bacteria encoding secreted or surface associated proteins is now described.

Construction of the pTREP1-nuc Series of Reporter Vectors (a) Construction of Expression Plasmid pTREP1

The pTREP1 plasmid is a high-copy number (40–80 per cell) theta-replicating gram positive plasmid, which is a derivative of the pTREX plasmid which is itself a derivative of the the previously published pIL253 plasmid. pIL253 incorporates the broad Gram-positive host range replicon of pAMβ1 (Simon and Chopin, 1988) and is non-mobilisable by the *L lactis* sex-factor. pIL253 also lacks the tra function which is necessary for transfer or efficient mobilisation by conjugative parent plasmids exemplified by pIL501. The Enterococcal pAMβ1 replicon has previously been transferred to various species including *Streptococcus, Lactobacillus* and *Bacillus* species as well as *Clostridium acetobutylicum*, (LeBlanc et al., *Proceedings of the National Academy of Science USA* 75:3484–3487 (1978)) indicating the potential broad host range utility. The pTREP1 plasmid represents a constitutive transcription vector.

The pTREX vector was constructed as follows. An artificial DNA fragment containing a putative RNA stabilising sequence, a translation initiation region (TIR), a multiple cloning site for insertion of the target genes and a transcription terminator was created by annealing 2 complementary oligonucleotides and extending with Tfl DNA polymerase. The sense and anti-sense oligonucleotides contained the recognition sites for NheI and BamHI at their 5' ends respectively to facilitate cloning. This fragment was cloned between the XbaI and BamHI sites in pUC19NT7, a derivative of pUC19 which contains the T7 expression cassette from pLET1 (Wells et al., *J. Appl. Bacteriol.* 74:629–636 (1993)) cloned between the EcoRI and HindIII sites. The resulting construct was designated pUCLEX. The complete expression cassette of pUCLEX was then removed by cutting with HindIII and blunting followed by cutting with EcoRI before cloning into EcoRI and SacI (blunted) sites of pIL253 to generate the vector pTREX (Wells and Schofield, In Current advances in metabolism, genetics and applications-NATO ASI Series. H 98:37–62. (1996)). The putative RNA stabilising sequence and TIR are derived from the *Escherichia coli* T7 bacteriophage sequence and modified at one nucleotide position to enhance the complementarity of the Shine Dalgarno (SD) motif to the ribosomal 16s RNA of *Lactococcus lactis* (Schofield et al. pers. coms. University of Cambridge Dept. Pathology.).

A *Lactococcus lactis* MG1363 chromosomal DNA fragment exhibiting promoter activity which was subsequently designated P7 was cloned between the EcoRI and BglII sites present in the expression cassette, creating pTREX7. This active promoter region had been previously isolated using the promoter probe vector pSB292 (Waterfield et al., *Gene* 165:9–15 (1995)). The promoter fragment was amplified by PCR using the Vent DNA polymerase according to the manufacturer.

The pTREP1 vector was then constructed as follows. An artificial DNA fragment which included a transcription terminator, the forward pUC sequencing primer, a promoter multiple cloning site region and a universal translation stop sequence was created by annealing two overlapping partially complementary synthetic oligonucleotides together and extending with sequenase according to manufacturers instructions. The sense and anti-sense (pTREP$_F$ and pTREP$_R$) oligonucleotides contained the recognition sites for EcoRV and BamHI at their 5' ends respectively to facilitate cloning into pTREX7. The transcription terminator was that of the *Bacillus penicillinase* gene, which has been shown to be effective in Lactococcus (Jos et al., *Applied and Environmental Microbiology* 50:540–542 (1985)). This was considered necessary as expression of target genes in the pTREX vectors was observed to be leaky and is thought to be the result of cryptic promoter activity in the origin region (Schofield et al. pers. coms. University of Cambridge Dept. Pathology.). The forward pUC primer sequencing was included to enable direct sequencing of cloned DNA fragments. The translation stop sequence which encodes a stop codon in 3 different frames was included to prevent translational fusions between vector genes and cloned DNA fragments. The pTREX7 vector was first digested with EcoRI and blunted using the 5'-3' polymerase activity of T4 DNA polymerase (NEB) according to manufacturer's instructions. The EcoRI digested and blunt ended pTREX7 vector was then digested with Bgl II thus removing the P7 promoter. The artificial DNA fragment derived from the annealed synthetic oligonucleotides was then digested with EcoRV and Bam HI and cloned into the EcoRI(blunted)-Bgl II digested pTREX7 vector to generate pTREP. A *Lactococcus lactis* MG1363 chromosomal promoter designated P1 was then cloned between the EcoRI and BglII sites present in the pTREP expression cassette forming pTREP1. This promoter was also isolated using the promoter probe vector pSB292 and characterised by Waterfield et al., (1995) [supra]. The P1 promoter fragment was originally amplified by PCR using vent DNA polymerase according to manufacturers instructions and cloned into the pTREX as an EcoRI-BglII DNA fragment. The EcoRI-BglII P1 promoter containing fragment was removed from pTREX1 by restriction enzyme digestion and used for cloning into pTREP (Schofield et al. pers. coms. University of Cambridge, Dept. Pathology.).

(b) PCR Amplification of the *S. aureus* nuc Gene.

The nucleotide sequence of the *S. aureus* nuc gene (EMBL database accession number V01281) was used to design synthetic oligonucleotide primers for PCR amplification. The primers were designed to amplify the mature form of the nuc gene designated nucA which is generated by proteolytic cleavage of the N-terminal 19 to 21 amino acids of the secreted propeptide designated Snase B (Shortle, 1983 [supra]). Three sense primers (nucS1, nucS2 and nucS3, shown in FIG. 3) were designed, each one having a blunt-ended restriction endonuclease cleavage site for EcoRV or SmaI in a different reading frame with respect to the nuc gene. Additionally BglII and BamHI were incorporated at the 5' ends of the sense and anti-sense primers respectively to facilitate cloning into BamHI and BglII cut pTREP1. The sequences of all the primers are given in FIG. 3. Three nuc gene DNA fragments encoding the mature form of the nuclease gene (NucA) were amplified by PCR using each of the sense primers combined with the anti-sense primer. The nuc gene fragments were amplified by PCR using *S. aureus* genomic DNA template, Vent DNA Polymerase (NEB) and the conditions recommended by the manufacturer. An initial denaturation step at 93° C. for 2 min was followed by 30 cycles of denaturation at 93° C. for 45 sec, annealing at 50° C. for 45 seconds, and extension 73° C. for 1 minute and then a final 5 min extension step at 73° C. The PCR amplified products were purified using a Wizard clean up column (Promega) to remove unincorporated nucleotides and primers.

(c) Construction of the pTREP1-nuc Vectors

The purified nuc gene fragments described in section b were digested with Bgl II and BamHI using standard conditions and ligated to BamHI and BglII cut and dephosphorylated pTREP1 to generate the pTREP1-nuc1, pTREP1-nuc2 and pTREP1-nuc3 series of reporter vectors. These vectors are described in FIG. 4. General molecular biology techniques were carried out using the reagents and buffers supplied by the manufacturer or using standard techniques (Sambrook and Maniatis, Molecular cloning: A laboratory manual. Cold Spring Harbor Laboratory Press: Cold Spring Harbour (1989)). In each of the pTREP1-nuc vectors the expression cassette comprises a transcription terminator, lactococcal promoter P1, unique cloning sites (BglII, EcoRV or SmaI) followed by the mature form of the nuc gene and a second transcription terminator. Note that the sequences required for translation and secretion of the nuc gene were deliberately excluded in this construction. Such elements can only be provided by appropriately digested foreign DNA fragments (representing the target bacterium) which can be cloned into the unique restriction sites present immediately upstream of the nuc gene.

(d) Screening for Secreted Proteins in Group B *Streptococcus*.

Genomic DNA isolated from and Group B *Streptococcus* (*S. agalactiae*) was digested with the restriction enzyme Tru9I. This enzyme which recognises the sequence 5'-TTAA-3' was used because it cuts A/T rich genomes efficiently and can generate random genomic DNA fragments within the preferred size range (usually averaging 0.5–1.0 kb). This size range was preferred because there is an increased probability that the P1 promoter can be utilised to transcribe a novel gene sequence. However, the P1 promoter may not be necessary in all cases as it is possible that many Streptococcal promoters are recognised in *L. lactis*. DNA fragments of different size ranges were purfied from partial Tru9I digests of and *S. agalactiae* genomic DNA. As the Tru 9I restriction enzyme generates staggered ends the DNA fragments had to be made blunt ended before ligation to the EcoRV or SmaI cut pTREP1-nuc vectors. This was achieved by the partial fill-in enzyme reaction using the 5'-3' polymerase activity of Klenow enzyme. Briefly Tru9I digested DNA was dissolved in a solution (usually between 10–20 µl in total) supplemented with T4 DNA ligase buffer (New England Biolabs; NEB) (1×) and 33 µM of each of the required dNTPs, in this case dATP and dTTP. Klenow enzyme was added (1 unit Klenow enzyme (NEB) per µg of DNA) and the reaction incubated at 25° C. for 15 minutes. The reaction was stoped by incubating the mix at 75° C. for 20 minutes. EcoRV or SmaI digested pTREP-nuc plasmid DNA was then added (usually between 200–400 ng). The mix was then supplemented with 400 units of T4 DNA ligase (NEB) and T4 DNA ligase buffer (1×) and incubated overnight at 16° C. The ligation mix was precipiated directly in 100% Ethanol and ¹/₁₀ volume of 3M sodium acetate (pH 5.2) and used to transform *L. lactis* MG1363 (Gasson, *J. Bacteriol*. 154:1–9 (1983)). Alternatively, the gene cloning site of the pTREP-nuc vectors also contains a BglII site which can be used to clone for example Sau3AI digested genomic DNA fragments.

*L. lactis* transformant colonies were grown on brain heart infusion agar and nuclease secreting (Nuc$^+$) clones were detected by a toluidine blue-DNA-agar overlay (0.05 M Tris pH 9.0, 10 g of agar per litre, 10 g of NaCl per liter, 0.1 mM CaCl2, 0.03% wt/vol. salmon sperm DNA and 90 mg of Toluidine blue 0 dye) essentially as described by Shortle, 1983 [supra], and Le Loir et al., 1994 [supra]). The plates were then incubated at 37° C. for up to 2 hours. Nuclease secreting clones develop an easily identifiable pink halo. Plasmid DNA was isolated from Nuc$^+$ recombinant *L. lactis* clones and DNA inserts were sequenced on one strand using the NucSeq sequencing primer described in FIG. 3, which sequences directly through the DNA insert.

Whilst the example described above related specifically to Group B *Streptococcus*, it will be apparent to one skilled in the art that the same screening technique may be used to detect exported and secreted proteins in other gram positive bacteria, for example *Streptococcus pneumoniae*.

EXAMPLE 2

Screening Group B Streptococcal Derived Genes in DNA Vaccination Experiments pcDNA3.1+ as a DNA Vaccine Vector The commercially available pcDNA3.1+ plasmid (Invitrogen), referred to as pcDNA3.1 henceforth, was used as a vector in all DNA immunisation experiments involving gene targets derived using the LEEP system. pcDNA 3.1 is designed for high-level stable and transient expression in mammalian cells and has been used widely and successfully as a host vector to test candidate genes from a variety of pathogens in DNA vaccination experiments (Zhang et al., 1997; Kurar and Splitter, 1997; Anderson et al., 1996).

The vector possesses a multiple cloning site which facilitates the cloning of multiple gene targets downstream of the human cytomegalovirus (CMV) immediate-early promoter/enhancer which permits efficient, high-level expression of the target gene in a wide variety of mammalian cells and cell types including both muscle and immune cells. This is important for optimal immune response as it remains unknown as to which cells types are most important in generating a protective response in vivo. The plasmid also contains the ColE1 origin of replication which allows convenient high-copy number replication and growth in *E. coli* and the ampicillin resistance gene (B-lactamase) for selection in *E. coli*. In addition pcDNA 3.1 possesses a T7 promoter/priming site upstream of the MCS which allows for in vitro transcription of a cloned gene in the sense orientation.

Preparation of DNA Vaccines

Oligonucleotide primers were designed for each individual gene of interest derived using the LEEP system. Each gene was examined thoroughly, and where possible, primers were designed such that they targeted that portion of the gene thought to encode only the mature portion of the protein (APPENDIX I). It was hoped that expressing those sequences that encode only the mature portion of a target gene protein, would facilitate its correct folding when expressed in mammalian cells. For example, in the majority of cases primers were designed such that putative N-terminal signal peptide sequences would not be included in the final amplification product to be cloned into the pcDNA3.1 expression vector. The signal peptide directs the polypeptide precursor to the cell membrane via the protein export pathway where it is normally cleaved off by signal peptidase I (or signal peptidase II if a lipoprotein). Hence the signal peptide does not make up any part of the mature protein whether it be displayed on the bacterium's surface or secreted. Where a N-terminal leader peptide sequence was not immediately obvious, primers were designed to target the whole of the gene sequence for cloning and ultimately, expression in pcDNA3.1.

All forward and reverse oligonucleotide primers incorporated appropriate restriction enzyme sites to facilitate cloning into the pCDNA3.1 MCS region. All forward primers were also designed to include the conserved Kozak nucleotide sequence 5'-gccacc-3' immediately upstream of an 'atg' translation initiation codon in frame with the target gene insert. The Kozak sequence facilitates the recognition of initiator sequences by eukaryotic ribosomes. Typically, a forward primer incorporating a BamHI restriction enzyme site for the primer would begin with the sequence 5'-cgggatccgccaccatg-3' (SEQ ID NO: 199), followed by a sequence homologous to the 5' end of that part of a gene being amplified. All reverse primers incorporated a Not I restriction enzyme site sequence 5'-ttgcggccgc-3' (SEQ ID NO:200). All gene-specific forward and reverse primers were designed with compatible melting temperatures to facilitate their amplification.

All gene targets were amplified by PCR from S. agalactiae genomic DNA template using Vent DNA polymerase (NEB) or rTth DNA polymerase (PE Applied Biosystems) using conditions recommended by the manufacturer. A typical amplification reaction involved an initial denaturation step at 95° C. for 2 minutes followed by 35 cycles of denaturation at 95° C. for 30 seconds, annealing at the appropriate melting temperature for 30 seconds, and extension at 72° C. for 1 minute (1 minute per kilobase of DNA being amplified). This was followed by a final extension period at 72° C. for 10 minutes. All PCR amplified products were extracted once with phenol chloroform (2:1:1) and once with chloroform (1:1) and ethanol precipitated.

Specific DNA fragments were isolated from agarose gels using the QIAquick Gel Extraction Kit (Qiagen). The purified amplification gene DNA fragments were digested with the appropriate restriction enzymes and cloned into the pcDNA3.1 plasmid vector using E. coli as a host. Successful cloning and maintenance of genes was confirmed by restriction mapping and by DNA sequencing. Recombinant plasmid DNA was isolated on a large scale (>1.5 mg) using Plasmid Mega Kits (Qiagen).

It was decided to include the S. agalactiae rib gene as a positive control in at least one trial of DNA immunisation experiments. Rabbit antiserum against the Rib protein (Stalhammar-Carleman et al., 1993) and highly purified preparations of the Rib protein itself (Larsson et al., 1999; Larsson et al., 1996) have been shown to confer protection against lethal infection with strains expressing the antigen. All serotype III strains have been shown to express the Rib antigen and Southern blot analysis performed in the laboratory has confirmed that S. agalactiae serotype III (strain 97/0099) does contain the rib gene, hence the rib gene as part of a DNA vaccine would represent a potential positive control for all DNA immunisation experiments. Oligonucleotide primers were designed (Appendix I) that targeted only the mature portion of the rib gene and which included appropriate restriction enzyme sites for cloning into pcDNA3.1. rib was amplified using rTth DNA polymerase (PE Applied Biosystems) using conditions recommended by the manufacturer. Conditions for cloning were similar to that described previously.

Preparation of a S. agalactiae Standard Inoculum
Strain Validation

S. agalactiae serotype III (strain 97/0099) is a recent clinical isolate derived from the cerebral spinal fluid of a new born baby suffering from meningitis. This haemolytic strain of Group B Streptococcus was epidemiologically tested and validated at the Respiratory and Systemic Infection Laboratory, PHLS Central Public health laboratory, 61 Collindale Avenue, London NW9 5HT. The strain was subcultured only twice prior to its arrival in the laboratory. Upon its arrival on a agar slope, a sweep of 4–5 colonies was immediately used to inoculate a Todd Hewitt/5% horse blood broth which was incubated overnight statically at 37 C. 0.5 ml aliquots of this overnight culture were then used to make 20% glycerol stocks of the bacterium for long term storage at −70 C. Glyerol stocks were streaked on Todd Hewitt/5% horse blood agar plates to confirm viability.

In vivo Passaging of Group B Streptoccocus

A frozen culture (described under strain validation) of S. agalactiae serotype III (strain 97/0099) was streaked to single colonies on Todd-Hewitt/5% blood agar plates which were incubated overnight at 37° C. A sweep of 4–5 colonies was used to inoculate a Todd Hewitt/5% horse blood broth which was again incubated overnight. A 0.5 ml aliquot from this overnight culture was used to inoculate a 50 ml Todd Hewitt broth (1:100 dilution) which was incubated at 37 C. 10-fold serial dilutions of the overnight culture were made (since virulence of this strain was unknown) and each were passaged intra-pentoneally (IP) in CBA/ca mice in duplicate. Viable counts were performed on the various inocula used in the passage. Groups of mice were challenged with various concentrations of the pathogen ranging from $10^8$ to $10^4$ colony forming units (cfu). Mice that developed symptoms were terminally anaesthetized and cardiac punctures were performed (Only mice that had been challenged with the highest doses, i.e. $1 \times 10^8$ cfu, developed symptoms). The retrieved unclotted blood was used to inoculate directly a 50 ml serum broth (Todd Hewitt/20% inactivated foetal calf serum). The culture was constantly monitored and allowed to grow to late logarithmic phase. The presence of blood in the medium interfered with $OD_{600}$ readings as it was being increasingly lysed with increasing growth of the bacterium, hence the requirement to constantly monitor the culture. Upon reaching late logarithmic phase/early stationary phase, the culture was transferred to a fresh 50 ml tube in order to exclude dead bacterial cells and remaining blood cells which would have sedimented at the bottom of the tube. 0.5 ml aliquots were then transferred to sterile cryovials, frozen in liquid nitrogen and stored at −70 C. A viable count was carried out on a single standard inoculum aliquot in order to determine bacterial numbers. This was determined to be approximately $5 \times 10^8$ cfu per ml.

Intra-peritoneal Challenge and Virulence Testing of Group B Streptococcus Standard Inoculum To determine if the standard inoculum was suitably virulent for use in a vaccine trial, challenges were carried out using a dose range. Frozen standard inoculum strain aliquots were allowed to thaw at room temperature. From viable count data the number of cfu per ml was already known for the standard inoculum. Initially, serial dilutions of the standard inoculum were made in Todd Hewitt broth and mice were challenged intra-peritoneally with doses ranging from $1\times10^8$ to $1\times10^4$ cfu in a 500 µl volume of Todd Hewitt broth. The survival times of mouse groups injected with different doses of the bacterium were compared. The standard inoculum was determined to be suitably virulent and a dose of $1\times10^6$ cfu was considered close to optimal for further use in vaccine trials. Further optimisation was carried out by comparing mice challenged with doses ranging between $5\times10^5$ and $5\times10^6$ cfu. The optimal dose was estimated to be approximately $2.5\times10^6$ cfu. This represented a 100% lethal dose and was repeatedly consistant with end-points as determined by survival times being clustered within a narrow time-range. Throughout all these experiments, challenged mice were constantly monitored to clarify symptoms, stages of symptom development as well as calculating survival times.

Vaccine Trials

Vaccine trials in mice were accomplished by the administration of DNA to 6 week old CBA/ca mice (Harlan, UK). Mice to be vaccinated were divided into groups of six and each group were immunised with recombinant pcDNA3.1 plasmid DNA containing a specific target-gene sequence derived using the LEEP system. A total of 100 µg of DNA in Dulbecco's PBS (Sigma) was injected intramuscularly into the tibialis anterior muscle of both hind legs. Four weeks later this procedure was repeated using the same amount of DNA. For comparison, control mice groups were included in all vaccine trials. These control groups were either not DNA-vaccinated or were immunised with non-recombinant pcDNA3.1 plasmid DNA only, using the same time course described above. Four weeks after the second immunisation, all mice groups were challenged intra-peritoneally with a lethal dose of S. agalactiae serotype III (strain 97/0099). The actual number of bacteria administered was determined by plating serial dilutions of the inoculum on Todd-Hewitt/5% blood agar plates. All mice were killed 3 or 4 days after infection. During the infection process, challenged mice were monitored for the development of symptoms associated with the onset of S. agalactiae induced-disease. Typical symptoms in an appropriate order included piloerection, an increasingly hunched posture, discharge from eyes, increased lethargy and reluctance to move which was often the result of apparent paralysis in the lower body/hind leg region. The latter symptoms usually coincided with the development of a moribund state at which stage the mice were culled to prevent further suffering. These mice were deemed to be very close to death, and the time of culling was used to determine a survival time for statistical analysis. Where mice were found dead, a survival time was calculated by averaging the time when a particular mouse was last observed alive and the time when found dead, in order to determine a more accurate time of death.

Interpretation of Results

A positive result was taken as any DNA sequence that was cloned and used in challenge experiments as described above and gave protection against that challenge. DNA sequences were determined to be protective;
   if that DNA sequence gave statistically significant protection (to a 95% confidence level (p>0.05) as determined using the Mann-Whitney U test.
   if that DNA sequence was marginal or non-significant using Mann-Whitney but showed some protective features. For example, one or more outlying mice may survive for significantly longer time periods when compared with control mice. Alternatively, the time to first death may also be prolonged when compared to counterpart mice in control groups.

It is acceptable to allow marginal or non-significant results to be considered as potential positives when it is possible that the clarity of some results may be affected by problems associated with the administration of the DNA vaccine. Indeed, much varied survival times may reflect different levels of immune response between different members of a given group.

Results Statistical analysis of survival times - LEEP DNA immunisation and GBS challenge Trial 1 (FIG. 4a)

| | Mean Survival Times (hours) | | | | |
|---|---|---|---|---|---|
| | pcDNA3.1 | 17(ID-8) | 18(ID-9) | 20(ID-25) | rib |
| 1 | 26.833 | 14.916 | 27.750 | 30.500 | 88.666 |
| 2 | 42.333 | 94.000 (T) | 34.333 | 33.333 | 28.166 |
| 3 | 47.916 | 45.166 | 41.083 | 34.083 | 37.250 |
| 4 | 28.333 | 30.750 | 47.083 | 23.500 | 37.250 |
| 5 | 42.333 | 74.666 | 94.000 (T) | 94.000 (T) | 94.000 (T) |
| 6 | 25.333 | 25.000 | 26.166 | 30.500 | 45.750 |
| Mean | 37.549 | 51.899 | 48.849 | 43.083 | 57.066 |
| sd | 9.3943 | 32.214 | 26.257 | 28.768 | 31.556 |
| p value 1 | | 0.4049 | 0.4049 | 0.5000 | 0.1481 |
| p value 2 | >39.0 | >39.0 | >39.0 | >39.0 | |

(T) terminated at conclusion of experiment but showing symptoms of infection.
p value 1 refers to statistical significance when compared to pcDNA3.1 controls.
p value 2 refers to statistical significance when compared to rib positive control.

All DNA vaccine's showed a pattern of protection similar to that obtained with the rib DNA vaccine, which was initially used as a positive control.

17 (ID-8)

Mice immunised with the '17 (ID-8)' DNA vaccine did not show significantly longer survival times when compared with the unvaccinated control group. However, there are two outlying mice one of which survived the term of the experiment despite developing symptoms. The group also exhibited a much wider range of survival times reflected by a mean survival value which is approximately 14 hours higher than that demonstrated by the unvaccinated control group.

18 (ID-9)

Mice immunised with the '18 (ID-9)' DNA vaccine did not show significantly longer survival times when compared with the unvaccinated control group. However, there is one outlying mouse which survived the term of the experiment despite developing symptoms.

20 (ID-25)

Mice immunised with the '20 (ID-25)' DNA vaccine did not show significantly longer survival times when compared with the unvaccinated control group. However, there was one outlying mouse which survived the term of the experiment despite developing symptoms.

Figure 4B:
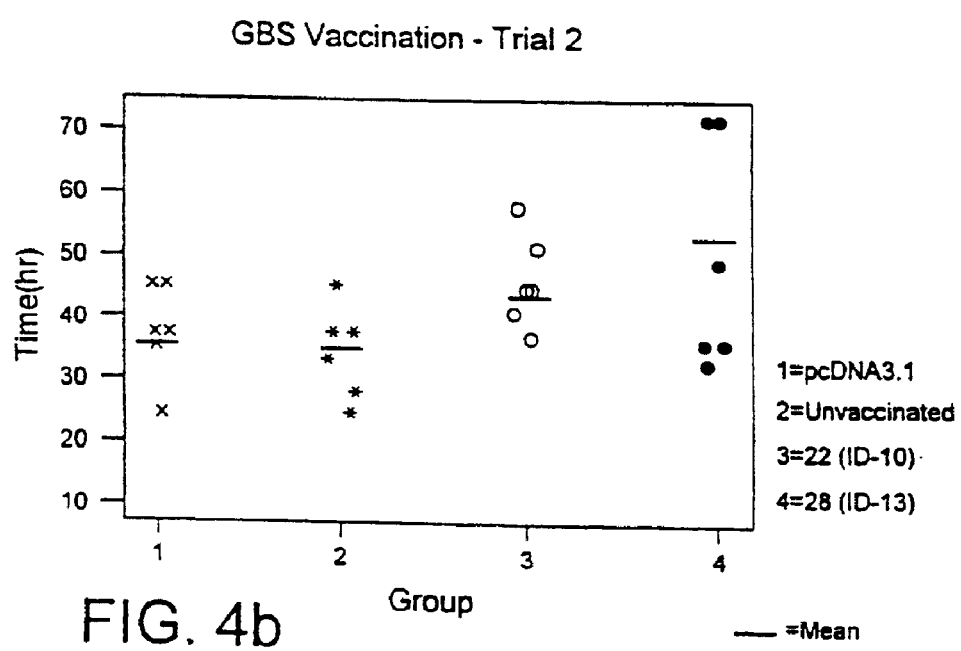

Statistical analysis of survival times - LEEP DNA immunisation and GBS challenge Trial 2 (FIG. 4b)

| | Mean Survival Times (hours) | | | |
|---|---|---|---|---|
| | pcDNA | UnVacc | 22(ID-10) | 28(ID-13) |
| 1 | 45.000 | 27.916 | 44.666 | 72.000 (T) |
| 2 | 37.333 | 45.083 | 51.416 | 33.000 |
| 3 | 37.333 | 37.583 | 40.791 | 36.083 |

-continued

Statistical analysis of survival times - LEEP DNA immunisation and GBS challenge Trial 2 (FIG. 4b)

Mean Survival Times (hours)

|   | pcDNA | UnVacc | 22(ID-10) | 28(ID-13) |
|---|---|---|---|---|
| 4 | 35.291 | 24.583 | 44.666 | 72.000 (T) |
| 5 | 24.333 | 37.583 | 36.916 | 49.166 |
| 6 | 45.000 | 33.166 | 57.833 | 36.083 |
| Mean | 35.858 | 34.549 | 43.691 | 52.449 |
| sd | 7.4342 | 8.2567 | 5.3825 | 18.850 |
| p value 1 |  | >39.0 | 0.1137 | 0.2340 |
| p value 2 | 0.4679 |  | 0.0323 | 0.1137 |

(T)-terminated at conclusion of experiment but showing symptoms of infection.
p value 1 refers to statistical significance when compared to pcDNA3.1 controls.
p value 2 refers to statistical significance when compared to unvaccinated controls.

There was no significant difference in the survival times exhibited by the pcDNA3.1 and unvaccinated control groups. This is confirmed by their very similar mean survival times of 35.858 hours (pcDNA3.1) and 34.166 hours (Unvaccinated).

22 (ID-10)

Mice immunised with the '22 (ID-10)' DNA vaccine exhibited significantly longer survival times when compared with the unvaccinated control group but not when compared with the pcDNA3.1 control group. In addition, the time to first death in this group was prolonged by approximately 12 hours when compared to the pcDNA3.1 and unvaccinated control groups. The mean survival time of 43.691 hours is also considerbly higher than that determined for both control groups.

28 (ID-13)

Mice immunised with the '28 (ID-13)' DNA vaccine did not show significantly longer survival times when compared with the pcDNA3.1 and unvaccinated control groups. However there are three outlying mice, two of which survived the term of the experiment despite showing symptoms. In addition, the time to first death in this group was prolonged by approximately 9 hours when compared to the pcDNA3.1 and unvaccinated control groups. The mean survival time of 52.449 hours is also considerbly higher than that determined for both control groups, as well demonstrating a wider range of survival times.

Figure 4C:
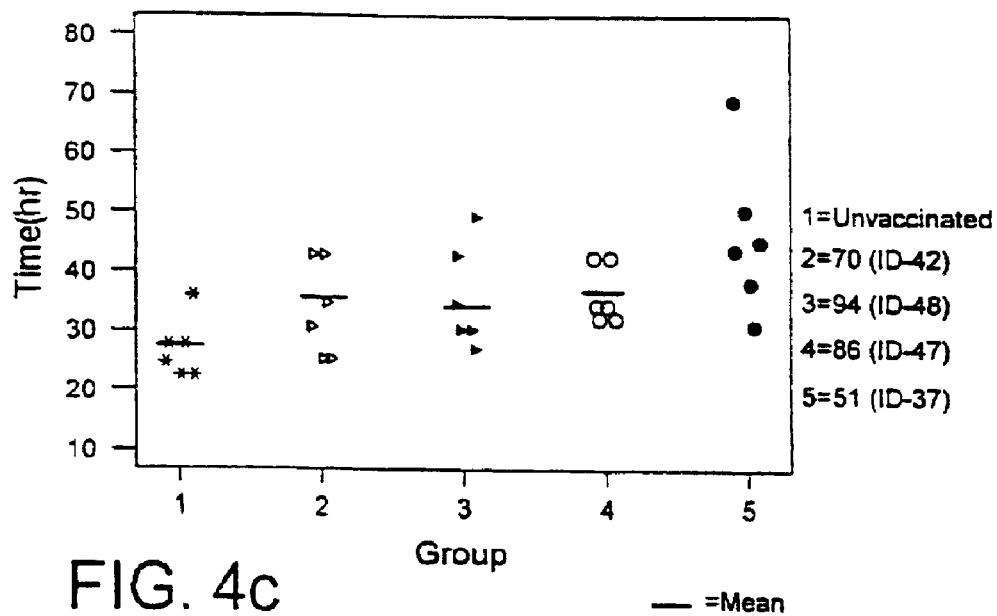

Statistical analysis of survival times - LEEP DNA immunisation and GBS challenge Trial 3 (FIG. 4c)

Mean Survival Times (hours)

|   | UnVacc. | 70(ID-42) | 94(ID-48) | 86(ID-47) | 51(ID-37) |
|---|---|---|---|---|---|
| 1 | 27.583 | 25.166 | 34.666 | 32.416 | 43.749 |
| 2 | 27.583 | 42.666 | 49.500 | 32.416 | 38.333 |
| 3 | 24.583 | 34.666 | 27.000 | 42.500 | 50.666 |
| 4 | 22.250 | 42.666 | 30.500 | 34.500 | 45.166 |
| 5 | 35.916 | 30.583 | 30.500 | 34.500 | 69.082 |
| 6 | 22.250 | 25.166 | 42.666 | 42.500 | 31.166 |
| Mean | 27.583 | 35.149 | 34.433 | 35.266 | 49.399 |
| sd | 5.1691 | 7.6444 | 8.8495 | 4.1758 | 11.846 |
| p value |  | 0.0628 | 0.0321 | 0.0153 | 0.0041 | p value refers to statistical significance when compared to unvaccinated controls.

Mice immunised with the '70 (ID-42)' DNA vaccine, marginally did not show significantly longer survival times when compared with the unvaccinated control group. However, the first death in this group is prolonged (by approximately 3 hours ) when compared with the unvaccinated group. In addition, the group has a mean survival time which is approximately 8 hours longer than the unvaccinated group.

94 (ID48)

Mice immunised with the '94 (ID-48)' DNA vaccine exhibited significantly longer survival times when compared with the unvaccinated control group.

86 (ID47)

Mice immunised with the '86 (ID-47)' DNA vaccine exhibited significantly longer survival times when compared with the unvaccinated control group.

51 (ID-37)

Mice immunised with the '51 (ID-37)' DNA vaccine exhibited significantly longer survival times when compared with the unvaccinated control group.

Figure 4D:
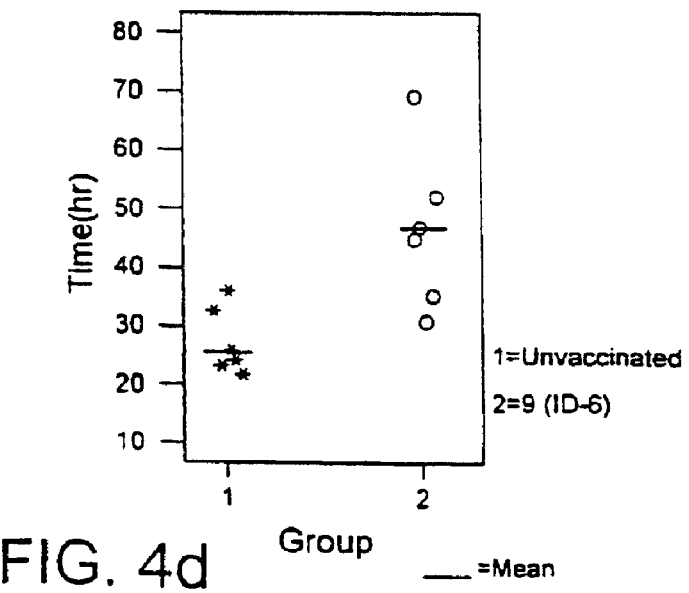

Statistical analysis of survival times - LEEP DNA immunisation and GBS challenge Trial 4 (FIG. 4d)

Mean Survival Times (hours)

|   | UnVacc | 9(ID-6) |
|---|---|---|
| 1 | 32.666 | 35.250 |
| 2 | 21.666 | 30.958 |
| 3 | 23.916 | 69.333 |
| 4 | 22.999 | 52.333 |
| 5 | 25.916 | 44.916 |
| 6 | 35.916 | 47.083 |
| Mean | 25.432 | 46.041 |
| sd | 4.3291 | 16.096 |
| p value |  | 0.0101 |

Figure 4E:
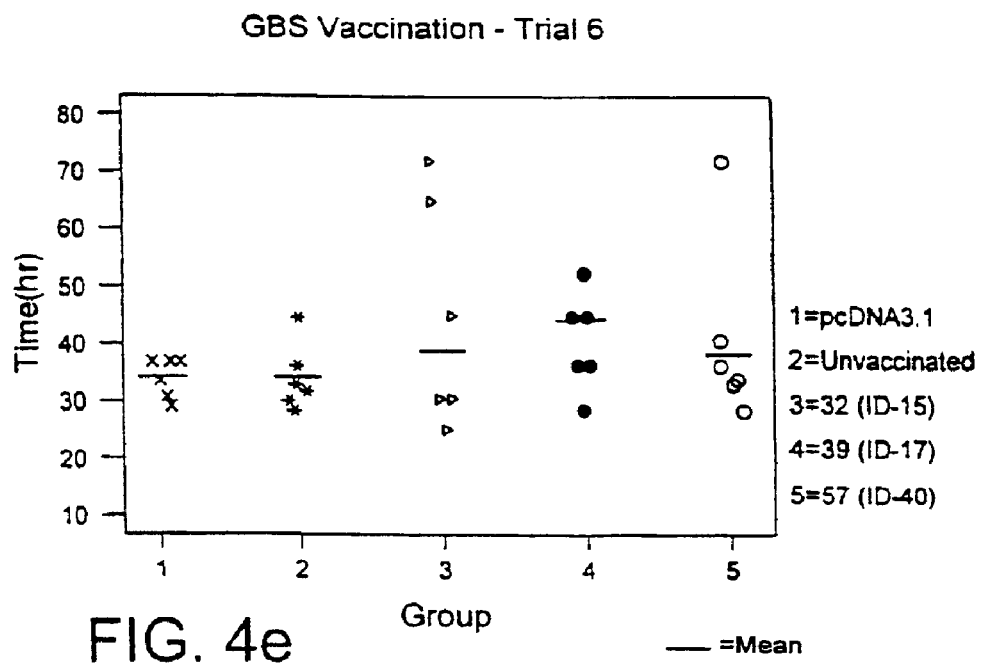

(T)-terminated at conclusion of experiment but showing symptoms of infection.
p value refers to statistical significance when compared to unvaccinated controls Statistical analysis of survival times - LEEP DNA immunisation and GBS challenge Trial 6 (FIG. 4e)

Mean Survival Times (hours)

|   | pcDNA | UnVacc | 32 (ID-15) | 39 (ID-17) | 57 (40) |
|---|---|---|---|---|---|
| 1 | 33.541 | 36.000 | 25.041 | 52.333 | 28.333 |
| 2 | 36.750 | 29.999 | 30.458 | 44.750 | 32.708 |
| 3 | 36.750 | 32.749 | 44.833 | 44.750 | 36.083 |
| 4 | 36.750 | 44.500 | 30.458 | 36.250 | 40.333 |
| 5 | 29.000 | 28.333 | 64.833 | 36.250 | 72.000 (T) |
| 6 | 30.750 | 31.666 | 72.000 (T) | 28.583 | 33.750 |
| Mean | 34.558 | 34.316 | 39.124 | 44.016 | 38.103 |
| sd | 3.4036 | 6.3921 | 16.140 | 13.833 | 12.986 |
| p value 1 |  | >39.0 | 0.4043 | 0.1867 | 0.4044 |
| p value 2 | 0.2862 |  | 0.2873 | 0.0458 | 0.2113 |

(T)-terminated at conclusion of experiment but showing symptoms of infection.
p value 1 refers to statistical significance when compared to pcDNA3.1 controls
p value 2 refers to statistical significance when compared to unvaccinated controls.

There was no significant difference in the survival times exhibited by the pcDNA3.1 and unvaccinated control groups. This is confirmed by their very similar mean survival times of 34.558 hours (pcDNA3.1) and 34.316 hours (Unvaccinated).

32 (ID-15)

Mice immunised with the '32 (ID-15)' DNA vaccine did not show significantly longer survival times when compared with the pcDNA3.1 and unvaccinated control groups. However, the '32 (ID-15)' group has two outlying mice one of which survived the term of the experiment despite showing symptoms. This group also exhibits a wide range of survival times.

39 (ID-17)

Mice immunised with the '39 (ID-17)' DNA vaccine exhibited significantly longer survival times when compared with the unvaccinated control group but was not significant when compared with the pcDNA3.1 control group. The group has a considerbly higher mean survival time of 44.016 hours than that determined for either of the control groups.

57 (ID-40)

Mice immunised with the '32 (ID-15)' DNA vaccine did not show significantly longer survival times when compared with the pcDNA3.1 and unvaccinated control groups. However, the '32 (ID-15)' group has one outlying mouse which survived the term of the experiment despite showing symptoms.

| Statistical analysis of survival times - LEEP DNA immunisation and GBS challenge Trial 3 (FIG. 5b) | | | |
|---|---|---|---|
| | Mean Survival Times (hours) | | |
| | UnVacc | 3-60(ID-65) | 3-5(ID-66) |
| 1 | 27.583 | 54.416 | 42.916 |
| 2 | 27.583 | 31.000 | 42.916 |
| 3 | 24.583 | 43.000 | 32.874 |
| 4 | 22.250 | 34.916 | 42.916 |
| 5 | 35.916 | 38.958 | 27.333 |
| 6 | 22.250 | 34.916 | 30.916 |
| Mean | 27.583 | 40.458 | 37.791 |
| sd | 5.1691 | 8.9959 | 7.2860 |
| p value | | 0.0098 | 0.0215 | p value refers to statistical significance when compared to unvaccinated controls.

Mice immunised with the 'b 3-60 (ID-65)' DNA vaccine exhibited significantly longer survival times when compared with the unvaccinated control group.

3-5 (ID-66)

Mice immunised with the '3-5 (ID-66)' DNA vaccine exhibited significantly longer survival times when compared with the unvaccinated control group.

| SURVIVAL DATA-SET B Statistical analysis of survival times - LEEP DNA immunisation and GBS challenge Trial 2 (FIG. 5a) | | | |
|---|---|---|---|
| | Mean Survival Times (hours) | | |
| | pcDNA | UnVacc | 13(ID-72) |
| 1 | 45.000 | 27.916 | 69.166 |
| 2 | 37.333 | 45.083 | 36.333 |
| 3 | 37.333 | 37.583 | 43.916 |
| 4 | 35.291 | 24.583 | 32.166 |
| 5 | 24.333 | 37.583 | 36.333 |
| 6 | 45.000 | 33.166 | 43.916 |
| Mean | 35.858 | 34.549 | 43.582 |
| sd | 7.4342 | 8.2567 | 14.917 |
| p value 1 | | >39.0 | 0.4679 |
| p value 2 | 0.4679 | | 0.1880 | p value 1 refers to statistical significance when compared to pcDNA3.1 controls.
p value 2 refers to statistical significance when compared to unvaccinated controls.

There was no significant difference in the survival times exhibited by the pcDNA3.1 and unvaccinated control groups. This is confirmed by their very similar mean survival times of 35.858 hours (pcDNA3.1) and 34.166 hours (Unvaccinated).

13 (ID-72)

Mice immunised with the '13 (ID-72)' DNA vaccine did not show significantly longer survival times when compared with the pcDNA3.1 and unvaccinated control groups. However, there is one outlying mouse which survived approximately 24 hours longer than the longest surviving mice in the pcDNA3.1 and unvaccinated control groups respectively. In addition, the time to first death in this group was prolonged when compared to the pcDNA3.1 and unvaccinated control groups. The mean survival time of 43.582 hours is considerbly higher than that determined for both control groups.

| Statistical analysis of survival times - LEEP DNA immunisation and GBS challenge Trial 4 (FIG. 5c) | | | | |
|---|---|---|---|---|
| | Mean Survival Times (hours) | | | |
| | UnVacc | 3-40(ID-67) | 3-30(ID-68) | 3-38(ID-69) |
| 1 | 32.666 | 79.750 | 35.500 | 68.583 |
| 2 | 21.666 | 35.833 | 28.333 | 29.916 |
| 3 | 23.916 | 30.500 | 31.208 | 29.916 |
| 4 | 22.999 | 22.708 | 98.000 (T) | 31.041 |
| 5 | 25.916 | 28.583 | 73.500 | 32.166 |
| 6 | 35.916 | 40.791 | 32.333 | 29.916 |
| Mean | 25.432 | 39.474 | 53.308 | 38.324 |
| sd | 4.3291 | 22.998 | 30.961 | 16.940 |
| p value | | 0.1149 | 0.0463 | 0.1132 |

(T) terminated at conclusion of experiment but showing symptoms of infection.
p value refers to statistical significance when compared to unvaccinated controls Mice immunised with the '3-40 (ID-67)' DNA vaccine did not show significantly longer survival times when compared with the unvaccinated control group. However, there is one outlying mouse which survived approximately 43 hours longer than the longest surviving mice in the unvaccinated control group.

3-30 (ID-68)

Mice immunised with the '3-30 (ID-68)' DNA vaccine exhibited significantly longer survival times when compared with the unvaccinated control group.

8 (ID-69)

Mice immunised with the '2-19 (ID-73)' DNA vaccine did not show significantly longer survival times when compared with the unvaccinated control group. However, there was one outlying mouse which survived approximately 32 hours longer than the longest surviving mice in the unvaccinated control group. In addition, the time to first death was prolonged (by approximately 8 hours) when compared to the unvaccinated controls.

Figure 5A:
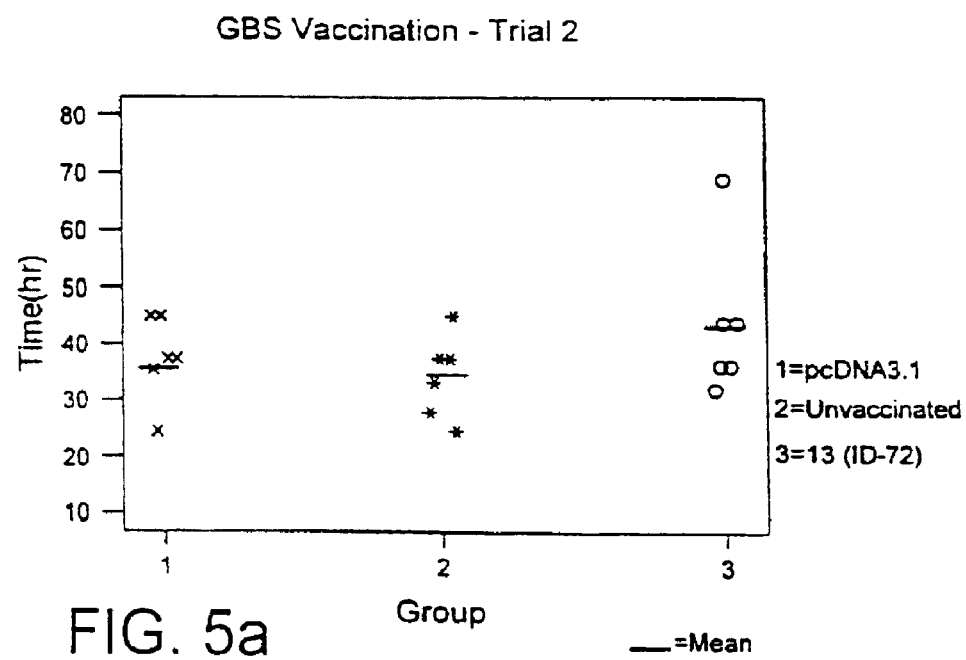
Figure 5B:
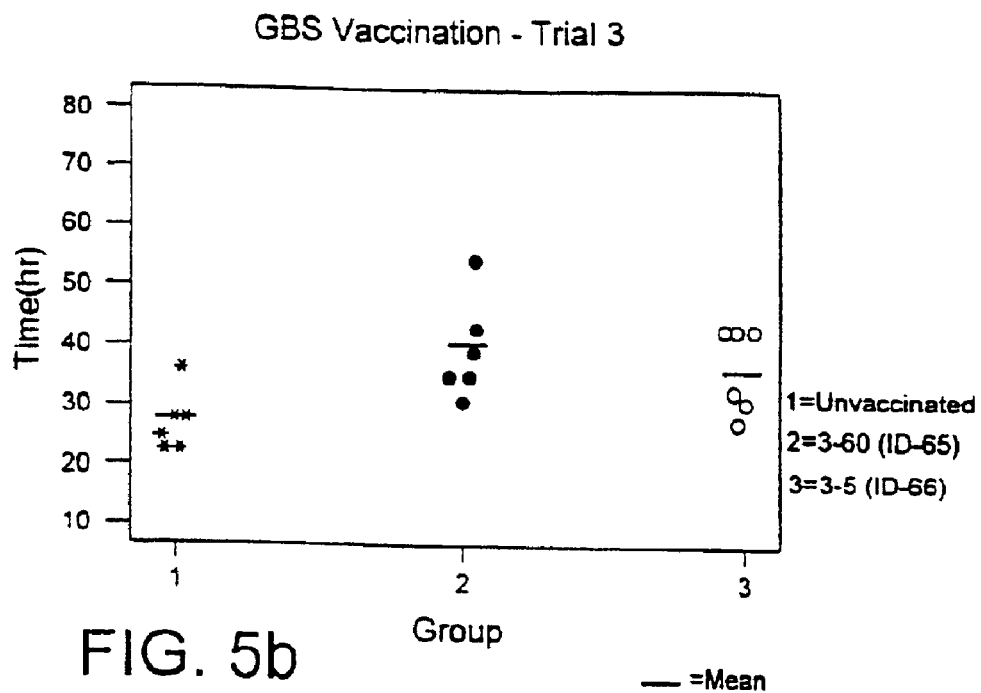
Figure 5C:
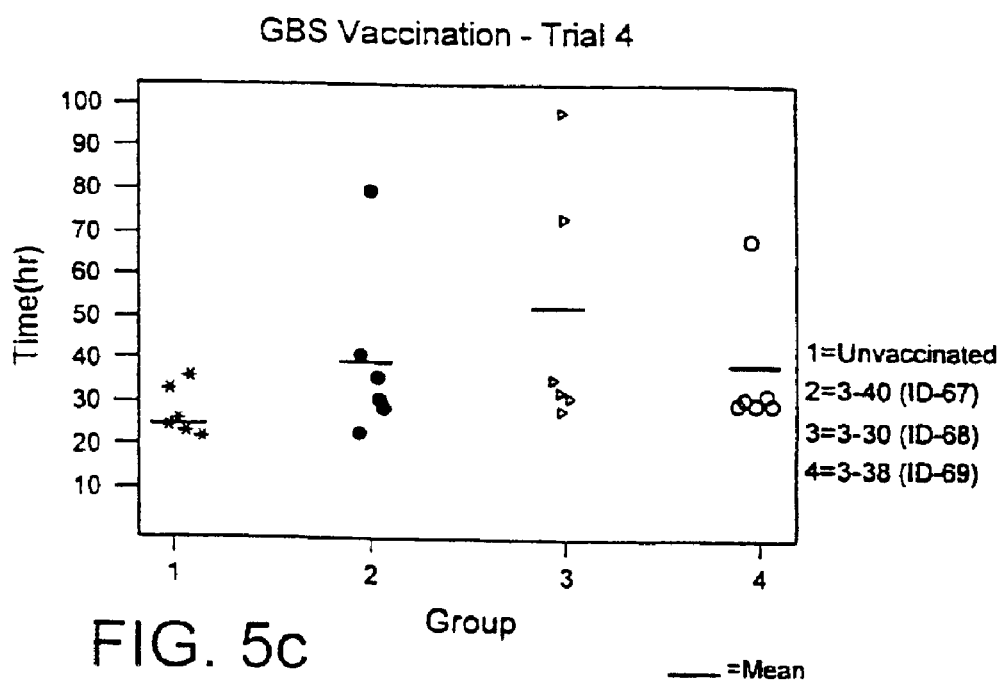
Figure 5D:
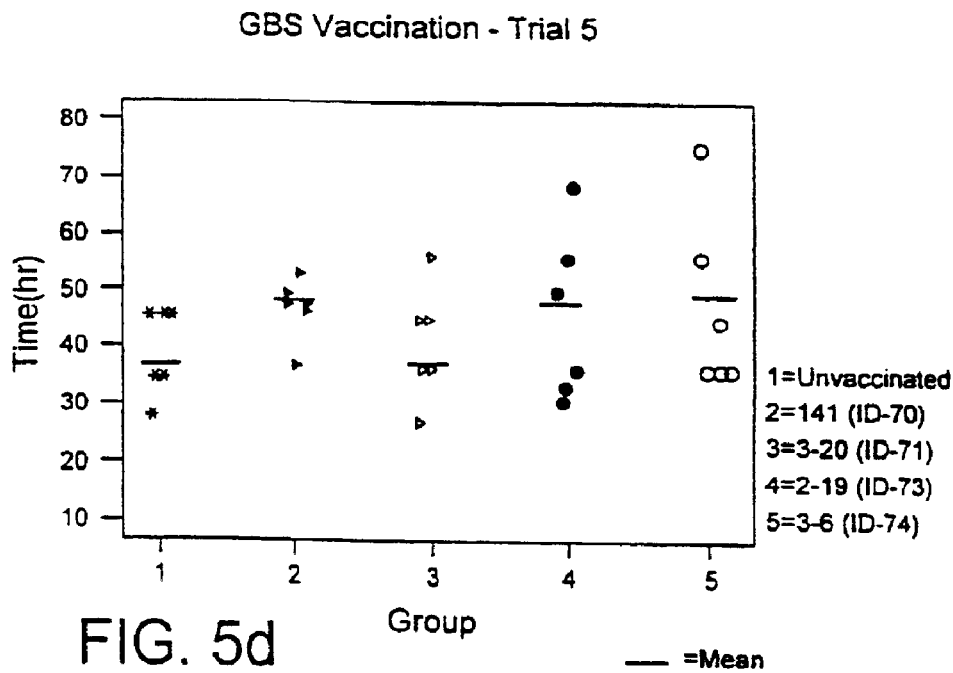

Statistical analysis of survival times - LEEP DNA
immunisation and GBS challenge Trial 5 (FIG. 5d)

Mean Survival Times (hours)

|   | UnVacc | 141(ID-70) | 3-20(ID-71) | 2-19(ID-73) | 3-6(ID-74) |
|---|---|---|---|---|---|
| 1 | 27.833 | 47.500 | 36.166 | 36.166 | 44.666 |
| 2 | 45.666 | 52.833 | 44.833 | 49.833 | 36.000 |
| 3 | 45.666 | 49.333 | 26.750 | 55.833 | 75.416 |
| 4 | 34.333 | 46.250 | 36.166 | 68.583 | 36.000 |
| 5 | 34.333 | 47.500 | 55.916 | 33.333 | 55.916 |
| 6 | 45.666 | 36.500 | 44.833 | 30.583 | 36.000 |
| Mean | 37.566 | 48.683 | 37.234 | 48.749 | 49.599 |
| sd | 7.8558 | 2.5672 | 8.4103 | 14.497 | 16.587 |
| p value |  | 0.0101 | 0.5000 | 0.2336 | 0.1854 | p value - refers to statistical significance when compared to unvaccinated controls.

141 (ID-70)

Mice immunised with the '141 (ID-70)' DNA vaccine exhibited significantly longer survival times when compared with the unvaccinated control group.

3-20 (ID-71)

Mice immunised with the '3-20 (ID-71)' DNA vaccine did not show significantly longer survival times when compared with the unvaccinated control group. However, there is one outlying mouse which survived approximately 10 hours longer than the longest surviving mice in the unvaccinated control group.

2-19 (ID-73)

Mice immunised with the '2-19 (ID-73)' DNA vaccine did not show significantly longer survival times when compared with the unvaccinated control group. However, there are three outlying mouse which survived approximately 4, 10 and 23 hours longer than the longest surviving mice in the unvaccinated control group. This is reflected in the higher mean survival time of 48.749 hours and a much wider range of survival times.

3-6 (ID-74)

Mice immunised with the '3-6 (ID-74)' DNA vaccine did not show significantly longer survival times when compared with the unvaccinated control group. However, there are three outlying mouse which survived approximately 4, 10 and 23 hours longer than the longest surviving mice in the unvaccinated control group. This is reflected in the higher mean survival time of 49.599 hours and a much wider range of survival times.

Figure 5E:
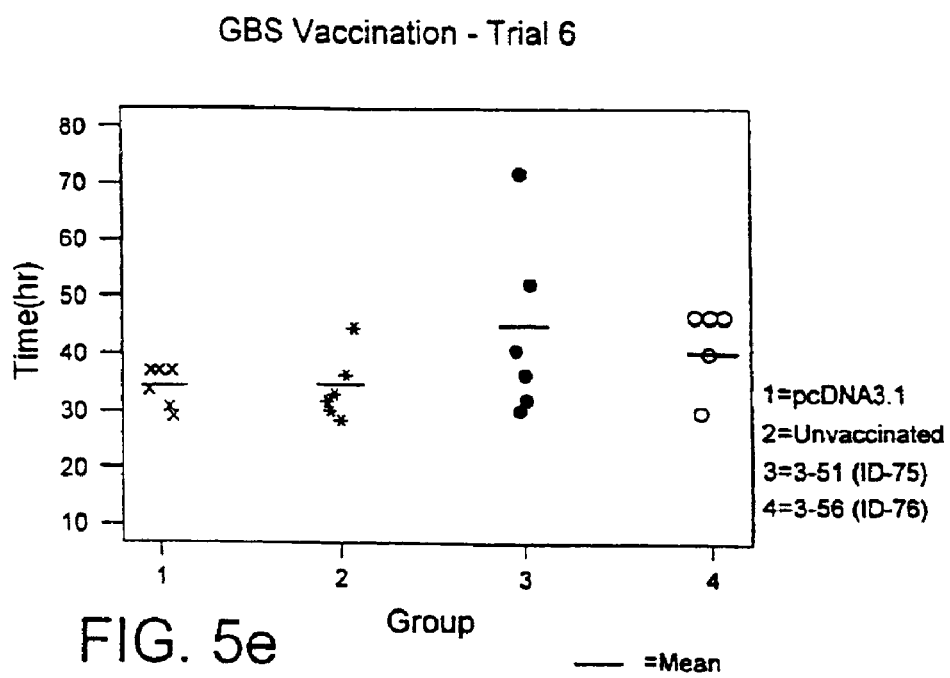

Statistical analysis of survival times - LEEP DNA
immunisation and GBS challenge Trial 6 (FIG. 5e)

Mean Survival Times (hours)

|   | pcDNA3.1 | UnVacc. | 3-51(ID-75) | 3-56(ID-76) |
|---|---|---|---|---|
| 1 | 33.541 | 36.000 | 36.333 | 46.583 |
| 2 | 36.750 | 29.999 | 30.291 | 29.833 |
| 3 | 36.750 | 32.749 | 32.000 | 40.166 |
| 4 | 36.750 | 44.500 | 52.333 | 46.583 |
| 5 | 29.000 | 28.333 | 72.000 (T) | 46.583 |
| 6 | 30.750 | 31.666 | 40.499 | — |
| Mean | 34.558 | 34.316 | 44.591 | 40.791 |
| sd | 3.4036 | 6.3921 | 16.615 | 7.9070 |

-continued

Statistical analysis of survival times - LEEP DNA
immunisation and GBS challenge Trial 6 (FIG. 5e)

Mean Survival Times (hours)

|   | pcDNA3.1 | UnVacc. | 3-51(ID-75) | 3-56(ID-76) |
|---|---|---|---|---|
| p value 1 |  | >39.0 | 0.1876 | 0.0386 |
| p value 2 | 0.2862 |  | 0.0867 | 0.0587 |

(T) terminated at conclusion of experiment but showing symptoms of infection.
p value 1 refers to statistical significance when compared to pcDNA3.1 controls
p value 2 refers to statistical significance when compared to unvaccinated controls.

There was no significant difference in the survival times exhibited by the pcDNA3.1 and unvaccinated control groups. This is confirmed by their very similar mean survival times of 34.558 hours (pcDNA3.1) and 34.316 hours (Unvaccinated).

3-51 (ID-75)

Mice immunised with the 'b 3-51 (ID-75)' DNA vaccine did not show significantly longer survival times when compared with the pcDNA3.1 control group but was relatively close to significant when compared with the unvaccinated control group. The '3-51' group has two outlying mouse one of which survived the term of the experiment despite developing symptoms. The mean survival time of 44.499 hours is considerbly higher than that determined for both control groups and the group also demonstrates as a much wider range of survival times.

3-56 (ID-76)

Mice immunised with the '3-56 (ID-76)' DNA vaccine exhibited significantly longer survival times when compared with the pcDNA3.1 control group but were marginally not significant when compared with unvaccinated control group.

EXAMPLE 3

Conservation and Varability of Candidate Vaccine Antigen Genes Among Different Isolates of Group B Strepococci An initial Southern blot analysis was carried out to determine cross-serotype conservation of novel Group B Streptococcal genes isolated using the LEEP system. Analysing the serotype distribution of a target gene will also determine their potential use as antigen components in a GBS vaccine. The Group B Streptococcal strains whose DNA was analysed as part of this study are listed in APPENDIX II.

Amplification and Labelling of Specific Target Genes as DNA Probes for Southern Blot Analysis.

Oligonucleotide primers were designed for each individual gene of interest derived using the LEEP system. Primers were designed to target the whole of the gene being investigated (All primers are listed in APPENDIX III). Specific gene targets were amplified by PCR using Vent DNA polymerase (NEB) according to the manufacturers instructions. Typical reactions were carried out in a 100 μl volume containing 50 ng of GBS template DNA, a one tenth volume of enzyme reaction buffer, 1 μM of each primer, 250 μM of each dNTP and 2 units of Vent DNA polymerase. A typical reaction contained an initial 2 minute denaturation at 95° C., followed by 35 cycles of denaturation at 95° C. for 30 seconds, annealing at the appropriate melting temperature for 30 seconds, and extension at 72° C. for 1 minute (1 minute per kilobase of DNA being amplified). The annealing temperature was determined by the lower melting temperature of the two oligonucleotide primers. The reaction was concluded with a final extension period of 10 minutes at 72° C.

All PCR amplified products were extracted once with phenol chloroform (2:1:1) and once with chloroform (1:1) and ethanol precipitated. Specific DNA fragments were isolated from agarose gels using the QIAquick Gel Extraction Kit (Qiagen). For use as DNA probes, purified amplified gene DNA fragments were labelled with digoxygenin using the DIG Nucleic Acid Labelling Kit (Boehringer Mannheim) according to the manufacturer's instructions.

Southern Blot Hybridisation Analysis of Group B Streptococcal Genomic DNA

Genomic DNA had previously been isolated from all strains of Group B *Streptococci* which were investigated for conservation of LEEP-derived gene targets. Appropriate DNA concentrations were digested using either Hin DIII, Eco RI or Bgl IIrestriction enzymes (NEB) according to manufacturer instructions and analysed by agarose gel electrophoresis. Following agarose gel electrophoresis of DNA samples, the gel was denatured in 0.25M HCl for 20 minutes and DNA was transferred onto Hybond™ N⁺ membrane (Amersham) by overnight capillary blotting. The method is essentially as described in Sambrook et al. (1989) using Whatman 3MM wicks on a platform over a reservoir of 0.4M NaOH. After transfer, the filter was washed briefly in 2×SSC and stored at 4 C in Saran wrap (Dow chemical company).

Filters were prehybridised, hybridised with the digoxygenin labelled DNA probes and washed using conditions recommended by Boehringer Mannheim when using their DIG Nucleic Acid Detection Kit. Filters were prehybridised at 68° C. for one hour in hybridisation buffer (1% w/v supplied blocking reagent, 5×SSC, 0.1% v/v N-lauryl sarcosine, 0.02% v/v sodium dodecyl sulphate[SDS]). The digoxygenin labelled DNA probe was denatured at 99.9° C. for 10 minutes before being added to the hybridisation buffer. Hybridisation was allowed to proceed overnight in a rotating Hybaid tube in a Hybaid Mini-hybridisation oven. Unbound probe was removed by washing the filter twice with 2×SSC-0.1% SDS for 5 minutes at room temperature. For increased stringency filters were then washed twice with 0.1×SSC-0.1% SDS for 15 minutes at 68° C. The DIG Nucleic Acid Detection Kit (Boehringer Mannheim) was used to immunologically detect specifically bound digoxygenin labelled DNA probes.

Results of Southern Blot Analysis

All genomic digests and their corresponding Southern blots followed an identical lane order as described in Table I.

TABLE I

| Lane | 1 | 2 | 3 | 4 | 5 | 6 | 7 |
|---|---|---|---|---|---|---|---|
| Strain | 1 kb molecular Weight Marker | 515 | A909 | SB35 | H36B | 18RS21 | 1954/92 |
| Serotype | | Ia | Ia | Ib | Ib | II | II |

| Lane | 8 | 9 | 10 | 11 | 12 | 13 | 14 |
|---|---|---|---|---|---|---|---|
| Strain | 118/158 | 97/0057 | BM110 | BS30 | M781 | 97/0099 | 3139 |
| Serotype | II | II | III | III | III | III | IV |

TABLE I-continued

| Lane | 15 | 16 | 17 | 18 | 19 | 20 |
|---|---|---|---|---|---|---|
| Strain | 1169-NT | GBS 6 | 7271 | JM9 | Group A Strepococcus | *Streptococcus pneumoniae* |
| Serotype | V | VI | VII | VIII | — | 14 |

For comparative purposes, it was decided to analyse the serotype distribution of the GBS rib gene, which encodes the known protective immunogen Rib. Rib has previously been shown to be present in serotype III and some strains of serotype II but not in serotypes Ia or Ib (Stalhammar-Carlemalm et al., 1993). Confirmation of this pattern would not only give increased confidence in interpreting subsequent results, it would also determine if a rib gene homologue was present in the remaining GBS serotypes being investigated here. Primers designed for the amplification of rib and its subsequent cloning into pcDNA3.1 (Appendix I), were used to generate a rib gene probe for Southern blot analysis.

Figure 6:
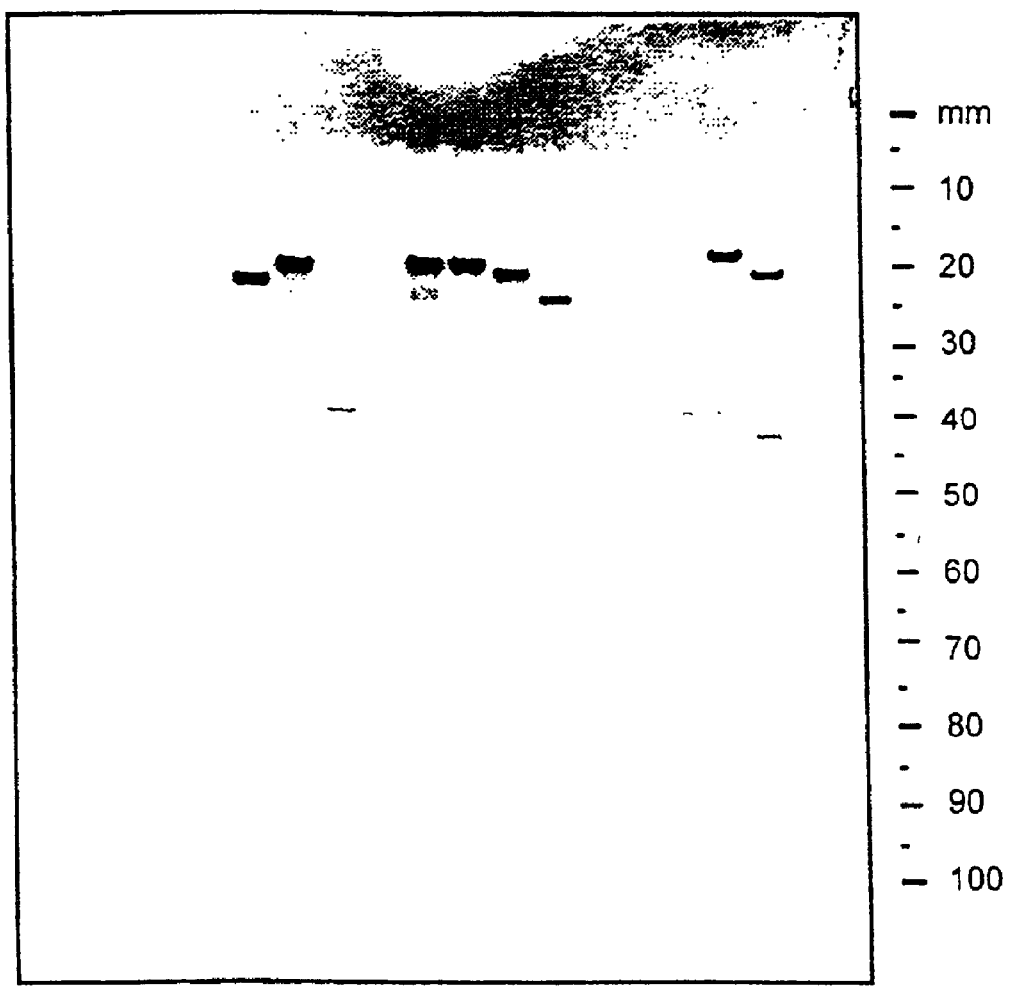

Southern Blot Analysis—Rib (FIG. 6)

1 2 3 4 5 6 7 8 9 10 11 12 13 14 15 16 17 18 19 20

Genomic DNA from each strain was digested completely with Hin DIII (NEB) and electrophoresed at 40 Volts for 6 hours in 0.8% agarose, transferred onto Hybond N⁺ (Amersham) membrane by Southern blot and hybridised with the digoxigenin-labelled rib gene probe. Specifically bound DNA probe was identified using the DIG Nucleic Acid'Detection Kit (Boehringer Mannheim).

Comment

Figure 7:
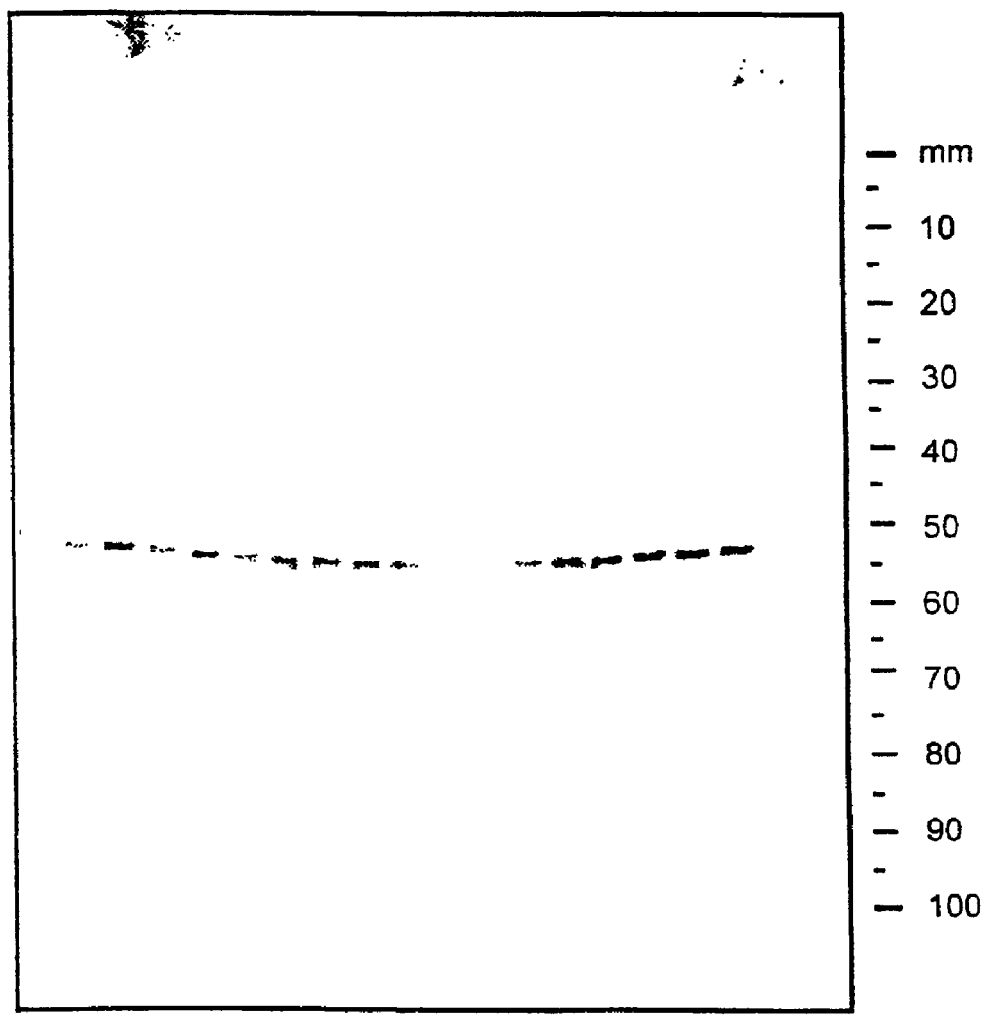

The Southern blot analysis described in FIG. 7 indicates that the rib gene is not conserved across all GBS serotypes. rib appears to be absent from all serotype Ia and Ib strains (lanes 2 to 5) and from strains 118/158 and 97/0057 of serotype II (lanes 8 and 9). However, rib would appear to present in strains 18RS21 and 1954/92 of serotype II (lanes 6 and 7) and in all strains of serotype III (lanes 10 to 13). This is in agreement with previously published data (Stalhammar-Carlemalm et al., 1993). rib would also appear to be present in strains representing serotypes VII and VII (lanes 17 and 18) but was absent from strains representing serotypes IV, V and V (lanes 14 to 16) as well as the control strains (lanes 19 and 20). The rib gene probe did hybridise with lower intensity to genomic DNA fragments from strains representing serotypes Ia, Ib, IV, VI, VII and serotype II strains 118/158 and 97/0057. This may indicate the presence of a gene in these strains with a lower level of homology to rib. These hybridising DNA fragments may contain a homologue of the GBS bca gene encoding the Ca protein antigen which has been shown to be closely homologous to the Rib protein (Wastfelt et al., 1996). If this is the case, it would be in agreement with previous work which showed all strains of serotypes Ia, Ib, II and III to be positive for one the two proteins (Stalhammar-Carlemalm et al., 1993). However, the apparent variable distribution of the rib gene amongst different GBS serotypes, makes it a less than ideal candidate for use in a GBS vaccine that is cross-protective against all serotypes.

Southern Blot Analysis—4 (ID-1) (photograph 7)

1 2 3 4 5 6 7 8 9 10 11 12 13 14 15 16 17 18 19 20

Genomic DNA from each strain was digested completely with Hin DIII (NEB) and electrophoresed at 40 Volts for 6 hours in 0.8% agarose, transferred onto Hybond N+ (Amersham) membrane by Southern blot and hybridised with the digoxigenin-labelled 4 (ID-1) gene probe. Specifically bound DNA probe was identified using the DIG Nucleic Acid Detection Kit (Boehringer Mannheim).

Comment

The Southern blot analysis described in FIG. 7 indicates that gene 4 (ID-1) is conserved across all GBS serotypes. The gene probe hybridised specifically to a Hin DIII-digested genomic DNA fragment of approximately 3.5 kb in DNA digests from all GBS representatives. but was absent from both the control strains (lanes 19 and 20).

Figure 8:
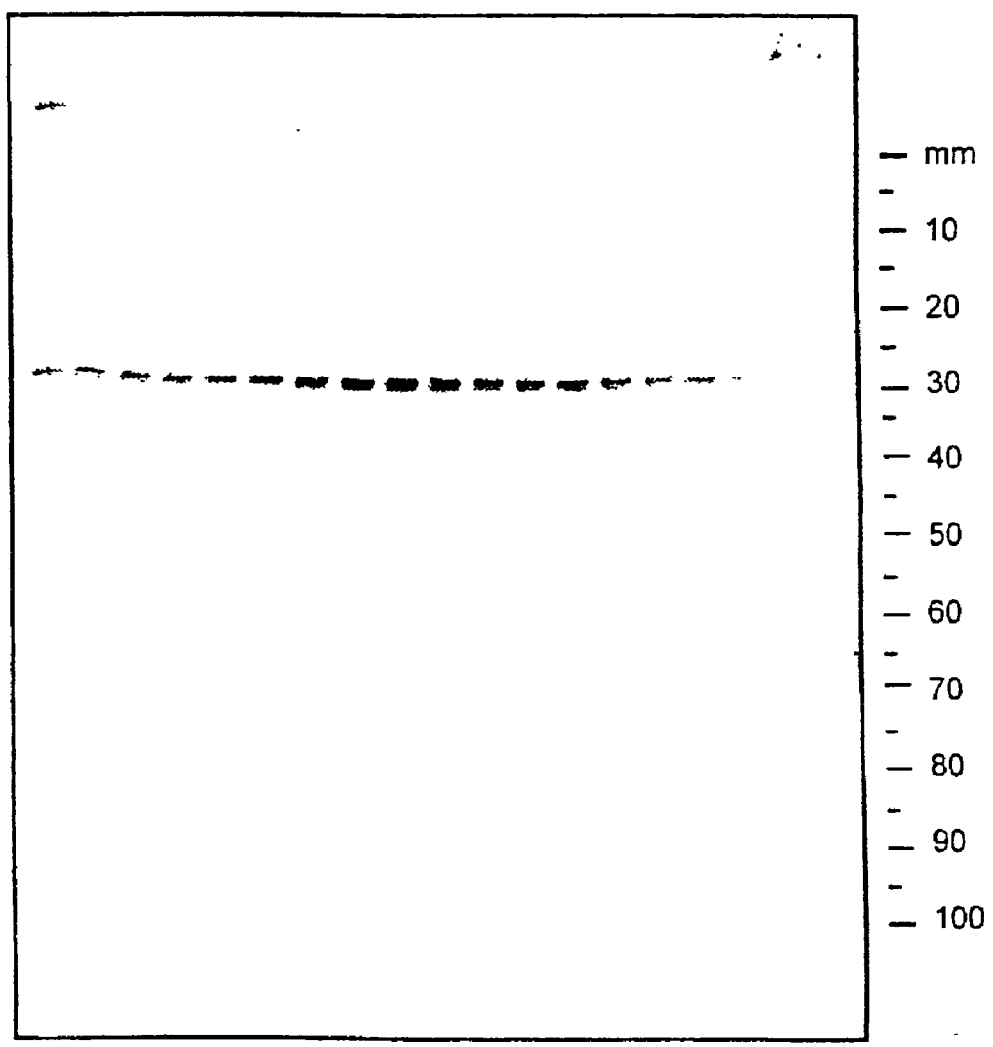

Southern Blot Analysis—5 (ID-2) (FIG. 8)

1 2 3 4 5 6 7 8 9 10 11 12 13 14 15 16 17 18 19 20

Genomic DNA from each strain was digested completely with Eco RI (NEB) and electrophoresed at 40 Volts for 6 hours in 0.8% agarose, transferred onto Hybond N+ (Amersham) membrane by Southern blot and hybridised with the digoxigenin-labelled 5 (ID-2) gene probe. Specifically bound DNA probe was identified using the DIG Nucleic Acid Detection Kit (Boehringer Mannheim).

Comment

The Southern blot analysis described in FIG. 7 indicates that gene 4 (ID-1) is conserved across all GBS serotypes. The gene probe hybridised specifically to a Eco RI-digested genomic DNA fragment of approximately 6.2 kb in DNA digests from all GBS representatives. but was absent from both the control strains (lanes 19 and 20).

Figure 9:
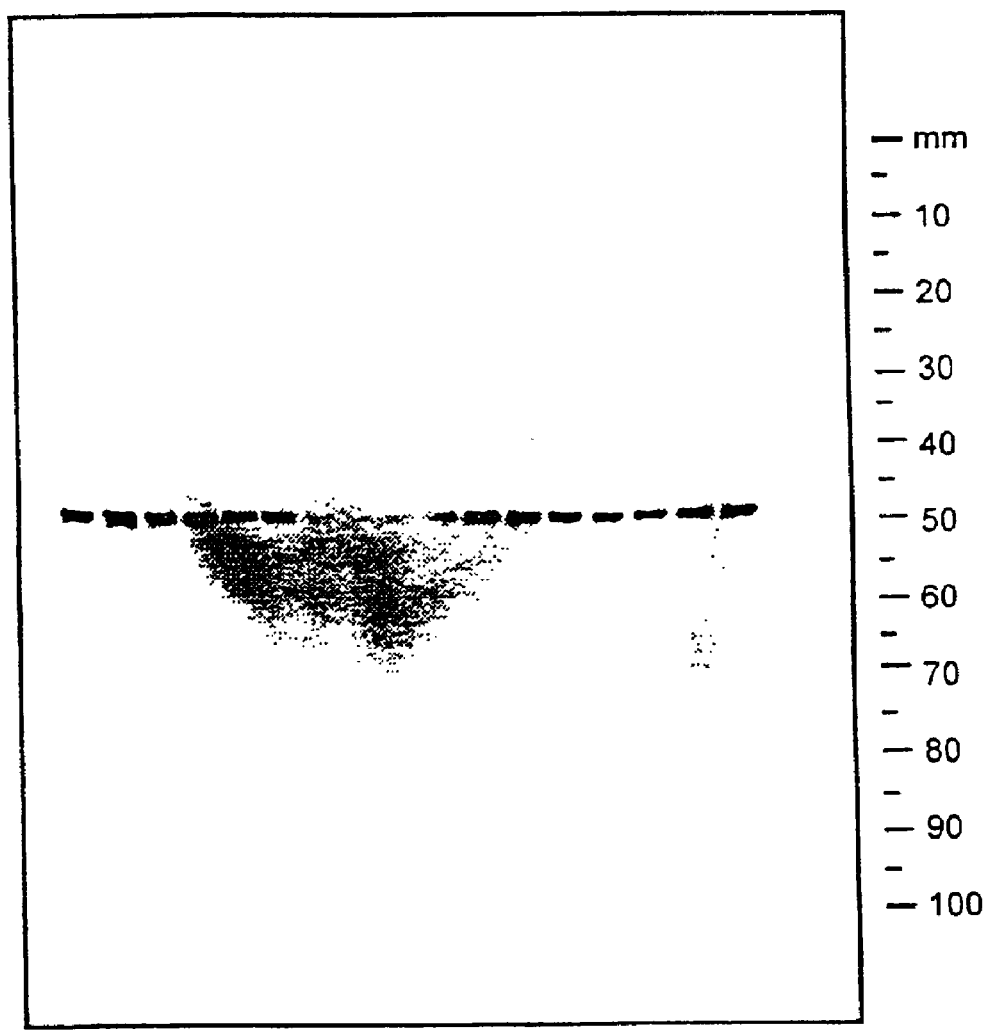

Southern Blot Analysis—15 (ID-7) (FIG. 9)

1 2 3 4 5 6 7 8 9 10 11 12 13 14 15 16 17 18 19 20

Genomic DNA from each strain was digested completely with Eco RI (NEB) and electrophoresed at 40 Volts for 6 hours in 0.8% agarose, transferred onto Hybond N+ (Amersham) membrane by Southern blot and hybridised with the digoxigenin-labelled 15 (ID-7) gene probe. Specifically bound DNA probe was identified using the DIG Nucleic Acid Detection Kit (Boehringer Mannheim).

Comment

The Southern blot analysis described in FIG. 7 indicates that gene 15 (ID-7) is conserved across all GBS serotypes. The gene probe hybridised specifically to a Eco RI-digested genomic DNA fragment of approximately 6.2 kb in DNA digests from all GBS representatives. but was absent from both the control strains (lanes 19 and 20). The gene probe hybridised specifically with Eco RI-digested DNA fragments ranging from approximately 3.5 kb to 5.2 kb in size.

Figure 10:
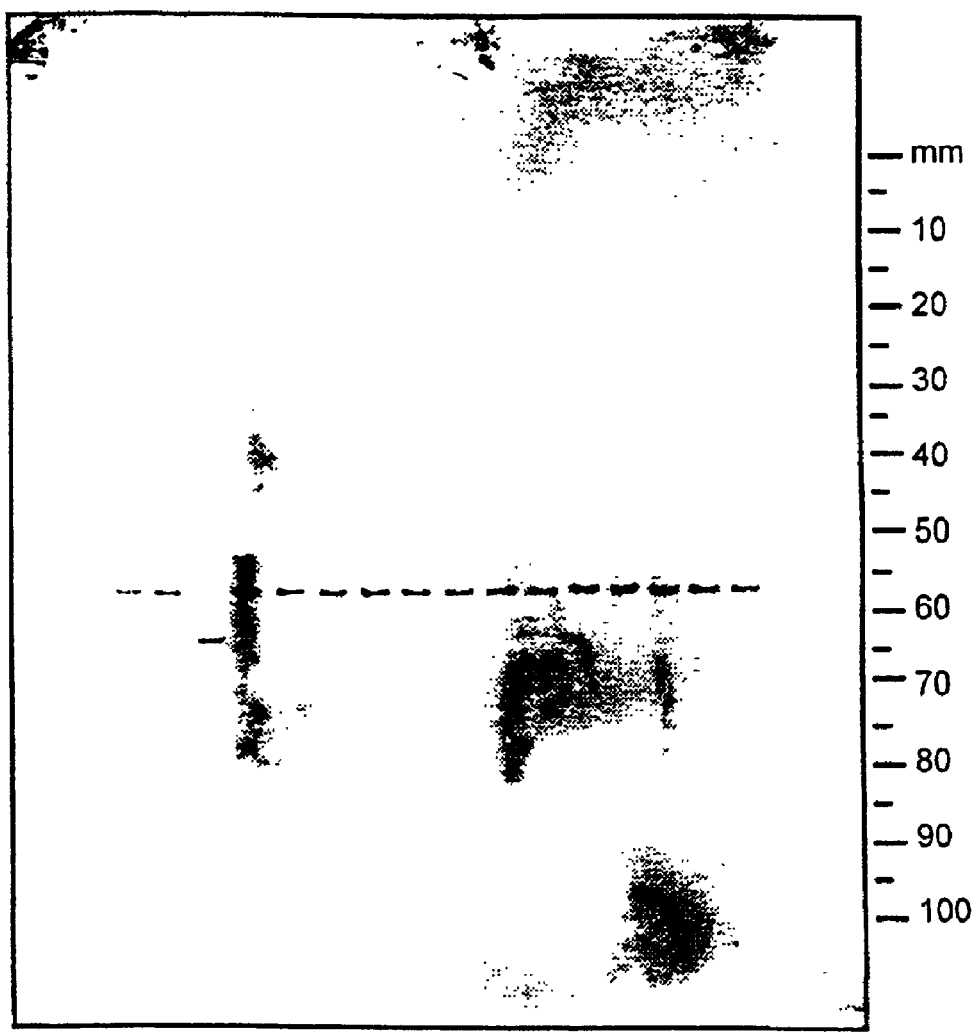

Southern Blot Analysis—17 (ID-8) (FIG. 10)

FIG. 5

1 2 3 4 5 6 7 8 9 10 11 12 13 14 15 16 17 18 19 20

Genomic DNA from each strain was digested completely with Hin DIII (NEB) and electrophoresed at 40 Volts for 6 hours in 0.8% agarose, transferred onto Hybond N+ (Amersham) membrane by Southern blot and hybridised with the digoxigenin-labelled 17 (ID-8) gene probe. Specifically bound DNA probe was identified using the DIG Nucleic Acid Detection Kit (Boehringer Mannheim).

Comment

The Southern blot analysis described in FIG. 7 indicates that gene 17 (ID-8) is conserved across all GBS serotypes. The gene probe hybridised specifically to a Hin DIII-digested genomic DNA fragment of approximately 2.3 kb in DNA digests from all GBS representatives. but was absent from both the control strains (lanes 19 and 20).

Figure 11:
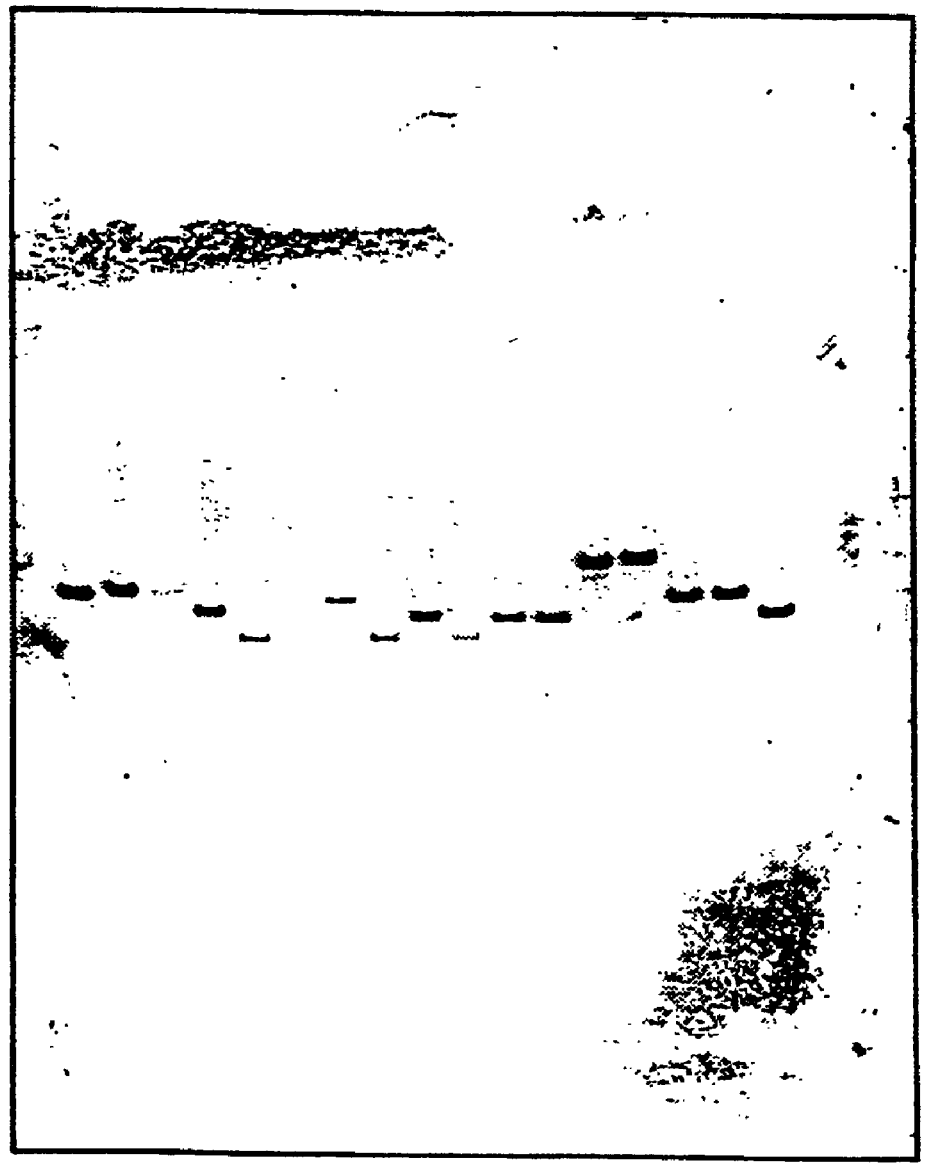

Southern Blot Analysis—22 (ID-10) (FIG. 11)

FIG. 6

1 2 3 4 5 6 7 8 9 10 11 12 13 14 15 16 17 18 19 20

Genomic DNA from each strain was digested completely with Bgl II (NEB) and electrophoresed at 40 Volts for 6 hours in 0.8% agarose, transferred onto Hybond N+ (Amersham) membrane by Southern blot and hybridised with the digoxigenin-labelled 22 (ID-10) gene probe. Specifically bound DNA probe was identified using the DIG Nucleic Acid Detection Kit (Boehringer Mannheim).

Comment

The Southern blot analysis described in FIG. 7 indicates that gene 22 (ID-10) is conserved across all GBS serotypes. The gene probe hybridised specifically to a Bgl II-digested genomic DNA fragment of approximately 3.1 kb in DNA digests from all GBS representatives except serotype Ib strain $H_{36}B$, where the gene probe hybridised specifically to a a Bgl II-digested genomic DNA fragment. Gene 22 (ID-10) was absent from both the control strains (lanes 19 and 20).

Conclusion

The Southern blot analyses described here, represents a preliminary investigation into the conservation level of LEEP-derived genes amongst different GBS serotypes. Initial results indicate that the genes 4 (ID-1), 5 (ID-2), 15 (ID-7), 17(ID-8) and 22 (ID-10) are present in all GBS serotypes and thus represent potential candidate genes for use in a GBS vaccine. Similar analyses are being currently carried out for each of the genes contained in this patent.

APPENDIX I

ID-8 (17)
  Forward Primer
    5'-cgggatccgccaccatgACCACTTCTCAAGCTGTTTTAGC-3' (SEQ ID NO:153)
  Reverse Primer
    5'ttgcggccgcACGATTATCAACAAAGTTCTG-3' (SEQ ID NO:154)
ID-9 (18)
  Forward Primer
    5'-cggatccgccaccatgGCTACTCATATTGGAAGTTACCAGC-3' (SEQ ID NO:155)
  Reverse Primer
    5'-ttgcggccgcAGGGTTTATTTGTTGAAGTGTCTTG-3' (SEQ ID NO:156)
ID-10 (22)
  Forward Primer
    5'-cggatccgccaccatgTATCTATATCATTTACCAATGCCC-3' (SEQ ID NO:157)
  Reverse Primer
    5'-ttgcggccgcTTTATGTATAGAAACAGCAGTCCC-3' (SEQ ID NO:158)
ID-13 (28)
  Forward Primer
    5'-cggatccgccaccatgAAAGGAAGAACAACCTATCGTTTAG-3' (SEQ ID NO:159)
  Reverse Primer
    5'-ttgcggccgcAAGAGCAAATTTTCGTATCCCCTC-3' (SEQ ID NO:160)
ID-15 (32)
  Forward Primer
    5'-cggatccgccaccATGATTGTTGGACACGGAATTG-3' (SEQ ID NO:161)

Reverse Primer
5'-ttgcggccgcTTTTTCTTCCTCCAAAATAACACTAGC-3' (SEQ ID NO:162)
ID-17 (39)
Forward Primer
5-cggatccgccaccatgGCGACTAAAGAGTTAGGTGTTAG-3' (SEQ ID NO:163)
Reverse Primer
5'-ttgcggccgcTATAGTTTTAGTTTCAACTTGTCTAGATG-3' (SEQ ID NO:164)
ID-25 (20)
Forward Primer
5'-cgggatccaccatgTATACGAGTTTACAACCAAATCATG-3' (SEQ ID NO:165)
Reverse Primer
5'-ttgcggccgcGTCAGCTCGTACTGTTTTTTAGC-3' (SEQ ID NO:166)
ID-37 (51)
Forward Primer
5'-cggatccgccaccatgTGTCAAATGAATAGTGAACATAAAAG-3' (SEQ ID NO:167)
Reverse Primer
5-ttgcggccgcCTCAAATAATTTACCTCCAATTTCG-3' (SEQ ID NO:168)
ID-40 (51)
Forward Primer
5'-cggatccgccaccatgGCTCCATTCGAATTTAAAGATTC-3' (SEQ ID NO:169)
Reverse Primer
5'-ttgcggccgcTGATTTACCAGTTTGGAAGAGTTC-3' (SEQ ID NO:170)
ID42 (70)
Forward Primer
5'-cggatccgccaccATGAATACTATTTATAATACATTGAGAACAG-3' (SEQ ID NO:171)
Reverse Primer
5'-ttgcggccgcTTCTTTGTTCCAACTTTCTGG-3' (SEQ ID NO:172)
ID-47 (86)
Forward Primer
5'-cggatccgccaccATGATAGAGTGGATTCAAACACATTTAC-3' (SEQ ID NO:173)
Reverse Primer
5'-ttgcggccgcTTTATGACTCAAGCGACGTTA-3' (SEQ ID NO:174)
ID-48 94
Forward Primer
5'-cggatccgccaccATGGAGTAGTAATTAGAGATATTCGTAAG-3' (SEQ ID NO:175)
Reverse Primer
5'-ttgcggccgcCTTGTCATATTCATCTCCCTTCAAC-3' (SEQ ID NO:176)
ID-67 (3-40)
Forward Primer
5'-cggatccgccaccatgGCTAGTTTTGTCATGAATCATAATGAC-3' (SEQ ID NO:177)
Reverse Primer
5'-ttgcggccgcGTTATTTGCTCGTTGTTTAGCTAAATC-3' (SEQ ID NO:178)
ID-68 (3-30)
Forward Primer
5'-cggatccgccaccatgGCTCTTAGTTTTTTATGGTTTCAGTTCAAGC-3' (SEQ ID NO:179)
Reverse Primer
5'-ttgcggccgcGAAGGCACCGCCACCTCC-3' (SEQ ID NO:180)
ID-69 (3-38)
Forward Primer
5'-cggatccgccaccatgGGTGAAACCCAAGATACCAATCAAGC-3' (SEQ ID NO:181)
Reverse Primer
5'ttgcggccgcAACACCTGGTGGGCGTTTGG-3' (SEQ ID NO:182)
ID-70 (141)
Forward Primer
5-cggatccgccaccATGGCTGGGAATCGTAATAACG-3' (SEQ ID NO:183)
Reverse Primer
5'-ttgcggccgcAGCCGTCTCTAAAACAGGCTTG-3' (SEQ ID NO:184)
ID-71 (3-20)
Forward Primer
5'-cggatccgccaccatgCTTCCAACGCAGCCGCAAAAC-3' (SEQ ID NO:185)
Reverse Primer
5'-ttgcggccgcATTTAGTGTTATTTCTCCTGTTCATAATCC-3' (SEQ ID NO:186)
ID-72 (13)
Forward Primer
5'-cgggatccaccatgTACACGCATATTGTTGAAAAAAG-3' (SEQ ID NO:187)
Reverse Primer
5'-ttgcggccgcAAATAATTTCTTTTGGTTGTTTG-3' (SEQ ID NO:188)
ID-73 (2-19)
Forward Primer
5'-cggatccgccaccatgAGTAATCAAGAAGTTTCAGCAAGC-3' (SEQ ID NO:189)
Reverse Primer
5'-ttgcggccgcCCATTGTGGAATATCAGCTGAAG-3' (SEQ ID NO:190)
ID-74 (3-6)
Forward Primer
5'-cggatccgccaccatgGTGCAGGCAGTGGTACCGCT-3' (SEQ ID NO:191)
Reverse Primer
5'-ttgcggccgcGCGCATTGTAACAAATTCCTCAG-3' (SEQ ID NO:192)
ID-75 (3-51)
Forward Primer
5'-cgggatccaccatgGCTGCCGAGAAGGATAAAG-3' (SEQ ID NO:193)
Reverse Primer
5'-ttgcggccgcATTATTTAGCTGCTTTTTTAATGG-3' (SEQ ID NO:194)
ID-76 (3-56)
Forward Primer
5'-cgggatccaccatgTGTCAGGTTGTTTATGCAAGTTTTC-3' (SEQ ID NO:195)
Reverse Primer
5'-ttgcggccgcTTTACTAATTGATAAAGAGCAACTTCG-3' (SEQ ID NO:196)
rib (control)
Forward Primer
5'-ggggtaccggccaccATGGCTGAAGTAATTTCAGGAAGT-3' (SEQ ID NO:197)
Reverse Primer
5'-cggaattccgTTAATCCTCTTTTTTTCTTAGAAACAGAT-3' (SEQ ID NO:198)

APPENDIX II

Listed below are the details (serotype and strain designation) of Group B *Streptococcus* strains whose DNA was analysed for gene conservation

| SEROTYPE | STRAIN |
|---|---|
| Ia | 515 |
| Ia | A909 |
| Ib | SB35 |
| Ib | H36B |
| II | 18RS21 |
| II | 1954/92 |
| II | 118/158 |
| II | 97/0057 |
| III | BM110 |
| III | BS30 |
| III | M781 |
| III | 97/0099 |
| IV | 3139 |
| V | 1169/NT |
| VI | GBS VI |
| VII | 7271 |
| VIII | JM9 |

A group A Streptococcal strain (serotype M1, strain NCTC8198) and *Streptococcus pneumoniae* (serotype 14) were also included in the analysis for control purposes.

APPENDIX III

ID-1 (4)
Forward Primer
5'-atggaaaaaatacttggaaaaaattac-3' (SEQ ID NO:201)
Reverse Primer
5'-ctattttgttttagcgatgtctttatc-3' (SEQ ID NO:202)
ID-2 (5)
Forward Primer
5'-atgtcaaaacaaaaagtaacggcaac-3' (SEQ ID NO:203)
Reverse Primer
5'-ttatttatggccaataccataagttaattg-3' (SEQ ID NO:204)
ID-6 (9)
Forward Primer
5'-atgaaaaaagttttttttctcatggctatg-3' (SEQ ID NO:205)
Reverse Primer
5'-ttacttcaactgttgatagagcacttcc-3' (SEQ ID NO:206)
ID-7 (15)
Forward Primer
5'-ttgttcaatttataggttttagaacttgg-3' (SEQ ID NO:207)
Reverse Primer
5'-ttaattttcattgcgtctcaaacc-3' (SEQ ID NO:208)
ID-8 (17)
Forward Primer
5'-atgacaaaaaaacttattattgctatattag-3' (SEQ ID NO:209)
Reverse Primer
5'-ttaacgattatcaacaaagttctgtac-3' (SEQ ID NO:210)
ID10 (22)
Forward Primer
5'-atgatacgccagttttttaagagaa-3' (SEQ ID NO:211)
Reverse Primer
5'-ttatttatgtatagaaacagcagtccc-3' (SEQ ID NO:212)

References

Anderson, R., Gao, X.-M., Papakonstantinopoulou, A., Roberts, M. and Dougan, G. (1996) Immune response in mice following immunisation with DNA encoding fragment C of tetanus toxin. *Infection and Immunity*, 64, 3168–3173.

Kurar, E. and Splitter, G. A. (1997) Nucleic acid vaccination of *Brucella abortus* ribosomal L7/L12 gene illicits immune response. *Vaccine*, 15, 1851–57.

Larsson, C., Stalhammer-Carlemalm, M., and Lindahl, G. 1996. Experimental vaccination against Group B *Streptococus*, an encapsulated bacterium, with highly purified preparations of cell surface proteins Rib and. *Infect. Immun.* 64: 3518–3523.

Larsson, C., Stalhammer-Carlemalm, M., and Lindahl, G. 1999. Protection against experimental infection with Group B *Streptococus* by immunization with a bivalent protein vaccine. *Vaccine*, 17: 454–458.

Stalhammer-carlemalm, M., Stenberg, L., and lindahl, G. 1993. Protein Rib: a novel Group B Streptococcal protein that confers protective immunity and is expressed by most strains causing invasive infections: *J. Exp. Med.* 177: 1593–1603.

Wastfelt, M., Stalhammer-Carlemalm, M., (1996) Identification of a family of Streptococcal surface proteins with extremely repetitive structure. *J. Biol. Chem.* 271: 18892–18897.

Zhang, D., Yang, X., Berry, J., Shen, C., McClarty, G. and Brunham, R. C. (1997) DNA vaccination with the major outer-membrane protein genes induces acquired immunity to *Chlamydia trachomatis* (mouse pneumonitis) infection. *Infection and Immunity*, 176, 1035–40.

What is claimed is:

1. An isolated protein or polypeptide, said protein or polypeptide selected from the group consisting of:
   a) Group B *Streptococcus* protein or polypeptide comprising the amino acid sequence of SEQ ID NO: 72, and
   b) a protein or polypeptide that is a derivative or variant of SEQ ID NO: 72, said protein or polypeptide comprising a sequence having at least 50% identity to SEQ ID NO: 72, wherein said derivative or variant is able to protect against Group B *Streptococcus* challenge.

2. The protein or polypeptide of claim 1, wherein said protein or polypeptide that is a derivative or variant of SEQ ID NO: 72 comprises a sequence having at least 70% identity to SEQ ID NO: 72.

3. An immunogenic composition comprising at least one protein or polypeptide of claim 1 or claim 2.

4. The immunogenic composition of claim 3, wherein said composition is a vaccine.

5. A kit for the detection of Group B *Streptococcus* comprising at least one Group B *Streptococcus* protein or polypeptide of claim 1 or claim 2.

6. Derivatives or variants of the proteins or polypeptides of claim 1 which show at least 90% identity to those proteins or polypeptides.

* * * * *

SEQUENCE LISTING

```
<160> NUMBER OF SEQ ID NOS: 212

<210> SEQ ID NO 1
<211> LENGTH: 1248
<212> TYPE: DNA
<213> ORGANISM: Streptococcus agalactiae

<400> SEQUENCE: 1
atggaaaaaa atacttggaa aaaattactt gttagtactg ctgctctttc agtagttgca      60
ggaggagcaa ttgctgctac tcactctaac tcagttgatg ctgcttcaaa aaaaactatc     120
aaactttggg tcccaacaga ttcaaaagcg tcttataaag caattgttaa aaaattcgag     180
aaggaaaaca aaggcgttac tgtaaaaatg attgagtcta atgactccaa agctcaagaa     240
aacgtaaaaa aagacccaag caaggcagcc gatgtattct cacttccaca tgaccaactt     300
ggtcaattag tagaatctgg tgttatccaa gaaattccag agcaatactc aaaagaaatt     360
```

```
gctaaaaacg acactaaaca atcacttact ggtgcacaat ataaagggaa aacttatgca    420
ttcccatttg gtattgaatc tcaagttctt tattataata aaacaaagtt aactgctgac    480
gacgttaaat catacgaaac aattacaagc aaagggaaat tcggtcaaca gcttaaagca    540
gctaactcat atgtaacagg tcctcttttc ctttctgtag gcgacacttt atttggtaaa    600
tctggtgaag atgctaaagg cactaactgg ggtaatgaag caggtgtttc tgtccttaaa    660
tggattgcag atcaaaagaa aaatgatggt tttgtcaact tgacagctga aaatacaatg    720
tctaaatttg gcgatggttc tgttcatgct tttgaaagtg gaccatggga ttacgacgct    780
gctaaaaaag ctgtcggtga agataaaatc ggtgttgctg tttacccaac aatgaaaatc    840
ggtgacaaag aagttcaaca aaaagcattc ttgggcgtta aactttatgc cgttaaccaa    900
gcacctgctg gttcaaacac taaacgaatc tcagctagct acaaactcgc tgcatatcta    960
actaatgctg aaagtcaaaa aattcaattc gaaaaacgtc atatcgttcc tgctaactca   1020
tcaattcaat cttctgatag cgtccaaaaa gatgaacttg caaaagcagt tatcgaaatg   1080
ggtagctcag ataaatatac aacggttatg cctaagttga gtcaaatgtc aacattctgg   1140
acagaaagtg ctgctattct tagcgatact tacagtggta aaatcaaatc tagcgattac   1200
cttaaacgtc taaacaatt cgataaagac atcgctaaaa caaaatag                 1248
```

<210> SEQ ID NO 2
<211> LENGTH: 415
<212> TYPE: PRT
<213> ORGANISM: Streptococcus agalactiae

<400> SEQUENCE: 2

```
Met Glu Lys Asn Thr Trp Lys Lys Leu Leu Val Ser Thr Ala Ala Leu
 1               5                  10                  15

Ser Val Val Ala Gly Gly Ala Ile Ala Ala Thr His Ser Asn Ser Val
                20                  25                  30

Asp Ala Ala Ser Lys Lys Thr Ile Lys Leu Trp Val Pro Thr Asp Ser
            35                  40                  45

Lys Ala Ser Tyr Lys Ala Ile Val Lys Lys Phe Glu Lys Glu Asn Lys
        50                  55                  60

Gly Val Thr Val Lys Met Ile Glu Ser Asn Asp Ser Lys Ala Gln Glu
 65                  70                  75                  80

Asn Val Lys Lys Asp Pro Ser Lys Ala Ala Asp Val Phe Ser Leu Pro
                85                  90                  95

His Asp Gln Leu Gly Gln Leu Val Glu Ser Gly Val Ile Gln Glu Ile
               100                 105                 110

Pro Glu Gln Tyr Ser Lys Glu Ile Ala Lys Asn Asp Thr Lys Gln Ser
           115                 120                 125

Leu Thr Gly Ala Gln Tyr Lys Gly Lys Thr Tyr Ala Phe Pro Phe Gly
       130                 135                 140

Ile Glu Ser Gln Val Leu Tyr Tyr Asn Lys Thr Lys Leu Thr Ala Asp
145                 150                 155                 160

Asp Val Lys Ser Tyr Glu Thr Ile Thr Ser Lys Gly Lys Phe Gly Gln
                165                 170                 175

Gln Leu Lys Ala Ala Asn Ser Tyr Val Thr Gly Pro Leu Phe Leu Ser
            180                 185                 190

Val Gly Asp Thr Leu Phe Gly Lys Ser Gly Glu Asp Ala Lys Gly Thr
        195                 200                 205

Asn Trp Gly Asn Glu Ala Gly Val Ser Val Leu Lys Trp Ile Ala Asp
```

```
               210                 215                 220
Gln Lys Lys Asn Asp Gly Phe Val Asn Leu Thr Ala Glu Asn Thr Met
225                 230                 235                 240

Ser Lys Phe Gly Asp Gly Ser Val His Ala Phe Glu Ser Gly Pro Trp
            245                 250                 255

Asp Tyr Asp Ala Ala Lys Lys Ala Val Gly Glu Asp Lys Ile Gly Val
                260                 265                 270

Ala Val Tyr Pro Thr Met Lys Ile Gly Asp Lys Glu Val Gln Gln Lys
            275                 280                 285

Ala Phe Leu Gly Val Lys Leu Tyr Ala Val Asn Gln Ala Pro Ala Gly
290                 295                 300

Ser Asn Thr Lys Arg Ile Ser Ala Ser Tyr Lys Leu Ala Ala Tyr Leu
305                 310                 315                 320

Thr Asn Ala Glu Ser Gln Lys Ile Gln Phe Glu Lys Arg His Ile Val
                325                 330                 335

Pro Ala Asn Ser Ser Ile Gln Ser Asp Ser Val Gln Lys Asp Glu
                340                 345                 350

Leu Ala Lys Ala Val Ile Glu Met Gly Ser Ser Asp Lys Tyr Thr Thr
            355                 360                 365

Val Met Pro Lys Leu Ser Gln Met Ser Thr Phe Trp Thr Glu Ser Ala
370                 375                 380

Ala Ile Leu Ser Asp Thr Tyr Ser Gly Lys Ile Lys Ser Ser Asp Tyr
385                 390                 395                 400

Leu Lys Arg Leu Lys Gln Phe Asp Lys Asp Ile Ala Lys Thr Lys
                405                 410                 415

<210> SEQ ID NO 3
<211> LENGTH: 1539
<212> TYPE: DNA
<213> ORGANISM: Streptococcus agalactiae

<400> SEQUENCE: 3
atgtcaaaac aaaaagtaac ggcaactttg ttgttatcca ctttagtctt atcgctatca      60
tcacctttag tgaccttagc agaaactatt aatccagaaa caagcctgac aatggcaaca     120
gcatcaacag aaagttcttc tgaagcagag aaacaggaaa aaacacaacc tacagattca     180
gaaactgctt caccttcagc cgaaggaagt atctcaacag aaaaaacaga gattggtacg     240
acagagacat catcaagcaa tgaatcatca tcaagttcat cacatcaatc ttcttccaac     300
gaagatgcta aacatctga ttctgcttca acagcatcta ctcctagcac taatactaca     360
aacagtagtc aagcagacag taagccaggt caatcaacaa agactgaatt aaaacctgag     420
cctaccttac cattagtaga gcctaaaata actcccgctc cgtctcagat agaaagtgtt     480
cagacaaatc agaatgcttc tgttcctgct ttatcctttg atgataactt attatcaaca     540
ccgatttcac cagtgacagc aacgccattc tacgtagaac actggtctgg tcaggatgcc     600
tactctcact atttattgtc acatcgttac ggtatcaaag ctgaacaatt agatgggtac     660
ttaaaatctt tagggattca aatgattct aatcgtatca atggtgctaa gttattacaa     720
tgggaaaaag atagtggttt agatgtccgt gctattgtag ctattgctgt ccttgaaagt     780
tcattgggaa ctcaaggagt ggctaaaatg ccaggtgcta atatgtttgg ttatggtgcc     840
tttgatcatg actctagcca tgctagtgct tataatgatg aagaagcaat tatgttgttg     900
acaaaaaata caattattaa aaacaacaac tctagctttg aaatccaaga tttgaaagca     960
cagaaattat cttctggaca acttaataca gttactgagg gtggtgttta ttatacagat    1020
```

```
aactctggaa ctggtaaacg tcgtgcccag attatggaag atttagaccg ctggattgat      1080
caacatggag ggacaccaga aattcctgct gccttgaaag ctttatcgac agcaagttta      1140
gcagatttac caagtggttt tagcttatca acagcggtta acacagctag ctatattgca      1200
tcaacttatc catggggtga atgtacatgg tatgtcttta accgcgctaa agagttaggt      1260
tatacatttg atccatttat gggtaatggt ggagattggc aacataaggc tgctttgaa       1320 acaacacatt caccaaaagt aggctatgct gtatcatttt caccaggaca agctggtgct      1380
gatggcactt acggtcacgt agctattgtt gaagaagtta aaaaagatgg ttcagttctc      1440
atttcagaat ctaatgcaat gggacgtggt attgtctctt accgtacttt tagttcagca      1500
caagctgcac aattaactta tggtattggc cataaataa                             1539

<210> SEQ ID NO 4
<211> LENGTH: 512
<212> TYPE: PRT
<213> ORGANISM: Streptococcus agalactiae

<400> SEQUENCE: 4

Met Ser Lys Gln Lys Val Thr Ala Thr Leu Leu Ser Thr Leu Val
 1               5                  10                  15

Leu Ser Leu Ser Ser Pro Leu Val Thr Leu Ala Glu Thr Ile Asn Pro
                 20                  25                  30

Glu Thr Ser Leu Thr Met Ala Thr Ala Ser Thr Glu Ser Ser Glu
             35                  40                  45

Ala Glu Lys Gln Glu Lys Thr Gln Pro Thr Asp Ser Glu Thr Ala Ser
     50                  55                  60

Pro Ser Ala Glu Gly Ser Ile Ser Thr Glu Lys Thr Glu Ile Gly Thr
 65                  70                  75                  80

Thr Glu Thr Ser Ser Ser Asn Glu Ser Ser Ser Ser Ser His Gln
                 85                  90                  95

Ser Ser Ser Asn Glu Asp Ala Lys Thr Ser Asp Ser Ala Ser Thr Ala
            100                 105                 110

Ser Thr Pro Ser Thr Asn Thr Thr Asn Ser Ser Gln Ala Asp Ser Lys
        115                 120                 125

Pro Gly Gln Ser Thr Lys Thr Glu Leu Lys Pro Glu Pro Thr Leu Pro
    130                 135                 140

Leu Val Glu Pro Lys Ile Thr Pro Ala Pro Ser Gln Ile Glu Ser Val
145                 150                 155                 160

Gln Thr Asn Gln Asn Ala Ser Val Pro Ala Leu Ser Phe Asp Asp Asn
                165                 170                 175

Leu Leu Ser Thr Pro Ile Ser Pro Val Thr Ala Thr Pro Phe Tyr Val
            180                 185                 190

Glu His Trp Ser Gly Gln Asp Ala Tyr Ser His Tyr Leu Leu Ser His
        195                 200                 205

Arg Tyr Gly Ile Lys Ala Glu Gln Leu Asp Gly Tyr Leu Lys Ser Leu
    210                 215                 220

Gly Ile Gln Tyr Asp Ser Asn Arg Ile Asn Gly Ala Lys Leu Leu Gln
225                 230                 235                 240

Trp Glu Lys Asp Ser Gly Leu Asp Val Arg Ala Ile Val Ala Ile Ala
                245                 250                 255

Val Leu Glu Ser Ser Leu Gly Thr Gln Gly Val Ala Lys Met Pro Gly
            260                 265                 270

Ala Asn Met Phe Gly Tyr Gly Ala Phe Asp His Asp Ser Ser His Ala
```

```
                    275               280               285
Ser Ala Tyr Asn Asp Glu Glu Ala Ile Met Leu Leu Thr Lys Asn Thr
    290                 295                 300

Ile Ile Lys Asn Asn Asn Ser Ser Phe Glu Ile Gln Asp Leu Lys Ala
305                 310                 315                 320

Gln Lys Leu Ser Ser Gly Gln Leu Asn Thr Val Thr Glu Gly Gly Val
            325                 330                 335

Tyr Tyr Thr Asp Asn Ser Gly Thr Gly Lys Arg Arg Ala Gln Ile Met
                340                 345                 350

Glu Asp Leu Asp Arg Trp Ile Asp Gln His Gly Gly Thr Pro Glu Ile
            355                 360                 365

Pro Ala Ala Leu Lys Ala Leu Ser Thr Ala Ser Leu Ala Asp Leu Pro
    370                 375                 380

Ser Gly Phe Ser Leu Ser Thr Ala Val Asn Thr Ala Ser Tyr Ile Ala
385                 390                 395                 400

Ser Thr Tyr Pro Trp Gly Glu Cys Thr Trp Tyr Val Phe Asn Arg Ala
                405                 410                 415

Lys Glu Leu Gly Tyr Thr Phe Asp Pro Phe Met Gly Asn Gly Gly Asp
            420                 425                 430

Trp Gln His Lys Ala Gly Phe Glu Thr Thr His Ser Pro Lys Val Gly
    435                 440                 445

Tyr Ala Val Ser Phe Ser Pro Gly Gln Ala Gly Ala Asp Gly Thr Tyr
    450                 455                 460

Gly His Val Ala Ile Val Glu Glu Val Lys Lys Asp Gly Ser Val Leu
465                 470                 475                 480

Ile Ser Glu Ser Asn Ala Met Gly Arg Gly Ile Val Ser Tyr Arg Thr
                485                 490                 495

Phe Ser Ser Ala Gln Ala Ala Gln Leu Thr Tyr Gly Ile Gly His Lys
            500                 505                 510

<210> SEQ ID NO 5
<211> LENGTH: 1293
<212> TYPE: DNA
<213> ORGANISM: Streptococcus agalactiae

<400> SEQUENCE: 5
gtgcatatgt tacaaaacat tggacaaaca ggcattcaag caactcgaat tgctttaggt        60
tgtatgagaa tgagtgactt gaaaggaaaa caagctgaag aagtagttgg aacagcatta      120
gatttgggta ttataaataa taaagtgcaa gaaagtgtct ctggcgtcaa agtgactaaa      180
tcattgtgtt atcaagaaca agaaattgct tcttttcaag agattaatca gatgactttc      240
gtgaagaaca tgcggaccat gacttatgat gtcatgtttg atcctttagt tcttcttttt      300
ataggtgcct cctacgtatt aacattggct atgggagctt ttatgatttc aaaaggtcaa      360
gttactgttg tgacttggt aacatttgtg acgtatttag atatgttggt atggcccttg       420
atggcgattg gtttcttgtt caatatggta cagcgtggta gtgtttctta taccgtatt       480 aatagtctac ttgagcaaga atcggatata actgatcctt aaatcctat caaacctgtt      540 gtcaatggaa cattaagata tgatattgat ttctttagat acgacaatga ggaaacctta      600
gccgatattc atttcacctt agaaaaaggt caaaccttag gttggtagg tcaaacggga      660 tcagggaaga caagtcttat taagttattg ctacgtgaac atgatgtgac tcagggaaa      720 attactttaa ataaacatga tatacgtgat tatcgattgt ctgagttacg tcaactaatc      780
ggttatgttc ctcaagatca gttttattt gctaccagta ttttagaaaa tgttcgcttt      840
```

-continued

```
ggaaatccaa ctctatctat caatgctgtc aaagaagcaa ctaaattggc acatgtttac      900
gatgacattg aacagatgcc agcaggattt gagactctaa ttggagaaaa aggagtctca      960
ttatctggtg acaaaaaaca aaggattgcg atgagtcgtg ccatgatttt agatccagat     1020
attcttattt tggatgattc tctatcagca gtggacgcta aaacggaaca tgctattgtt     1080
gagaatctta aaacgaatcg tcaagggaaa tcgactatta tttcagcaca tcgtttatca     1140
gctgttgtgc acgcagacct tatcttagtt atgcgagacg gcagagtcat tgagcgaggt     1200
caacatcaag agttgctaaa taaaggtggt tggtatgctg aaacgtatgc ctcacagcaa     1260
ttagaaatgg aggaagcatt tgatgaagtc taa                                  1293
```

<210> SEQ ID NO 6
<211> LENGTH: 430
<212> TYPE: PRT
<213> ORGANISM: Streptococcus agalactiae

<400> SEQUENCE: 6

```
Met His Met Leu Gln Asn Ile Gly Gln Thr Gly Ile Gln Ala Thr Arg
 1               5                  10                  15

Ile Ala Leu Gly Cys Met Arg Met Ser Asp Leu Lys Gly Lys Gln Ala
                20                  25                  30

Glu Glu Val Val Gly Thr Ala Leu Asp Leu Gly Ile Ile Asn Asn Lys
            35                  40                  45

Val Gln Glu Ser Val Ser Gly Val Lys Val Thr Lys Ser Leu Cys Tyr
        50                  55                  60

Gln Glu Gln Glu Ile Ala Ser Phe Gln Glu Ile Asn Gln Met Thr Phe
65                  70                  75                  80

Val Lys Asn Met Arg Thr Met Thr Tyr Asp Val Met Phe Asp Pro Leu
                85                  90                  95

Val Leu Leu Phe Ile Gly Ala Ser Tyr Val Leu Thr Leu Ala Met Gly
            100                 105                 110

Ala Phe Met Ile Ser Lys Gly Gln Val Thr Val Gly Asp Leu Val Thr
        115                 120                 125

Phe Val Thr Tyr Leu Asp Met Leu Val Trp Pro Leu Met Ala Ile Gly
    130                 135                 140

Phe Leu Phe Asn Met Val Gln Arg Gly Ser Val Ser Tyr Asn Arg Ile
145                 150                 155                 160

Asn Ser Leu Leu Glu Gln Glu Ser Asp Ile Thr Asp Pro Leu Asn Pro
                165                 170                 175

Ile Lys Pro Val Val Asn Gly Thr Leu Arg Tyr Asp Ile Asp Phe Phe
            180                 185                 190

Arg Tyr Asp Asn Glu Glu Thr Leu Ala Asp Ile His Phe Thr Leu Glu
        195                 200                 205

Lys Gly Gln Thr Leu Gly Leu Val Gly Gln Thr Gly Ser Gly Lys Thr
    210                 215                 220

Ser Leu Ile Lys Leu Leu Leu Arg Glu His Asp Val Thr Gln Gly Lys
225                 230                 235                 240

Ile Thr Leu Asn Lys His Asp Ile Arg Asp Tyr Arg Leu Ser Glu Leu
                245                 250                 255

Arg Gln Leu Ile Gly Tyr Val Pro Gln Asp Gln Phe Leu Phe Ala Thr
            260                 265                 270

Ser Ile Leu Glu Asn Val Arg Phe Gly Asn Pro Thr Leu Ser Ile Asn
        275                 280                 285
```

-continued

Ala Val Lys Glu Ala Thr Lys Leu Ala His Val Tyr Asp Asp Ile Glu
    290             295                 300

Gln Met Pro Ala Gly Phe Glu Thr Leu Ile Gly Lys Gly Val Ser
305             310                 315                 320

Leu Ser Gly Gly Gln Lys Gln Arg Ile Ala Met Ser Arg Ala Met Ile
                325                 330                 335

Leu Asp Pro Asp Ile Leu Ile Leu Asp Asp Ser Leu Ser Ala Val Asp
            340                 345                 350

Ala Lys Thr Glu His Ala Ile Val Glu Asn Leu Lys Thr Asn Arg Gln
        355                 360                 365

Gly Lys Ser Thr Ile Ile Ser Ala His Arg Leu Ser Ala Val Val His
370                 375                 380

Ala Asp Leu Ile Leu Val Met Arg Asp Gly Arg Val Ile Glu Arg Gly
385                 390                 395                 400

Gln His Gln Glu Leu Leu Asn Lys Gly Gly Trp Tyr Ala Glu Thr Tyr
                405                 410                 415

Ala Ser Gln Gln Leu Glu Met Glu Glu Ala Phe Asp Glu Val
            420                 425                 430

<210> SEQ ID NO 7
<211> LENGTH: 999
<212> TYPE: DNA
<213> ORGANISM: Streptococcus agalactiae

<400> SEQUENCE: 7
ttgatgaagt ctaatcaatg gcaagtcttt aagagattaa tctcctattt acgcccttat      60
aaatggttta cagtattagc tctatctctc ttattgttga cgactgttgt taaaaatatt     120
attcctttaa ttgcttcaca ttttattgat cactatctga caaatgttaa tcaaacagca     180
gttcttattt tagtgggata ttattcaatg tatgtcttgc agaccttaat tcaatatttt     240
gggaatctct ttttgcgcg tgtttcttat agtattgtta gagatattcg tagagatgct     300
tttgctaata tggaaaggct aggcatgtct tattttgata ggacaccggc aggatctatt     360
gtgtcacgta ttactaatga tactgaagca atatctgata tgttttcggg tattttatca     420
agttttatct cggcgatatt tattttaca gttactctgt acactatgtt gatgctagac     480
attaaactaa caggactcgt cgctcttttg ttacctgtta tctttatatt agtgaatgtc     540
tatcggaaaa aatcagtcac tgtcattgct aaaacgagaa gtttacttag tgatatcaac     600
agtaaattat caggaagtat tgaaggaatt cgcattgtac aggcttttgg tcaagaagag     660
cgcttgaaga ctgaatttga ggaaattaac aaagagcatg ttgtgtatgc caatcgttct     720
atggctcttg atagtctctt cttaagaccg gcgatgtctc ttttaaaact cctagcatat     780
gctgttctta tgtcttattt tggatttaca ggagttaaag gaggtcttac ggcaggatta     840
atgtatgctt ttattcagta cgttaatcgt ctatttgacc cttttaattga agtaacgcaa     900
aattttttcaa ccttacaaac atcaatggta tcagcagggc gtgtgtttga tctgattgat     960
gaaacaggtt ttgaaccaag ccaaaaaaat acagaagct                           999

<210> SEQ ID NO 8
<211> LENGTH: 332
<212> TYPE: PRT
<213> ORGANISM: Streptococcus agalactiae

<400> SEQUENCE: 8

Met Lys Ser Asn Gln Trp Gln Val Phe Lys Arg Leu Ile Ser Tyr Leu
  1               5                  10                  15

-continued

```
Arg Pro Tyr Lys Trp Phe Thr Val Leu Ala Leu Ser Leu Leu Leu Leu
                 20                  25                  30

Thr Thr Val Val Lys Asn Ile Ile Pro Leu Ile Ala Ser His Phe Ile
         35                  40                  45

Asp His Tyr Leu Thr Asn Val Asn Gln Thr Ala Val Leu Ile Leu Val
     50                  55                  60

Gly Tyr Tyr Ser Met Tyr Val Leu Gln Thr Leu Ile Gln Tyr Phe Gly
 65                  70                  75                  80

Asn Leu Phe Phe Ala Arg Val Ser Tyr Ser Ile Val Arg Asp Ile Arg
                 85                  90                  95

Arg Asp Ala Phe Ala Asn Met Glu Arg Leu Gly Met Ser Tyr Phe Asp
                100                 105                 110

Arg Thr Pro Ala Gly Ser Ile Val Ser Arg Ile Thr Asn Asp Thr Glu
            115                 120                 125

Ala Ile Ser Asp Met Phe Ser Gly Ile Leu Ser Ser Phe Ile Ser Ala
        130                 135                 140

Ile Phe Ile Phe Thr Val Thr Leu Tyr Thr Met Leu Met Leu Asp Ile
145                 150                 155                 160

Lys Leu Thr Gly Leu Val Ala Leu Leu Leu Pro Val Ile Phe Ile Leu
                165                 170                 175

Val Asn Val Tyr Arg Lys Lys Ser Val Thr Val Ile Ala Lys Thr Arg
            180                 185                 190

Ser Leu Leu Ser Asp Ile Asn Ser Lys Leu Ser Gly Ser Ile Glu Gly
        195                 200                 205

Ile Arg Ile Val Gln Ala Phe Gly Gln Glu Arg Leu Lys Thr Glu
    210                 215                 220

Phe Glu Glu Ile Asn Lys Glu His Val Val Tyr Ala Asn Arg Ser Met
225                 230                 235                 240

Ala Leu Asp Ser Leu Phe Leu Arg Pro Ala Met Ser Leu Leu Lys Leu
                245                 250                 255

Leu Ala Tyr Ala Val Leu Met Ser Tyr Phe Gly Phe Thr Gly Val Lys
            260                 265                 270

Gly Gly Leu Thr Ala Gly Leu Met Tyr Ala Phe Ile Gln Tyr Val Asn
        275                 280                 285

Arg Leu Phe Asp Pro Leu Ile Glu Val Thr Gln Asn Phe Ser Thr Leu
    290                 295                 300

Gln Thr Ser Met Val Ser Ala Gly Arg Val Phe Asp Leu Ile Asp Glu
305                 310                 315                 320

Thr Gly Phe Glu Pro Ser Gln Lys Asn Thr Glu Ala
                325                 330
```

<210> SEQ ID NO 9
<211> LENGTH: 3753
<212> TYPE: DNA
<213> ORGANISM: Streptococcus agalactiae

<400> SEQUENCE: 9

| | | | | | | |
|---|---|---|---|---|---|---|
| atgaaaagaa | aagacttatt | tggtgataaa | caaactcaat | acacgattag | aaagttaagt | 60 |
| gttggagtag | cttcagttgc | aacaggggta | tgtatttttc | ttcatagtcc | acagtatttt | 120 |
| gctgaagaag | taagtgtttc | tcctgcaact | acagcgattc | caaagtcgaa | tattaatcag | 180 |
| gttgacaacc | ggcaatctac | taatttaaaa | gatgacataa | actcaaactc | tgagacggtt | 240 |
| gtgacaccct | cagatatgcc | ggataccaag | caattagtat | cagatgaaac | tgacactcaa | 300 |

-continued

```
aaaggagtga cagagccgga taaggcgaca agcctgcttg aagaaaataa aggtcctgtt     360
tcagataaaa ataccttaga tttaaaagtg gcaccatcta cattgcaaaa tactcccgac    420
aaaacttctc aagctatagg tgctccaagt ccgaccttga aagttgctaa tcaagctcca    480
cagattgaaa atggttactt taggttacat cttaaagaat tgcctcaagg tcatcctgta    540
gaaagcactg gctttggat atggggagat gttgatcaac cgtctagtaa ttggccaaat     600
ggtgctatcc ctatgactaa tgctaagaaa gatgattacg gttattatgt tgattttaaa    660
ttatctgaaa aacaacgaaa acaaatatct tttttaatta ataacaaagc aggaacaaat    720
ttaagcggcg atcatcatat tccattatta cgacctgaga tgaaccaagt ttggattgat    780
gaaaagtacg gtatacatac ttatcagccc ctcaaagaag ggtatgtccg tattaactat    840
ttgagttcat ctggtaacta tgaccactta tcagcatggc tctttaaaga tgttgcaacc    900
ccctcaacaa cttggccaga tggtagtaat tttgtgaatc aaggactata tggaaggtat    960
attgatgtac cactgaaaac taatgccaaa gagattggtt ttctaatctt agatgaaagt   1020
aagacaggag atgcagtgaa agttcaaccc aacgactatg ttttagaga tttagctaac   1080 cataaccaaa tttttgtaaa agataaggat ccaaaggttt ataataatcc ttattacatt   1140
gatcaagtgc agctaaagga tgctcaacaa actgatttaa caagtattca agcaagtttt   1200
acaactctag atggggtaga taaaactgaa attttaaaag aattgaaagt gacagataaa   1260
aatcaaaatg ctatacaaat ttctgatatc actctcgata ctagtaaatc tcttttaata   1320
atcaaaggcg actttaatcc taaacaaggt catttcaata tatcttataa tggtaacaat   1380
gtcacgacaa ggcaatcttg ggaatttaaa gaccaacttt atgcttatag tggaaattta   1440
ggtgcagttc tcaatcaaga tggttcaaaa gttgaagcca gcctctggtc accgagtgct   1500
gatagtgtca ctatgattat ttatgacaaa gataatcaaa acagggttgt agcgactacc   1560
ccccttgtga aaataataa aggtgtttgg cagacgatac ttgatactaa attaggtatt    1620
aaaaactata ctggttacta ttatctttac gaaataaaaa gaggtaagga taaggttaag   1680
attttagatc cttatgcaaa gtcattagca gagtgggata gtaatactgt taatgacgat   1740
ataaaaacgg ctaaagcagc ttttgtaaat ccaagtcaac ttggacctaa aaatttaagt   1800
tttgctaaaa ttgctaattt taaggaaaa caagatgctg ttatatacga agcacatgta    1860
agagacttca cttctgatca atctttggac ggaaaattaa aaaatcaact tggtaccttt   1920
gcagcctttt cagagaaact agattattta cagaaattag gagttacaca cattcagctt   1980
ttaccggtat tgagttattt ttatgttaat gaaatggata agtcacgctc aacagcttac   2040
acttcctcag acaataatta caattggggc tatgacccac agagctattt tgctctttct   2100
ggaatgtatt cagagaaacc aaaagatcca tcagcacgta tcgccgaatt aaaacaatta   2160
atacatgata ttcataaacg tggcatgggg gttatacttg atgtcgtcta taatcacact   2220
gcaaaaactt atctctttga ggatatagaa cctaattatt atcactttat gaatgaagat   2280
ggttcaccaa gagaaagttt tggaggggga cgtttaggaa ccactcatgc aatgagtcgt   2340
cgtgttttgg ttgattccat taaatatctt acaagtgaat ttaaagttga tggtttccgt   2400
tttgatatga tgggagatca tgatgcggct gcgattgaat tagcttataa agaagctaaa   2460
gctattaatc ctaatatgat tatgattggt gagggctgga gaacattcca aggcgatcaa   2520
ggtaagccgg ttaaaccagc tgaccaagat tggatgaagt caaccgatac agttggcgtc   2580
ttttcagatg atattcgtaa tagcttgaaa tctggttttc caaatgaagg tactccagct   2640
ttcatcacag gtggcccaca atctttacaa ggtattttta aaaatatcaa agcacaacct   2700
```

```
gggaattttg aagcagattc gccaggagat gtggtgcagt atattgctgc acatgataac   2760
cttaccttgc atgatgtgat tgcaaaatca attaataaag accctaaggt agctgaagaa   2820
gatattcata gacgtctgcg tttaggaaat gtaatgattt taacatctca agggacagca   2880
ttcattcatt ctggtcaaga gtatggtcgt acgaagcgtt tacttaaccc tgattacatg   2940
acaaaagttt cagatgacaa attgcctaat aaagcaacac ttattgaagc tgttaaagaa   3000
tacccatatt ttattcatga ttcatatgat tcttcagatg ccattaatca ttttgattgg   3060
gcagcagcca cagataataa caaacaccca atttcaacga aaacacaggc ctatacagca   3120
ggtttaatca cattaaggcg ttcaacagat gctttccgga aattgagcaa agcagaaatt   3180
gatcgtgagg ttagcttgat tacagaggta ggtcaaggtg atattaaaga aaaagatttg   3240
gttattgctt accaaacaat agattctaaa ggcgatattt acgcagtatt tgttaatgct   3300
gatagtaaag ctagaaacgt tttactaggt gaaaaatata acacctttt aaaagggcaa   3360
gtaattgttg atgctgatca agcggggatt aaaccaatct caactcctag aggtgttcat   3420
tttgaaaaag atagtttgct gattgatcca ttaacagcaa ttgtgattaa agttggcaaa   3480
gttgctccta gccctaagga ggaattgcaa gcagattatc ccaaaacaca atctttcaag   3540
ggatctaaaa cggtagaaaa agtaaataga atagctaata agacctcaat aactcctgta   3600
gtttctaata agaccgattc atatctgaca aatgaagcta atttgccaaa actggagat   3660
aagtcatcaa aaatactaag tgtagtagga ataagcattc tagcaagtct acttgctcta   3720
ctaggtctct ctttaaagag gaatcgcact taa                                3753

<210> SEQ ID NO 10
<211> LENGTH: 1250
<212> TYPE: PRT
<213> ORGANISM: Streptococcus agalactiae

<400> SEQUENCE: 10

Met Lys Arg Lys Asp Leu Phe Gly Asp Lys Gln Thr Gln Tyr Thr Ile
 1               5                  10                  15

Arg Lys Leu Ser Val Gly Val Ala Ser Val Ala Thr Gly Val Cys Ile
            20                  25                  30

Phe Leu His Ser Pro Gln Val Phe Ala Glu Glu Val Ser Val Ser Pro
        35                  40                  45

Ala Thr Thr Ala Ile Ala Lys Ser Asn Ile Asn Gln Val Asp Asn Arg
    50                  55                  60

Gln Ser Thr Asn Leu Lys Asp Asp Ile Asn Ser Asn Ser Glu Thr Val
65                  70                  75                  80

Val Thr Pro Ser Asp Met Pro Asp Thr Lys Gln Leu Val Ser Asp Glu
                85                  90                  95

Thr Asp Thr Gln Lys Gly Val Thr Glu Pro Asp Lys Ala Thr Ser Leu
            100                 105                 110

Leu Glu Glu Asn Lys Gly Pro Val Ser Asp Lys Asn Thr Leu Asp Leu
        115                 120                 125

Lys Val Ala Pro Ser Thr Leu Gln Asn Thr Pro Asp Lys Thr Ser Gln
    130                 135                 140

Ala Ile Gly Ala Pro Ser Pro Thr Leu Lys Val Ala Asn Gln Ala Pro
145                 150                 155                 160

Gln Ile Glu Asn Gly Tyr Phe Arg Leu His Leu Lys Glu Leu Pro Gln
                165                 170                 175

Gly His Pro Val Glu Ser Thr Gly Leu Trp Ile Trp Gly Asp Val Asp
```

```
                180             185             190
Gln Pro Ser Ser Asn Trp Pro Asn Gly Ala Ile Pro Met Thr Asn Ala
            195                 200                 205
Lys Lys Asp Asp Tyr Gly Tyr Tyr Val Asp Phe Lys Leu Ser Glu Lys
            210                 215                 220
Gln Arg Lys Gln Ile Ser Phe Leu Ile Asn Asn Lys Ala Gly Thr Asn
225                 230                 235                 240
Leu Ser Gly Asp His His Ile Pro Leu Leu Arg Pro Glu Met Asn Gln
                245                 250                 255
Val Trp Ile Asp Glu Lys Tyr Gly Ile His Thr Tyr Gln Pro Leu Lys
            260                 265                 270
Glu Gly Tyr Val Arg Ile Asn Tyr Leu Ser Ser Gly Asn Tyr Asp
            275                 280                 285
His Leu Ser Ala Trp Leu Phe Lys Asp Val Ala Thr Pro Ser Thr Thr
    290                 295                 300
Trp Pro Asp Gly Ser Asn Phe Val Asn Gln Gly Leu Tyr Gly Arg Tyr
305                 310                 315                 320
Ile Asp Val Pro Leu Lys Thr Asn Ala Lys Glu Ile Gly Phe Leu Ile
                325                 330                 335
Leu Asp Glu Ser Lys Thr Gly Asp Ala Val Lys Val Gln Pro Asn Asp
            340                 345                 350
Tyr Val Phe Arg Asp Leu Ala Asn His Asn Gln Ile Phe Val Lys Asp
            355                 360                 365
Lys Asp Pro Lys Val Tyr Asn Asn Pro Tyr Tyr Ile Asp Gln Val Gln
370                 375                 380
Leu Lys Asp Ala Gln Gln Thr Asp Leu Thr Ser Ile Gln Ala Ser Phe
385                 390                 395                 400
Thr Thr Leu Asp Gly Val Asp Lys Thr Glu Ile Leu Lys Glu Leu Lys
                405                 410                 415
Val Thr Asp Lys Asn Gln Asn Ala Ile Gln Ile Ser Asp Ile Thr Leu
            420                 425                 430
Asp Thr Ser Lys Ser Leu Leu Ile Ile Lys Gly Asp Phe Asn Pro Lys
            435                 440                 445
Gln Gly His Phe Asn Ile Ser Tyr Asn Gly Asn Asn Val Thr Thr Arg
450                 455                 460
Gln Ser Trp Glu Phe Lys Asp Gln Leu Tyr Ala Tyr Ser Gly Asn Leu
465                 470                 475                 480
Gly Ala Val Leu Asn Gln Asp Gly Ser Lys Val Glu Ala Ser Leu Trp
                485                 490                 495
Ser Pro Ser Ala Asp Ser Val Thr Met Ile Ile Tyr Asp Lys Asp Asn
            500                 505                 510
Gln Asn Arg Val Val Ala Thr Thr Pro Leu Val Lys Asn Asn Lys Gly
            515                 520                 525
Val Trp Gln Thr Ile Leu Asp Thr Lys Leu Gly Ile Lys Asn Tyr Thr
            530                 535                 540
Gly Tyr Tyr Tyr Leu Tyr Glu Ile Lys Arg Gly Lys Asp Lys Val Lys
545                 550                 555                 560
Ile Leu Asp Pro Tyr Ala Lys Ser Leu Ala Glu Trp Asp Ser Asn Thr
                565                 570                 575
Val Asn Asp Asp Ile Lys Thr Ala Lys Ala Phe Val Asn Pro Ser
            580                 585                 590
Gln Leu Gly Pro Lys Asn Leu Ser Phe Ala Lys Ile Ala Asn Phe Lys
            595                 600                 605
```

```
Gly Lys Gln Asp Ala Val Ile Tyr Glu Ala His Val Arg Asp Phe Thr
    610                 615                 620
Ser Asp Gln Ser Leu Asp Gly Lys Leu Lys Asn Gln Leu Gly Thr Phe
625                 630                 635                 640
Ala Ala Phe Ser Glu Lys Leu Asp Tyr Leu Gln Lys Leu Gly Val Thr
                645                 650                 655
His Ile Gln Leu Leu Pro Val Leu Ser Tyr Phe Tyr Val Asn Glu Met
            660                 665                 670
Asp Lys Ser Arg Ser Thr Ala Tyr Thr Ser Ser Asp Asn Asn Tyr Asn
        675                 680                 685
Trp Gly Tyr Asp Pro Gln Ser Tyr Phe Ala Leu Ser Gly Met Tyr Ser
690                 695                 700
Glu Lys Pro Lys Asp Pro Ser Ala Arg Ile Ala Glu Leu Lys Gln Leu
705                 710                 715                 720
Ile His Asp Ile His Lys Arg Gly Met Gly Val Ile Leu Asp Val Val
                725                 730                 735
Tyr Asn His Thr Ala Lys Thr Tyr Leu Phe Glu Asp Ile Glu Pro Asn
            740                 745                 750
Tyr Tyr His Phe Met Asn Glu Asp Gly Ser Pro Arg Glu Ser Phe Gly
        755                 760                 765
Gly Gly Arg Leu Gly Thr Thr His Ala Met Ser Arg Arg Val Leu Val
770                 775                 780
Asp Ser Ile Lys Tyr Leu Thr Ser Glu Phe Lys Val Asp Gly Phe Arg
785                 790                 795                 800
Phe Asp Met Met Gly Asp His Asp Ala Ala Ile Glu Leu Ala Tyr
                805                 810                 815
Lys Glu Ala Lys Ala Ile Asn Pro Asn Met Ile Met Ile Gly Glu Gly
                820                 825                 830
Trp Arg Thr Phe Gln Gly Asp Gln Gly Lys Pro Val Lys Pro Ala Asp
            835                 840                 845
Gln Asp Trp Met Lys Ser Thr Asp Thr Val Gly Val Phe Ser Asp Asp
850                 855                 860
Ile Arg Asn Ser Leu Lys Ser Gly Phe Pro Asn Glu Gly Thr Pro Ala
865                 870                 875                 880
Phe Ile Thr Gly Gly Pro Gln Ser Leu Gln Ile Phe Lys Asn Ile
                885                 890                 895
Lys Ala Gln Pro Gly Asn Phe Glu Ala Asp Ser Pro Gly Asp Val Val
                900                 905                 910
Gln Tyr Ile Ala Ala His Asp Asn Leu Thr Leu His Asp Val Ile Ala
            915                 920                 925
Lys Ser Ile Asn Lys Asp Pro Lys Val Ala Glu Glu Asp Ile His Arg
        930                 935                 940
Arg Leu Arg Leu Gly Asn Val Met Ile Leu Thr Ser Gln Gly Thr Ala
945                 950                 955                 960
Phe Ile His Ser Gly Gln Glu Tyr Gly Arg Thr Lys Arg Leu Leu Asn
                965                 970                 975
Pro Asp Tyr Met Thr Lys Val Ser Asp Lys Leu Pro Asn Lys Ala
                980                 985                 990
Thr Leu Ile Glu Ala Val Lys Glu Tyr Pro Tyr Phe Ile His Asp Ser
            995                 1000                1005
Tyr Asp Ser Ser Asp Ala Ile Asn His Phe Asp Trp Ala Ala Ala Thr
        1010                1015                1020
```

Asp Asn Asn Lys His Pro Ile Ser Thr Lys Thr Gln Ala Tyr Thr Ala
1025                1030                1035                1040

Gly Leu Ile Thr Leu Arg Arg Ser Thr Asp Ala Phe Arg Lys Leu Ser
            1045                1050                1055

Lys Ala Glu Ile Asp Arg Glu Val Ser Leu Ile Thr Glu Val Gly Gln
        1060                1065                1070

Gly Asp Ile Lys Glu Lys Asp Leu Val Ile Ala Tyr Gln Thr Ile Asp
    1075                1080                1085

Ser Lys Gly Asp Ile Tyr Ala Val Phe Val Asn Ala Asp Ser Lys Ala
    1090                1095                1100

Arg Asn Val Leu Leu Gly Glu Lys Tyr Lys His Leu Leu Lys Gly Gln
1105                1110                1115                1120

Val Ile Val Asp Ala Asp Gln Ala Gly Ile Lys Pro Ile Ser Thr Pro
            1125                1130                1135

Arg Gly Val His Phe Glu Lys Asp Ser Leu Leu Ile Asp Pro Leu Thr
        1140                1145                1150

Ala Ile Val Ile Lys Val Gly Lys Val Ala Pro Ser Pro Lys Glu Glu
    1155                1160                1165

Leu Gln Ala Asp Tyr Pro Lys Thr Gln Ser Phe Lys Gly Ser Lys Thr
    1170                1175                1180

Val Glu Lys Val Asn Arg Ile Ala Asn Lys Thr Ser Ile Thr Pro Val
1185                1190                1195                1200

Val Ser Asn Lys Thr Asp Ser Tyr Leu Thr Asn Glu Ala Asn Leu Pro
            1205                1210                1215

Lys Thr Gly Asp Lys Ser Ser Lys Ile Leu Ser Val Val Gly Ile Ser
        1220                1225                1230

Ile Leu Ala Ser Leu Leu Ala Leu Leu Gly Leu Ser Leu Lys Arg Asn
    1235                1240                1245

Arg Thr
  1250

<210> SEQ ID NO 11
<211> LENGTH: 921
<212> TYPE: DNA
<213> ORGANISM: Streptococcus agalactiae

<400> SEQUENCE: 11
atgaaaaaag ttttttttct catggctatg gttgtgagtt tagtaatgat agcagggtgt        60
gataagtcag caaaccccaa acagcctacg caaggcatgt cagttgtaac cagcttttac       120
ccaatgtatg cgatgacaaa agaagtatct ggagacctaa atgatgtgag gatgatccaa       180
tcaggtgcag gcattcattc ctttgaaccg tctgtaaatg atgtggcagc tatttatgac       240
gcggatttgt ttgtttacca atcacatacc ttagaagctt gggcaaggga tctagaccct       300
aatttaaaaa aatcaaaggt taatgtgttt gaagcgtcaa aacctctgac actagataga       360
gtcaaagggc tagaagatat ggaagtcaca caaggcattg accctgcgac actttatgac       420
ccacataccc tggacggatcc cgttttagct ggtgaggaag ctgttaatat cgctaaagag       480
ctaggacatt tggatcctaa acacaaagac agttacacta aaaggctaa ggctttcaaa       540 aaagaagcag agcaactaac tgaagaatac actcaaaaat ttaaaaaggt gcgctcaaaa       600
acatttgtga cgcaacacac ggcattttct tatctggcta acgattcgg cttgaaacaa       660 cttggtatct cgggtatttc tccagagcaa gagccctctc ctcgccaatt gaaagaaatt       720
caagactttg ttaagaata acgtcaag actatttttg cagaagacaa cgtcaacccc       780

```
aaaattgctc atgctattgc gaaatcaaca ggagctaaag taaagacatt aagtccactt    840
gaagctgctc caagcggaaa caagacatat ctagaaaatc ttagagcaaa tttggaagtg    900
ctctatcaac agttgaagta a                                              921
```

<210> SEQ ID NO 12
<211> LENGTH: 306
<212> TYPE: PRT
<213> ORGANISM: Streptococcus agalactiae

<400> SEQUENCE: 12

```
Met Lys Lys Val Phe Phe Leu Met Ala Met Val Val Ser Leu Val Met
 1               5                  10                  15

Ile Ala Gly Cys Asp Lys Ser Ala Asn Pro Lys Gln Pro Thr Gln Gly
            20                  25                  30

Met Ser Val Val Thr Ser Phe Tyr Pro Met Tyr Ala Met Thr Lys Glu
        35                  40                  45

Val Ser Gly Asp Leu Asn Asp Val Arg Met Ile Gln Ser Gly Ala Gly
    50                  55                  60

Ile His Ser Phe Glu Pro Ser Val Asn Asp Val Ala Ala Ile Tyr Asp
65                  70                  75                  80

Ala Asp Leu Phe Val Tyr Gln Ser His Thr Leu Glu Ala Trp Ala Arg
                85                  90                  95

Asp Leu Asp Pro Asn Leu Lys Lys Ser Lys Val Asn Val Phe Glu Ala
            100                 105                 110

Ser Lys Pro Leu Thr Leu Asp Arg Val Lys Gly Leu Glu Asp Met Glu
        115                 120                 125

Val Thr Gln Gly Ile Asp Pro Ala Thr Leu Tyr Asp Pro His Thr Trp
    130                 135                 140

Thr Asp Pro Val Leu Ala Gly Glu Glu Ala Val Asn Ile Ala Lys Glu
145                 150                 155                 160

Leu Gly His Leu Asp Pro Lys His Lys Asp Ser Tyr Thr Lys Lys Ala
                165                 170                 175

Lys Ala Phe Lys Lys Glu Ala Glu Gln Leu Thr Glu Glu Tyr Thr Gln
            180                 185                 190

Lys Phe Lys Lys Val Arg Ser Lys Thr Phe Val Thr Gln His Thr Ala
        195                 200                 205

Phe Ser Tyr Leu Ala Lys Arg Phe Gly Leu Lys Gln Leu Gly Ile Ser
    210                 215                 220

Gly Ile Ser Pro Glu Gln Glu Pro Ser Pro Arg Gln Leu Lys Glu Ile
225                 230                 235                 240

Gln Asp Phe Val Lys Glu Tyr Asn Val Lys Thr Ile Phe Ala Glu Asp
                245                 250                 255

Asn Val Asn Pro Lys Ile Ala His Ala Ile Ala Lys Ser Thr Gly Ala
            260                 265                 270

Lys Val Lys Thr Leu Ser Pro Leu Glu Ala Ala Pro Ser Gly Asn Lys
        275                 280                 285

Thr Tyr Leu Glu Asn Leu Arg Ala Asn Leu Glu Val Leu Tyr Gln Gln
    290                 295                 300

Leu Lys
305
```

<210> SEQ ID NO 13
<211> LENGTH: 657
<212> TYPE: DNA
<213> ORGANISM: Streptococcus agalactiae

<400> SEQUENCE: 13

```
ttgttcaata aaataggttt tagaacttgg aaatcaggaa agctttggct ttatatggga      60
gtgctaggat caactattat tttaggatca agtcctgtat ctgctatgga tagtgttgga     120
aatcaaagtc aaggtaatgt tttagagcgt cgccaacgtg atgcggaaaa caaaagtcag     180
ggtaatgttt tagagcgtcg ccaacgtgat gcggaaaaca agagccaagg caatgtttta     240
gagcgtcgtc aacgcgatgt tgagaataag agccaaggca atgttttaga gcgtcgtcaa     300
cgtgatgcgg aaaacaaaag tcagggcaat gttctagagc cgccaacg tgatgcggat      360
aacaagagcc aagtaggtca acttataggg aaaaatccac ttttttcaaa gccaactgta     420
tctagagaaa ataatcactc tagtcaaggt gactctaaca acagtcatt ctctaaaaaa      480
gtatctcagg ttactaatgt agctaataga ccgatgttaa ctaataattc tagaacaatt     540
tcagtgataa ataaattacc taaaacaggt ggtgatcaaa atgtcatttt taaacttgta     600
ggttttggtt taatttttgtt aacaagtcgc tgcggtttga gacgcaatga aaattaa      657
```

<210> SEQ ID NO 14
<211> LENGTH: 218
<212> TYPE: PRT
<213> ORGANISM: Streptococcus agalactiae

<400> SEQUENCE: 14

```
Met Phe Asn Lys Ile Gly Phe Arg Thr Trp Lys Ser Gly Lys Leu Trp
  1               5                  10                  15

Leu Tyr Met Gly Val Leu Gly Ser Thr Ile Ile Leu Gly Ser Ser Pro
             20                  25                  30

Val Ser Ala Met Asp Ser Val Gly Asn Gln Ser Gln Gly Asn Val Leu
         35                  40                  45

Glu Arg Arg Gln Arg Asp Ala Glu Asn Lys Ser Gln Gly Asn Val Leu
     50                  55                  60

Glu Arg Arg Gln Arg Asp Ala Glu Asn Lys Ser Gln Gly Asn Val Leu
 65                  70                  75                  80

Glu Arg Arg Gln Arg Asp Val Glu Asn Lys Ser Gln Gly Asn Val Leu
                 85                  90                  95

Glu Arg Arg Gln Arg Asp Ala Glu Asn Lys Ser Gln Gly Asn Val Leu
            100                 105                 110

Glu Arg Arg Gln Arg Asp Ala Asp Asn Lys Ser Gln Val Gly Gln Leu
        115                 120                 125

Ile Gly Lys Asn Pro Leu Phe Ser Lys Pro Thr Val Ser Arg Glu Asn
    130                 135                 140

Asn His Ser Ser Gln Gly Asp Ser Asn Lys Gln Ser Phe Ser Lys Lys
145                 150                 155                 160

Val Ser Gln Val Thr Asn Val Ala Asn Arg Pro Met Leu Thr Asn Asn
                165                 170                 175

Ser Arg Thr Ile Ser Val Ile Asn Lys Leu Pro Lys Thr Gly Gly Asp
            180                 185                 190

Gln Asn Val Ile Phe Lys Leu Val Gly Phe Gly Leu Ile Leu Leu Thr
        195                 200                 205

Ser Arg Cys Gly Leu Arg Arg Asn Glu Asn
    210                 215
```

<210> SEQ ID NO 15
<211> LENGTH: 1029
<212> TYPE: DNA

<213> ORGANISM: Streptococcus agalactiae

<400> SEQUENCE: 15

```
atgacaaaaa aacttattat tgctatatta gcactatgca ctatcttaac cacttctcaa      60
gctgttttag ctaagaaaaa atcacaaact gttaccataa aaacaacta ttcggtctat     120
attaaaaaag aaaaaagaga caagccggat aataaaaagc aaatcagcga gacacttaaa     180
gttcctttaa aacccaaaaa agtagttgtt tttgatatgg gagctttgga tactatcaca     240
gctttaggag ctgaaaaatc tgttattggt atcccgaagg ctaaaaatgc tctaagttta     300
ttgcccaata acgtcaaatc tgtttataaa gctaagagat accaagacgt aggaagtctc     360
ttcgaaccaa actttgaagc tattgctcgt atgcaacctg atgtggtttt cctaggagca     420
cgtatggctt ctgttgataa tattgaaaaa ttaaaggagg ctgcacctaa agcagcatta     480
gtatatgctg gagtcgactc aaaaaaagta tttgacaaag gagttgctga gcgtgtcaca     540
atgttaggga aaatcttcga ccaaaataaa aaggcaaaaa cctttaataa agatatcgca     600
caagctgttc ttaaattgca gaaaactatt gagaaaaaag gtaaacctac agctctattt     660
gtaatggcaa acagcggtga acttttaact caatcaccct ctggtcgttt tggttggatt     720
ttctctgtag gtggatttaa agcagtcaat gaaaatgaaa aactaagttc acatggtact     780
cccgtatctt atgaatacat cgctgaaaaa atcctaact atctctttgt tttagatcgt     840
ggagcgacta ttggacaagg agcttcatca aaagaacttt ttaataacga tgttattaaa     900
gcaactgatg ctgtcaaaaa caacgtgtt catgaggtag atggaaaaga ttggtatatc     960
aattcaggcg gaagccgagt aacactccgt atgattaaag atgtacagaa ctttgttgat    1020
aatcgttaa                                                            1029
```

<210> SEQ ID NO 16
<211> LENGTH: 342
<212> TYPE: PRT
<213> ORGANISM: Streptococcus agalactiae

<400> SEQUENCE: 16

```
Met Thr Lys Lys Leu Ile Ile Ala Ile Leu Ala Leu Cys Thr Ile Leu
 1               5                   10                  15

Thr Thr Ser Gln Ala Val Leu Ala Lys Glu Lys Ser Gln Thr Val Thr
            20                  25                  30

Ile Lys Asn Asn Tyr Ser Val Tyr Ile Lys Lys Glu Lys Arg Asp Lys
        35                  40                  45

Pro Asp Asn Lys Lys Gln Ile Ser Glu Thr Leu Lys Val Pro Leu Lys
    50                  55                  60

Pro Lys Lys Val Val Phe Asp Met Gly Ala Leu Asp Thr Ile Thr
65                  70                  75                  80

Ala Leu Gly Ala Glu Lys Ser Val Ile Gly Ile Pro Lys Ala Lys Asn
                85                  90                  95

Ala Leu Ser Leu Leu Pro Asn Asn Val Lys Ser Val Tyr Lys Ala Lys
            100                 105                 110

Arg Tyr Gln Asp Val Gly Ser Leu Phe Glu Pro Asn Phe Glu Ala Ile
        115                 120                 125

Ala Arg Met Gln Pro Asp Val Val Phe Leu Gly Ala Arg Met Ala Ser
    130                 135                 140

Val Asp Asn Ile Glu Lys Leu Lys Glu Ala Ala Pro Lys Ala Ala Leu
145                 150                 155                 160

Val Tyr Ala Gly Val Asp Ser Lys Lys Val Phe Asp Lys Gly Val Ala
```

```
                           165                 170                 175
Glu Arg Val Thr Met Leu Gly Lys Ile Phe Asp Gln Asn Lys Lys Ala
                180                 185                 190
Lys Thr Phe Asn Lys Asp Ile Ala Gln Ala Val Leu Lys Leu Gln Lys
            195                 200                 205
Thr Ile Glu Lys Lys Gly Lys Pro Thr Ala Leu Phe Val Met Ala Asn
        210                 215                 220
Ser Gly Glu Leu Leu Thr Gln Ser Pro Ser Gly Arg Phe Gly Trp Ile
225                 230                 235                 240
Phe Ser Val Gly Gly Phe Lys Ala Val Asn Glu Asn Glu Lys Leu Ser
                245                 250                 255
Ser His Gly Thr Pro Val Ser Tyr Glu Tyr Ile Ala Glu Lys Asn Pro
                260                 265                 270
Asn Tyr Leu Phe Val Leu Asp Arg Gly Ala Thr Ile Gly Gln Gly Ala
            275                 280                 285
Ser Ser Lys Glu Leu Phe Asn Asn Asp Val Ile Lys Ala Thr Asp Ala
        290                 295                 300
Val Lys Asn Lys Arg Val His Glu Val Asp Gly Lys Asp Trp Tyr Ile
305                 310                 315                 320
Asn Ser Gly Gly Ser Arg Val Thr Leu Arg Met Ile Lys Asp Val Gln
                325                 330                 335
Asn Phe Val Asp Asn Arg
            340

<210> SEQ ID NO 17
<211> LENGTH: 2469
<212> TYPE: DNA
<213> ORGANISM: Streptococcus agalactiae

<400> SEQUENCE: 17
gtgaagaaaa catatggtta tatcggctca gttgctgcta ttttactagc tactcatatt      60
ggaagttacc agcttggtaa gcatcatatg ggtctagcaa caaaggacaa tcagattgcc     120
tatattgatg atagcaaagg taaggtaaaa gccctaaaa caaacaaaac gatggatcaa     180
atcagtgctg aagaaggcat ctctgctgaa cagatcgtag tcaaaattac tgaccaaggt     240
tatgttacct cacacggtga ccattatcat ttttacaatg ggaaagttcc ttatgatgcg     300
attattagtg aagagttgtt gatgacggat cctaattacc attttaaaca atcagacgtt     360
atcaatgaaa tcttagacgg ttacgttatt aaagtcaatg caactatta tgtttacctc     420
aagccaggta gtaagcgcaa aacattcga accaaacaac aaattgctga gcaagtagcc     480
aaaggaacta agaagctaa agaaaaaggt ttagctcaag tggcccatct cagtaaagaa     540
gaagttgcgg cagtcaatga agcaaaaaga caaggacgct atactacaga cgatggctat     600
atttttagtc cgacagatat cattgatgat ttaggagatg cttatttagt acctcatggt     660
aatcactatc attatattcc taaaaaagat ttgtctccaa gtgagctagc tgctgcacaa     720
gcctactgga gtcaaaaaca aggtcgaggt gctagaccgt ctgattaccg cccgacacca     780
gccccaggtc gtaggaaagc cccaattcct gatgtgacgc taaccctgg acaaggtcat     840
cagccagata cggtggtta tcatccagcg cctcctaggc aaatgatgc gtcacaaaac     900
aaacaccaaa gagatgagtt taaggaaaa acctttaagg aactttaga tcatctacac     960
cgtcttgatt tgaaataccg tcatgtggaa gaagatgggt tgattttga accgactcaa    1020
gtgatcaaat caacgctttt tgggtatgtg gtgcctcatg gagatcatta tcatattatc    1080
```

```
ccaagaagtc agttatcacc tcttgaaatg gaattagcag atcgatactt agccggccaa   1140
actgatgaca acgactcagg ttcagatcac tcaaaaccat cagataaaga agtgacacat   1200 accttcttg gtcatcgcat caaagcttac ggaaaaggct tagatggtaa accatatgat   1260
```
(acctttcttg gtcatcgcat caaagcttac ggaaaaggct tagatggtaa accatatgat   1260)
```
acgagtgatg cttatgtttt tagtaaagaa tccattcatt cagtggataa atcaggagtt   1320
acagctaaac acggagatca tttccactat ataggatttg agaacttga acaatatgag   1380 ttggatgagg tcgctaactg ggtgaaagca aaaggtcaag ctgatgagct tgttgctgct   1440
ttggatcagg aacaaggcaa agaaaaacca ctctttgaca ctaaaaaagt gagtcgcaaa   1500
gtaacaaaag atggtaaagt gggctatatt atgccaaaag atggcaagga ctatttctat   1560
gctcgttatc aacttgattt gactcagatt gcctttgccg aacaagaact aatgcttaaa   1620
gataagaagc attaccgtta tgacattgtt gatacaggca ttgagccacg acttgctgta   1680
gatgtgtcaa gtctgccgat gcatgctggt aatgctactt acgatactgg aagttcgttt   1740
gttatcccac atattgatca tatccatgtc gttccgtatt catggttgac gcgcaatcag   1800
attgcaacaa tcaagtatgt gatgcaacac cccgaagttc gtccggatgt atggtctaag   1860
ccagggcatg aagagtcagg ttcggtcatt ccaaatgtta cgcctcttga taaacgtgct   1920
ggtatgccaa actggcaaat tatccattct gctgaagaag ttcaaaaagc cctagcagaa   1980
ggtcgttttg cagcaccaga cggctatatt ttcgatccac gagatgtttt ggcaaaagaa   2040
acttttgtat ggaaagatgg ctcctttagc atcccaagag cagatggcag ttcattgaga   2100
accattaata aatccgatct atcccaagct gagtggcaac aagctcaaga gttattggca   2160
aagaaaaatg ctggtgatgc tactgatacg gataaacctg aagaaagca acaggcagat   2220
```
(aagaaaaatg ctggtgatgc tactgatacg gataaacctg aagaaaagca acaggcagat   2220)
```
aagagcaatg aaaaccaaca gccaagtgaa gccagtaaag aagaaaaga atcagatgac   2280
```
(aagagcaatg aaaaccaaca gccaagtgaa gccagtaaag aagaaaaaga atcagatgac   2280)
```
tttatagaca gtttaccaga ctatggtcta gatagagcaa ccctagaaga tcatatcaat   2340
caattagcac aaaaagctaa tatcgatcct aagtatctca ttttccaacc agaaggtgtc   2400 caatttata ataaaaatgg tgaattggta acttatgata tcaagacact tcaacaaata   2460
```
(caatttttata ataaaaatgg tgaattggta acttatgata tcaagacact tcaacaaata   2460)
```
aacccttaa                                                           2469
```

<210> SEQ ID NO 18
<211> LENGTH: 822
<212> TYPE: PRT
<213> ORGANISM: Streptococcus agalactiae

<400> SEQUENCE: 18

Met Lys Lys Thr Tyr Gly Tyr Ile Gly Ser Val Ala Ala Ile Leu Leu
1               5                   10                  15

Ala Thr His Ile Gly Ser Tyr Gln Leu Gly Lys His His Met Gly Leu
                20                  25                  30

Ala Thr Lys Asp Asn Gln Ile Ala Tyr Ile Asp Asp Ser Lys Gly Lys
            35                  40                  45

Val Lys Ala Pro Lys Thr Asn Lys Thr Met Asp Gln Ile Ser Ala Glu
        50                  55                  60

Glu Gly Ile Ser Ala Glu Gln Ile Val Lys Ile Thr Asp Gln Gly
65                  70                  75                  80

Tyr Val Thr Ser His Gly Asp His Tyr His Phe Tyr Asn Gly Lys Val
                85                  90                  95

Pro Tyr Asp Ala Ile Ile Ser Glu Glu Leu Leu Met Thr Asp Pro Asn
            100                 105                 110

Tyr His Phe Lys Gln Ser Asp Val Ile Asn Glu Ile Leu Asp Gly Tyr
        115                 120                 125

```
Val Ile Lys Val Asn Gly Asn Tyr Tyr Val Tyr Leu Lys Pro Gly Ser
    130                 135                 140

Lys Arg Lys Asn Ile Arg Thr Lys Gln Gln Ile Ala Glu Gln Val Ala
145                 150                 155                 160

Lys Gly Thr Lys Glu Ala Lys Glu Lys Gly Leu Ala Gln Val Ala His
                165                 170                 175

Leu Ser Lys Glu Glu Val Ala Ala Val Asn Glu Ala Lys Arg Gln Gly
                180                 185                 190

Arg Tyr Thr Thr Asp Asp Gly Tyr Ile Phe Ser Pro Thr Asp Ile Ile
                195                 200                 205

Asp Asp Leu Gly Asp Ala Tyr Leu Val Pro His Gly Asn His Tyr His
    210                 215                 220

Tyr Ile Pro Lys Lys Asp Leu Ser Pro Ser Glu Leu Ala Ala Ala Gln
225                 230                 235                 240

Ala Tyr Trp Ser Gln Lys Gln Gly Arg Gly Ala Arg Pro Ser Asp Tyr
                245                 250                 255

Arg Pro Thr Pro Ala Pro Gly Arg Arg Lys Ala Pro Ile Pro Asp Val
                260                 265                 270

Thr Pro Asn Pro Gly Gln Gly His Gln Pro Asp Asn Gly Gly Tyr His
    275                 280                 285

Pro Ala Pro Pro Arg Pro Asn Asp Ala Ser Gln Asn Lys His Gln Arg
    290                 295                 300

Asp Glu Phe Lys Gly Lys Thr Phe Lys Glu Leu Leu Asp His Leu His
305                 310                 315                 320

Arg Leu Asp Leu Lys Tyr Arg His Val Glu Glu Asp Gly Leu Ile Phe
                325                 330                 335

Glu Pro Thr Gln Val Ile Lys Ser Asn Ala Phe Gly Tyr Val Val Pro
                340                 345                 350

His Gly Asp His Tyr His Ile Ile Pro Arg Ser Gln Leu Ser Pro Leu
    355                 360                 365

Glu Met Glu Leu Ala Asp Arg Tyr Leu Ala Gly Gln Thr Asp Asp Asn
370                 375                 380

Asp Ser Gly Ser Asp His Ser Lys Pro Ser Asp Lys Glu Val Thr His
385                 390                 395                 400

Thr Phe Leu Gly His Arg Ile Lys Ala Tyr Gly Lys Gly Leu Asp Gly
                405                 410                 415

Lys Pro Tyr Asp Thr Ser Asp Ala Tyr Val Phe Ser Lys Glu Ser Ile
                420                 425                 430

His Ser Val Asp Lys Ser Gly Val Thr Ala Lys His Gly Asp His Phe
                435                 440                 445

His Tyr Ile Gly Phe Gly Glu Leu Glu Gln Tyr Glu Leu Asp Glu Val
    450                 455                 460

Ala Asn Trp Val Lys Ala Lys Gly Gln Ala Asp Glu Leu Val Ala Ala
465                 470                 475                 480

Leu Asp Gln Glu Gln Gly Lys Glu Lys Pro Leu Phe Asp Thr Lys Lys
                485                 490                 495

Val Ser Arg Lys Val Thr Lys Asp Gly Lys Val Gly Tyr Ile Met Pro
                500                 505                 510

Lys Asp Gly Lys Asp Tyr Phe Tyr Ala Arg Tyr Gln Leu Asp Leu Thr
                515                 520                 525

Gln Ile Ala Phe Ala Glu Gln Glu Leu Met Leu Lys Asp Lys Lys His
    530                 535                 540
```

| | | | | | | | | | | | | | | |
|---|---|---|---|---|---|---|---|---|---|---|---|---|---|---|
| Tyr | Arg | Tyr | Asp | Ile | Val | Asp | Thr | Gly | Ile | Glu | Pro | Arg | Leu | Ala | Val |
| 545 | | | | 550 | | | | | 555 | | | | | 560 |

Tyr Arg Tyr Asp Ile Val Asp Thr Gly Ile Glu Pro Arg Leu Ala Val
545                 550                 555                 560

Asp Val Ser Ser Leu Pro Met His Ala Gly Asn Ala Thr Tyr Asp Thr
                565                 570                 575

Gly Ser Ser Phe Val Ile Pro His Ile Asp His Ile His Val Val Pro
            580                 585                 590

Tyr Ser Trp Leu Thr Arg Asn Gln Ile Ala Thr Ile Lys Tyr Val Met
        595                 600                 605

Gln His Pro Glu Val Arg Pro Asp Val Trp Ser Lys Pro Gly His Glu
    610                 615                 620

Glu Ser Gly Ser Val Ile Pro Asn Val Thr Pro Leu Asp Lys Arg Ala
625                 630                 635                 640

Gly Met Pro Asn Trp Gln Ile Ile His Ser Ala Glu Glu Val Gln Lys
                645                 650                 655

Ala Leu Ala Glu Gly Arg Phe Ala Ala Pro Asp Gly Tyr Ile Phe Asp
                660                 665                 670

Pro Arg Asp Val Leu Ala Lys Glu Thr Phe Val Trp Lys Asp Gly Ser
            675                 680                 685

Phe Ser Ile Pro Arg Ala Asp Gly Ser Ser Leu Arg Thr Ile Asn Lys
        690                 695                 700

Ser Asp Leu Ser Gln Ala Glu Trp Gln Gln Ala Gln Glu Leu Leu Ala
705                 710                 715                 720

Lys Lys Asn Ala Gly Asp Ala Thr Asp Thr Asp Lys Pro Glu Glu Lys
                725                 730                 735

Gln Gln Ala Asp Lys Ser Asn Glu Asn Gln Gln Pro Ser Glu Ala Ser
                740                 745                 750

Lys Glu Glu Lys Glu Ser Asp Asp Phe Ile Asp Ser Leu Pro Asp Tyr
            755                 760                 765

Gly Leu Asp Arg Ala Thr Leu Glu Asp His Ile Asn Gln Leu Ala Gln
    770                 775                 780

Lys Ala Asn Ile Asp Pro Lys Tyr Leu Ile Phe Gln Pro Glu Gly Val
785                 790                 795                 800

Gln Phe Tyr Asn Lys Asn Gly Glu Leu Val Thr Tyr Asp Ile Lys Thr
                805                 810                 815

Leu Gln Gln Ile Asn Pro
        820

<210> SEQ ID NO 19
<211> LENGTH: 939
<212> TYPE: DNA
<213> ORGANISM: Streptococcus agalactiae

<400> SEQUENCE: 19

```
atgatacgcc agttttaag agaacacttg atttggtata ttttatatat catgatgttt      60
gtcctatttt ttattagttt ctatctatat catttaccaa tgccctattt gtttaattcc     120
ttaggtttaa atgttattgt tttactagga attagtattt ggcaatacag tcgttacagg     180
aaaaaaatgt tacatctcaa atattttaat agtagtcagg acccctcttt cgaacttcaa     240
ccgagtgatt acgcttattt taatattatt acacaattag aagctagaga agcgcaaaaa     300
gtttctgaaa caattgaaca aaccaatcat gttgcactta tgataaagat gtggtcgcac     360
caaatgaaag ttccattggc agctatttca ttaatggccc agacaaatca tctcgatcct     420
aaggaagttg aacaacaatt attgaaattg caacattatc ttgaaacgtt gttagcattt     480
ttgaaattta gacaatatcg tgacgatttt cgttttgaag ctgttagcct tagagaagta     540
```

-continued

```
gtagtagaaa ttataaaatc gtataaggtt atttgtctat ccaaaagctt atctatcata        600
attgaaggcg ataatatctg aaaacagac aaaaagtggt taacttttgc tctttcacag         660
gtgctagata atgccataaa atattctaat cctgagtcaa agataataat aagcatagga        720
gaagagagta ttagaataca agactacggt atcggcatac tcgaagagga tatccctaga       780 cttttttgaag atggctttac gggttacaac ggtcatgagc accaaaaggc aacaggcatg       840
gggttatata tgacaaaaga agtcttatct agtctgaatt tgtccatttc ggtggatagc        900
aaaattaatt atgggactgc tgtttctata cataaataa                                939
```

<210> SEQ ID NO 20
<211> LENGTH: 312
<212> TYPE: PRT
<213> ORGANISM: Streptococcus agalactiae

<400> SEQUENCE: 20

```
Met Ile Arg Gln Phe Leu Arg Glu His Leu Ile Trp Tyr Ile Leu Tyr
  1               5                  10                  15

Ile Met Met Phe Val Leu Phe Phe Ile Ser Phe Tyr Leu Tyr His Leu
                 20                  25                  30

Pro Met Pro Tyr Leu Phe Asn Ser Leu Gly Leu Asn Val Ile Val Leu
             35                  40                  45

Leu Gly Ile Ser Ile Trp Gln Tyr Ser Arg Tyr Arg Lys Lys Met Leu
         50                  55                  60

His Leu Lys Tyr Phe Asn Ser Ser Gln Asp Pro Ser Phe Glu Leu Gln
  65                  70                  75                  80

Pro Ser Asp Tyr Ala Tyr Phe Asn Ile Ile Thr Gln Leu Glu Ala Arg
                 85                  90                  95

Glu Ala Gln Lys Val Ser Glu Thr Ile Glu Gln Thr Asn His Val Ala
            100                 105                 110

Leu Met Ile Lys Met Trp Ser His Gln Met Lys Val Pro Leu Ala Ala
        115                 120                 125

Ile Ser Leu Met Ala Gln Thr Asn His Leu Asp Pro Lys Glu Val Glu
    130                 135                 140

Gln Gln Leu Leu Lys Leu Gln His Tyr Leu Glu Thr Leu Leu Ala Phe
145                 150                 155                 160

Leu Lys Phe Arg Gln Tyr Arg Asp Asp Phe Arg Glu Ala Val Ser
                165                 170                 175

Leu Arg Glu Val Val Glu Ile Ile Lys Ser Tyr Lys Val Ile Cys
            180                 185                 190

Leu Ser Lys Ser Leu Ser Ile Ile Glu Gly Asp Asn Ile Trp Lys
        195                 200                 205

Thr Asp Lys Lys Trp Leu Thr Phe Ala Leu Ser Gln Val Leu Asp Asn
    210                 215                 220

Ala Ile Lys Tyr Ser Asn Pro Glu Ser Lys Ile Ile Ser Ile Gly
225                 230                 235                 240

Glu Glu Ser Ile Arg Ile Gln Asp Tyr Gly Ile Gly Ile Leu Glu Glu
                245                 250                 255

Asp Ile Pro Arg Leu Phe Glu Asp Gly Phe Thr Gly Tyr Asn Gly His
            260                 265                 270

Glu His Gln Lys Ala Thr Gly Met Gly Leu Tyr Met Thr Lys Glu Val
        275                 280                 285

Leu Ser Ser Leu Asn Leu Ser Ile Ser Val Asp Ser Lys Ile Asn Tyr
    290                 295                 300
```

Gly Thr Ala Val Ser Ile His Lys
305             310

<210> SEQ ID NO 21
<211> LENGTH: 942
<212> TYPE: DNA
<213> ORGANISM: Streptococcus agalactiae

<400> SEQUENCE: 21

```
atgacttatc aaaaaacagt tgttttggct ggtgattatt cctacattag acaaattgaa      60
accacattaa aatctctctg tgtctatcat gagaatctct caatttttat ttttaatcaa     120
gatattcctc aagaatggtt tttagctatg aaagataggg ttggacaaac tggaaatcaa     180
attcaggatg taaagctctt ccatgatcac ttatccccaa aatgggaaaa taaaaagctt     240
aatcatatta attatatgac ctatgctcgt tatttcatac ctcagtacat ctcagctgat     300
acagttttat atcttgactc tgacttagtt gttactacta atttagataa cctctttcaa     360
atttcactag acaatgcata tttagctgca gttccagctc ttttttgggct tggatatggg   420
tttaatgctg gagtaatggt aattaacaac caacgttggc gacaagaaaa tatgactatt     480
aaattaattg aaaaaaatca aaaggaaatt gagaatgcca acgaagggga tcaaacaatt     540
cttaatcgca tgtttgaaaa tcaggtaatt tatttagatg ataccctacaa ttttcaaatt   600
ggttttgata tgggagctgc tatcgatggg cataaattta tttttgacat cccaattacc    660
ccactcccaa aaattattca ctacatttcg ggaatcaaac cttggcaaac attatcaaat    720
atgagactcc gtgaggtatg gtggcactat aatttacttg aatggtcaag tatcatatct    780
agtaaaaaag tatttggttt agaccaccca attaaaacac aaaattatcg tctcaatttc    840
cttattgcta caacttctga ttgtatacca tctatctcag aattagtcac tgcccttcca    900
gattgtctat ttcacattgc atgcaccaac agttatgtct ga                        942
```

<210> SEQ ID NO 22
<211> LENGTH: 313
<212> TYPE: PRT
<213> ORGANISM: Streptococcus agalactiae

<400> SEQUENCE: 22

Met Thr Tyr Gln Lys Thr Val Val Leu Ala Gly Asp Tyr Ser Tyr Ile
1               5                   10                  15

Arg Gln Ile Glu Thr Thr Leu Lys Ser Leu Cys Val Tyr His Glu Asn
            20                  25                  30

Leu Ser Ile Phe Ile Phe Asn Gln Asp Ile Pro Gln Glu Trp Phe Leu
        35                  40                  45

Ala Met Lys Asp Arg Val Gly Gln Thr Gly Asn Gln Ile Gln Asp Val
    50                  55                  60

Lys Leu Phe His Asp His Leu Ser Pro Lys Trp Glu Asn Lys Lys Leu
65                  70                  75                  80

Asn His Ile Asn Tyr Met Thr Tyr Ala Arg Tyr Phe Ile Pro Gln Tyr
                85                  90                  95

Ile Ser Ala Asp Thr Val Leu Tyr Leu Asp Ser Asp Leu Val Val Thr
            100                 105                 110

Thr Asn Leu Asp Asn Leu Phe Gln Ile Ser Leu Asp Asn Ala Tyr Leu
        115                 120                 125

Ala Ala Val Pro Ala Leu Phe Gly Leu Gly Tyr Gly Phe Asn Ala Gly
    130                 135                 140

```
Val Met Val Ile Asn Asn Gln Arg Trp Arg Gln Glu Asn Met Thr Ile
145                 150                 155                 160

Lys Leu Ile Glu Lys Asn Gln Lys Glu Ile Glu Asn Ala Asn Glu Gly
                165                 170                 175

Asp Gln Thr Ile Leu Asn Arg Met Phe Glu Asn Gln Val Ile Tyr Leu
            180                 185                 190

Asp Asp Thr Tyr Asn Phe Gln Ile Gly Phe Asp Met Gly Ala Ala Ile
        195                 200                 205

Asp Gly His Lys Phe Ile Phe Asp Ile Pro Ile Thr Pro Leu Pro Lys
    210                 215                 220

Ile Ile His Tyr Ile Ser Gly Ile Lys Pro Trp Gln Thr Leu Ser Asn
225                 230                 235                 240

Met Arg Leu Arg Glu Val Trp Trp His Tyr Asn Leu Leu Glu Trp Ser
                245                 250                 255

Ser Ile Ile Ser Ser Lys Lys Val Phe Gly Leu Asp His Pro Ile Lys
                260                 265                 270

Thr Gln Asn Tyr Arg Leu Asn Phe Leu Ile Ala Thr Thr Ser Asp Cys
            275                 280                 285

Ile Pro Ser Ile Ser Glu Leu Val Thr Ala Leu Pro Asp Cys Leu Phe
        290                 295                 300

His Ile Ala Cys Thr Asn Ser Tyr Val
305                 310
```

<210> SEQ ID NO 23
<211> LENGTH: 1146
<212> TYPE: DNA
<213> ORGANISM: Streptococcus agalactiae

<400> SEQUENCE: 23

```
gtgaagaaaa catattgtta tatcggctca gttgctgcta ttttactagc tactcatatt        60
ggaagttacc agcttggtaa gcatcatatg ggtctagcaa caaggacaa tcagattgcc        120
tatattgatg atagcaaagg taaggtaaaa gcccctaaaa caaacaaaac gatggatcaa        180
atcagtgctg aagaaggcat ctctgctgaa cagatcgtag tcaaaattac tgaccaaggt        240
tatgttacct cacacggtga ccattatcat ttttacaatg ggaaagttcc ttatgatgcg        300
attattagtg aagagttgtt gatgacggat cctaattacc attttaaaca atcagacgtt        360
atcaatgaaa tcttagacgg ttacgttatt aaagtcaatg caactatta tgtttacctc        420
aagccaggta gtaagcgcaa aaacattcga accaaacaac aaattgctga gcaagtagcc        480
aaaggaacta agaagctaa agaaaaaggt ttagctcaag tggcccatct cagtaaagaa        540
gaagttgcgg cagtcaatga agcaaaaaga caaggacgct atactacaga cgatggctat        600
atttttagtc gacagatat cattgatgat ttaggagatg cttatttagt acctcatggt        660
aatcactatc attatattcc taaaaaagat ttgtctccaa gtgagctagc tgctgcacaa        720
gcctactgga gtcaaaaaca aggtcgaggt gctagaccgt ctgattaccg cccgacacca        780
gccccaggtc gtaggaaagc cccacttcct gatgtgacgc taaccctgg acaaggtcat        840
cagccagata acggtggtta tcatccagcg cctcctaggc caaatgatgc gtcacaaaac        900
aaacaccaaa gagatgagtt taaggaaaa acctttaagg aacttttaga tcaactacac        960
cgtcttgatt tgaaataccg tcatgtggaa gaagatgggt tgattttga accgactcaa       1020
gtgatcaaat caaacgcttt tgggtatgtg gtgcctcatg gagatcatta tcatattatc       1080
ccaagaagtc agttatcacc tcttgaaatg gaattagcag atcgatactt aacccggcca       1140
``` aactga 1146

<210> SEQ ID NO 24
<211> LENGTH: 381
<212> TYPE: PRT
<213> ORGANISM: Streptococcus agalactiae

<400> SEQUENCE: 24

```
Met Lys Lys Thr Tyr Cys Tyr Ile Gly Ser Val Ala Ala Ile Leu Leu
  1               5                  10                  15

Ala Thr His Ile Gly Ser Tyr Gln Leu Gly Lys His His Met Gly Leu
             20                  25                  30

Ala Thr Lys Asp Asn Gln Ile Ala Tyr Ile Asp Asp Ser Lys Gly Lys
         35                  40                  45

Val Lys Ala Pro Lys Thr Asn Lys Thr Met Asp Gln Ile Ser Ala Glu
 50                  55                  60

Glu Gly Ile Ser Ala Glu Gln Ile Val Val Lys Ile Thr Asp Gln Gly
 65                  70                  75                  80

Tyr Val Thr Ser His Gly Asp His Tyr His Phe Tyr Asn Gly Lys Val
                 85                  90                  95

Pro Tyr Asp Ala Ile Ile Ser Glu Glu Leu Leu Met Thr Asp Pro Asn
            100                 105                 110

Tyr His Phe Lys Gln Ser Asp Val Ile Asn Glu Ile Leu Asp Gly Tyr
        115                 120                 125

Val Ile Lys Val Asn Gly Asn Tyr Tyr Val Tyr Leu Lys Pro Gly Ser
130                 135                 140

Lys Arg Lys Asn Ile Arg Thr Lys Gln Gln Ile Ala Glu Gln Val Ala
145                 150                 155                 160

Lys Gly Thr Lys Glu Ala Lys Glu Lys Gly Leu Ala Gln Val Ala His
                165                 170                 175

Leu Ser Lys Glu Glu Val Ala Ala Val Asn Glu Ala Lys Arg Gln Gly
            180                 185                 190

Arg Tyr Thr Thr Asp Asp Gly Tyr Ile Phe Ser Pro Thr Asp Ile Ile
        195                 200                 205

Asp Asp Leu Gly Asp Ala Tyr Leu Val Pro His Gly Asn His Tyr His
    210                 215                 220

Tyr Ile Pro Lys Lys Asp Leu Ser Pro Ser Glu Leu Ala Ala Ala Gln
225                 230                 235                 240

Ala Tyr Trp Ser Gln Lys Gln Gly Arg Gly Ala Arg Pro Ser Asp Tyr
                245                 250                 255

Arg Pro Thr Pro Ala Pro Gly Arg Arg Lys Ala Pro Leu Pro Asp Val
            260                 265                 270

Thr Pro Asn Pro Gly Gln Gly His Gln Pro Asp Asn Gly Gly Tyr His
        275                 280                 285

Pro Ala Pro Pro Arg Pro Asn Asp Ala Ser Gln Asn Lys His Gln Arg
    290                 295                 300

Asp Glu Phe Lys Gly Lys Thr Phe Lys Glu Leu Leu Asp Gln Leu His
305                 310                 315                 320

Arg Leu Asp Leu Lys Tyr Arg His Val Glu Glu Asp Gly Leu Ile Phe
                325                 330                 335

Glu Pro Thr Gln Val Ile Lys Ser Asn Ala Phe Gly Tyr Val Val Pro
            340                 345                 350

His Gly Asp His Tyr His Ile Ile Pro Arg Ser Gln Leu Ser Pro Leu
        355                 360                 365
```

Glu Met Glu Leu Ala Asp Arg Tyr Leu Thr Arg Pro Asn
    370                 375                 380

<210> SEQ ID NO 25
<211> LENGTH: 660
<212> TYPE: DNA
<213> ORGANISM: Streptococcus agalactiae

<400> SEQUENCE: 25

```
atggtaaatg atatattaga agaatgtat  aaagagaata ttccaaaatc ttaccttaca    60
tccgtcccat tagttatttc tcaaaaagga agaacaacct attcgtttag tatgactggt   120
ggtcaacaaa tagatggagt gaaattcaca cagatatatg aggactatat gaaattactc   180
agtcaaggta aggatatcgc agagttatat caaaaatatt ctaaagaaga gttggcaaat   240
ctaggcatta atatttatca atccaatgat atagaaagga ctgaggaaag aactttgat   300
gaaattatca gttgggtttc caaccttat  gcaacaagac caattcaaga aaggcacact   360
attcaattag agccaacaag attttcacta gaggataaga aaagaattga gaagctgca   420
gctcaaggac taagcgaaat cgaccttatt gatttagttg acctatgta  tattaattta   480
gacaatacaa gcgtcaatcg ccatattgtg gggttattga ctaataacac ccaagtaaca   540
tactatttcc aagaacaatt aaataaggag ttgctgtcaa tggctcacgc tttagataac   600
gtacaacagg cctttattaa attattaagt gaagaggaga tacgaaaatt tgctctttaa   660
```

<210> SEQ ID NO 26
<211> LENGTH: 219
<212> TYPE: PRT
<213> ORGANISM: Streptococcus agalactiae

<400> SEQUENCE: 26

Met Val Asn Asp Ile Leu Glu Arg Met Tyr Lys Glu Asn Ile Pro Lys
  1               5                  10                  15

Ser Tyr Leu Thr Ser Val Pro Leu Val Ile Ser Gln Lys Gly Arg Thr
             20                  25                  30

Thr Tyr Ser Phe Ser Met Thr Gly Gly Gln Gln Ile Asp Gly Val Lys
         35                  40                  45

Phe Thr Gln Ile Tyr Glu Asp Tyr Met Lys Leu Leu Ser Gln Gly Lys
     50                  55                  60

Asp Ile Ala Glu Leu Tyr Gln Lys Tyr Ser Lys Glu Glu Leu Ala Asn
 65                  70                  75                  80

Leu Gly Ile Asn Ile Tyr Gln Ser Asn Asp Ile Glu Arg Thr Glu Glu
                 85                  90                  95

Arg Thr Phe Asp Glu Ile Ile Ser Trp Val Ser Asn Pro Tyr Ala Thr
            100                 105                 110

Arg Pro Ile Gln Glu Arg His Thr Ile Gln Leu Glu Pro Thr Arg Phe
        115                 120                 125

Ser Leu Glu Asp Lys Lys Arg Ile Glu Glu Ala Ala Gln Gly Leu
    130                 135                 140

Ser Glu Ile Asp Leu Ile Asp Leu Val Asp Leu Tyr Asp Ile Asn Leu
145                 150                 155                 160

Asp Asn Thr Ser Val Asn Arg His Ile Val Gly Leu Leu Thr Asn Asn
                165                 170                 175

Thr Gln Val Thr Tyr Tyr Phe Gln Glu Gln Leu Asn Lys Glu Leu Leu
            180                 185                 190

Ser Met Ala His Ala Leu Asp Asn Val Gln Gln Ala Phe Ile Lys Leu
        195                 200                 205

-continued

```
Leu Ser Glu Glu Glu Ile Arg Lys Phe Ala Leu
    210                 215

<210> SEQ ID NO 27
<211> LENGTH: 653
<212> TYPE: DNA
<213> ORGANISM: Streptococcus agalactiae

<400> SEQUENCE: 27
atgaataaaa gaagaaaatt atcaaaattg aatgtaaaaa aacaacattt agcttatgga      60
gctatcactt tagtagccct tttttcatgt attttggctg taacggtcat ctttaaaagt     120
tcacaagtta ctactgaatc tttgtcaaaa gcagataaag ttcgcgtagc caaaaaatca     180
aaaatgacta aggcgacatc taaatcaaaa gtagaagatg taaaacaggc tccaaaacct     240
tctcaggcat ctaatgaagc cccaaaatca agttctcaat ctacagaagc taattctcag     300
caacaagtta ctgcgagtga agaggcggct gtagaacaag cagttgtaac agaaaatacc     360
cctgctacca gtcaggcaca acaaacttat gctgttactg agacaactta caaacctgct     420
caacaccaga caagtggcca agtattgagc aatggaaata ctgcagggc ggtcggatct      480 gctgctgcag cacaaatggc tgctgcaaca ggagtccctc agtctacttg ggaacatatt     540
attgcccgtg aatcaaatgg taatcctaat gttgctaatg cctcagggc ttcaggactt      600 ttccaaacga tgccaggttg gggttcaaca gctacagttc aggatcaagt taa           653

<210> SEQ ID NO 28
<211> LENGTH: 234
<212> TYPE: PRT
<213> ORGANISM: Streptococcus agalactiae

<400> SEQUENCE: 28

Met Asn Lys Arg Arg Lys Leu Ser Lys Leu Asn Val Lys Lys Gln His
  1               5                  10                  15

Leu Ala Tyr Gly Ala Ile Thr Leu Val Ala Leu Phe Ser Cys Ile Leu
                 20                  25                  30

Ala Val Thr Val Ile Phe Lys Ser Ser Gln Val Thr Thr Glu Ser Leu
             35                  40                  45

Ser Lys Ala Asp Lys Val Arg Val Ala Lys Lys Ser Lys Met Thr Lys
     50                  55                  60

Ala Thr Ser Lys Ser Lys Val Glu Asp Val Lys Gln Ala Pro Lys Pro
 65                  70                  75                  80

Ser Gln Ala Ser Asn Glu Ala Pro Lys Ser Ser Gln Ser Thr Glu
                 85                  90                  95

Ala Asn Ser Gln Gln Gln Val Thr Ala Ser Glu Glu Ala Ala Val Glu
            100                 105                 110

Gln Ala Val Val Thr Glu Asn Thr Pro Ala Thr Ser Gln Ala Gln Gln
        115                 120                 125

Thr Tyr Ala Val Thr Glu Thr Thr Tyr Lys Pro Ala Gln His Gln Thr
    130                 135                 140

Ser Gly Gln Val Leu Ser Asn Gly Asn Thr Ala Gly Ala Val Gly Ser
145                 150                 155                 160

Ala Ala Ala Ala Gln Met Ala Ala Ala Thr Gly Val Pro Gln Ser Thr
                165                 170                 175

Trp Glu His Ile Ile Ala Arg Glu Ser Asn Gly Asn Pro Asn Val Ala
            180                 185                 190

Asn Ala Ser Gly Ala Ser Gly Leu Phe Gln Thr Met Pro Gly Trp Gly
```

195                 200                 205
Ser Thr Ala Thr Val Gln Asp Gln Val Asn Ser Ala Ile Lys Ala Tyr
    210                 215                 220

Arg Ala Gln Gly Leu Ser Ala Trp Gly Tyr
225                 230

<210> SEQ ID NO 29
<211> LENGTH: 360
<212> TYPE: DNA
<213> ORGANISM: Streptococcus agalactiae

<400> SEQUENCE: 29
atgattgttg gacacggaat tgatttacaa gagatagagg cgattactaa agcatatgag    60
cgtaatcaac gttttgcaga acgcgttttg accgaacaag aattgcttct ttttaaagga   120
atttccaatc ccaagcgtca gatgtctttt taacagggc gatgggcagc aaaagaggct   180
tatagcaaag cacttggaac aggaattggg aaagttaatt ttcatgatat cgaaatttta   240
tcggatgata aaggagcgcc tttgattaca aaagaaccgt taatggaaa atcttttgtt   300 tcaatatctc atagtggtaa ttatgcacaa gctagtgtta ttttggagga agaaaaatga   360

<210> SEQ ID NO 30
<211> LENGTH: 119
<212> TYPE: PRT
<213> ORGANISM: Streptococcus agalactiae

<400> SEQUENCE: 30

Met Ile Val Gly His Gly Ile Asp Leu Gln Glu Ile Glu Ala Ile Thr
  1               5                  10                  15

Lys Ala Tyr Glu Arg Asn Gln Arg Phe Ala Glu Arg Val Leu Thr Glu
             20                  25                  30

Gln Glu Leu Leu Leu Phe Lys Gly Ile Ser Asn Pro Lys Arg Gln Met
         35                  40                  45

Ser Phe Leu Thr Gly Arg Trp Ala Ala Lys Glu Ala Tyr Ser Lys Ala
     50                  55                  60

Leu Gly Thr Gly Ile Gly Lys Val Asn Phe His Asp Ile Glu Ile Leu
 65                  70                  75                  80

Ser Asp Asp Lys Gly Ala Pro Leu Ile Thr Lys Glu Pro Phe Asn Gly
                 85                  90                  95

Lys Ser Phe Val Ser Ile Ser His Ser Gly Asn Tyr Ala Gln Ala Ser
            100                 105                 110

Val Ile Leu Glu Glu Glu Lys
        115

<210> SEQ ID NO 31
<211> LENGTH: 474
<212> TYPE: DNA
<213> ORGANISM: Streptococcus agalactiae

<400> SEQUENCE: 31 atgattttg tcacagtggg gacacatgaa cagcagttca accgtcttat taaagaagtt    60
gatagattaa aagggacagg tgctattgat caagaagtgt tcattcaaac gggttactca   120
gacttcgaac ctcagaattg tcagtggtca aaatttctct catatgatga tatgaactct   180
tacatgaaag aagctgagat tgttatcaca catggcggcc cagcgacgtt tatgtcagtt   240
atttctttag ggaaattacc agttgttgtt cctaggagaa agcagtttgg tgaacatatc   300
aatgatcatc aaatacaatt tttaaaaaaa attgcccacc tgtatccctt ggcttggatt   360

-continued

```
gaagatgtag atggacttgc ggaagcgttg aaaaggaata tagctacaga aaaatatcag    420
ggaaataatg atatgttttg tcataaatta gaaaaaatta taggtgaaat atga          474
```

<210> SEQ ID NO 32
<211> LENGTH: 157
<212> TYPE: PRT
<213> ORGANISM: Streptococcus agalactiae

<400> SEQUENCE: 32

```
Met Ile Phe Val Thr Val Gly Thr His Glu Gln Gln Phe Asn Arg Leu
  1               5                  10                  15

Ile Lys Glu Val Asp Arg Leu Lys Gly Thr Gly Ala Ile Asp Gln Glu
                 20                  25                  30

Val Phe Ile Gln Thr Gly Tyr Ser Asp Phe Glu Pro Gln Asn Cys Gln
             35                  40                  45

Trp Ser Lys Phe Leu Ser Tyr Asp Asp Met Asn Ser Tyr Met Lys Glu
         50                  55                  60

Ala Glu Ile Val Ile Thr His Gly Gly Pro Ala Thr Phe Met Ser Val
 65                  70                  75                  80

Ile Ser Leu Gly Lys Leu Pro Val Val Pro Arg Arg Lys Gln Phe
                 85                  90                  95

Gly Glu His Ile Asn Asp His Gln Ile Gln Phe Leu Lys Lys Ile Ala
                100                 105                 110

His Leu Tyr Pro Leu Ala Trp Ile Glu Asp Val Asp Gly Leu Ala Glu
            115                 120                 125

Ala Leu Lys Arg Asn Ile Ala Thr Glu Lys Tyr Gln Gly Asn Asn Asp
        130                 135                 140

Met Phe Cys His Lys Leu Glu Lys Ile Ile Gly Glu Ile
145                 150                 155
```

<210> SEQ ID NO 33
<211> LENGTH: 1203
<212> TYPE: DNA
<213> ORGANISM: Streptococcus agalactiae

<400> SEQUENCE: 33

```
ttggaagaca aattattcaa caaacatttt ataggcatta ctattttaaa ctttattgtt     60
tatatggtct attatttgtt caccgttatc atagctttta ttgcgactaa agagttaggt    120
gttagcacta gccaagcagg attagcaacg gggatttata ttgtaggga tttgattgct    180 cgtcttatat ttggtaagca attagaagtt ctaggacgta agttagtttt acgtggaggg    240
gctatttttt acttactaac aactttagct tatttttata tgccaagtat cggagtaatg    300
tatttagttc gtttcctaaa tggttttggt tatggcgtcg tgtcaacagc aactaatact    360
attgtaacag cctatatacc agctgataaa agaggtgagg ggattaactt ttacggtcta    420
tcaacaagtt tagccgcagc tattggtcct tttgtaggaa catttatgct agacaacctt    480
catattaact ttaaaatggt tattgtatta tgtagtattt taattgcgat tgtagtgttg    540
ggagcatttg ttttcccagt caaaaatatt actttaaatc cagaacagtt agctaaatca    600
aaatcatgga ctattgatag tttcattgag aaaaaagcaa ttttttatcac aattattgca    660 tttttgatgg gtatctccta tgcttccgtg ttaggtttcc aaaaattata caacagaa     720 attaatttga tgacagtagg agcttatttc tttattgttt atgcacttgt catcacttta    780
accagaccat ctatgggaag attaatggac gctaagggag ataagtgggt gctttatcca    840
```

-continued

```
agttatctgt tcttaacttt gggacttgct ttattaggga gtgctatggg aagtgttacc      900
taccttctat caggtgcttt gattggtttt ggttatggca cctttatgtc ttgtggccaa      960
gcagcatcaa tcaaaggtgt tgaggaacat cgtttcaata cagccatgtc aacttacatg     1020
ataggtcttg atttagggtt aggtgctgga ccttacattt tgggacttgt taaagatggt     1080
tttcttggag ctggtgtgca atcctttaga gaattattct ggatagcagc gattattcct     1140
gttgtttgtg gtattctata tttcttaaaa tcatctagac aagttgaaac taaaactata     1200
taa                                                                   1203
```

<210> SEQ ID NO 34
<211> LENGTH: 400
<212> TYPE: PRT
<213> ORGANISM: Streptococcus agalactiae

<400> SEQUENCE: 34

```
Met Glu Asp Lys Leu Phe Asn Lys His Phe Ile Gly Ile Thr Ile Leu
  1               5                  10                  15

Asn Phe Ile Val Tyr Met Val Tyr Leu Phe Thr Val Ile Ile Ala
                 20                  25                  30

Phe Ile Ala Thr Lys Glu Leu Gly Val Ser Thr Ser Gln Ala Gly Leu
             35                  40                  45

Ala Thr Gly Ile Tyr Ile Val Gly Thr Leu Ile Ala Arg Leu Ile Phe
         50                  55                  60

Gly Lys Gln Leu Glu Val Leu Gly Arg Lys Leu Val Leu Arg Gly Gly
 65                  70                  75                  80

Ala Ile Phe Tyr Leu Leu Thr Thr Leu Ala Tyr Phe Tyr Met Pro Ser
                 85                  90                  95

Ile Gly Val Met Tyr Leu Val Arg Phe Leu Asn Gly Phe Gly Tyr Gly
                100                 105                 110

Val Val Ser Thr Ala Thr Asn Thr Ile Val Thr Ala Tyr Ile Pro Ala
            115                 120                 125

Asp Lys Arg Gly Glu Gly Ile Asn Phe Tyr Gly Leu Ser Thr Ser Leu
        130                 135                 140

Ala Ala Ala Ile Gly Pro Phe Val Gly Thr Phe Met Leu Asp Asn Leu
145                 150                 155                 160

His Ile Asn Phe Lys Met Val Ile Val Leu Cys Ser Ile Leu Ile Ala
                165                 170                 175

Ile Val Val Leu Gly Ala Phe Val Phe Pro Val Lys Asn Ile Thr Leu
            180                 185                 190

Asn Pro Glu Gln Leu Ala Lys Ser Lys Ser Trp Thr Ile Asp Ser Phe
        195                 200                 205

Ile Glu Lys Lys Ala Ile Phe Ile Thr Ile Ile Ala Phe Leu Met Gly
    210                 215                 220

Ile Ser Tyr Ala Ser Val Leu Gly Phe Gln Lys Leu Tyr Thr Thr Glu
225                 230                 235                 240

Ile Asn Leu Met Thr Val Gly Ala Tyr Phe Phe Ile Val Tyr Ala Leu
                245                 250                 255

Val Ile Thr Leu Thr Arg Pro Ser Met Gly Arg Leu Met Asp Ala Lys
            260                 265                 270

Gly Asp Lys Trp Val Leu Tyr Pro Ser Tyr Leu Phe Thr Leu Gly
        275                 280                 285

Leu Ala Leu Leu Gly Ser Ala Met Gly Ser Val Thr Tyr Leu Leu Ser
    290                 295                 300
```

```
Gly Ala Leu Ile Gly Phe Gly Tyr Gly Thr Phe Met Ser Cys Gly Gln
305                 310                 315                 320

Ala Ala Ser Ile Lys Gly Val Glu Glu His Arg Phe Asn Thr Ala Met
            325                 330                 335

Ser Thr Tyr Met Ile Gly Leu Asp Leu Gly Leu Gly Ala Gly Pro Tyr
            340                 345                 350

Ile Leu Gly Leu Val Lys Asp Gly Phe Leu Gly Ala Gly Val Gln Ser
        355                 360                 365

Phe Arg Glu Leu Phe Trp Ile Ala Ala Ile Ile Pro Val Val Cys Gly
    370                 375                 380

Ile Leu Tyr Phe Leu Lys Ser Ser Arg Gln Val Glu Thr Lys Thr Ile
385                 390                 395                 400
```

<210> SEQ ID NO 35
<211> LENGTH: 393
<212> TYPE: DNA
<213> ORGANISM: Streptococcus agalactiae

<400> SEQUENCE: 35

```
atgaatagtg aacctaaaag tcagtcaaac gaagtaaaaa atagcaagca atcagaagtg      60
aagaaagata aaaaaatgac aaaaaaagaa caattagcct atctcaaaga gcatgagcaa     120
gaaatcatag attatgtaaa attacataac aaccaaattg agtccgttca attcgattgg     180
tcaagtgtaa aagtagaaca agcgggaat ggaactccac aagggggtga ttataatctt      240
tcactgagag gaaagtttaa tcatctacaa aattcaaaat taatagttga tttttattta     300
gctcataaaa atgatatccc aaatatcaaa tcaatgggaa tgctaaataa gccatatata     360
cataaaaatg gtatttggca catttatgaa tag                                   393
```

<210> SEQ ID NO 36
<211> LENGTH: 137
<212> TYPE: PRT
<213> ORGANISM: Streptococcus agalactiae

<400> SEQUENCE: 36

```
Met Ile Leu Gly Gly Cys Gln Met Asn Ser Glu Pro Lys Ser Gln Ser
1               5                   10                  15

Asn Glu Val Lys Asn Ser Lys Gln Ser Glu Val Lys Lys Asp Lys Lys
            20                  25                  30

Met Thr Lys Lys Glu Gln Leu Ala Tyr Leu Lys Glu His Glu Gln Glu
        35                  40                  45

Ile Ile Asp Tyr Val Lys Leu His Asn Asn Gln Ile Glu Ser Val Gln
    50                  55                  60

Phe Asp Trp Ser Ser Val Lys Val Glu Gln Ser Gly Asn Gly Thr Pro
65                  70                  75                  80

Gln Gly Gly Asp Tyr Asn Leu Ser Leu Arg Gly Lys Phe Asn His Leu
                85                  90                  95

Gln Asn Ser Lys Leu Ile Val Asp Phe Tyr Leu Ala His Lys Asn Asp
            100                 105                 110

Ile Pro Asn Ile Lys Ser Met Gly Met Leu Asn Lys Pro Tyr Ile His
        115                 120                 125

Lys Asn Gly Ile Trp His Ile Tyr Glu
    130                 135
```

<210> SEQ ID NO 37
<211> LENGTH: 927
<212> TYPE: DNA

<213> ORGANISM: Streptococcus agalactiae

<400> SEQUENCE: 37

```
atgaaaaaga ttcgattatc aaagtttatt aaaatgattg ttgttatttt gtttttaatt      60
agtgtagcag ctagttttta ttttttccac gttgcccaag ttcgagatga taaatccttt     120
atttcaaatg gtcaacgtaa gcctggaaac tctttatatg cttatgataa atcctttgat     180
aagctattaa agcaaaaaat agaaatgaca accaaaata taaagcaagt tgcttggtat      240
gttcctgctg ctaagaaaac tcataagaca gttgttgtcg ttcatggttt tgcgaatagc     300
aaagagaata tgaaggcata tggttggctg tttcataagt taggatacaa tgttcttatg     360
cctgacaaca ttgcacatgg tgaaagtcat gggcagttga taggctatgg ctggaacgac     420
cgcgagaaca ttatcaaatg gacagaaatg atagtggata gaatccatc aagccaaatt      480
actttatttg gtgtttcaat gggtggagca acagtcatga tggctagtgg tgaaaaatta     540
cctagtcagg ttgttaatat cattgaagat tgtggttatt ctagtgtttg ggatgaatta     600
aaatttcagg ctaaagagat gtatggttta ccagccttcc cactcttata tgaagtttca     660
acaatttcta aaatcagagc aggttttccg tatggacaag caagtagtgt cgaacaattg     720
aaaaagaata atttaccagc cctctttatt catggtgata aggataattt tgttccaaca     780
agtatggttt atgacaacta taagctaca gcaggtaaga aagagcttta tattgtaaaa       840
ggggcaaaac atgcgaaatc ttttgaaaca gagccagaaa aatatgagaa acgtatctct     900
agttttttga aaaatatga aaaataa                                          927
```

<210> SEQ ID NO 38
<211> LENGTH: 308
<212> TYPE: PRT
<213> ORGANISM: Streptococcus agalactiae

<400> SEQUENCE: 38

```
Met Lys Lys Ile Arg Leu Ser Lys Phe Ile Lys Met Ile Val Val Ile
  1               5                  10                  15

Leu Phe Leu Ile Ser Val Ala Ala Ser Phe Tyr Phe Phe His Val Ala
             20                  25                  30

Gln Val Arg Asp Asp Lys Ser Phe Ile Ser Asn Gly Gln Arg Lys Pro
         35                  40                  45

Gly Asn Ser Leu Tyr Ala Tyr Asp Lys Ser Phe Asp Lys Leu Leu Lys
     50                  55                  60

Gln Lys Ile Glu Met Thr Asn Gln Asn Ile Lys Gln Val Ala Trp Tyr
 65                  70                  75                  80

Val Pro Ala Ala Lys Lys Thr His Lys Thr Val Val Val His Gly
                 85                  90                  95

Phe Ala Asn Ser Lys Glu Asn Met Lys Ala Tyr Gly Trp Leu Phe His
            100                 105                 110

Lys Leu Gly Tyr Asn Val Leu Met Pro Asp Asn Ile Ala His Gly Glu
        115                 120                 125

Ser His Gly Gln Leu Ile Gly Tyr Gly Trp Asn Asp Arg Glu Asn Ile
    130                 135                 140

Ile Lys Trp Thr Glu Met Ile Val Asp Lys Asn Pro Ser Ser Gln Ile
145                 150                 155                 160

Thr Leu Phe Gly Val Ser Met Gly Gly Ala Thr Val Met Met Ala Ser
                165                 170                 175

Gly Glu Lys Leu Pro Ser Gln Val Val Asn Ile Ile Glu Asp Cys Gly
            180                 185                 190
```

```
Tyr Ser Ser Val Trp Asp Glu Leu Lys Phe Gln Ala Lys Glu Met Tyr
        195                 200                 205

Gly Leu Pro Ala Phe Pro Leu Leu Tyr Glu Val Ser Thr Ile Ser Lys
        210                 215                 220

Ile Arg Ala Gly Phe Ser Tyr Gly Gln Ala Ser Ser Val Glu Gln Leu
225                 230                 235                 240

Lys Lys Asn Asn Leu Pro Ala Leu Phe Ile His Gly Asp Lys Asp Asn
                245                 250                 255

Phe Val Pro Thr Ser Met Val Tyr Asp Asn Tyr Lys Ala Thr Ala Gly
            260                 265                 270

Lys Lys Glu Leu Tyr Ile Val Lys Gly Ala Lys His Ala Lys Ser Phe
        275                 280                 285

Glu Thr Glu Pro Glu Lys Tyr Glu Lys Arg Ile Ser Ser Phe Leu Lys
        290                 295                 300

Lys Tyr Glu Lys
305
```

<210> SEQ ID NO 39
<211> LENGTH: 546
<212> TYPE: DNA
<213> ORGANISM: Streptococcus agalactiae

<400> SEQUENCE: 39

```
ttgaggagta atatggtaaa gacagcagtt ttaatggcga catacaatgg cgaaaaattt    60
atatctgaac aacttgattc aattcgccaa cagacattaa aaccagatta tgtattattg   120
agggatgatt gttcaacgga tgaaacagtc aatgtcgtca ataactatat cgcaaaacat   180
gagttagaag gctggaaaat tgttaaaaac gacaaaaact taggctggcg tttaaatttt   240
cgtcaattac ttattgatgt gttagcctat gaggttgact atgtcttttt tagtgatcaa   300
gatgatattt ggtatcttga taaaaacgaa cgacagtttg ccattatgtc agataaccct   360
caaattgagg ttttgagtgc agacgttgat atcaaaacga tgtctacaga agccagtgtt   420
ccacattttc taactttttc ttctagtgat agaatcagtc agtatcctaa agtatatgat   480
tatcaaacat tccgtcccgg atggaccatt gctatgaaga gagattttgc gcaagctatc   540
gcttga                                                              546
```

<210> SEQ ID NO 40
<211> LENGTH: 181
<212> TYPE: PRT
<213> ORGANISM: Streptococcus agalactiae

<400> SEQUENCE: 40

```
Met Arg Ser Asn Met Val Lys Thr Ala Val Leu Met Ala Thr Tyr Asn
1               5                   10                  15

Gly Glu Lys Phe Ile Ser Glu Gln Leu Asp Ser Ile Arg Gln Gln Thr
            20                  25                  30

Leu Lys Pro Asp Tyr Val Leu Leu Arg Asp Asp Cys Ser Thr Asp Glu
        35                  40                  45

Thr Val Asn Val Val Asn Asn Tyr Ile Ala Lys His Glu Leu Glu Gly
    50                  55                  60

Trp Lys Ile Val Lys Asn Asp Lys Asn Leu Gly Trp Arg Leu Asn Phe
65                  70                  75                  80

Arg Gln Leu Leu Ile Asp Val Leu Ala Tyr Glu Val Asp Tyr Val Phe
                85                  90                  95
```

```
Phe Ser Asp Gln Asp Asp Ile Trp Tyr Leu Asp Lys Asn Glu Arg Gln
            100                 105                 110

Phe Ala Ile Met Ser Asp Asn Pro Gln Ile Glu Val Leu Ser Ala Asp
        115                 120                 125

Val Asp Ile Lys Thr Met Ser Thr Glu Ala Ser Val Pro His Phe Leu
    130                 135                 140

Thr Phe Ser Ser Asp Arg Ile Ser Gln Tyr Pro Lys Val Tyr Asp
145                 150                 155                 160

Tyr Gln Thr Phe Arg Pro Gly Trp Thr Ile Ala Met Lys Arg Asp Phe
                165                 170                 175

Ala Gln Ala Ile Ala
            180

<210> SEQ ID NO 41
<211> LENGTH: 579
<212> TYPE: DNA
<213> ORGANISM: Streptococcus agalactiae

<400> SEQUENCE: 41
atgattcatg agattcacga ttgtcaattt attgaaaaag gaagttacgt ttatttgaat      60
tatattaatg ctgagggcga gagagtagtt attataatca tagattttgt ccgtagtgtt     120
agtcctattt tatatcgtct atttatgatt ttacttgcac aagaagtacc tcacttgcat     180
gattacatct ataatgcaag agatgatcac tacgatactt ggaagtttaa agaattaaag     240
gagtcaaacc atccagtcct tttggcattc tctgaaaggt ggcacgatag tcgcttgact     300
tctaaaagcc ttgcagaatg tttacaatta accgaccttg atgaagaagt gaaatcgacc     360
atcattcaat taagacagtt cgaaaaatca gtcagaaatc ctttggctca cctgattaaa     420 cctttttgatg agcaagaact atatcgtaca actcaatttt cttctcaagc attttttagac    480 cagattatct tcttggcaaa ggtaattggt gttgagtatg atactgttaa ttttcactac     540
gatacggtta caagcttat tataaagata cttgagtaa                              579

<210> SEQ ID NO 42
<211> LENGTH: 192
<212> TYPE: PRT
<213> ORGANISM: Streptococcus agalactiae

<400> SEQUENCE: 42

Met Ile His Glu Ile His Asp Cys Gln Phe Ile Glu Lys Gly Ser Tyr
  1               5                  10                  15

Val Tyr Leu Asn Tyr Ile Asn Ala Glu Gly Glu Arg Val Val Ile Ile
            20                  25                  30

Ile Ile Asp Phe Val Arg Ser Val Ser Pro Ile Leu Tyr Arg Leu Phe
        35                  40                  45

Met Ile Leu Leu Ala Gln Glu Val Pro His Leu His Asp Tyr Ile Tyr
    50                  55                  60

Asn Ala Arg Asp Asp His Tyr Asp Thr Trp Lys Phe Lys Glu Leu Lys
 65                  70                  75                  80

Glu Ser Asn His Pro Val Leu Leu Ala Phe Ser Glu Arg Trp His Asp
                85                  90                  95

Ser Arg Leu Thr Ser Lys Ser Leu Ala Glu Cys Leu Gln Leu Thr Asp
            100                 105                 110

Leu Asp Glu Glu Val Lys Ser Thr Ile Ile Gln Leu Arg Gln Phe Glu
        115                 120                 125

Lys Ser Val Arg Asn Pro Leu Ala His Leu Ile Lys Pro Phe Asp Glu
```

```
                130              135              140
Gln Glu Leu Tyr Arg Thr Thr Gln Phe Ser Ser Gln Ala Phe Leu Asp
145                 150                 155                 160

Gln Ile Ile Phe Leu Ala Lys Val Ile Gly Val Glu Tyr Asp Thr Val
                165                 170                 175

Asn Phe His Tyr Asp Thr Val Asn Lys Leu Ile Ile Lys Ile Leu Glu
            180                 185                 190
```

<210> SEQ ID NO 43
<211> LENGTH: 465
<212> TYPE: DNA
<213> ORGANISM: Streptococcus agalactiae

<400> SEQUENCE: 43

```
atggtaaaag tttcaaattt agggtatcca cgtcttggtg aacagcgcga atggaagcaa      60
gcgatcgaag ctttctgggc agggaatctt gaacaaaaag atttagaaaa acaactaaaa     120
caattacgta tcaatcattt aaagaaacaa aaagaggcag gtattgacct tattccagtg     180
ggggattttt cttgttatga tcatgttttg gatttgtcat ttcaattcaa tgtaatccca     240
aagcgtttcg atgagtatga gaggaattta gacctttatt ttgctattgc aagaggtgac     300
aaagataatg tcgcatcatc tatgaaaaag tggtttaata ccaactacca ctacatagtc     360
ccagaatggg aggttgagac taaacctcac ttgcagaata attacttact tgatctttat     420
ctagaagcta gggaagtagt tggtgataaa gcaaagccgg ttatc                     465
```

<210> SEQ ID NO 44
<211> LENGTH: 159
<212> TYPE: PRT
<213> ORGANISM: Streptococcus agalactiae

<400> SEQUENCE: 44

```
Met Glu Glu Ile Met Val Lys Val Ser Asn Leu Gly Tyr Pro Arg Leu
1               5                   10                  15

Gly Glu Gln Arg Glu Trp Lys Gln Ala Ile Glu Ala Phe Trp Ala Gly
            20                  25                  30

Asn Leu Glu Gln Lys Asp Leu Glu Lys Gln Leu Lys Gln Leu Arg Ile
        35                  40                  45

Asn His Leu Lys Lys Gln Lys Glu Ala Gly Ile Asp Leu Ile Pro Val
    50                  55                  60

Gly Asp Phe Ser Cys Tyr Asp His Val Leu Asp Leu Ser Phe Gln Phe
65                  70                  75                  80

Asn Val Ile Pro Lys Arg Phe Asp Glu Tyr Glu Arg Asn Leu Asp Leu
                85                  90                  95

Tyr Phe Ala Ile Ala Arg Gly Asp Lys Asp Asn Val Ala Ser Ser Met
            100                 105                 110

Lys Lys Trp Phe Asn Thr Asn Tyr His Tyr Ile Val Pro Glu Trp Glu
        115                 120                 125

Val Glu Thr Lys Pro His Leu Gln Asn Asn Tyr Leu Leu Asp Leu Tyr
    130                 135                 140

Leu Glu Ala Arg Glu Val Val Gly Asp Lys Ala Lys Pro Val Ile
145                 150                 155
```

<210> SEQ ID NO 45
<211> LENGTH: 124
<212> TYPE: DNA
<213> ORGANISM: Streptococcus agalactiae

<400> SEQUENCE: 45

| | |
|---|---|
| atggtgttac ttttattgct aatggtagcc aagtcaagtt tgatggttac atggctgttt | 60 |
| ataacgatac tgacaaaaat aaaatgttac cagatatgga ggaaggagaa agttatcaag | 120 |
| ttaa | 124 |

<210> SEQ ID NO 46
<211> LENGTH: 41
<212> TYPE: PRT
<213> ORGANISM: Streptococcus agalactiae

<400> SEQUENCE: 46

```
Met Val Leu Leu Leu Leu Met Val Ala Lys Ser Ser Leu Met Val
 1               5                  10                  15
Thr Trp Leu Phe Ile Thr Ile Leu Thr Lys Ile Lys Cys Tyr Gln Ile
            20                  25                  30
Trp Arg Lys Glu Lys Val Ile Lys Leu
        35                  40
```

<210> SEQ ID NO 47
<211> LENGTH: 669
<212> TYPE: DNA
<213> ORGANISM: Streptococcus agalactiae

<400> SEQUENCE: 47

| | |
|---|---|
| atgaacaaaa aaatttccgg gatcggcttg gcttcgattg cagtacttag tttagctgca | 60 |
| tgtggacatc gtggtgcttc taaatctggt ggtaaatcag atagcttgaa ggttgcaatg | 120 |
| gtaacagata ccgtggtgt tgatgataaa tcatttaacc aatctggttg ggaaggtatg | 180 |
| caagcttggg gcaagaagaa tggccttaaa aaggagctg gttttgacta tttccaatcg | 240 |
| gcaagtgaat ctgattatgc aactaactta gatacagctg tgtctagtgg ttataaattg | 300 |
| attttcggta ttggattttc tcttcatgat gctattgata aagcagcaga caataacaaa | 360 |
| gatgttaatt acgtcatcgt tgatgatgtt attaaaggga agataatgt tgcaagtgtt | 420 |
| gtctttgcgg ataatgaatc agcttactta gcaggtattg cagccgctaa aactaccaaa | 480 |
| acaaaaacag ttggctttgt aggtggtatg gaatctgagg ttattacccg ttttgaaaaa | 540 |
| ggttttgaag caggtgtcaa atcagttgat aaatcaatta aaattaaagt tgactatgct | 600 |
| ggttcattcg gtgatgctgc taagggtaag acaattgcag ccgcacaata tgcttctggc | 660 |
| gcagatatt | 669 |

<210> SEQ ID NO 48
<211> LENGTH: 223
<212> TYPE: PRT
<213> ORGANISM: Streptococcus agalactiae

<400> SEQUENCE: 48

```
Met Asn Lys Lys Ile Ser Gly Ile Gly Leu Ala Ser Ile Ala Val Leu
 1               5                  10                  15
Ser Leu Ala Ala Cys Gly His Arg Gly Ala Ser Lys Ser Gly Gly Lys
            20                  25                  30
Ser Asp Ser Leu Lys Val Ala Met Val Thr Asp Thr Gly Val Asp
        35                  40                  45
Asp Lys Ser Phe Asn Gln Ser Gly Trp Glu Gly Met Gln Ala Trp Gly
    50                  55                  60
Lys Lys Asn Gly Leu Lys Lys Gly Ala Gly Phe Asp Tyr Phe Gln Ser
65                  70                  75                  80
```

```
Ala Ser Glu Ser Asp Tyr Ala Thr Asn Leu Asp Thr Ala Val Ser Ser
                85                  90                  95

Gly Tyr Lys Leu Ile Phe Gly Ile Gly Phe Ser Leu His Asp Ala Ile
            100                 105                 110

Asp Lys Ala Ala Asp Asn Asn Lys Asp Val Asn Tyr Val Ile Val Asp
        115                 120                 125

Asp Val Ile Lys Gly Lys Asp Asn Val Ala Ser Val Phe Ala Asp
    130                 135                 140

Asn Glu Ser Ala Tyr Leu Ala Gly Ile Ala Ala Lys Thr Thr Lys
145                 150                 155                 160

Thr Lys Thr Val Gly Phe Val Gly Gly Met Glu Ser Glu Val Ile Thr
                165                 170                 175

Arg Phe Glu Lys Gly Phe Glu Ala Gly Val Lys Ser Val Asp Lys Ser
            180                 185                 190

Ile Lys Ile Lys Val Asp Tyr Ala Gly Ser Phe Gly Asp Ala Ala Lys
        195                 200                 205

Gly Lys Thr Ile Ala Ala Ala Gln Tyr Ala Ser Gly Ala Asp Ile
    210                 215                 220

<210> SEQ ID NO 49
<211> LENGTH: 609
<212> TYPE: DNA
<213> ORGANISM: Streptococcus agalactiae

<400> SEQUENCE: 49
atgttacatt ctaaaaaaat acattcctta tcgcttattg ccgttctctc tttagcaaca    60
tatacgagtt tacaaccaaa tcatgtagcg gctgaacaat cacaaaaaac atcaactgtt   120
cttatgagtc aaaaaactat tgaacataag ttaaagttg cagataaaga agctgctcct   180
ctctacgcta aaatcgacca tatccaacga catattgaag tcaaaaaagc aaaagattta   240
aaagttattg aattgtatat taacaaagat atcaaccaac tagagaagca aaataaacgt   300
ctactaacta aattctatac ttctattgat aatcaaacat gggatagcac aagtgaagtc   360
aaaaaattga ttgataagac aaccctatcc actaacgaaa aagatagatt aaaattatat   420
tttgaacaac gtgcttacct tgagacaagg ttgaacgacc gctatcaaaa atttgataac   480
tctattgaaa ccaaaataa agaactaaaa atattaacgt caaaaataga aaaatctat    540 caaaaacatg gtattacaaa agaggtatta aaaacttact atgctaaaaa aacagtacga   600
gctgactga                                                          609

<210> SEQ ID NO 50
<211> LENGTH: 202
<212> TYPE: PRT
<213> ORGANISM: Streptococcus agalactiae

<400> SEQUENCE: 50

Met Leu His Ser Lys Lys Ile His Ser Leu Ser Leu Ile Ala Val Leu
 1               5                  10                  15

Ser Leu Ala Thr Tyr Thr Ser Leu Gln Pro Asn His Val Ala Ala Glu
            20                  25                  30

Gln Ser Gln Lys Thr Ser Thr Val Leu Met Ser Gln Lys Thr Ile Glu
        35                  40                  45

His Lys Leu Lys Val Ala Asp Lys Glu Ala Ala Pro Leu Tyr Ala Lys
    50                  55                  60

Ile Asp His Ile Gln Arg His Ile Glu Val Lys Lys Ala Lys Asp Leu
```

```
                65                  70                  75                  80
Lys Val Ile Glu Leu Tyr Ile Asn Lys Asp Ile Asn Gln Leu Glu Lys
                    85                  90                  95

Gln Asn Lys Arg Leu Leu Thr Lys Phe Tyr Thr Ser Ile Asp Asn Gln
                100                 105                 110

Thr Trp Asp Ser Thr Ser Glu Val Lys Lys Leu Ile Asp Lys Thr Thr
            115                 120                 125

Leu Ser Thr Asn Glu Lys Asp Arg Leu Lys Leu Tyr Phe Glu Gln Arg
        130                 135                 140

Ala Tyr Leu Glu Thr Arg Leu Asn Asp Arg Tyr Gln Lys Phe Asp Asn
145                 150                 155                 160

Ser Ile Glu Asn Gln Asn Lys Glu Leu Lys Ile Leu Thr Ser Lys Ile
                165                 170                 175

Glu Lys Ile Tyr Gln Lys His Gly Ile Thr Lys Glu Val Leu Lys Thr
            180                 185                 190

Tyr Tyr Ala Lys Lys Thr Val Arg Ala Asp
        195                 200

<210> SEQ ID NO 51
<211> LENGTH: 600
<212> TYPE: DNA
<213> ORGANISM: Streptococcus agalactiae

<400> SEQUENCE: 51
ctgaattccc aaaaacgcta caatcaaact tggtatccta cttatggttt ttctgatact      60
tatgcattca tggttactaa agagtttgcc agacagaata aaatcaccaa gatctctgat     120
ctcaaaaagt tatcaacaac tatgaaggca ggggttgata gttcatggat gaatcgcgag     180
ggagatggat acactgattt cgctaaaaca tacggttttg aattttcaca tatttaccct     240
atgcaaattg gcttagtcta tgatgcggtt gaaagtaaca aaatgcaatc tgtattaggc     300
tactccactg acggtcgtat ttcgagctat gatttagaaa ttttaaggga tgataaaaaa     360
ttctttcctc cttatgaagc ctctatggtt gtcaacaatt ctatcatcaa aaagatcct      420 aaactaaaaa aattactcca tcgactcgat ggtaaaatca atttaaaaac gatgcaaaac     480
cttaattata tggtagatga taaacttttt gaagcttggc gtaatcatgg tcatagctgt     540
ttcctgtgtg aaattgttat ccgctcacaa ttccacacaa catacgagcc ggaagcataa     600

<210> SEQ ID NO 52
<211> LENGTH: 199
<212> TYPE: PRT
<213> ORGANISM: Streptococcus agalactiae

<400> SEQUENCE: 52

Leu Asn Ser Gln Lys Arg Tyr Asn Gln Thr Trp Tyr Pro Thr Tyr Gly
 1               5                  10                  15

Phe Ser Asp Thr Tyr Ala Phe Met Val Thr Lys Glu Phe Ala Arg Gln
                20                  25                  30

Asn Lys Ile Thr Lys Ile Ser Asp Leu Lys Lys Leu Ser Thr Thr Met
            35                  40                  45

Lys Ala Gly Val Asp Ser Ser Trp Met Asn Arg Glu Gly Asp Gly Tyr
        50                  55                  60

Thr Asp Phe Ala Lys Thr Tyr Gly Phe Glu Phe Ser His Ile Tyr Pro
65                  70                  75                  80

Met Gln Ile Gly Leu Val Tyr Asp Ala Val Glu Ser Asn Lys Met Gln
                85                  90                  95
```

```
Ser Val Leu Gly Tyr Ser Thr Asp Gly Arg Ile Ser Tyr Asp Leu
            100                 105                 110

Glu Ile Leu Arg Asp Asp Lys Lys Phe Phe Pro Tyr Glu Ala Ser
            115                 120                 125

Met Val Val Asn Asn Ser Ile Ile Lys Lys Asp Pro Lys Leu Lys Lys
            130                 135                 140

Leu Leu His Arg Leu Asp Gly Lys Ile Asn Leu Lys Thr Met Gln Asn
145                 150                 155                 160

Leu Asn Tyr Met Val Asp Asp Lys Leu Leu Glu Ala Trp Arg Asn His
                165                 170                 175

Gly His Ser Cys Phe Leu Cys Glu Ile Val Ile Arg Ser Gln Phe His
                180                 185                 190

Thr Thr Tyr Glu Pro Glu Ala
            195
```

<210> SEQ ID NO 53
<211> LENGTH: 849
<212> TYPE: DNA
<213> ORGANISM: Streptococcus agalactiae

<400> SEQUENCE: 53

```
atgaaaaaat tactttccct aacatgtcta atcatgatgt ctttatgttt agtggcatgt      60
actaagcaag caatgtcgtc taagcaagca atgtcgtcta agcaaattaa agataagaat     120
agtaaagaaa aggtgattac tgttgcaact tacagcaaac ctacatctac cttttttagat   180
ttgattaaag ataatgtaaa agaaaaagga tatactttaa aggttgtcat ggtctctgac     240
tatattcagg ctaacattgc tttagaaaac aaagaacatg atgctaacct tttacaacat     300
gaatttttca tgagtatctt taataaggaa aatgatggtc atctagtgtc aattacacca     360
atttatcatt cattggctgg tttttatggt caacatttga aaatattgc cgagcttaaa     420
gacggtgcta aggtagcgat tccgtctgat cctgccaata tgactagagc tctgctatta     480
ttgcaagaaa agaaacttat caccttaaag aatacgtcca aaagaccaa ggctatcgaa       540
gatattatta ctaaccctaa aaattacga attgaacctg tagcattact taacctcaat     600
caggcctatt ttgaatatga ccttgtcttt aatttccctg atatgtgac aaaaatcaat     660
ctagttccta aagggatag attattatat gagaaaaaac cagatatccg ttttgcaggt     720
gccttggtag ctcgtgaaga ataataaaaat agtgataaaa taaagtact taaagaagta     780
ctaacaagta aagagattcg tcactatatc actaaggaga ttccaagtga agcagacgtt     840
gcgttctag                                                             849
```

<210> SEQ ID NO 54
<211> LENGTH: 282
<212> TYPE: PRT
<213> ORGANISM: Streptococcus agalactiae

<400> SEQUENCE: 54

```
Met Lys Lys Leu Leu Ser Leu Thr Cys Leu Ile Met Met Ser Leu Cys
  1                 5                  10                  15

Leu Val Ala Cys Thr Lys Gln Ala Met Ser Ser Lys Gln Ala Met Ser
             20                  25                  30

Ser Lys Gln Ile Lys Asp Lys Asn Ser Lys Glu Lys Val Ile Thr Val
         35                  40                  45

Ala Thr Tyr Ser Lys Pro Thr Ser Thr Phe Leu Asp Leu Ile Lys Asp
     50                  55                  60
```

Asn Val Lys Glu Lys Gly Tyr Thr Leu Lys Val Met Val Ser Asp
 65                  70                  75                  80

Tyr Ile Gln Ala Asn Ile Ala Leu Glu Asn Lys Glu His Asp Ala Asn
                 85                  90                  95

Leu Leu Gln His Glu Phe Met Ser Ile Phe Asn Lys Glu Asn Asp
            100                 105                 110

Gly His Leu Val Ser Ile Thr Pro Ile Tyr His Ser Leu Ala Gly Phe
        115                 120                 125

Tyr Gly Gln His Leu Lys Asn Ile Ala Glu Leu Lys Asp Gly Ala Lys
    130                 135                 140

Val Ala Ile Pro Ser Asp Pro Ala Asn Met Thr Arg Ala Leu Leu Leu
145                 150                 155                 160

Leu Gln Glu Lys Lys Leu Ile Thr Leu Lys Asn Thr Ser Lys Lys Thr
                165                 170                 175

Lys Ala Ile Glu Asp Ile Ile Thr Asn Pro Lys Lys Leu Arg Ile Glu
            180                 185                 190

Pro Val Ala Leu Leu Asn Leu Asn Gln Ala Tyr Phe Glu Tyr Asp Leu
        195                 200                 205

Val Phe Asn Phe Pro Gly Tyr Val Thr Lys Ile Asn Leu Val Pro Lys
    210                 215                 220

Arg Asp Arg Leu Leu Tyr Glu Lys Lys Pro Asp Ile Arg Phe Ala Gly
225                 230                 235                 240

Ala Leu Val Ala Arg Glu Asp Asn Lys Asn Ser Asp Lys Ile Lys Val
                245                 250                 255

Leu Lys Glu Val Leu Thr Ser Lys Glu Ile Arg His Tyr Ile Thr Lys
            260                 265                 270

Glu Ile Pro Ser Glu Ala Asp Val Ala Phe
        275                 280

<210> SEQ ID NO 55
<211> LENGTH: 711
<212> TYPE: DNA
<213> ORGANISM: Streptococcus agalactiae

<400> SEQUENCE: 55
ctgttggcta aggaaaccac tatgtctgtc ctttggtatc aaaattctgc agaagccaag      60
gctttatatt tacaaggtta taatgttgct aaaatgaagt tagatgattg gttacaaaag     120
cccagtgaaa aaccatattc aattatctta gatttagatg aaacagtttt agataatagc     180
ccatatcaag caaagaatat taaagatggc tctagtttca cgccagagag ttgggataaa     240
tgggtgcaaa agaaatcagc taaggctgtt gcgggtgcca aagaattttt gaagtatgct     300
aatgaaaagg gaataaaaat ttattatgtc tcagatcgta cagatgctca agttgatgcg     360
actaagaaaa atttagagaa ggaaggtata cctgttcaag ggaaagacca cttgcttttc     420
cttaaaaaag gaatgaaatc taagagagt cgccgtcagg cagttcaaaa agataccaat     480
ttaattatgc ttttttggaga taatttagtt gattttgctg atttttctaa atcatctagt     540
acagatagag aacaactact aactaaactt caaagtgagt ttggtagtaa atttattgtt     600
ttcccaaatc ctatgtacgg ttcttgggaa agtgctattt atcaaggaaa acatctggat     660
gttcaaaaac aattgaaaga acgacaaaaa atgttgcatt cgtatgatta a              711

<210> SEQ ID NO 56
<211> LENGTH: 236
<212> TYPE: PRT

<213> ORGANISM: Streptococcus agalactiae

<400> SEQUENCE: 56

| | | | | | | | | | | | | | | |
|---|---|---|---|---|---|---|---|---|---|---|---|---|---|---|
| Leu | Leu | Ala | Lys | Glu | Thr | Thr | Met | Ser | Val | Leu | Trp | Tyr | Gln | Asn | Ser |
| 1 | | | | 5 | | | | | 10 | | | | | 15 | |
| Ala | Glu | Ala | Lys | Ala | Leu | Tyr | Leu | Gln | Gly | Tyr | Asn | Val | Ala | Lys | Met |
| | | | | 20 | | | | | 25 | | | | | 30 | |
| Lys | Leu | Asp | Asp | Trp | Leu | Gln | Lys | Pro | Ser | Glu | Lys | Pro | Tyr | Ser | Ile |
| | | | 35 | | | | | 40 | | | | | 45 | | |
| Ile | Leu | Asp | Leu | Asp | Glu | Thr | Val | Leu | Asp | Asn | Ser | Pro | Tyr | Gln | Ala |
| | | 50 | | | | | 55 | | | | | 60 | | | |
| Lys | Asn | Ile | Lys | Asp | Gly | Ser | Ser | Phe | Thr | Pro | Glu | Ser | Trp | Asp | Lys |
| 65 | | | | | 70 | | | | | 75 | | | | | 80 |
| Trp | Val | Gln | Lys | Lys | Ser | Ala | Lys | Ala | Val | Ala | Gly | Ala | Lys | Glu | Phe |
| | | | | 85 | | | | | 90 | | | | | 95 | |
| Leu | Lys | Tyr | Ala | Asn | Glu | Lys | Gly | Ile | Lys | Ile | Tyr | Tyr | Val | Ser | Asp |
| | | | | 100 | | | | | 105 | | | | | 110 | |
| Arg | Thr | Asp | Ala | Gln | Val | Asp | Ala | Thr | Lys | Glu | Asn | Leu | Glu | Lys | Glu |
| | | | 115 | | | | | 120 | | | | | 125 | | |
| Gly | Ile | Pro | Val | Gln | Gly | Lys | Asp | His | Leu | Leu | Phe | Leu | Lys | Lys | Gly |
| | | 130 | | | | | 135 | | | | | 140 | | | |
| Met | Lys | Ser | Lys | Glu | Ser | Arg | Arg | Gln | Ala | Val | Gln | Lys | Asp | Thr | Asn |
| 145 | | | | | 150 | | | | | 155 | | | | | 160 |
| Leu | Ile | Met | Leu | Phe | Gly | Asp | Asn | Leu | Val | Asp | Phe | Ala | Asp | Phe | Ser |
| | | | | 165 | | | | | 170 | | | | | 175 | |
| Lys | Ser | Ser | Ser | Thr | Asp | Arg | Glu | Gln | Leu | Leu | Thr | Lys | Leu | Gln | Ser |
| | | | 180 | | | | | 185 | | | | | 190 | | |
| Glu | Phe | Gly | Ser | Lys | Phe | Ile | Val | Phe | Pro | Asn | Pro | Met | Tyr | Gly | Ser |
| | | | | 195 | | | | | 200 | | | | | 205 | |
| Trp | Glu | Ser | Ala | Ile | Tyr | Gln | Gly | Lys | His | Leu | Asp | Val | Gln | Lys | Gln |
| | | | 210 | | | | | 215 | | | | | 220 | | |
| Leu | Lys | Glu | Arg | Gln | Lys | Met | Leu | His | Ser | Tyr | Asp | | | | |
| 225 | | | | | 230 | | | | | 235 | | | | | |

<210> SEQ ID NO 57
<211> LENGTH: 128
<212> TYPE: DNA
<213> ORGANISM: Streptococcus agalactiae

<400> SEQUENCE: 57

```
atggataata aaggtaataa cgccaatgtg attgatgcaa tcgctgaggg tgcaagcaca      60
ggtgcacaaa tggctttctc aattggtgct agtttgattg cctttgttgg tttagtttct     120
ttgattaa                                                              128
```

<210> SEQ ID NO 58
<211> LENGTH: 42
<212> TYPE: PRT
<213> ORGANISM: Streptococcus agalactiae

<400> SEQUENCE: 58

| | | | | | | | | | | | | | | |
|---|---|---|---|---|---|---|---|---|---|---|---|---|---|---|
| Met | Asp | Asn | Lys | Gly | Asn | Asn | Ala | Asn | Val | Ile | Asp | Ala | Ile | Ala | Glu |
| 1 | | | | 5 | | | | | 10 | | | | | 15 | |
| Gly | Ala | Ser | Thr | Gly | Ala | Gln | Met | Ala | Phe | Ser | Ile | Gly | Ala | Ser | Leu |
| | | | | 20 | | | | | 25 | | | | | 30 | |
| Ile | Ala | Phe | Val | Gly | Leu | Val | Ser | Leu | Ile | | | | | | |
| | | | | 35 | | | | | 40 | | | | | | |

<210> SEQ ID NO 59
<211> LENGTH: 573
<212> TYPE: DNA
<213> ORGANISM: Streptococcus agalactiae

<400> SEQUENCE: 59

```
atgaaaaaga aaacaaatc ctctaacatt gctataattg caatcttttt tgctattatg      60
cttgtcattc attttttgtc atcatttatt tttagttttt ggttagtccc tattaaacct     120
actttgatgc atatcccagt tattattgca tctatagcct atggacctcg tattggtgca     180
actctaggcg ccttaatggg ggggatcagc gtagctaaca gcagcattgt tctattacca     240
acgagttacc tcttctcacc ttttgttgaa atggtaatt tttattcgct aattattgca     300
cttgtaccac gtattctaat cgggattatt ccttatttcg tttacaaatt actacacaac     360
cgctttggtt tggctatctc aggtgctata ggctctctaa caaacacagt atttgtttta     420
tctggaattt ttatctttttt ttcaagtact tataatggga atatcaagct aatgctcgct     480
gggattattt catctaattc attagctgag atggtcattg cagctatcat tgtatatcta     540
actgatcctc gtattctcaa tattaaacat taa                                   573
```

<210> SEQ ID NO 60
<211> LENGTH: 190
<212> TYPE: PRT
<213> ORGANISM: Streptococcus agalactiae

<400> SEQUENCE: 60

Met Lys Lys Asn Lys Ser Ser Asn Ile Ala Ile Ile Ala Ile Phe
1               5                   10                  15

Phe Ala Ile Met Leu Val Ile His Phe Leu Ser Ser Phe Ile Phe Ser
            20                  25                  30

Phe Trp Leu Val Pro Ile Lys Pro Thr Leu Met His Ile Pro Val Ile
        35                  40                  45

Ile Ala Ser Ile Ala Tyr Gly Pro Arg Ile Gly Ala Thr Leu Gly Ala
    50                  55                  60

Leu Met Gly Gly Ile Ser Val Ala Asn Ser Ser Ile Val Leu Leu Pro
65                  70                  75                  80

Thr Ser Tyr Leu Phe Ser Pro Phe Val Glu Asn Gly Asn Phe Tyr Ser
                85                  90                  95

Leu Ile Ile Ala Leu Val Pro Arg Ile Leu Ile Gly Ile Ile Pro Tyr
            100                 105                 110

Phe Val Tyr Lys Leu Leu His Asn Arg Phe Gly Leu Ala Ile Ser Gly
        115                 120                 125

Ala Ile Gly Ser Leu Thr Asn Thr Val Phe Val Leu Ser Gly Ile Phe
    130                 135                 140

Ile Phe Phe Ser Ser Thr Tyr Asn Gly Asn Ile Lys Leu Met Leu Ala
145                 150                 155                 160

Gly Ile Ile Ser Ser Asn Ser Leu Ala Glu Met Val Ile Ala Ala Ile
                165                 170                 175

Ile Val Tyr Leu Thr Asp Pro Arg Ile Leu Asn Ile Lys His
            180                 185                 190

<210> SEQ ID NO 61
<211> LENGTH: 251
<212> TYPE: DNA
<213> ORGANISM: Streptococcus agalactiae

<400> SEQUENCE: 61

```
ttgaatatga cattacaaga cgaaatcaaa aaacgccgta cttttgccat catctctcac      60
ccggatgctg gtaagacgac tattactgag caattattat attttggtgg tgaaattaga    120
gaagcaggga cagtaaaagg gaaaaaatca ggtactttg caaagtccga ctggatggat     180
attgaaaagc aacggggtat ctctgttact tcatctgtta tgcaatttga ttacgcgggt    240
aaacgtgtta a                                                         251
```

<210> SEQ ID NO 62
<211> LENGTH: 83
<212> TYPE: PRT
<213> ORGANISM: Streptococcus agalactiae

<400> SEQUENCE: 62

```
Met Asn Met Thr Leu Gln Asp Glu Ile Lys Lys Arg Arg Thr Phe Ala
  1               5                  10                  15
Ile Ile Ser His Pro Asp Ala Gly Lys Thr Thr Ile Thr Glu Gln Leu
             20                  25                  30
Leu Tyr Phe Gly Gly Glu Ile Arg Glu Ala Gly Thr Val Lys Gly Lys
         35                  40                  45
Lys Ser Gly Thr Phe Ala Lys Ser Asp Trp Met Asp Ile Glu Lys Gln
     50                  55                  60
Arg Gly Ile Ser Val Thr Ser Ser Val Met Gln Phe Asp Tyr Ala Gly
 65                  70                  75                  80
Lys Arg Val
```

<210> SEQ ID NO 63
<211> LENGTH: 303
<212> TYPE: DNA
<213> ORGANISM: Streptococcus agalactiae

<400> SEQUENCE: 63

```
atggcagata aaacagaac atttaaactt gtaggtgcag gatcttctag cacacaagaa       60
aaaattgaaa agcctgctct ttcgtttatg caagatgcgt ggcgtcgctt gaaaaaaaac    120
aaattagcag tagtttcact ctatttatta gctcttttac ttactttttc gttagcctca    180
aatttatttg taactcagaa ggatgctaat gggtttgatt cgaaaaaagt aacgacatat    240
cgcaacttac cacctaaatt gagttcaaac cttcctttt ggaatggtag cattaatcca    300
tca                                                                  303
```

<210> SEQ ID NO 64
<211> LENGTH: 101
<212> TYPE: PRT
<213> ORGANISM: Streptococcus agalactiae

<400> SEQUENCE: 64

```
Met Ala Asp Lys Asn Arg Thr Phe Lys Leu Val Gly Ala Gly Ser Ser
  1               5                  10                  15
Ser Thr Gln Glu Lys Ile Glu Lys Pro Ala Leu Ser Phe Met Gln Asp
             20                  25                  30
Ala Trp Arg Arg Leu Lys Lys Asn Lys Leu Ala Val Val Ser Leu Tyr
         35                  40                  45
Leu Leu Ala Leu Leu Leu Thr Phe Ser Leu Ala Ser Asn Leu Phe Val
     50                  55                  60
Thr Gln Lys Asp Ala Asn Gly Phe Asp Ser Lys Lys Val Thr Thr Tyr
 65                  70                  75                  80
```

-continued

Arg Asn Leu Pro Pro Lys Leu Ser Ser Asn Leu Pro Phe Trp Asn Gly
                85                  90                  95

Ser Ile Asn Pro Ser
            100

<210> SEQ ID NO 65
<211> LENGTH: 154
<212> TYPE: DNA
<213> ORGANISM: Streptococcus agalactiae

<400> SEQUENCE: 65
atgaaaagaa aacagtttat aaaattagga attgcaacct tactaacggt tatttcgctt      60
tacacaccaa taaacctagc tacaaatcat accacagaaa atattgttac tgctcaagag     120
tataaaacaa agagaatggt actttacctt ttaa                                 154

<210> SEQ ID NO 66
<211> LENGTH: 51
<212> TYPE: PRT
<213> ORGANISM: Streptococcus agalactiae

<400> SEQUENCE: 66

Met Lys Arg Lys Gln Phe Ile Lys Leu Gly Ile Ala Thr Leu Leu Thr
  1               5                  10                  15

Val Ile Ser Leu Tyr Thr Pro Ile Asn Leu Ala Thr Asn His Thr Thr
                20                  25                  30

Glu Asn Ile Val Thr Ala Gln Glu Tyr Lys Thr Lys Glu Asn Ile Leu
            35                  40                  45

Phe Leu Leu
    50

<210> SEQ ID NO 67
<211> LENGTH: 144
<212> TYPE: DNA
<213> ORGANISM: Streptococcus agalactiae

<400> SEQUENCE: 67
atgttttata atcctttact ttttattgta ctaattacaa ttgctgtatt tttcttagct      60 aagaaaaat ggcaattacc gacatttact tcattggtt tgctatttat ctataaccaa       120
gggctgtggg aacagttgat taat                                            144

<210> SEQ ID NO 68
<211> LENGTH: 48
<212> TYPE: PRT
<213> ORGANISM: Streptococcus agalactiae

<400> SEQUENCE: 68

Met Phe Tyr Asn Pro Leu Leu Phe Ile Val Leu Ile Thr Ile Ala Val
  1               5                  10                  15

Phe Phe Leu Ala Lys Lys Lys Trp Gln Leu Pro Thr Phe Thr Phe Ile
                20                  25                  30

Gly Leu Leu Phe Ile Tyr Asn Gln Gly Leu Trp Glu Gln Leu Ile Asn
            35                  40                  45

<210> SEQ ID NO 69
<211> LENGTH: 453
<212> TYPE: DNA
<213> ORGANISM: Streptococcus agalactiae

<400> SEQUENCE: 69

```
gtggtgcaaa taatgaaaaa acatataaaa agtatcatac caatagttct tattggtatg    60
atactaggag gctgtcaaat gaatagtgaa cataaaagtc agtataatga aacaaaaagt   120
agcaagcaat cagaagtgaa gaaagataaa aaaatgacaa aaaaagaaca attagcttat   180
ctcaaagagc atgaacaaga aataattgat tttgtaaaat ctcagaataa aagatagaa    240 tctgtacaaa ttgattggaa tgatgttcga tggagtaaag ggggaaatgg tacacctcaa   300
ggaggaggag agggggatttt actttttggg gagattaata atgattctga atcaagttgg   360
agagttgata ttgatataga aaaggacgg ctagacctaa aaaatatgta tttaggacaa    420
cctatacgaa ttggaggtaa attatttgag taa                                453

<210> SEQ ID NO 70
<211> LENGTH: 150
<212> TYPE: PRT
<213> ORGANISM: Streptococcus agalactiae

<400> SEQUENCE: 70

Met Val Gln Ile Met Lys Lys His Ile Lys Ser Ile Ile Pro Ile Val
  1               5                  10                  15

Leu Ile Gly Met Ile Leu Gly Gly Cys Gln Met Asn Ser Glu His Lys
                 20                  25                  30

Ser Gln Tyr Asn Glu Thr Lys Ser Ser Lys Gln Ser Glu Val Lys Lys
         35                   40                  45

Asp Lys Lys Met Thr Lys Lys Glu Gln Leu Ala Tyr Leu Lys Glu His
     50                  55                  60

Glu Gln Glu Ile Ile Asp Phe Val Lys Ser Gln Asn Lys Lys Ile Glu
 65                  70                  75                  80

Ser Val Gln Ile Asp Trp Asn Asp Val Arg Trp Ser Lys Gly Gly Asn
                 85                  90                  95

Gly Thr Pro Gln Gly Gly Gly Glu Gly Ile Leu Leu Phe Gly Glu Ile
                100                 105                 110

Asn Asn Asp Ser Glu Ser Ser Trp Arg Val Asp Ile Asp Ile Glu Lys
             115                 120                 125

Gly Arg Leu Asp Leu Lys Asn Met Tyr Leu Gly Gln Pro Ile Arg Ile
         130                 135                 140

Gly Gly Lys Leu Phe Glu
145                 150

<210> SEQ ID NO 71
<211> LENGTH: 1455
<212> TYPE: DNA
<213> ORGANISM: Streptococcus agalactiae

<400> SEQUENCE: 71
atggaatttt tggcttataa tgctttcaca gcaatcggtg tttctattcc gcacggtaat    60
catttccact ttattcacta taaggatatg tctccattag agttagaagc aacaaggatg   120
gtggcagagc atagaggaca tcatattgat gcattaggga aaaaagattc tacagagaaa   180
ccaaagcata tttctcatga acctaataag gaacctcaca cagaggaaga acaccatgca   240
gtaacaccga agaccaacg taaggcaaa ccaaatagcc agattgtcta cagtgctcaa   300
gaaattgaag aggcaaaaaa agctggtaaa tacacaacat ctgatggtta cattttttgat   360 gctaaagata ttaaaaaaga tacaggtaca ggttatgtca ttccacatat gacacatgag   420
cattgggtac caaagaaaga tttatcagag tcggaattaa aagcagctca agaatttctt   480
```

```
tcaggaaaat ctgaagcaaa tcaagacaaa ccaaaaacag gtaaaacagc tcaagaaatc    540
tatgaggcaa ttgaaccaaa agcaattgtt aaacctgaag atttattatt tggaattgca    600
caagcgacag actataagaa tggtacattt gtaattcctc ataaagatca ttaccattat    660
gtggaattaa aatggtttga tgaagaaaaa gatcttttag ctgattcaga taagacatat    720
tctttagaag actatttagc tacggctaaa tattacatga tgcacccaga aaaacgtcct    780
aaagttgaag gatgggtaa agatgctgaa atttataagg aaaaggactc taataaagca    840
gataaaccaa gtcctgcacc aactgataat aaatcaacat caaattctag tgacaaaaac    900
ttaagtgctg cagaagtatt caaacaagca aaaccgaaaa aaattgtacc gcttgataaa    960
attgctgctc acatggcata tgcagttgga tttgaagatg atcaattgat tgttcctcat   1020
catgatcatt atcataatgt tcctatggca tggtttgaca agggtggttt atggaaagca   1080
ccagaaggct atacattaca acaactcttc tcaacaatta aatactacat ggaacatcct   1140
aatgaattac caaagaaaa gggttgggga cacgacagtg atcataacaa aggctcaaat   1200
aaagacaata aagccaaaaa ttatgctcca gatgaagaac ctgaagattc agggaaagta   1260
actcacaact atggtttta tgatgttaat aaaggttcag acgaagaaga accagaaaaa   1320
caagaagatg aatcagagct agatgaatat gaactaggaa tggcacaaaa cgctaagaaa   1380
tatggtatgg atagacaatc ttttgaaaag caactcatcc aattatcaaa taaatatagt   1440
gtaagttttg aaagc                                                    1455

<210> SEQ ID NO 72
<211> LENGTH: 485
<212> TYPE: PRT
<213> ORGANISM: Streptococcus agalactiae

<400> SEQUENCE: 72

Met Glu Phe Leu Ala Tyr Asn Ala Phe Thr Ala Ile Gly Val Ser Ile
  1               5                  10                  15

Pro His Gly Asn His Phe His Phe Ile His Tyr Lys Asp Met Ser Pro
                 20                  25                  30

Leu Glu Leu Glu Ala Thr Arg Met Val Ala Glu His Arg Gly His His
             35                  40                  45

Ile Asp Ala Leu Gly Lys Lys Asp Ser Thr Glu Lys Pro Lys His Ile
         50                  55                  60

Ser His Glu Pro Asn Lys Glu Pro His Thr Glu Glu His His Ala
     65                  70                  75                  80

Val Thr Pro Lys Asp Gln Arg Lys Gly Lys Pro Asn Ser Gln Ile Val
                 85                  90                  95

Tyr Ser Ala Gln Glu Ile Glu Glu Ala Lys Lys Ala Gly Lys Tyr Thr
                100                 105                 110

Thr Ser Asp Gly Tyr Ile Phe Asp Ala Lys Asp Ile Lys Lys Asp Thr
            115                 120                 125

Gly Thr Gly Tyr Val Ile Pro His Met Thr His Glu His Trp Val Pro
        130                 135                 140

Lys Lys Asp Leu Ser Glu Ser Glu Leu Lys Ala Ala Gln Glu Phe Leu
145                 150                 155                 160

Ser Gly Lys Ser Glu Ala Asn Gln Asp Lys Pro Lys Thr Gly Lys Thr
                165                 170                 175

Ala Gln Glu Ile Tyr Glu Ala Ile Glu Pro Lys Ala Ile Val Lys Pro
            180                 185                 190

Glu Asp Leu Leu Phe Gly Ile Ala Gln Ala Thr Asp Tyr Lys Asn Gly
```

-continued

```
                195                 200                 205
Thr Phe Val Ile Pro His Lys Asp His Tyr His Tyr Val Glu Leu Lys
    210                 215                 220

Trp Phe Asp Glu Glu Lys Asp Leu Leu Ala Asp Ser Asp Lys Thr Tyr
225                 230                 235                 240

Ser Leu Glu Asp Tyr Leu Ala Thr Ala Lys Tyr Tyr Met Met His Pro
                245                 250                 255

Glu Lys Arg Pro Lys Val Glu Gly Trp Gly Lys Asp Ala Glu Ile Tyr
                260                 265                 270

Lys Glu Lys Asp Ser Asn Lys Ala Asp Lys Pro Ser Pro Ala Pro Thr
            275                 280                 285

Asp Asn Lys Ser Thr Ser Asn Ser Ser Asp Lys Asn Leu Ser Ala Ala
    290                 295                 300

Glu Val Phe Lys Gln Ala Lys Pro Glu Lys Ile Val Pro Leu Asp Lys
305                 310                 315                 320

Ile Ala Ala His Met Ala Tyr Ala Val Gly Phe Glu Asp Asp Gln Leu
                325                 330                 335

Ile Val Pro His His Asp His Tyr His Asn Val Pro Met Ala Trp Phe
                340                 345                 350

Asp Lys Gly Gly Leu Trp Lys Ala Pro Glu Gly Tyr Thr Leu Gln Gln
            355                 360                 365

Leu Phe Ser Thr Ile Lys Tyr Tyr Met Glu His Pro Asn Glu Leu Pro
    370                 375                 380

Lys Glu Lys Gly Trp Gly His Asp Ser Asp His Asn Lys Gly Ser Asn
385                 390                 395                 400

Lys Asp Asn Lys Ala Lys Asn Tyr Ala Pro Asp Glu Pro Glu Asp
                405                 410                 415

Ser Gly Lys Val Thr His Asn Tyr Gly Phe Tyr Asp Val Asn Lys Gly
                420                 425                 430

Ser Asp Glu Glu Pro Lys Gln Glu Asp Glu Ser Glu Leu Asp
            435                 440                 445

Glu Tyr Glu Leu Gly Met Ala Gln Asn Ala Lys Lys Tyr Gly Met Asp
    450                 455                 460

Arg Gln Ser Phe Glu Lys Gln Leu Ile Gln Leu Ser Asn Lys Tyr Ser
465                 470                 475                 480

Val Ser Phe Glu Ser
                485
```

<210> SEQ ID NO 73
<211> LENGTH: 855
<212> TYPE: DNA
<213> ORGANISM: Streptococcus agalactiae

<400> SEQUENCE: 73

```
atgaggaaac gttttttcctt gctaaatttt attgttgtta cttttatttt cttttttcttt    60 attctttttc cgcttttaa ggccaaagat tgtcaggttg tttatgcaag ttttcaagga    120
gatcattggg acatttgtaa cgcatttgat tttccgtatt tacatcgctt tgatctcatt    180
aaaggtaaag aaaatcaact ttactttata ggttgtacaa ttgctaacag taaagcctac    240
actgaggatt ggagtgataa aggccgaatt tttgttgctc gttttaatac tcaaaaccat    300
acattggaag gattgcaaca attgcctcaa actttattaa aaaatcatgg atactatgcc    360
attcaggatg aaggatattc attgattact tcagtagaag gggtactcaa actcacttat    420
ccagaatttt ctactacagg cgactggcaa ttagaacggc ttttcgatga ggagacaagc    480
```

-continued

```
gatgtggtga aagtggatat taatcaggat ggtaaggatg agtatgtgat catccaaggt    540
tttcatggag atcgtttacg tatcttcact gaagatttcg gtcgagaatt attccattat    600
cctgaaaaaa ccccatttgg tcacgctatt tggagtggtc gtttacttaa tcagacttgt    660
ttcgtattcg ggtggcgatc agaaaaagca gaattaaggc ttttttcactt tgtagatggg    720 cacttggttt cagaattagt agatgcaaaa gcagcttcta gtaatgtctt agcttttgaa    780
aaagatggaa aagcttatct tttctcagcc aataacggac gtggcgaagt tgctctttat    840
caattagtaa aataa                                                     855
```

<210> SEQ ID NO 74
<211> LENGTH: 284
<212> TYPE: PRT
<213> ORGANISM: Streptococcus agalactiae

<400> SEQUENCE: 74

```
Met Arg Lys Arg Phe Ser Leu Leu Asn Phe Ile Val Val Thr Phe Ile
1               5                   10                  15

Phe Phe Phe Phe Ile Leu Phe Pro Leu Phe Lys Ala Lys Asp Cys Gln
            20                  25                  30

Val Val Tyr Ala Ser Phe Gln Gly Asp His Trp Asp Ile Cys Asn Ala
        35                  40                  45

Phe Asp Phe Pro Tyr Leu His Arg Phe Asp Leu Ile Lys Gly Lys Glu
    50                  55                  60

Asn Gln Leu Tyr Phe Ile Gly Cys Thr Ile Ala Asn Ser Lys Ala Tyr
65                  70                  75                  80

Thr Glu Asp Trp Ser Asp Lys Gly Arg Ile Phe Val Ala Arg Phe Asn
                85                  90                  95

Thr Gln Asn His Thr Leu Glu Gly Leu Gln Gln Leu Pro Gln Thr Leu
            100                 105                 110

Leu Lys Asn His Gly Tyr Tyr Ala Ile Gln Asp Glu Gly Tyr Ser Leu
        115                 120                 125

Ile Thr Ser Val Glu Gly Val Leu Lys Leu Thr Tyr Pro Glu Phe Ser
    130                 135                 140

Thr Thr Gly Asp Trp Gln Leu Glu Arg Leu Phe Asp Glu Thr Ser
145                 150                 155                 160

Asp Val Val Lys Val Asp Ile Asn Gln Asp Gly Lys Asp Glu Tyr Val
                165                 170                 175

Ile Ile Gln Gly Phe His Gly Asp Arg Leu Arg Ile Phe Thr Glu Asp
            180                 185                 190

Phe Gly Arg Glu Leu Phe His Tyr Pro Glu Lys Thr Pro Phe Gly His
        195                 200                 205

Ala Ile Trp Ser Gly Arg Leu Leu Asn Gln Thr Cys Phe Val Phe Gly
    210                 215                 220

Trp Arg Ser Glu Lys Ala Glu Leu Arg Leu Phe His Phe Val Asp Gly
225                 230                 235                 240

His Leu Val Ser Glu Leu Val Asp Ala Lys Ala Ala Ser Ser Asn Val
                245                 250                 255

Leu Ala Phe Glu Lys Asp Gly Lys Ala Tyr Leu Phe Ser Ala Asn Asn
            260                 265                 270

Gly Arg Gly Glu Val Ala Leu Tyr Gln Leu Val Lys
        275                 280
```

<210> SEQ ID NO 75

<211> LENGTH: 2070
<212> TYPE: DNA
<213> ORGANISM: Streptococcus agalactiae

<400> SEQUENCE: 75

| | |
|---|---|
| atgaagcaca agttaaaagc ttttacgctt gctttactct caatattctt tgtgtttggt | 60 |
| ggaaaggtca gtgcagagac tgtgaatatt gtttctgata cagcatacgc tccattcgaa | 120 |
| tttaaagatt ctgatcaaac ttataaagga atcgatgttg acatcgttaa cgaagtcgct | 180 |
| aagcgtgctg gctggaatgt taacatgacg tatccaggtt ttgatgccgc agttaacgct | 240 |
| gttcaatctg gacaggcaga tgcgctaatg ccggaactac tgttactga agcacgtaaa | 300 |
| aaagtcttta atttctcaga tacttattac gatacttccg ttattcttta tactaaaaat | 360 |
| aataataaag tcacaaacta caaacaacta aaggaaaag tagtcggtgt aaaaaatgga | 420 |
| acagctgctc aaagcttctt agaagaaaat aaatctaaat acggctataa agttaaaaca | 480 |
| tttgatacaa gcgacctaat gaataacagc cttgattctg ttctatttta cgccgctatg | 540 |
| gacgatcaac cagttgtgca atttgcgata atcaaggaa agcttacgc cattaacatg | 600 |
| gaaggcgaag cagttggtag ctttgcattt gctgtcaaaa aaggtagtgg acacgataat | 660 |
| ctaattaaag aatttaacac agcttttgca caaatgaaat cagatggcac ttataatgac | 720 |
| atcatggata aatggcttgg aaaagacgct acaaaaacaa gcggcaaagc aacaggtaat | 780 |
| gccaatgaaa aagcaactcc tgtaaagcca agttataaaa ttgtttctga ttcttcattc | 840 |
| gcaccattcg aatatcaaaa cggtaaaggg aaatatactg gttttgatat ggaattaatc | 900 |
| acgaaaattg ctaaacagca aggttttaaa cttgatatct caaatccagg ttttgatgcc | 960 |
| gctttaaatg ctgtccaatc tgggcaagct gacggtgtta ttgcaggagc cacaatcaca | 1020 |
| gaagcacgcc aaaaaatctt tgatttttct gatccttatt acacatctag cgttatctta | 1080 |
| gcggttaaaa aaggaagcaa tgtcaaatca taccaagatt taaaggaaa acagttggt | 1140 |
| gctaaaaatg gtactgcctc atatacttgg ttatcagacc acgcagataa gtacaactat | 1200 |
| catgttaaag catttgatga agcatctaca atgtatgata gtatgaactc aggttcaatt | 1260 |
| gatgctctaa tggatgacga agccgttctt gcttacgcta ttaatcaagg tcgtaaattt | 1320 |
| gaaacaccta tcaaaggtga aaaatcaggc gatatcggat ttgcagtgaa aaaaggggca | 1380 |
| aatccagaat taattaaaat gtttaacaac ggtcttgctt cactcaaaaa atcgggtgag | 1440 |
| tacgataaac ttgttaaaaa atacctttcc acagccagca cttcttcaaa cgataaagct | 1500 |
| gctaaacctg tagatgaatc aactattta ggttaattt ctaataacta caaacaattg | 1560 |
| ctatctggta ttggaactac tttaagttta actcttatct cgtttgcgat tgctatggtt | 1620 |
| attggtatta tctttggtat gatgagcgta tcaccaagta atactctccg cacaatttca | 1680 |
| atgattttg ttgatattgt ccgtggtatt ccactcatga ttgtggccgc ttttattttc | 1740 |
| tggggtattc ctaatttaat cgaaagcatc acaggtcacc aaagtccaat taatgacttc | 1800 |
| gttgctgcta ctatcgctct ttctttaaat ggtggtgcgt acattgctga aattgtacgt | 1860 |
| ggtggtattg aagctgttcc ttctggtcaa atggaagcaa gtcgcagctt aggtatttct | 1920 |
| tacggcaaaa ctatgcaaaa ggttatctta cctcaagcag tacgccttat gttaccaaac | 1980 |
| tttatcaacc aatttgtcat ctcattaaag gatacaacaa ttgtatcagc aatcggactt | 2040 |
| gtggaactct ccaaactgg taaatcataa | 2070 |

<210> SEQ ID NO 76
<211> LENGTH: 689

<212> TYPE: PRT
<213> ORGANISM: Streptococcus agalactiae

<400> SEQUENCE: 76

```
Met Lys His Lys Leu Lys Ala Phe Thr Leu Ala Leu Leu Ser Ile Phe
  1               5                  10                  15

Phe Val Phe Gly Gly Lys Val Ser Ala Glu Thr Val Asn Ile Val Ser
             20                  25                  30

Asp Thr Ala Tyr Ala Pro Phe Glu Phe Lys Asp Ser Asp Gln Thr Tyr
         35                  40                  45

Lys Gly Ile Asp Val Asp Ile Val Asn Glu Val Ala Lys Arg Ala Gly
 50                  55                  60

Trp Asn Val Asn Met Thr Tyr Pro Gly Phe Asp Ala Ala Val Asn Ala
 65                  70                  75                  80

Val Gln Ser Gly Gln Ala Asp Ala Leu Met Ala Gly Thr Thr Val Thr
                 85                  90                  95

Glu Ala Arg Lys Lys Val Phe Asn Phe Ser Asp Thr Tyr Tyr Asp Thr
            100                 105                 110

Ser Val Ile Leu Tyr Thr Lys Asn Asn Asn Lys Val Thr Asn Tyr Lys
        115                 120                 125

Gln Leu Lys Gly Lys Val Val Gly Val Lys Asn Gly Thr Ala Ala Gln
    130                 135                 140

Ser Phe Leu Glu Glu Asn Lys Ser Lys Tyr Gly Tyr Lys Val Lys Thr
145                 150                 155                 160

Phe Asp Thr Ser Asp Leu Met Asn Asn Ser Leu Asp Ser Gly Ser Ile
                165                 170                 175

Tyr Ala Ala Met Asp Asp Gln Pro Val Val Gln Phe Ala Ile Asn Gln
            180                 185                 190

Gly Lys Ala Tyr Ala Ile Asn Met Glu Gly Glu Ala Val Gly Ser Phe
        195                 200                 205

Ala Phe Ala Val Lys Lys Gly Ser His Asp Asn Leu Ile Lys Glu
    210                 215                 220

Phe Asn Thr Ala Phe Ala Gln Met Lys Ser Asp Gly Thr Tyr Asn Asp
225                 230                 235                 240

Ile Met Asp Lys Trp Leu Gly Lys Asp Ala Thr Lys Thr Ser Gly Lys
                245                 250                 255

Ala Thr Gly Asn Ala Asn Glu Lys Ala Thr Pro Val Lys Pro Ser Tyr
            260                 265                 270

Lys Ile Val Ser Asp Ser Ser Phe Ala Pro Phe Glu Tyr Gln Asn Gly
        275                 280                 285

Lys Gly Lys Tyr Thr Gly Phe Asp Met Glu Leu Ile Thr Lys Ile Ala
    290                 295                 300

Lys Gln Gln Gly Phe Lys Leu Asp Ile Ser Asn Pro Gly Phe Asp Ala
305                 310                 315                 320

Ala Leu Asn Ala Val Gln Ser Gly Gln Ala Asp Gly Val Ile Ala Gly
                325                 330                 335

Ala Thr Ile Thr Glu Ala Arg Gln Lys Ile Phe Asp Phe Ser Asp Pro
            340                 345                 350

Tyr Tyr Thr Ser Ser Val Ile Leu Ala Val Lys Lys Gly Ser Asn Val
        355                 360                 365

Lys Ser Tyr Gln Asp Leu Lys Gly Lys Thr Val Gly Ala Lys Asn Gly
    370                 375                 380

Thr Ala Ser Tyr Thr Trp Leu Ser Asp His Ala Asp Lys Tyr Asn Tyr
385                 390                 395                 400
```

```
His Val Lys Ala Phe Asp Glu Ala Ser Thr Met Tyr Asp Ser Met Asn
                405                 410                 415
Ser Gly Ser Ile Asp Ala Leu Met Asp Asp Glu Ala Val Leu Ala Tyr
            420                 425                 430
Ala Ile Asn Gln Gly Arg Lys Phe Glu Thr Pro Ile Lys Gly Glu Lys
        435                 440                 445
Ser Gly Asp Ile Gly Phe Ala Val Lys Lys Gly Ala Asn Pro Glu Leu
    450                 455                 460
Ile Lys Met Phe Asn Asn Gly Leu Ala Ser Leu Lys Lys Ser Gly Glu
465                 470                 475                 480
Tyr Asp Lys Leu Val Lys Lys Tyr Leu Ser Thr Ala Ser Thr Ser Ser
                485                 490                 495
Asn Asp Lys Ala Ala Lys Pro Val Asp Glu Ser Thr Ile Leu Gly Leu
            500                 505                 510
Ile Ser Asn Asn Tyr Lys Gln Leu Leu Ser Gly Ile Gly Thr Thr Leu
        515                 520                 525
Ser Leu Thr Leu Ile Ser Phe Ala Ile Ala Met Val Ile Gly Ile Ile
    530                 535                 540
Phe Gly Met Met Ser Val Ser Pro Ser Asn Thr Leu Arg Thr Ile Ser
545                 550                 555                 560
Met Ile Phe Val Asp Ile Val Arg Gly Ile Pro Leu Met Ile Val Ala
                565                 570                 575
Ala Phe Ile Phe Trp Gly Ile Pro Asn Leu Ile Glu Ser Ile Thr Gly
            580                 585                 590
His Gln Ser Pro Ile Asn Asp Phe Val Ala Ala Thr Ile Ala Leu Ser
        595                 600                 605
Leu Asn Gly Gly Ala Tyr Ile Ala Glu Ile Val Arg Gly Gly Ile Glu
    610                 615                 620
Ala Val Pro Ser Gly Gln Met Glu Ala Ser Arg Ser Leu Gly Ile Ser
625                 630                 635                 640
Tyr Gly Lys Thr Met Gln Lys Val Ile Leu Pro Gln Ala Val Arg Leu
                645                 650                 655
Met Leu Pro Asn Phe Ile Asn Gln Phe Val Ile Ser Leu Lys Asp Thr
            660                 665                 670
Thr Ile Val Ser Ala Ile Gly Leu Val Glu Leu Phe Gln Thr Gly Lys
        675                 680                 685
Ser
```

```
<210> SEQ ID NO 77
<211> LENGTH: 149
<212> TYPE: DNA
<213> ORGANISM: Streptococcus agalactiae

<400> SEQUENCE: 77
ttggaaggtt tacttattgc attgattccc atgtttgcgt ggggaagtat tggatttgtt     60
agtaataaaa ttggagggcg tccaaatcaa caaacatttg gaatgacttt aggagcattg    120
ctatttgcga ttatcgtatg tttatttaa                                      149

<210> SEQ ID NO 78
<211> LENGTH: 49
<212> TYPE: PRT
<213> ORGANISM: Streptococcus agalactiae

<400> SEQUENCE: 78
```

Met Gly Leu Leu Ile Ala Leu Ile Pro Met Phe Ala Trp Gly Ser
1               5                   10                  15

Ile Gly Phe Val Ser Asn Lys Ile Gly Gly Arg Pro Asn Gln Gln Thr
                20                  25                  30

Phe Gly Met Thr Leu Gly Ala Leu Leu Phe Ala Ile Ile Val Cys Leu
        35                  40                  45

Phe

<210> SEQ ID NO 79
<211> LENGTH: 963
<212> TYPE: DNA
<213> ORGANISM: Streptococcus agalactiae

<400> SEQUENCE: 79

```
atgaatacta tttataatac attgagaaca gataaaggtt ataaagttta tgagggtat      60
ttatatgaaa ttactggtga agaatgtgaa gaagccttag accttgtgat tcctaagaat    120
attgtatttg cagatacaga tacttgtggc tacactttt tactcaatga agatggaaca    180
gtttatgatg atgtgacttt ctacaaattt gatgataaat attggttggc tagtcataaa    240
gctttggatt cttatttaga caacatcaat tttgactata ccgtaacaga tatttctgac    300
gagtataaaa tgctgcaaat tgaaggaaga tattcgggag aaattgctca gtcatttat     360
gaatatgata tttcaacact taattttcgt actcttcgca tagagatgga cttcatcaaa    420
ggtgaggaaa ggttatcttg gcgtagattt ggttttctg gagaatttgg ctatcaattt     480
ttcctaccat cttctattt tgctactttt gtttcggatg tctgtgaagg tatagcagag    540
tgtggggatg aacttgatag atatttaagg tttgaagtgg acaacccat tactgatatt     600
tatcaacaag aagaatattc tttatatgaa ataggttatt cttggaatct agatttcaca    660
aaggaagaat ttagaggtcg cgatagcttg ttagagcaca tcagatcagc aacagttaaa    720
agtgttggat tctcaacgaa ggaaaaactc gcttcaggaa caccagtgct atttgatgac    780
caaattgttg aaagattttt tggatagca gacgagaaac actcttcgga aaattaccta    840
ggtttgatga ttgttaacca aacatatgct cattcaggag ttacttttgt aacagaagat    900
ggccaaattt tgaaaacaca atcaagccct tattgtatcc cagaaagttg gaacaaagaa    960
tga                                                                  963
```

<210> SEQ ID NO 80
<211> LENGTH: 320
<212> TYPE: PRT
<213> ORGANISM: Streptococcus agalactiae

<400> SEQUENCE: 80

Met Asn Thr Ile Tyr Asn Thr Leu Arg Thr Asp Lys Gly Tyr Lys Val
1               5                   10                  15

Tyr Glu Gly Tyr Leu Tyr Glu Ile Thr Gly Glu Glu Cys Glu Glu Ala
                20                  25                  30

Leu Asp Leu Val Ile Pro Lys Asn Ile Val Phe Ala Asp Thr Asp Thr
        35                  40                  45

Cys Gly Tyr Thr Phe Leu Leu Asn Glu Asp Gly Thr Val Tyr Asp Asp
    50                  55                  60

Val Thr Phe Tyr Lys Phe Asp Asp Lys Tyr Trp Leu Ala Ser His Lys
65                  70                  75                  80

Ala Leu Asp Ser Tyr Leu Asp Asn Ile Asn Phe Asp Tyr Thr Val Thr
                85                  90                  95

-continued

```
Asp Ile Ser Asp Glu Tyr Lys Met Leu Gln Ile Glu Gly Arg Tyr Ser
                100                 105                 110
Gly Glu Ile Ala Gln Ser Phe Tyr Glu Tyr Asp Ile Ser Thr Leu Asn
            115                 120                 125
Phe Arg Thr Leu Arg Ile Glu Met Asp Phe Ile Lys Gly Glu Glu Arg
        130                 135                 140
Leu Ser Trp Arg Arg Phe Gly Phe Ser Gly Glu Phe Gly Tyr Gln Phe
145                 150                 155                 160
Phe Leu Pro Ser Ser Ile Phe Ala Thr Phe Val Ser Asp Val Cys Glu
                165                 170                 175
Gly Ile Ala Glu Cys Gly Asp Glu Leu Asp Arg Tyr Leu Arg Phe Glu
            180                 185                 190
Val Gly Gln Pro Ile Thr Asp Ile Tyr Gln Gln Glu Glu Tyr Ser Leu
        195                 200                 205
Tyr Glu Ile Gly Tyr Ser Trp Asn Leu Asp Phe Thr Lys Glu Glu Phe
    210                 215                 220
Arg Gly Arg Asp Ser Leu Leu Glu His Ile Arg Ser Ala Thr Val Lys
225                 230                 235                 240
Ser Val Gly Phe Ser Thr Lys Glu Lys Leu Ala Ser Gly Thr Pro Val
                245                 250                 255
Leu Phe Asp Asp Gln Ile Val Gly Lys Ile Phe Trp Ile Ala Asp Glu
            260                 265                 270
Lys His Ser Ser Glu Asn Tyr Leu Gly Leu Met Ile Val Asn Gln Thr
        275                 280                 285
Tyr Ala His Ser Gly Val Thr Phe Val Thr Glu Asp Gly Gln Ile Leu
    290                 295                 300
Lys Thr Gln Ser Ser Pro Tyr Cys Ile Pro Glu Ser Trp Asn Lys Glu
305                 310                 315                 320
```

<210> SEQ ID NO 81
<211> LENGTH: 702
<212> TYPE: DNA
<213> ORGANISM: Streptococcus agalactiae

<400> SEQUENCE: 81

```
atggagttag taattagaga tattcgtaag cggtttcagg aaacagaggt cttgagagga     60
gcaagttacc gattttattc aggtaaaata acagggtct taggtaggaa tggtgctggg    120
aaaacaactt tatttaatat actttatggg gatcttgcag ctgacaacgg gaccatttgt    180
ttattgaagg ataatcacga gtatcctctt accgataagg atattggtat tgtttattcc    240
gaaaactacc ttccagaatt tttaacaggg tatgaatttg taaaattta catggattta    300
catccttcag atgatttaat gacaatagat gattatttag attttatgga aataggacaa    360
acagagcgtc atagaattat caaaggatat tctgatggaa tgaagagtaa gctctcatta    420
atttgcctga tgatttctaa gccaaaagta attttactag atgagccact gactgcagtt    480
gatgttgtat caagtattgc aataaaacgc cttttgttgg aattaagtga ggatcatatt    540
attatattat caactcatat aatggcctta gcagaagatc tatgtgatat tgtggctgta    600
ttagacaaag gaaaactcca aacattagat attgatcgta acatgaaca attcgaagag    660
cgtcttcttc aagtgttgaa gggagatgaa tatgacaagt aa                      702
```

<210> SEQ ID NO 82
<211> LENGTH: 233
<212> TYPE: PRT
<213> ORGANISM: Streptococcus agalactiae

<400> SEQUENCE: 82

```
Met Glu Leu Val Ile Arg Asp Ile Arg Lys Arg Phe Gln Glu Thr Glu
 1               5                  10                  15
Val Leu Arg Gly Ala Ser Tyr Arg Phe Tyr Ser Gly Lys Ile Thr Gly
            20                  25                  30
Val Leu Gly Arg Asn Gly Ala Gly Lys Thr Thr Leu Phe Asn Ile Leu
        35                  40                  45
Tyr Gly Asp Leu Ala Ala Asp Asn Gly Thr Ile Cys Leu Leu Lys Asp
 50                  55                  60
Asn His Glu Tyr Pro Leu Thr Asp Lys Asp Ile Gly Ile Val Tyr Ser
 65                  70                  75                  80
Glu Asn Tyr Leu Pro Glu Phe Leu Thr Gly Tyr Glu Phe Val Lys Phe
                85                  90                  95
Tyr Met Asp Leu His Pro Ser Asp Asp Leu Met Thr Ile Asp Asp Tyr
            100                 105                 110
Leu Asp Phe Met Glu Ile Gly Gln Thr Glu Arg His Arg Ile Ile Lys
        115                 120                 125
Gly Tyr Ser Asp Gly Met Lys Ser Lys Leu Ser Leu Ile Cys Leu Met
130                 135                 140
Ile Ser Lys Pro Lys Val Ile Leu Leu Asp Glu Pro Leu Thr Ala Val
145                 150                 155                 160
Asp Val Val Ser Ser Ile Ala Ile Lys Arg Leu Leu Glu Leu Ser
                165                 170                 175
Glu Asp His Ile Ile Ile Leu Ser Thr His Ile Met Ala Leu Ala Glu
            180                 185                 190
Asp Leu Cys Asp Ile Val Ala Val Leu Asp Lys Gly Lys Leu Gln Thr
        195                 200                 205
Leu Asp Ile Asp Arg Lys His Glu Gln Phe Glu Glu Arg Leu Leu Gln
    210                 215                 220
Val Leu Lys Gly Asp Glu Tyr Asp Lys
225                 230
```

<210> SEQ ID NO 83
<211> LENGTH: 774
<212> TYPE: DNA
<213> ORGANISM: Streptococcus agalactiae

<400> SEQUENCE: 83

```
ttgtttatga gatatacaaa tggaaatttt gaagcctttg caagacctcg aaaacctgaa      60
ggtgtggata aaaatccgc ttatattgtt ggttctggtt tagcaggatt agctgccgct     120
gtctttttaa tacgtgacgg tcaaatggat ggtcaacgta ttcatatttt tgaagaacta     180
cctctttctg gaggatcact tgacggtgtc aaacgacctg atatcggttt tgtaacgcgt     240
ggtggtcgtg aaatggaaaa tcacttcgaa tgtatgtggg atatgtaccg ttccatcccc     300
tctctcgaag ttccagatgc ttcttatcta gatgaatttt attggcttga caaggatgat     360
cccaattcat ctaactgtcg cctcattcat aaacagggga atcgcttaga atctgatggt     420
gattttacac tcggaacaca ttccaaagag ttagttaagc tagtcatgga gactgaagag     480
tctttaggtg ctaagacgat tgaagaagtt ttttcaaaag aatttttga agtaattttt     540
tggacttatt gggctactat gtttgccttt gagaaatggc attcagcgat tgaaatgcgt     600
cgatatgcta tgcgctttat ccatcatatt ggtggtctgc ctgatttcac ttcattaaaa     660
tttaataaat ataatcaata tgattctatg gtgaaaccaa tcatcagtta tttagagtct     720
```
cataatgtag atgttcaatt tgatagcaag gtaactaata tctccgtaga cttt    774

<210> SEQ ID NO 84
<211> LENGTH: 258
<212> TYPE: PRT
<213> ORGANISM: Streptococcus agalactiae

<400> SEQUENCE: 84

Met Phe Met Arg Tyr Thr Asn Gly Asn Phe Glu Ala Phe Ala Arg Pro
1               5                   10                  15

Arg Lys Pro Glu Gly Val Asp Lys Lys Ser Ala Tyr Ile Val Gly Ser
            20                  25                  30

Gly Leu Ala Gly Leu Ala Ala Ala Val Phe Leu Ile Arg Asp Gly Gln
        35                  40                  45

Met Asp Gly Gln Arg Ile His Ile Phe Glu Glu Leu Pro Leu Ser Gly
    50                  55                  60

Gly Ser Leu Asp Gly Val Lys Arg Pro Asp Ile Gly Phe Val Thr Arg
65                  70                  75                  80

Gly Gly Arg Glu Met Glu Asn His Phe Glu Cys Met Trp Asp Met Tyr
                85                  90                  95

Arg Ser Ile Pro Ser Leu Glu Val Pro Asp Ala Ser Tyr Leu Asp Glu
            100                 105                 110

Phe Tyr Trp Leu Asp Lys Asp Pro Asn Ser Ser Asn Cys Arg Leu
        115                 120                 125

Ile His Lys Gln Gly Asn Arg Leu Glu Ser Asp Gly Asp Phe Thr Leu
    130                 135                 140

Gly Thr His Ser Lys Glu Leu Val Lys Leu Val Met Glu Thr Glu Glu
145                 150                 155                 160

Ser Leu Gly Ala Lys Thr Ile Glu Glu Val Phe Ser Lys Glu Phe Phe
                165                 170                 175

Glu Ser Asn Phe Trp Thr Tyr Trp Ala Thr Met Phe Ala Phe Glu Lys
            180                 185                 190

Trp His Ser Ala Ile Glu Met Arg Arg Tyr Ala Met Arg Phe Ile His
        195                 200                 205

His Ile Gly Gly Leu Pro Asp Phe Thr Ser Leu Lys Phe Asn Lys Tyr
    210                 215                 220

Asn Gln Tyr Asp Ser Met Val Lys Pro Ile Ile Ser Tyr Leu Glu Ser
225                 230                 235                 240

His Asn Val Asp Val Gln Phe Asp Ser Lys Val Thr Asn Ile Ser Val
                245                 250                 255

Asp Phe

<210> SEQ ID NO 85
<211> LENGTH: 903
<212> TYPE: DNA
<213> ORGANISM: Streptococcus agalactiae

<400> SEQUENCE: 85
ttgttggctt ctttatttat cgtccgtttg tcaaaatcgc tttcgctaag gaggagcaat    60
atgaaaaaat tacttagatg gcttcctcct gtacttttca ttattatcct tataggaatg   120
actatcttag gtaagtccta tatcaataaa gtaacagctc acaaaataaa actctataac   180
tctcgaatga ctcctactat tttaatttca ggatccagtg ctactcaaga acgatttaac   240
agcatgttag cacagctcaa ccaaatggga gaaaaacata gcgttttaaa gttaactgtc   300

-continued

```
aaaaaagaca atagcattat ctacaatgga caaattagcg gcaatgacca caaaccctac    360
attgtcattg gatttgaaaa taatgaagat ggttatagta acatcaaaaa acaaacaaaa    420
tggctacaga ttgctatgaa tgatcttcag aagaaatata aatttaaacg ttttaacgct    480
atcggtcatt caaatggtgg cttatcatgg actatttttcc tagaagatta ttacgactct   540
gatgaatttg atatgaaatc attgttaaca atgggaacac cttttaactt gaagaaagt    600 aacacctcaa atcatactca aatgcttaaa gatttaatca gtaataaagg aaatattcca    660
tcaagtctca tggtatacaa tttggcagga actaattcat atgatggtga taaaattgtt    720
ccatttgcta gtgtggagac tggtaaatat attttccaag aaaccgctaa acactatacc    780
caactaacag taactggtaa taatgctaca cattctgact tgcctgataa tcctgaagtt    840
atccaatatg tcgcagaaaa aattcttaaa aatgagaaag gtaaattacc aaaacctcac    900
taa                                                                  903
```

<210> SEQ ID NO 86
<211> LENGTH: 300
<212> TYPE: PRT
<213> ORGANISM: Streptococcus agalactiae

<400> SEQUENCE: 86

```
Met Leu Ala Ser Leu Phe Ile Val Arg Leu Ser Lys Ser Leu Ser Leu
 1               5                  10                  15

Arg Arg Ser Asn Met Lys Lys Leu Leu Arg Trp Leu Pro Pro Val Leu
            20                  25                  30

Phe Ile Ile Ile Leu Ile Gly Met Thr Ile Leu Gly Lys Ser Tyr Ile
        35                  40                  45

Asn Lys Val Thr Ala His Lys Ile Lys Leu Tyr Asn Ser Arg Met Thr
    50                  55                  60

Pro Thr Ile Leu Ile Ser Gly Ser Ser Ala Thr Gln Glu Arg Phe Asn
65                  70                  75                  80

Ser Met Leu Ala Gln Leu Asn Gln Met Gly Glu Lys His Ser Val Leu
                85                  90                  95

Lys Leu Thr Val Lys Lys Asp Asn Ser Ile Ile Tyr Asn Gly Gln Ile
            100                 105                 110

Ser Gly Asn Asp His Lys Pro Tyr Ile Val Ile Gly Phe Glu Asn Asn
        115                 120                 125

Glu Asp Gly Tyr Ser Asn Ile Lys Lys Gln Thr Lys Trp Leu Gln Ile
    130                 135                 140

Ala Met Asn Asp Leu Gln Lys Lys Tyr Lys Phe Lys Arg Phe Asn Ala
145                 150                 155                 160

Ile Gly His Ser Asn Gly Gly Leu Ser Trp Thr Ile Phe Leu Glu Asp
                165                 170                 175

Tyr Tyr Asp Ser Asp Glu Phe Asp Met Lys Ser Leu Leu Thr Met Gly
            180                 185                 190

Thr Pro Phe Asn Phe Glu Glu Ser Asn Thr Ser Asn His Thr Gln Met
        195                 200                 205

Leu Lys Asp Leu Ile Ser Asn Lys Gly Asn Ile Pro Ser Ser Leu Met
    210                 215                 220

Val Tyr Asn Leu Ala Gly Thr Asn Ser Tyr Asp Gly Asp Lys Ile Val
225                 230                 235                 240

Pro Phe Ala Ser Val Glu Thr Gly Lys Tyr Ile Phe Gln Glu Thr Ala
                245                 250                 255

Lys His Tyr Thr Gln Leu Thr Val Thr Gly Asn Asn Ala Thr His Ser
```

-continued

```
              260                 265                 270
Asp Leu Pro Asp Asn Pro Glu Val Ile Gln Tyr Val Ala Glu Lys Ile
            275                 280                 285

Leu Lys Asn Glu Lys Gly Lys Leu Pro Lys Pro His
        290                 295                 300
```

<210> SEQ ID NO 87
<211> LENGTH: 912
<212> TYPE: DNA
<213> ORGANISM: Streptococcus agalactiae

<400> SEQUENCE: 87

| | | | | | |
|---|---|---|---|---|---|
| ttgaaattag | gtattacaac | attcggagag | acaacaatcc | ttgaagaaac | aaaccaaagc | 60 |
| tattcacatc | ctgagaggat | tcgccaatta | gttgctgaga | ttgaactagc | tgatcaagtt | 120 |
| ggtttagatg | tatatggtat | tggagagcac | catcgtgaag | attttgcggt | ctctgcaccc | 180 |
| gaaattatcc | tagcagcagg | agcggttaga | actaataata | tccgtttatc | tagtgcagta | 240 |
| acgattctct | cttccaatga | tcctattcgc | gtctatcagc | aattttcaac | gattgacgca | 300 |
| ctttcaaatg | gtagagcaga | aattatggca | gggcgtggtt | cctttattga | gtcttttcca | 360 |
| ttgtttggat | acgatttagc | ggattatgat | gatttattta | atgaaaaaat | ggatatgttg | 420 |
| ttagcaatta | actcagcgac | aaatctcgat | tggaaaggtc | atttgacaca | aacagttaat | 480 |
| gagcgaccaa | tttatccaag | agcattacaa | agacagttat | caatatgggt | ggcaacagga | 540 |
| ggaaatgttg | attctacaat | tcgtattgca | gaacaaggtt | tgccaattgt | ttatgcaact | 600 |
| attggtggga | atcccaaagc | ctttcgtcaa | ttggtccata | tttataaaga | agttggtaag | 660 |
| tccgtaatgg | acacaaacca | ggaacaacta | aaagttgctg | ctcactcttg | gggatggatt | 720 |
| gaagaggata | atcaaaccgc | tattgaccgt | tattttttcc | ctacgaaaca | gaccgtcgat | 780 |
| aatattgcta | agggacgccc | tcattggtct | gaaatgacta | agagcagta | tttacgttca | 840 |
| ataggtccag | aaggtgctat | ttttgtagga | aatcctgaag | tggttgcaca | taaaattata | 900 |
| ggactttggt | ga | | | | | 912 |

<210> SEQ ID NO 88
<211> LENGTH: 303
<212> TYPE: PRT
<213> ORGANISM: Streptococcus agalactiae

<400> SEQUENCE: 88

```
Met Lys Leu Gly Ile Thr Thr Phe Gly Glu Thr Thr Ile Leu Glu Glu
 1               5                  10                  15

Thr Asn Gln Ser Tyr Ser His Pro Glu Arg Ile Arg Gln Leu Val Ala
            20                  25                  30

Glu Ile Glu Leu Ala Asp Gln Val Gly Leu Asp Val Tyr Gly Ile Gly
        35                  40                  45

Glu His His Arg Glu Asp Phe Ala Val Ser Ala Pro Glu Ile Ile Leu
    50                  55                  60

Ala Ala Gly Ala Val Arg Thr Asn Asn Ile Arg Leu Ser Ser Ala Val
65                  70                  75                  80

Thr Ile Leu Ser Ser Asn Asp Pro Ile Arg Val Tyr Gln Gln Phe Ser
                85                  90                  95

Thr Ile Asp Ala Leu Ser Asn Gly Arg Ala Glu Ile Met Ala Gly Arg
            100                 105                 110

Gly Ser Phe Ile Glu Ser Phe Pro Leu Phe Gly Tyr Asp Leu Ala Asp
        115                 120                 125
```

```
Tyr Asp Asp Leu Phe Asn Glu Lys Met Asp Met Leu Leu Ala Ile Asn
    130                 135                 140

Ser Ala Thr Asn Leu Asp Trp Lys Gly His Leu Thr Gln Thr Val Asn
145                 150                 155                 160

Glu Arg Pro Ile Tyr Pro Arg Ala Leu Gln Arg Gln Leu Ser Ile Trp
                165                 170                 175

Val Ala Thr Gly Gly Asn Val Asp Ser Thr Ile Arg Ile Ala Glu Gln
            180                 185                 190

Gly Leu Pro Ile Val Tyr Ala Thr Ile Gly Gly Asn Pro Lys Ala Phe
        195                 200                 205

Arg Gln Leu Val His Ile Tyr Lys Glu Val Gly Lys Ser Val Met Asp
    210                 215                 220

Thr Asn Gln Glu Gln Leu Lys Val Ala Ala His Ser Trp Gly Trp Ile
225                 230                 235                 240

Glu Glu Asp Asn Gln Thr Ala Ile Asp Arg Tyr Phe Phe Pro Thr Lys
                245                 250                 255

Gln Thr Val Asp Asn Ile Ala Lys Gly Arg Pro His Trp Ser Glu Met
            260                 265                 270

Thr Lys Glu Gln Tyr Leu Arg Ser Ile Gly Pro Glu Gly Ala Ile Phe
        275                 280                 285

Val Gly Asn Pro Glu Val Val Ala His Lys Ile Ile Gly Leu Trp
    290                 295                 300
```

<210> SEQ ID NO 89
<211> LENGTH: 693
<212> TYPE: DNA
<213> ORGANISM: Streptococcus agalactiae

<400> SEQUENCE: 89

```
atgatagagt ggattcaaac acatttacca aatgtatatc aaatgggttg ggaaggtgct      60
tacggctggc agacagctat tgtacaaacc ctttatatga cttttggtc gttccttatt     120
ggaggtttaa tgggattgtt aggaggttta ttccttgttt taactagtcc tagaggagtt     180
attgctaata aattagtatt tggagttta gataaagttg tttctgtttt tagagctctg     240
cccttcatta ttcttcttgc tttgattgcg ccagtaactc gcgtaattgt aggaacaaca     300
cttggttcac cagcagcttt ggtacctctt tctttggcag ttttcccatt ttttgctcgt     360
caagttcaag ttgttttagc tgaacttgat ggtggagtta ttgaggctgc acaagcctca     420
ggtggaacac tttgggatat tattgtagtt tatcttcgtg aaggtctacc agatttaatt     480
cgagtatcaa cggttacttt gatttcttta gtaggtgaaa cagctatggc tggcgctatt     540
ggtgcaggag gattgggttc tgttgctatt actaaggat ataactattc tcgtgatgat     600
attactttag tagcgactat tctgatttta ttattaattt tctttatcca ttttttaggt     660
gattttttaa cacgtcgctt gagtcataaa taa                                  693
```

<210> SEQ ID NO 90
<211> LENGTH: 230
<212> TYPE: PRT
<213> ORGANISM: Streptococcus agalactiae

<400> SEQUENCE: 90

```
Met Ile Glu Trp Ile Gln Thr His Leu Pro Asn Val Tyr Gln Met Gly
1               5                   10                  15

Trp Glu Gly Ala Tyr Gly Trp Gln Thr Ala Ile Val Gln Thr Leu Tyr
            20                  25                  30
```

```
Met Thr Phe Trp Ser Phe Leu Ile Gly Gly Leu Met Gly Leu Leu Gly
         35                  40                  45
Gly Leu Phe Leu Val Leu Thr Ser Pro Arg Gly Val Ile Ala Asn Lys
 50                  55                  60
Leu Val Phe Gly Val Leu Asp Lys Val Val Ser Val Phe Arg Ala Leu
 65                  70                  75                  80
Pro Phe Ile Ile Leu Leu Ala Leu Ile Ala Pro Val Thr Arg Val Ile
                 85                  90                  95
Val Gly Thr Thr Leu Gly Ser Pro Ala Ala Leu Val Pro Leu Ser Leu
                100                 105                 110
Ala Val Phe Pro Phe Phe Ala Arg Gln Val Gln Val Leu Ala Glu
            115                 120                 125
Leu Asp Gly Gly Val Ile Glu Ala Ala Gln Ala Ser Gly Gly Thr Leu
130                 135                 140
Trp Asp Ile Ile Val Val Tyr Leu Arg Glu Gly Leu Pro Asp Leu Ile
145                 150                 155                 160
Arg Val Ser Thr Val Thr Leu Ile Ser Leu Val Gly Glu Thr Ala Met
                165                 170                 175
Ala Gly Ala Ile Gly Ala Gly Gly Leu Gly Ser Val Ala Ile Thr Lys
                180                 185                 190
Gly Tyr Asn Tyr Ser Arg Asp Asp Ile Thr Leu Val Ala Thr Ile Leu
                195                 200                 205
Ile Leu Leu Leu Ile Phe Phe Ile Gln Phe Leu Gly Asp Phe Leu Thr
210                 215                 220
Arg Arg Leu Ser His Lys
225                 230

<210> SEQ ID NO 91
<211> LENGTH: 759
<212> TYPE: DNA
<213> ORGANISM: Streptococcus agalactiae

<400> SEQUENCE: 91
ttggcagtta gttttcatga agtatttggt tgggattctg cttttttat tatgattatc      60
aatattccat tgctccttct ttgctacttt ggcttaggta acaaacctt ttttaaaact     120
gtctatggtt cttggatttt tcctgttttt attaagttaa cacaaagtgt accaactttg    180
acccacaact cactcctcgc agcactttt ggaggtgtta ttgtaggatg tggtttgggg     240
attgttttt ggagcgactc ttcaactggt ggaacgggga ttatcattca attcttagga    300
aaatatactc ctataagcct tggacaaggg gttatattga ttgatggact tgttacaatt    360
gttggtttcc tagcttttga cagtgatacg gttatgtttt ctattattgg gttgataact    420
attagttata ttattaatgc tatccaaact ggatttacaa ccttaagcac tgtcttaatc    480
gtttctcaag agcaccaaaa aattaagaca tatatcaata ctgtcgcaga tagaggagta    540
acagaaattc ccgttaaagg gggatattct ggaactaatc aaatcatgct tatgacaact    600
attgctggtt atgagtttgc taaattacaa gaggcaatag cagaaattga cgaaacagcc    660
ttcataacag taactccaac atcacaagct tctggacgtg gatttagtct tcaaaaaaat    720
catggacgtc ttgatgaaga cattcttatg ccaatgtaa                           759

<210> SEQ ID NO 92
<211> LENGTH: 252
<212> TYPE: PRT
<213> ORGANISM: Streptococcus agalactiae
```

<400> SEQUENCE: 92

| | | | | | | | | | | | | | | |
|---|---|---|---|---|---|---|---|---|---|---|---|---|---|---|
|Met|Ala|Val|Ser|Phe|His|Glu|Val|Phe|Gly|Trp|Asp|Ser|Ala|Phe|Phe|
|1| | | |5| | | | |10| | | | |15|
|Ile|Met|Ile|Ile|Asn|Ile|Pro|Leu|Leu|Leu|Cys|Tyr|Phe|Gly|Leu|
| | | | |20| | | | |25| | | | |30|
|Gly|Lys|Gln|Thr|Phe|Leu|Lys|Thr|Val|Tyr|Gly|Ser|Trp|Ile|Phe|Pro|
| | | |35| | | | |40| | | | |45| |
|Val|Phe|Ile|Lys|Leu|Thr|Gln|Ser|Val|Pro|Thr|Leu|Thr|His|Asn|Ser|
| | |50| | | | |55| | | | |60| | |
|Leu|Leu|Ala|Ala|Leu|Phe|Gly|Gly|Val|Ile|Val|Gly|Cys|Gly|Leu|Gly|
|65| | | | |70| | | | |75| | | | |80|
|Ile|Val|Phe|Trp|Ser|Asp|Ser|Ser|Thr|Gly|Gly|Thr|Gly|Ile|Ile|Ile|
| | | | |85| | | | |90| | | | |95| |
|Gln|Phe|Leu|Gly|Lys|Tyr|Thr|Pro|Ile|Ser|Leu|Gly|Gln|Gly|Val|Ile|
| | | |100| | | | |105| | | | |110| | |
|Leu|Ile|Asp|Gly|Leu|Val|Thr|Ile|Val|Gly|Phe|Leu|Ala|Phe|Asp|Ser|
| | |115| | | | |120| | | | |125| | | |
|Asp|Thr|Val|Met|Phe|Ser|Ile|Ile|Gly|Leu|Ile|Thr|Ile|Ser|Tyr|Ile|
|130| | | | |135| | | | |140| | | | | |
|Ile|Asn|Ala|Ile|Gln|Thr|Gly|Phe|Thr|Thr|Leu|Ser|Thr|Val|Leu|Ile|
|145| | | | |150| | | | |155| | | | |160|
|Val|Ser|Gln|Glu|His|Gln|Lys|Ile|Lys|Thr|Tyr|Ile|Asn|Thr|Val|Ala|
| | | | |165| | | | |170| | | | |175| |
|Asp|Arg|Gly|Val|Thr|Glu|Ile|Pro|Val|Lys|Gly|Gly|Tyr|Ser|Gly|Thr|
| | | |180| | | | |185| | | | |190| | |
|Asn|Gln|Ile|Met|Leu|Met|Thr|Thr|Ile|Ala|Gly|Tyr|Glu|Phe|Ala|Lys|
| | |195| | | | |200| | | | |205| | | |
|Leu|Gln|Glu|Ala|Ile|Ala|Glu|Ile|Asp|Glu|Thr|Ala|Phe|Ile|Thr|Val|
| |210| | | | |215| | | | |220| | | | |
|Thr|Pro|Thr|Ser|Gln|Ala|Ser|Gly|Arg|Gly|Phe|Ser|Leu|Gln|Lys|Asn|
|225| | | | |230| | | | |235| | | | |240|
|His|Gly|Arg|Leu|Asp|Glu|Asp|Ile|Leu|Met|Pro|Met| | | | |
| | | |245| | | | |250| | | | | | | |

<210> SEQ ID NO 93
<211> LENGTH: 549
<212> TYPE: DNA
<213> ORGANISM: Streptococcus agalactiae

<400> SEQUENCE: 93

| | | |
|---|---|---|
|atgaaagaaa aacagtcgaa aaggcttatt tatatactac tgattgttcc cattatcttt|60|
|ataagtgttt ttacatacag tattagccag ccttctaaac tacttccacc aaaagaatta|120|
|gttattctaa gtccaaatag tcaagccatt ttaacaggaa cgattccagc ttttgaggaa|180|
|aaatacggta taaaagttaa gcttattcaa ggtgggacag ggcaactaat agatagatta|240|
|agtaaggagg gtaagcagtt gaaggcggat attttctttg gaggaaatta tacgcaattt|300|
|gaaagtcata aggcattgtt tgagtcttac gtatcaaaga atgttcatac tgttattcca|360|
|gactatatcc atccgagtga tacggcgaca cctatactca taatgggagt gtcttgatt|420|
|gtaaataacg aattagctaa gggacttacc atcaagagtt atgaagattt attacagcct|480|
|tccttaaaag gtaaaattgc ctttgcagat cctctagagt cgacctgcaa gcatgcaagc|540|
|ttggcgtaa|549|

<210> SEQ ID NO 94
<211> LENGTH: 182
<212> TYPE: PRT
<213> ORGANISM: Streptococcus agalactiae

<400> SEQUENCE: 94

```
Met Lys Glu Lys Gln Ser Lys Arg Leu Ile Tyr Ile Leu Leu Ile Val
  1               5                  10                  15
Pro Ile Ile Phe Ile Ser Val Phe Thr Tyr Ser Ile Ser Gln Pro Ser
                 20                  25                  30
Lys Leu Leu Pro Pro Lys Glu Leu Val Ile Leu Ser Pro Asn Ser Gln
             35                  40                  45
Ala Ile Leu Thr Gly Thr Ile Pro Ala Phe Glu Glu Lys Tyr Gly Ile
         50                  55                  60
Lys Val Lys Leu Ile Gln Gly Gly Thr Gly Gln Leu Ile Asp Arg Leu
 65                  70                  75                  80
Ser Lys Glu Gly Lys Gln Leu Lys Ala Asp Ile Phe Phe Gly Gly Asn
                 85                  90                  95
Tyr Thr Gln Phe Glu Ser His Lys Ala Leu Phe Glu Ser Tyr Val Ser
            100                 105                 110
Lys Asn Val His Thr Val Ile Pro Asp Tyr Ile His Pro Ser Asp Thr
        115                 120                 125
Ala Thr Pro Tyr Thr Ile Asn Gly Ser Val Leu Ile Val Asn Asn Glu
    130                 135                 140
Leu Ala Lys Gly Leu Thr Ile Lys Ser Tyr Glu Asp Leu Leu Gln Pro
145                 150                 155                 160
Ser Leu Lys Gly Lys Ile Ala Phe Ala Asp Pro Leu Glu Ser Thr Cys
                165                 170                 175
Lys His Ala Ser Leu Ala
            180
```

<210> SEQ ID NO 95
<211> LENGTH: 368
<212> TYPE: DNA
<213> ORGANISM: Streptococcus agalactiae

<400> SEQUENCE: 95

```
cctcctatca aatgatgaca aacgtgagag gtacatggaa caaatgctct ttaaaattga     60
aaatgcaacc tggcagcgtg tggtaagagc actttatcgt aaatacaata aggaattttt    120
tacatatcca gccgccaaaa caaaccacca cgcttttgaa tcaggattgg catatcacac    180
ggcaacaatg gttcgtttgg cagatagtat cggagatatc tatccagaac ttaataaaag    240
tttgatgttt gctggtatta tgctacatga tttagccaag gtcatagagt tatcgggtcc    300
tgataataca gaatatacta ttcgaggtaa tcttatcggt catatttcac ttattgatga    360
ggaattaa                                                              368
```

<210> SEQ ID NO 96
<211> LENGTH: 122
<212> TYPE: PRT
<213> ORGANISM: Streptococcus agalactiae

<400> SEQUENCE: 96

```
Leu Leu Ser Asn Asp Asp Lys Arg Glu Arg Tyr Met Glu Gln Met Leu
  1               5                  10                  15
Phe Lys Ile Glu Asn Ala Thr Trp Gln Arg Val Val Arg Ala Leu Tyr
                 20                  25                  30
```

```
Arg Lys Tyr Asn Lys Glu Phe Phe Thr Tyr Pro Ala Ala Lys Thr Asn
            35                  40                  45

His His Ala Phe Glu Ser Gly Leu Ala Tyr His Thr Ala Thr Met Val
        50                  55                  60

Arg Leu Ala Asp Ser Ile Gly Asp Ile Tyr Pro Glu Leu Asn Lys Ser
 65                  70                  75                  80

Leu Met Phe Ala Gly Ile Met Leu His Asp Leu Ala Lys Val Ile Glu
                85                  90                  95

Leu Ser Gly Pro Asp Asn Thr Glu Tyr Thr Ile Arg Gly Asn Leu Ile
            100                 105                 110

Gly His Ile Ser Leu Ile Asp Glu Glu Leu
        115                 120

<210> SEQ ID NO 97
<211> LENGTH: 753
<212> TYPE: DNA
<213> ORGANISM: Streptococcus agalactiae

<400> SEQUENCE: 97
```

| | | | | | |
|---|---|---|---|---|---|
| atgaaaaaaa | ataaaattat | ccgattcagt | ttagttggtg | ttctacttgc | gatactatgc | 60 |
| tttagtcttt | ttgctttatt | gaagcctaac | agtcaacaat | catcatctca | aaagttgagg | 120 |
| aatgaggata | taaaaaagac | atcctctcaa | aaaagaaata | gaaattacg | attaccagct | 180 |
| gtatcatcaa | aagattggaa | cttgattttg | gtcaatcgtg | accataaaca | tgaagaatta | 240 |
| agtccagatg | tggtgcctgt | tgaaaatatt | tatttggata | aacgtattac | gaagcaagct | 300 |
| actcagtttt | tagaggctgc | tagagcaatt | gattcacgag | aacatttaat | ttcgggttat | 360 |
| cgtagtgttg | cctatcagga | gaagttgttc | aattcttatg | ttactcaaga | gatgactagt | 420 |
| aaccctaatt | tgacgagggg | acaagcagaa | aagttggtaa | aaacttactc | tcagcctgca | 480 |
| ggtgctagtg | aacaccagac | tggattagcg | atggatatga | gtactgtaga | ttctttgaat | 540 |
| gagagcgatc | ctagagtagt | cagtcagttg | aaaaagatag | ctccacaata | tggttttgtc | 600 |
| ttacggtttc | cggatggtaa | aacagcagaa | acagggtag | gttatgaaga | ttggcattac | 660 |
| cgctatgttg | gggtagagtc | tgcaaaatat | atggtcaaac | atcatttaac | attagaagaa | 720 |
| tacataactt | tattaaagga | gaataaccaa | tga | | | 753 |

```
<210> SEQ ID NO 98
<211> LENGTH: 250
<212> TYPE: PRT
<213> ORGANISM: Streptococcus agalactiae

<400> SEQUENCE: 98

Met Lys Lys Asn Lys Ile Ile Arg Phe Ser Leu Val Gly Val Leu Leu
  1               5                  10                  15

Ala Ile Leu Cys Phe Ser Leu Phe Ala Leu Leu Lys Pro Asn Ser Gln
                20                  25                  30

Gln Ser Ser Ser Gln Lys Leu Arg Asn Glu Asp Ile Lys Lys Thr Ser
            35                  40                  45

Ser Gln Lys Arg Asn Lys Lys Leu Arg Leu Pro Ala Val Ser Ser Lys
 50                  55                  60

Asp Trp Asn Leu Ile Leu Val Asn Arg Asp His Lys His Glu Glu Leu
 65                  70                  75                  80

Ser Pro Asp Val Val Pro Val Glu Asn Ile Tyr Leu Asp Lys Arg Ile
                85                  90                  95
```

Thr Lys Gln Ala Thr Gln Phe Leu Glu Ala Ala Arg Ala Ile Asp Ser
                100                 105                 110

Arg Glu His Leu Ile Ser Gly Tyr Arg Ser Val Ala Tyr Gln Glu Lys
            115                 120                 125

Leu Phe Asn Ser Tyr Val Thr Gln Glu Met Thr Ser Asn Pro Asn Leu
        130                 135                 140

Thr Arg Gly Gln Ala Glu Lys Leu Val Lys Thr Tyr Ser Gln Pro Ala
145                 150                 155                 160

Gly Ala Ser Glu His Gln Thr Gly Leu Ala Met Asp Met Ser Thr Val
                165                 170                 175

Asp Ser Leu Asn Glu Ser Asp Pro Arg Val Val Ser Gln Leu Lys Lys
            180                 185                 190

Ile Ala Pro Gln Tyr Gly Phe Val Leu Arg Phe Pro Asp Gly Lys Thr
        195                 200                 205

Ala Glu Thr Gly Val Gly Tyr Glu Asp Trp His Tyr Arg Tyr Val Gly
    210                 215                 220

Val Glu Ser Ala Lys Tyr Met Val Lys His His Leu Thr Leu Glu Glu
225                 230                 235                 240

Tyr Ile Thr Leu Leu Lys Glu Asn Asn Gln
                245                 250

<210> SEQ ID NO 99
<211> LENGTH: 351
<212> TYPE: DNA
<213> ORGANISM: Streptococcus agalactiae

<400> SEQUENCE: 99
ctgttatgtg gatttcttcc atcaattcct gtgtctaatt ccggggggta tggtataata      60
acagttatga aaataaaaa aatcttattt gggactggcc ttgctggtgt gggtttactg     120
gcagctgctg gttataccct aactaaaaaa gtaacagatt ataaacgtca gcaaatcact     180
cagaccttaa gagaactttt tagtcagatg ggtgatattc aggtatttta ttttaatgaa     240
tttgaatctg atattaaaat gaccagtggt ggtcttgtct tggaagatgg cagaattttc     300
gaattcattt atcgtcaagg tgttcttgat tatgtggagg tgagcaaatg a              351

<210> SEQ ID NO 100
<211> LENGTH: 116
<212> TYPE: PRT
<213> ORGANISM: Streptococcus agalactiae

<400> SEQUENCE: 100

Leu Leu Cys Gly Phe Leu Pro Ser Ile Pro Val Ser Asn Ser Gly Gly
 1               5                  10                  15

Tyr Gly Ile Ile Thr Val Met Lys Asn Lys Lys Ile Leu Phe Gly Thr
            20                  25                  30

Gly Leu Ala Gly Val Gly Leu Leu Ala Ala Ala Gly Tyr Thr Leu Thr
        35                  40                  45

Lys Lys Val Thr Asp Tyr Lys Arg Gln Gln Ile Thr Gln Thr Leu Arg
    50                  55                  60

Glu Leu Phe Ser Gln Met Gly Asp Ile Gln Val Phe Tyr Phe Asn Glu
65                  70                  75                  80

Phe Glu Ser Asp Ile Lys Met Thr Ser Gly Gly Leu Val Leu Glu Asp
                85                  90                  95

Gly Arg Ile Phe Glu Phe Ile Tyr Arg Gln Gly Val Leu Asp Tyr Val
            100                 105                 110

-continued

Glu Val Ser Lys
          115

<210> SEQ ID NO 101
<211> LENGTH: 310
<212> TYPE: DNA
<213> ORGANISM: Streptococcus agalactiae

<400> SEQUENCE: 101

```
atgtatcaaa ctcagacaaa taaggaaaaa tttgttttat ttttgaaatt atttatccca      60
gtattgattt atcaatttgc taattttca gctacttta ttgattcggt tatgactgga     120
cagtatagtc agctacattt ggcaggtgtg tcaactgcta gtaatttatg gactccgttt     180
ttcgctttat tagtaggtat gatttcagca ttagtaccag tagttggtca acatttgggt     240
agaggaaata aagaacaaat tcgcacagaa tttcatcaat ttctatattt aggtttgata     300
ctgtccttaa                                                             310
```

<210> SEQ ID NO 102
<211> LENGTH: 103
<212> TYPE: PRT
<213> ORGANISM: Streptococcus agalactiae

<400> SEQUENCE: 102

Met Tyr Gln Thr Gln Thr Asn Lys Glu Lys Phe Val Leu Phe Leu Lys
1               5                  10                  15

Leu Phe Ile Pro Val Leu Ile Tyr Gln Phe Ala Asn Phe Ser Ala Thr
            20                  25                  30

Phe Ile Asp Ser Val Met Thr Gly Gln Tyr Ser Gln Leu His Leu Ala
        35                  40                  45

Gly Val Ser Thr Ala Ser Asn Leu Trp Thr Pro Phe Ala Leu Leu
    50                  55                  60

Val Gly Met Ile Ser Ala Leu Val Pro Val Val Gly Gln His Leu Gly
65                  70                  75                  80

Arg Gly Asn Lys Glu Gln Ile Arg Thr Glu Phe His Gln Phe Leu Tyr
                85                  90                  95

Leu Gly Leu Ile Leu Ser Leu
            100

<210> SEQ ID NO 103
<211> LENGTH: 1098
<212> TYPE: DNA
<213> ORGANISM: Streptococcus agalactiae

<400> SEQUENCE: 103

```
ctgctctttt tagctaactt ttctaattta tggtataatt gtatggattg tttagctaga      60
atggagaaga tgatgcaaga tgttttcatt ataggaagta gagggttgcc agctcgttac     120
ggtggttttg aaacttttgt ttcagaattg attaatcatc aaaaaagttc cgacataaaa     180
taccatgttg catgccttag tgataaagaa catcatactc attttaactt tgctgacgct     240
gattgtttta ctataaatcc tccccaatta gggccagcac gtgtgattgc ttatgatatt     300
atggccatta ttatgccct tgacttggtt aagacacatg atttaaaaga gcctatttt     360
tatattttag gaaatacaat tggtgccttt atttggcatt tgccaataa atacataaa     420
gtcggtggct tattgtatgt taatccggat ggtttagagt ggaagcgatc aaagtggtct     480
cgtcccacac agcgttattt aaaatacgcc gaaaaatgta tgactaaaaa tgcagaccta     540
attatttctg ataatattgg tattgaaaat tacattcaat ctacctactc taatgtgaag     600
```

-continued

```
acaaggttca ttgcttacgg tacagagatt aattctagga aattatcgtc agatgatcca      660
cgtgtcaaac agttgtttaa aaaatggaat attaagtcta agggttacta tctaatcgtt      720
ggtcgatttg tccctgaaaa caattatgaa acggctatta gggagttcat ggcttcagat      780
actaagcgtg atttagttat tatctgtaac catcaaaata ccccctactt tgaaaagttg      840
tccttaaaga caaaccttca acaagataaa agagttaagt ttgtaggtac gctctatgaa      900
aaagatctgc tggattatgt tcgtcaacaa gcctttgctt atattcatgg gcatgaagtt      960
ggcggtacta atccaggact gcttgaggct ttagctaata ctgatttgaa tcttgttcta     1020
gatgttgatt tcaacaaatc agtagcaggt ctctcaagtt tttactggac taaaaaagag     1080
ggggatttag ctaagctt                                                   1098
```

<210> SEQ ID NO 104
<211> LENGTH: 366
<212> TYPE: PRT
<213> ORGANISM: Streptococcus agalactiae

<400> SEQUENCE: 104

```
Met Leu Phe Leu Ala Asn Phe Ser Asn Leu Trp Tyr Asn Cys Met Asp
  1               5                  10                  15

Cys Leu Ala Arg Met Glu Lys Met Met Gln Asp Val Phe Ile Ile Gly
                 20                  25                  30

Ser Arg Gly Leu Pro Ala Arg Tyr Gly Gly Phe Glu Thr Phe Val Ser
             35                  40                  45

Glu Leu Ile Asn His Gln Lys Ser Ser Asp Ile Lys Tyr His Val Ala
         50                  55                  60

Cys Leu Ser Asp Lys Glu His His Thr His Phe Asn Phe Ala Asp Ala
     65                  70                  75                  80

Asp Cys Phe Thr Ile Asn Pro Pro Gln Leu Gly Pro Ala Arg Val Ile
                 85                  90                  95

Ala Tyr Asp Ile Met Ala Ile Asn Tyr Ala Leu Asp Leu Val Lys Thr
            100                 105                 110

His Asp Leu Lys Glu Pro Ile Phe Tyr Ile Leu Gly Asn Thr Ile Gly
        115                 120                 125

Ala Phe Ile Trp His Phe Ala Asn Lys Ile His Lys Val Gly Gly Leu
    130                 135                 140

Leu Tyr Val Asn Pro Asp Gly Leu Glu Trp Lys Arg Ser Lys Trp Ser
145                 150                 155                 160

Arg Pro Thr Gln Arg Tyr Leu Lys Tyr Ala Glu Lys Cys Met Thr Lys
                165                 170                 175

Asn Ala Asp Leu Ile Ile Ser Asp Asn Ile Gly Ile Glu Asn Tyr Ile
            180                 185                 190

Gln Ser Thr Tyr Ser Asn Val Lys Thr Arg Phe Ile Ala Tyr Gly Thr
        195                 200                 205

Glu Ile Asn Ser Arg Lys Leu Ser Ser Asp Pro Arg Val Lys Gln
    210                 215                 220

Leu Phe Lys Lys Trp Asn Ile Lys Ser Lys Gly Tyr Tyr Leu Ile Val
225                 230                 235                 240

Gly Arg Phe Val Pro Glu Asn Asn Tyr Glu Thr Ala Ile Arg Glu Phe
                245                 250                 255

Met Ala Ser Asp Thr Lys Arg Asp Leu Val Ile Ile Cys Asn His Gln
            260                 265                 270

Asn Asn Pro Tyr Phe Glu Lys Leu Ser Leu Lys Thr Asn Leu Gln Gln
```

```
              275                 280                 285
Asp Lys Arg Val Lys Phe Val Gly Thr Leu Tyr Glu Lys Asp Leu Leu
        290                 295                 300

Asp Tyr Val Arg Gln Gln Ala Phe Ala Tyr Ile His Gly His Glu Val
305                 310                 315                 320

Gly Gly Thr Asn Pro Gly Leu Leu Glu Ala Leu Ala Asn Thr Asp Leu
                325                 330                 335

Asn Leu Val Leu Asp Val Asp Phe Asn Lys Ser Val Ala Gly Leu Ser
            340                 345                 350

Ser Phe Tyr Trp Thr Lys Lys Glu Gly Asp Leu Ala Lys Leu
        355                 360                 365

<210> SEQ ID NO 105
<211> LENGTH: 546
<212> TYPE: DNA
<213> ORGANISM: Streptococcus agalactiae

<400> SEQUENCE: 105
ttgaggagta atatggtaaa gacagcagtt ttaatggcga catacaatgg cgaaaaattt    60
atatctgaac aacttgattc aattcgccaa cagacattaa aaccagatta tgtattattg   120
agggatgatt gttcaacgga tgaaacagtc aatgtcgtca ataactatat cgcaaaacat   180
gagttagaag gctggaaaat tgttaaaaac gacaaaaact taggctggcg tttaaatttt   240
cgtcaattac ttattgatgt gttagcctat gaggttgact atgtcttttt tagtgatcaa   300
gatgatattt ggtatcttga taaaaacgaa cgacagtttg ccattatgtc agataaccct   360
caaattgagg ttttgagtgc agacgttgat atcaaaacga tgtctacaga agccagtgtt   420
ccacattttc taacttttc ttctagtgat agaatcagtc agtatcctaa agtatatgat   480
tatcaaacat tccgtcccgg atggaccatt gctatgaaga gagattttgc gcaagctatc   540
gcttga                                                              546

<210> SEQ ID NO 106
<211> LENGTH: 181
<212> TYPE: PRT
<213> ORGANISM: Streptococcus agalactiae

<400> SEQUENCE: 106

Met Arg Ser Asn Met Val Lys Thr Ala Val Leu Met Ala Thr Tyr Asn
1               5                   10                  15

Gly Glu Lys Phe Ile Ser Glu Gln Leu Asp Ser Ile Arg Gln Gln Thr
            20                  25                  30

Leu Lys Pro Asp Tyr Val Leu Leu Arg Asp Asp Cys Ser Thr Asp Glu
        35                  40                  45

Thr Val Asn Val Val Asn Asn Tyr Ile Ala Lys His Glu Leu Glu Gly
    50                  55                  60

Trp Lys Ile Val Lys Asn Asp Lys Asn Leu Gly Trp Arg Leu Asn Phe
65                  70                  75                  80

Arg Gln Leu Leu Ile Asp Val Leu Ala Tyr Glu Val Asp Tyr Val Phe
                85                  90                  95

Phe Ser Asp Gln Asp Asp Ile Trp Tyr Leu Asp Lys Asn Glu Arg Gln
            100                 105                 110

Phe Ala Ile Met Ser Asp Asn Pro Gln Ile Glu Val Leu Ser Ala Asp
        115                 120                 125

Val Asp Ile Lys Thr Met Ser Thr Glu Ala Ser Val Pro His Phe Leu
    130                 135                 140
```

```
Thr Phe Ser Ser Asp Arg Ile Ser Gln Tyr Pro Lys Val Tyr Asp
145                 150                 155                 160

Tyr Gln Thr Phe Arg Pro Gly Trp Thr Ile Ala Met Lys Arg Asp Phe
            165                 170                 175

Ala Gln Ala Ile Ala
            180

<210> SEQ ID NO 107
<211> LENGTH: 639
<212> TYPE: DNA
<213> ORGANISM: Streptococcus agalactiae

<400> SEQUENCE: 107
gtgattatgg ataagtctat tcctaaagca actgctaaac gtttatcact gtactaccgt      60
atttttaaac gttttaatac tgatggcatc gaaaaagcta gttccaaaca aattgcagat     120
gccctaggta tcgattctgc tactgttcga cgtgattttt cttatttggg tgaactagga     180
cgccgtggtt ttggttatga tgtcaaaaaa cttatgaact ctttgcaga aatattgaac      240 gatcattcta caacaaatgt tatgctggtg gggtgtggaa atatcggtag agctctcttg     300
cattatcgtt tccacgatcg caataaaatg caaatttcaa tggcttttga tttagatagc     360
aatgatttag ttggtaaaac aaccgaggat ggaattcctg tctacggtat ttcgactatc     420
aatgaccatt taatagatag tgatattgaa actgctatcc taacagtacc tagtacagaa     480
gcccaagaag ttgctgacat cttagtcaaa gcaggtataa aaggcatctt gagttttttct    540 ccagttcatt taacattacc aaaagatatc attgttcagt atgtagattt aacaagcgaa     600
ttacaaactt tactttattt catgaaccag cagcgataa                            639

<210> SEQ ID NO 108
<211> LENGTH: 212
<212> TYPE: PRT
<213> ORGANISM: Streptococcus agalactiae

<400> SEQUENCE: 108

Met Ile Met Asp Lys Ser Ile Pro Lys Ala Thr Ala Lys Arg Leu Ser
 1               5                  10                  15

Leu Tyr Tyr Arg Ile Phe Lys Arg Phe Asn Thr Asp Gly Ile Glu Lys
            20                  25                  30

Ala Ser Ser Lys Gln Ile Ala Asp Ala Leu Gly Ile Asp Ser Ala Thr
        35                  40                  45

Val Arg Arg Asp Phe Ser Tyr Phe Gly Glu Leu Gly Arg Arg Gly Phe
    50                  55                  60

Gly Tyr Asp Val Lys Lys Leu Met Asn Phe Phe Ala Glu Ile Leu Asn
65                  70                  75                  80

Asp His Ser Thr Thr Asn Val Met Leu Val Gly Cys Gly Asn Ile Gly
                85                  90                  95

Arg Ala Leu Leu His Tyr Arg Phe His Asp Arg Asn Lys Met Gln Ile
            100                 105                 110

Ser Met Ala Phe Asp Leu Asp Ser Asn Asp Leu Val Gly Lys Thr Thr
        115                 120                 125

Glu Asp Gly Ile Pro Val Tyr Gly Ile Ser Thr Ile Asn Asp His Leu
    130                 135                 140

Ile Asp Ser Asp Ile Glu Thr Ala Ile Leu Thr Val Pro Ser Thr Glu
145                 150                 155                 160

Ala Gln Glu Val Ala Asp Ile Leu Val Lys Ala Gly Ile Lys Gly Ile
```

```
                    165                 170                 175
Leu Ser Phe Ser Pro Val His Leu Thr Leu Pro Lys Asp Ile Ile Val
            180                 185                 190

Gln Tyr Val Asp Leu Thr Ser Glu Leu Gln Thr Leu Leu Tyr Phe Met
        195                 200                 205

Asn Gln Gln Arg
    210

<210> SEQ ID NO 109
<211> LENGTH: 476
<212> TYPE: DNA
<213> ORGANISM: Streptococcus agalactiae

<400> SEQUENCE: 109
atgggtgcta aaggagcaga tgtcattctc gttttatcac actctggcat tggagatgat      60
cgatatgaag aaggtgaaga aaacgttggc tatcaaattg ccagcatcaa gggagtggat     120
gccgttgtta cgggacactc acacgctgaa tttccatcag gtaacggtac tggcttctat     180
gaaaaataca ctggagttga tggtatcaat ggaaaaataa atggaacacc tgttacaatg     240
gcaggcaagt acgggatca ccttggtatt attgatttag gacttagtta tactaatgga      300
aaatggcaag tctccgaaag cagtgctaaa atccgtaaaa ttgatatgaa ctcaacaact     360
gctgacgagc gtatcattgc attggctaag gaagcacacg atggcactat caactatgtt     420
cgccaacaag taggtacaac aactgcgcca attacaagtt actttgcact agttaa        476

<210> SEQ ID NO 110
<211> LENGTH: 158
<212> TYPE: PRT
<213> ORGANISM: Streptococcus agalactiae

<400> SEQUENCE: 110

Met Gly Ala Lys Gly Ala Asp Val Ile Leu Val Leu Ser His Ser Gly
  1               5                  10                  15

Ile Gly Asp Asp Arg Tyr Glu Glu Gly Glu Glu Asn Val Gly Tyr Gln
                 20                  25                  30

Ile Ala Ser Ile Lys Gly Val Asp Ala Val Val Thr Gly His Ser His
             35                  40                  45

Ala Glu Phe Pro Ser Gly Asn Gly Thr Gly Phe Tyr Glu Lys Tyr Thr
         50                  55                  60

Gly Val Asp Gly Ile Asn Gly Lys Ile Asn Gly Thr Pro Val Thr Met
 65                  70                  75                  80

Ala Gly Lys Tyr Gly Asp His Leu Gly Ile Ile Asp Leu Gly Leu Ser
                 85                  90                  95

Tyr Thr Asn Gly Lys Trp Gln Val Ser Glu Ser Ser Ala Lys Ile Arg
                100                 105                 110

Lys Ile Asp Met Asn Ser Thr Thr Ala Asp Glu Arg Ile Ile Ala Leu
            115                 120                 125

Ala Lys Glu Ala His Asp Gly Thr Ile Asn Tyr Val Arg Gln Gln Val
        130                 135                 140

Gly Thr Thr Thr Ala Pro Ile Thr Ser Tyr Phe Ala Leu Val
145                 150                 155

<210> SEQ ID NO 111
<211> LENGTH: 170
<212> TYPE: DNA
<213> ORGANISM: Streptococcus agalactiae
```

<400> SEQUENCE: 111

```
ttgtcaataa ggtttcaaat cagcttgaaa tatgataaaa taaaacagat tgtaagtgac    60
tgtttaagct tgttttttcag agaggttttt atgaatacaa acacaataaa aaaggttgta  120
gcgactggaa ttggagctgc acttttttatc attataggta tgctagttaa             170
```

<210> SEQ ID NO 112
<211> LENGTH: 56
<212> TYPE: PRT
<213> ORGANISM: Streptococcus agalactiae

<400> SEQUENCE: 112

```
Met Ser Ile Arg Phe Gln Ile Ser Leu Lys Tyr Asp Lys Ile Lys Gln
  1               5                  10                  15
Ile Val Ser Asp Cys Leu Ser Leu Phe Phe Arg Glu Val Phe Met Asn
             20                  25                  30
Thr Asn Thr Ile Lys Lys Val Val Ala Thr Gly Ile Gly Ala Ala Leu
         35                  40                  45
Phe Ile Ile Ile Gly Met Leu Val
     50                  55
```

<210> SEQ ID NO 113
<211> LENGTH: 242
<212> TYPE: DNA
<213> ORGANISM: Streptococcus agalactiae

<400> SEQUENCE: 113

```
atgaaacatt taaaatttca atcggtcttc gacattattg gtcctgttat gattggacca    60
tcaagtagtc atactgcagg agctgtccgc attggtaaag ttgtccattc tattttttggt  120
gaacctagtg aagtaacctt tcatttatac aattcttttg ctaaaactta ccaaggacac  180
ggtactgata aagcattggt tgcagggatt ctaggaatgg atacagataa tccagatatt  240
aa                                                                  242
```

<210> SEQ ID NO 114
<211> LENGTH: 80
<212> TYPE: PRT
<213> ORGANISM: Streptococcus agalactiae

<400> SEQUENCE: 114

```
Met Lys His Leu Lys Phe Gln Ser Val Phe Asp Ile Ile Gly Pro Val
  1               5                  10                  15
Met Ile Gly Pro Ser Ser Ser His Thr Ala Gly Ala Val Arg Ile Gly
             20                  25                  30
Lys Val Val His Ser Ile Phe Gly Glu Pro Ser Glu Val Thr Phe His
         35                  40                  45
Leu Tyr Asn Ser Phe Ala Lys Thr Tyr Gln Gly His Gly Thr Asp Lys
     50                  55                  60
Ala Leu Val Ala Gly Ile Leu Gly Met Asp Thr Asp Asn Pro Asp Ile
 65                  70                  75                  80
```

<210> SEQ ID NO 115
<211> LENGTH: 122
<212> TYPE: DNA
<213> ORGANISM: Streptococcus agalactiae

<400> SEQUENCE: 115

```
gtgtcagaag gtgttttaat gtttctaaaa gaagatgacg tagagacttt tcttcatatc    60
```

| | |
|---|---|
| ctgacaaatt catttagcca atttatggca caatttgatt tgtgtcataa ggaaatgatt | 120 |
| aa | 122 |

<210> SEQ ID NO 116
<211> LENGTH: 83
<212> TYPE: DNA
<213> ORGANISM: Streptococcus agalactiae

<400> SEQUENCE: 116

| | |
|---|---|
| atgacctaca aagattacac aggtttagat cggactgaac ttttgagtaa agtgcgtcat | 60 |
| atgatgtccg acaaacgttt taa | 83 |

<210> SEQ ID NO 117
<211> LENGTH: 27
<212> TYPE: PRT
<213> ORGANISM: Streptococcus agalactiae

<400> SEQUENCE: 117

Met Thr Tyr Lys Asp Tyr Thr Gly Leu Asp Arg Thr Glu Leu Leu Ser
1               5                   10                  15

Lys Val Arg His Met Met Ser Asp Lys Arg Phe
            20                  25

<210> SEQ ID NO 118
<211> LENGTH: 94
<212> TYPE: DNA
<213> ORGANISM: Streptococcus agalactiae

<400> SEQUENCE: 118

| | |
|---|---|
| ctgagttggg tcttggaaac ggtcctgtca atcatactag ctatcaagga gactaaaatg | 60 |
| tatttagaac aactaaaaga ggtaaatcct ttaa | 94 |

<210> SEQ ID NO 119
<211> LENGTH: 31
<212> TYPE: PRT
<213> ORGANISM: Streptococcus agalactiae

<400> SEQUENCE: 119

Met Ser Trp Val Leu Glu Thr Val Leu Ser Ile Ile Leu Ala Ile Lys
1               5                   10                  15

Glu Thr Lys Met Tyr Leu Glu Gln Leu Lys Glu Val Asn Pro Leu
            20                  25                  30

<210> SEQ ID NO 120
<211> LENGTH: 1230
<212> TYPE: DNA
<213> ORGANISM: Streptococcus agalactiae

<400> SEQUENCE: 120

| | |
|---|---|
| gtgaaaaaaa aattagtctc atcacttcta aagtgttctc taatcattat tgttagcttt | 60 |
| gctggtggag catttgctag ttttgtcatg aatcataatg acaatattcc aaatggtggt | 120 |
| gtcactaaaa ctagtaaagt aaattataat aacataacgc ctacaacaaa agctgttaaa | 180 |
| aaggtacaaa atagtgttgt ttctgttatc aattataaac aacaagagag tcgttctgac | 240 |
| ctatcagact tctatagtca tttttttggt aatcaggggg gcaacactga taagggctta | 300 |
| caagtttacg gtgaaggctc tggagtcatc tataaaaaag atggtaaaaa tgcctatgtt | 360 |
| gtcactaata accacgtcat tgatggggct aaacaaattg aaattcaact agctgatggc | 420 |
| tcaaaagcag ttgggaaact tgttgggtca gatacctact ctgatttagc cgtcgtcaaa | 480 |

-continued

```
attccatcag ataaagtttc aaatattgca gaatttgctg attcatcaaa actcaacatt        540
ggtgaaactg ctatagcgat cggaagccct cttggaactg agtatgcaaa ttctgtaact        600
caaggtattg tatctagttt aaaaagaact gtaacaatga ctaatgaaga aggacaaaca        660
gtttctacaa atgctatcca gacggatgct gctatcaatc ctggtaattc aggtggagca        720
cttatcaata ttgaaggaca ggttattgga attaattcta gtaaaatttc ttctacatca        780
aatcaaacct caggacaatc gtcaggaaat agcgttgaag gtatgggatt tgccattcct        840
tcaaatgatg ttgttaagat tatcaatcaa cttgagagta acggacaagt agagagacct        900
gctctaggta tttctatggc tggattaagt aatttaccat ccgatgttat tagtaaactg        960
aaaatcccaa gtaatgttac taatggtatt gtagtagcat ctatccaatc tggcatgcca       1020
gctcaaggca aactaaagaa atacgatgtc attactaaag ttgacgataa agaagtagca       1080
tctccaagtg atttcaaaag tttactctat ggccaccagg tagggattc cataacagta       1140 acctttatc gtggtgaaaa taaacaaaca gtcactataa aacttactaa aactagtaaa       1200
gatttagcta acaacgagc aaataactaa                                        1230
```

<210> SEQ ID NO 121
<211> LENGTH: 409
<212> TYPE: PRT
<213> ORGANISM: Streptococcus agalactiae

<400> SEQUENCE: 121

```
Met Lys Lys Leu Val Ser Ser Leu Leu Lys Cys Ser Leu Ile Ile
  1               5                  10                  15

Ile Val Ser Phe Ala Gly Gly Ala Phe Ala Ser Phe Val Met Asn His
                 20                  25                  30

Asn Asp Asn Ile Pro Asn Gly Val Thr Lys Thr Ser Lys Val Asn
             35                  40                  45

Tyr Asn Asn Ile Thr Pro Thr Lys Ala Val Lys Lys Val Gln Asn
         50                  55                  60

Ser Val Val Ser Val Ile Asn Tyr Lys Gln Gln Glu Ser Arg Ser Asp
 65                  70                  75                  80

Leu Ser Asp Phe Tyr Ser His Phe Phe Gly Asn Gln Gly Gly Asn Thr
                 85                  90                  95

Asp Lys Gly Leu Gln Val Tyr Gly Glu Gly Ser Gly Val Ile Tyr Lys
            100                 105                 110

Lys Asp Gly Lys Asn Ala Tyr Val Val Thr Asn Asn His Val Ile Asp
            115                 120                 125

Gly Ala Lys Gln Ile Glu Ile Gln Leu Ala Asp Gly Ser Lys Ala Val
            130                 135                 140

Gly Lys Leu Val Gly Ser Asp Thr Tyr Ser Asp Leu Ala Val Val Lys
145                 150                 155                 160

Ile Pro Ser Asp Lys Val Ser Asn Ile Ala Glu Phe Ala Asp Ser Ser
                165                 170                 175

Lys Leu Asn Ile Gly Glu Thr Ala Ile Ala Ile Gly Ser Pro Leu Gly
            180                 185                 190

Thr Glu Tyr Ala Asn Ser Val Thr Gln Gly Ile Val Ser Ser Leu Lys
            195                 200                 205

Arg Thr Val Thr Met Thr Asn Glu Glu Gly Gln Thr Val Ser Thr Asn
        210                 215                 220

Ala Ile Gln Thr Asp Ala Ala Ile Asn Pro Gly Asn Ser Gly Gly Ala
225                 230                 235                 240
```

```
Leu Ile Asn Ile Glu Gly Gln Val Ile Gly Ile Asn Ser Ser Lys Ile
                245                 250                 255

Ser Ser Thr Ser Asn Gln Thr Ser Gly Gln Ser Ser Gly Asn Ser Val
            260                 265                 270

Glu Gly Met Gly Phe Ala Ile Pro Ser Asn Asp Val Lys Ile Ile
        275                 280                 285

Asn Gln Leu Glu Ser Asn Gly Gln Val Glu Arg Pro Ala Leu Gly Ile
    290                 295                 300

Ser Met Ala Gly Leu Ser Asn Leu Pro Ser Asp Val Ile Ser Lys Leu
305                 310                 315                 320

Lys Ile Pro Ser Asn Val Thr Asn Gly Ile Val Val Ala Ser Ile Gln
                325                 330                 335

Ser Gly Met Pro Ala Gln Gly Lys Leu Lys Lys Tyr Asp Val Ile Thr
            340                 345                 350

Lys Val Asp Asp Lys Glu Val Ala Ser Pro Ser Asp Leu Gln Ser Leu
        355                 360                 365

Leu Tyr Gly His Gln Val Gly Asp Ser Ile Thr Val Thr Phe Tyr Arg
    370                 375                 380

Gly Glu Asn Lys Gln Thr Val Thr Ile Lys Leu Thr Lys Thr Ser Lys
385                 390                 395                 400

Asp Leu Ala Lys Gln Arg Ala Asn Asn
                405
```

```
<210> SEQ ID NO 122
<211> LENGTH: 1923
<212> TYPE: DNA
<213> ORGANISM: Streptococcus agalactiae

<400> SEQUENCE: 122
atgttaaaat ggtatacaaa caaaggaggg aggatgataa tgaagaaatg ttttttggct    60
atttgtttag ctcttagttt ttttatggtt tcagttcaag cagatgaggt ggactataac   120
attcctcatt atgagggtaa tctaactatt cacaatgata atagtgctga ttttacagag   180
aaggttactt accaatttga ttcgtcctat aatggacagt atgtcacgtt aggtacggcg   240
ggtaagttat ctgacaattt tgatattaat aataagccac aggttgaagt ttcaattaat   300
ggtaaagtaa ggaaagttag ttaccagata gaagatttgg aggatggcta ccgtttgaaa   360
gtgtttaatg gtggtgaagc aggtgatact gttaaagtca atgttcagtg gaaactaaaa   420
aatgttctat ttatgcataa ggatgttggt gaacttaact ggattcctat tagcgactgg   480
gataaaacgt tagagaaagt agattttttgg atatcaactg acaaaaaggt tgctctttct   540
cgtctttggg ggcacttggg ttatcttaaa actcctccta aaataagaca aaataataat   600
cgttaccatt tgacagcttt taatgtaaac aaacgattag aatttcatgg ttattgggat   660
agatcttatt ttaatctacc tacaaacagt aaaaataatt acaagaaaaa aattgaacat   720
caagagaaga atatagagcg tcatggtttt atcctaagtt tcttgttaag gatattatta   780
ccttcattct ttattattgt gacactattc atctcaatta gggtgttcct gtttagaaaa   840
aaagttaata atacgggca attccctaag gatcatcatt tatatgaagc acctgaggac   900
cttttcaccat tagagttaac tcaaagcatt tatagtatga gctttaaaaa ttttcaagat   960
gaggagaaga aaactcacct tatcagtcaa gaacaactca tacagtcaat tctattagac  1020
ttgattgata gaaagtatt tgaattatgat gataacttgt tatctctagc taacttagat  1080
agagcttctg atgcagaaat agattttata gagtttgctt ttgcggattc tacgagtttg  1140
```

-continued

```
aagccagatc aactcttttc taattaccaa tttagttata aagaaacact acgtgaactg    1200
aaaaagcagc acaaggcttc agatctgcaa aatcaaatga gacgccgagg aagtaatgcc    1260
ttatcaagaa ttacgcgtct cacaaggttg atttctaaag acaatataaa ctctcttaga    1320
agaaagggaa tttcatcccc ttatcgtaaa atgtcttcag aagagtctaa agaattatct    1380
aggttaaaaa gattcagtta cctatcaccct cttatttctt ttgttgttat aatttatacg    1440 cttttttaa attattttac ctatttctgt atctatctct tattgtttgg tgttatcctg     1500
ttgttgaata aaatcatttt tatgatgaca agaaaaataa gtaacggtta tattgtaact    1560
gaagatggag caagtcgtgt ctaccaatgg actagtttta ggaacatgct aagggatatc    1620
aaatcgtttg atcgttcaga gttagaaagt atcgtattat ggaatcgaat attggtttac    1680
gctactttat tcggctacgc tgaccgtgtt gagaaagtac tcagagtgaa ccaaatagat    1740
attccagaaa gatttgcaaa cattgatagt catcgatttg cgatttcagt caatcaatct    1800
agtaatcatt tttcaacgat aactgaagat gttagtcacg cttctaattt tagtgttaat    1860
tcaggcggtt cttcaggtgg tttctcaggc ggcggaggcg gcggaggtgg cggtgccttc    1920
taa                                                                  1923
```

<210> SEQ ID NO 123
<211> LENGTH: 640
<212> TYPE: PRT
<213> ORGANISM: Streptococcus agalactiae

<400> SEQUENCE: 123

```
Met Leu Lys Trp Tyr Thr Asn Lys Gly Gly Arg Met Ile Met Lys Lys
  1               5                  10                  15

Cys Phe Leu Ala Ile Cys Leu Ala Leu Ser Phe Phe Met Val Ser Val
                 20                  25                  30

Gln Ala Asp Glu Val Asp Tyr Asn Ile Pro His Tyr Glu Gly Asn Leu
             35                  40                  45

Thr Ile His Asn Asp Asn Ser Ala Asp Phe Thr Glu Lys Val Thr Tyr
         50                  55                  60

Gln Phe Asp Ser Ser Tyr Asn Gly Gln Tyr Val Thr Leu Gly Thr Ala
 65                  70                  75                  80

Gly Lys Leu Ser Asp Asn Phe Asp Ile Asn Asn Lys Pro Gln Val Glu
                 85                  90                  95

Val Ser Ile Asn Gly Lys Val Arg Lys Val Ser Tyr Gln Ile Glu Asp
            100                 105                 110

Leu Glu Asp Gly Tyr Arg Leu Lys Val Phe Asn Gly Gly Glu Ala Gly
        115                 120                 125

Asp Thr Val Lys Val Asn Val Gln Trp Lys Leu Lys Asn Val Leu Phe
    130                 135                 140

Met His Lys Asp Val Gly Glu Leu Asn Trp Ile Pro Ile Ser Asp Trp
145                 150                 155                 160

Asp Lys Thr Leu Glu Lys Val Asp Phe Trp Ile Ser Thr Asp Lys Lys
                165                 170                 175

Val Ala Leu Ser Arg Leu Trp Gly His Leu Gly Tyr Leu Lys Thr Pro
            180                 185                 190

Pro Lys Ile Arg Gln Asn Asn Asn Arg Tyr His Leu Thr Ala Phe Asn
        195                 200                 205

Val Asn Lys Arg Leu Glu Phe His Gly Tyr Trp Asp Arg Ser Tyr Phe
    210                 215                 220
```

```
Asn Leu Pro Thr Asn Ser Lys Asn Asn Tyr Lys Lys Ile Glu His
225                 230                 235                 240

Gln Glu Lys Ile Ile Glu Arg His Gly Phe Ile Leu Ser Phe Leu Leu
                245                 250                 255

Arg Ile Leu Leu Pro Ser Phe Phe Ile Ile Val Thr Leu Phe Ile Ser
            260                 265                 270

Ile Arg Val Phe Leu Phe Arg Lys Lys Val Asn Lys Tyr Gly Gln Phe
        275                 280                 285

Pro Lys Asp His His Leu Tyr Glu Ala Pro Glu Asp Leu Ser Pro Leu
    290                 295                 300

Glu Leu Thr Gln Ser Ile Tyr Ser Met Ser Phe Lys Asn Phe Gln Asp
305                 310                 315                 320

Glu Glu Lys Lys Thr His Leu Ile Ser Gln Glu Gln Leu Ile Gln Ser
                325                 330                 335

Ile Leu Leu Asp Leu Ile Asp Arg Lys Val Leu Asn Tyr Asp Asp Asn
            340                 345                 350

Leu Leu Ser Leu Ala Asn Leu Asp Arg Ala Ser Asp Ala Glu Ile Asp
        355                 360                 365

Phe Ile Glu Phe Ala Phe Ala Asp Ser Thr Ser Leu Lys Pro Asp Gln
    370                 375                 380

Leu Phe Ser Asn Tyr Gln Phe Ser Tyr Lys Glu Thr Leu Arg Glu Leu
385                 390                 395                 400

Lys Lys Gln His Lys Ala Ser Asp Leu Gln Asn Gln Met Arg Arg Arg
                405                 410                 415

Gly Ser Asn Ala Leu Ser Arg Ile Thr Arg Leu Thr Arg Leu Ile Ser
            420                 425                 430

Lys Asp Asn Ile Asn Ser Leu Arg Arg Lys Gly Ile Ser Ser Pro Tyr
        435                 440                 445

Arg Lys Met Ser Ser Glu Glu Ser Lys Glu Leu Ser Arg Leu Lys Arg
    450                 455                 460

Phe Ser Tyr Leu Ser Pro Leu Ile Ser Phe Val Val Ile Ile Tyr Thr
465                 470                 475                 480

Leu Phe Leu Asn Tyr Phe Thr Tyr Phe Cys Ile Tyr Leu Leu Leu Phe
                485                 490                 495

Gly Val Ile Leu Leu Leu Asn Lys Ile Ile Phe Met Met Thr Arg Lys
            500                 505                 510

Ile Ser Asn Gly Tyr Ile Val Thr Glu Asp Gly Ala Ser Arg Val Tyr
        515                 520                 525

Gln Trp Thr Ser Phe Arg Asn Met Leu Arg Asp Ile Lys Ser Phe Asp
    530                 535                 540

Arg Ser Glu Leu Glu Ser Ile Val Leu Trp Asn Arg Ile Leu Val Tyr
545                 550                 555                 560

Ala Thr Leu Phe Gly Tyr Ala Asp Arg Val Glu Lys Val Leu Arg Val
                565                 570                 575

Asn Gln Ile Asp Ile Pro Glu Arg Phe Ala Asn Ile Asp Ser His Arg
            580                 585                 590

Phe Ala Ile Ser Val Asn Gln Ser Asn His Phe Ser Thr Ile Thr
        595                 600                 605

Glu Asp Val Ser His Ala Ser Asn Phe Ser Val Asn Ser Gly Gly Ser
    610                 615                 620

Ser Gly Gly Phe Ser Gly Gly Gly Gly Gly Gly Gly Ala Phe
625                 630                 635                 640
```

-continued

<210> SEQ ID NO 124
<211> LENGTH: 2712
<212> TYPE: DNA
<213> ORGANISM: Streptococcus agalactiae

<400> SEQUENCE: 124

| | | | | | | |
|---|---|---|---|---|---|---|
| atgatgattg | tgaataatgg | ttatctagaa | gggagaaaaa | tgaaaagag | acaaaaaata | 60 |
| tggagagggt | tatcagttac | tttactaatc | ctgtcccaaa | ttccatttgg | tatattggta | 120 |
| caaggtgaaa | cccaagatac | caatcaagca | cttggaaaag | taattgttaa | aaaaacggga | 180 |
| gacaatgcta | caccattagg | caaagcgact | tttgtgttaa | aaaatgacaa | tgataagtca | 240 |
| gaaacaagtc | acgaaacggt | agagggttct | ggagaagcaa | cctttgaaaa | cataaaacct | 300 |
| ggagactaca | cattaagaga | agaaacagca | ccaattggtt | ataaaaaaac | tgataaaacc | 360 |
| tggaaagtta | agttgcaga | taacggagca | acaataatcg | agggtatgga | tgcagataaa | 420 |
| gcagagaaac | gaaagaagt | tttgaatgcc | caatatccaa | aatcagctat | ttatgaggat | 480 |
| acaaaagaaa | attacccatt | agttaatgta | gagggttcca | agttggtga | acaatacaaa | 540 |
| gcattgaatc | caataaatgg | aaaagatggt | cgaagagaga | ttgctgaagg | ttggttatca | 600 |
| aaaaaaaatc | cagggggtcaa | tgatctcgat | aagaataaat | ataaaattga | attaactgtt | 660 |
| gagggtaaaa | ccactgttga | aacgaaagaa | cttaatcaac | cactagatgt | cgttgtgcta | 720 |
| ttagataatt | caaatagtat | gaataatgaa | agagccaata | attctcaaag | agcattaaaa | 780 |
| gctggggaag | cagttgaaaa | gctgattgat | aaaattacat | caaataaaga | caatagagta | 840 |
| gctcttgtga | catatgcctc | aaccattttt | gatggtactg | aagcgaccgt | atcaaaggga | 900 |
| gttgccgatc | aaaatggtaa | agcgctgaat | gatagtgtat | catgggatta | tcataaaact | 960 |
| acttttacag | caactacaca | taattacagt | tatttaaatt | taacaaatga | tgctaacgaa | 1020 |
| gttaatattc | taaagtcaag | aattccaaag | gaagcggagc | atataaatgg | ggatcgcacg | 1080 |
| ctctatcaat | ttggtgcgac | atttactcaa | aaagctctaa | tgaaagcaaa | tgaaatttta | 1140 |
| gagacacaaa | gttctaatgc | tagaaaaaaa | cttatttttc | acgtaactga | tggtgtccct | 1200 |
| acgatgtctt | atgccataaa | ttttaatcct | tatatatcaa | catcttacca | aaaccagttt | 1260 |
| aattctttt | taaataaaat | accagataga | agtggtattc | tccaagagga | ttttataatc | 1320 |
| aatggtgatg | attatcaaat | agtaaaagga | gatggagaga | gtttaaact | gttttcggat | 1380 |
| agaaaagttc | ctgttactgg | aggaacgaca | caagcagctt | atcgagtacc | gcaaaatcaa | 1440 |
| ctctctgtaa | tgagtaatga | gggatatgca | attaatagtg | gatatattta | tctctattgg | 1500 |
| agagattaca | actgggtcta | tccatttgat | cctaagacaa | agaaagtttc | tgcaacgaaa | 1560 |
| caaatcaaaa | ctcatggtga | gccaacaaca | ttatacttta | tggaaatat | aagacctaaa | 1620 |
| ggttatgaca | tttttactgt | tgggattggt | gtaaacggag | atcctggtgc | aactcctctt | 1680 |
| gaagctgaga | aatttatgca | atcaatatca | gtaaaacag | aaaattatac | taatgttgat | 1740 |
| gatacaaata | aaatttatga | tgagctaaat | aaatacttta | aaacaattgt | tgaggaaaaa | 1800 |
| cattctattg | ttgatggaaa | tgtgactgat | cctatgggag | agatgattga | attccaatta | 1860 |
| aaaaatggtc | aaagttttac | acatgatgat | tacgttttgg | ttggaaatga | tggcagtcaa | 1920 |
| ttaaaaaatg | gtgtggctct | tggtggacca | acagtgatg | ggggaatttt | aaaagatgtt | 1980 |
| acagtgactt | atgataagac | atctcaaacc | atcaaaatca | atcatttgaa | cttaggaagt | 2040 |
| ggacaaaaag | tagttcttac | ctatgatgta | cgtttaaaag | ataactatat | aagtaacaaa | 2100 |
| ttttacaata | caaataatcg | tacaacgcta | agtccgaaga | gtgaaaaaga | accaaatact | 2160 |

-continued

```
attcgtgatt tcccaattcc caaaattcgt gatgttcgtg agtttccggt actaaccatc    2220
agtaatcaga agaaaatggg tgaggttgaa tttattaaag ttaataaaga caaacattca    2280
gaatcgcttt tgggagctaa gtttcaactt cagatagaaa aagatttttc tgggtataag    2340
caatttgttc cagagggaag tgatgttaca acaaagaatg atggtaaaat ttattttaaa    2400
gcacttcaag atggtaacta taaattatat gaaatttcaa gtccagatgg ctatatagag    2460
gttaaaacga aacctgttgt gacatttaca attcaaaatg gagaagttac gaacctgaaa    2520
gcagatccaa atgctaataa aaatcaaatc gggtatcttg aaggaaatgg taaacatctt    2580
attaccaaca ctcccaaacg cccaccaggt gtttttccta aaacaggggg aattggtaca    2640
attgtctata tattagttgg ttctactttt atgatactta ccatttgttc tttccgtcgt    2700
aaacaattgt aa                                                       2712
```

<210> SEQ ID NO 125
<211> LENGTH: 903
<212> TYPE: PRT
<213> ORGANISM: Streptococcus agalactiae

<400> SEQUENCE: 125

```
Met Met Ile Val Asn Asn Gly Tyr Leu Glu Gly Arg Lys Met Lys Lys
  1               5                  10                  15

Arg Gln Lys Ile Trp Arg Gly Leu Ser Val Thr Leu Leu Ile Leu Ser
             20                  25                  30

Gln Ile Pro Phe Gly Ile Leu Val Gln Gly Glu Thr Gln Asp Thr Asn
         35                  40                  45

Gln Ala Leu Gly Lys Val Ile Val Lys Lys Thr Gly Asp Asn Ala Thr
     50                  55                  60

Pro Leu Gly Lys Ala Thr Phe Val Leu Lys Asn Asp Asn Asp Lys Ser
 65                  70                  75                  80

Glu Thr Ser His Glu Thr Val Glu Gly Ser Gly Glu Ala Thr Phe Glu
                 85                  90                  95

Asn Ile Lys Pro Gly Asp Tyr Thr Leu Arg Glu Glu Thr Ala Pro Ile
            100                 105                 110

Gly Tyr Lys Lys Thr Asp Lys Thr Trp Lys Val Lys Val Ala Asp Asn
        115                 120                 125

Gly Ala Thr Ile Ile Glu Gly Met Asp Ala Asp Lys Ala Glu Lys Arg
    130                 135                 140

Lys Glu Val Leu Asn Ala Gln Tyr Pro Lys Ser Ala Ile Tyr Glu Asp
145                 150                 155                 160

Thr Lys Glu Asn Tyr Pro Leu Val Asn Val Glu Gly Ser Lys Val Gly
                165                 170                 175

Glu Gln Tyr Lys Ala Leu Asn Pro Ile Asn Gly Lys Asp Gly Arg Arg
            180                 185                 190

Glu Ile Ala Glu Gly Trp Leu Ser Lys Asn Pro Gly Val Asn Asp
        195                 200                 205

Leu Asp Lys Asn Lys Tyr Lys Ile Glu Leu Thr Val Glu Gly Lys Thr
    210                 215                 220

Thr Val Glu Thr Lys Glu Leu Asn Gln Pro Leu Asp Val Val Val Leu
225                 230                 235                 240

Leu Asp Asn Ser Asn Ser Met Asn Asn Glu Arg Ala Asn Asn Ser Gln
                245                 250                 255

Arg Ala Leu Lys Ala Gly Glu Ala Val Glu Lys Leu Ile Asp Lys Ile
            260                 265                 270
```

```
Thr Ser Asn Lys Asp Asn Arg Val Ala Leu Val Thr Tyr Ala Ser Thr
        275                 280                 285

Ile Phe Asp Gly Thr Glu Ala Thr Val Ser Lys Gly Val Ala Asp Gln
        290                 295                 300

Asn Gly Lys Ala Leu Asn Asp Ser Val Ser Trp Asp Tyr His Lys Thr
305                 310                 315                 320

Thr Phe Thr Ala Thr Thr His Asn Tyr Ser Tyr Leu Asn Leu Thr Asn
                325                 330                 335

Asp Ala Asn Glu Val Asn Ile Leu Lys Ser Arg Ile Pro Lys Glu Ala
            340                 345                 350

Glu His Ile Asn Gly Asp Arg Thr Leu Tyr Gln Phe Gly Ala Thr Phe
        355                 360                 365

Thr Gln Lys Ala Leu Met Lys Ala Asn Glu Ile Leu Glu Thr Gln Ser
        370                 375                 380

Ser Asn Ala Arg Lys Lys Leu Ile Phe His Val Thr Asp Gly Val Pro
385                 390                 395                 400

Thr Met Ser Tyr Ala Ile Asn Phe Asn Pro Tyr Ile Ser Thr Ser Tyr
                405                 410                 415

Gln Asn Gln Phe Asn Ser Phe Leu Asn Lys Ile Pro Asp Arg Ser Gly
            420                 425                 430

Ile Leu Gln Glu Asp Phe Ile Ile Asn Gly Asp Asp Tyr Gln Ile Val
        435                 440                 445

Lys Gly Asp Gly Glu Ser Phe Lys Leu Phe Ser Asp Arg Lys Val Pro
        450                 455                 460

Val Thr Gly Gly Thr Thr Gln Ala Ala Tyr Arg Val Pro Gln Asn Gln
465                 470                 475                 480

Leu Ser Val Met Ser Asn Glu Gly Tyr Ala Ile Asn Ser Gly Tyr Ile
                485                 490                 495

Tyr Leu Tyr Trp Arg Asp Tyr Asn Trp Val Tyr Pro Phe Asp Pro Lys
            500                 505                 510

Thr Lys Lys Val Ser Ala Thr Lys Gln Ile Lys Thr His Gly Glu Pro
        515                 520                 525

Thr Thr Leu Tyr Phe Asn Gly Asn Ile Arg Pro Lys Gly Tyr Asp Ile
        530                 535                 540

Phe Thr Val Gly Ile Gly Val Asn Gly Asp Pro Gly Ala Thr Pro Leu
545                 550                 555                 560

Glu Ala Glu Lys Phe Met Gln Ser Ile Ser Ser Lys Thr Glu Asn Tyr
                565                 570                 575

Thr Asn Val Asp Asp Thr Asn Lys Ile Tyr Asp Glu Leu Asn Lys Tyr
            580                 585                 590

Phe Lys Thr Ile Val Glu Glu Lys His Ser Ile Val Asp Gly Asn Val
        595                 600                 605

Thr Asp Pro Met Gly Glu Met Ile Glu Phe Gln Leu Lys Asn Gly Gln
        610                 615                 620

Ser Phe Thr His Asp Asp Tyr Val Leu Val Gly Asn Asp Gly Ser Gln
625                 630                 635                 640

Leu Lys Asn Gly Val Ala Leu Gly Gly Pro Asn Ser Asp Gly Gly Ile
                645                 650                 655

Leu Lys Asp Val Thr Val Thr Tyr Asp Lys Thr Ser Gln Thr Ile Lys
            660                 665                 670

Ile Asn His Leu Asn Leu Gly Ser Gly Gln Lys Val Val Leu Thr Tyr
        675                 680                 685

Asp Val Arg Leu Lys Asp Asn Tyr Ile Ser Asn Lys Phe Tyr Asn Thr
```

| | | | | | | | | | | |
|---|---|---|---|---|---|---|---|---|---|---|
| | | | | 690 | | 695 | | 700 | | |
| Asn | Asn | Arg | Thr | Thr | Leu | Ser | Pro | Lys | Ser | Glu Lys Glu Pro Asn Thr |
| 705 | | | | 710 | | | | 715 | | 720 |
| Ile | Arg | Asp | Phe | Pro | Ile | Pro | Lys | Ile | Arg | Asp Val Arg Glu Phe Pro |
| | | | | 725 | | | | 730 | | 735 |
| Val | Leu | Thr | Ile | Ser | Asn | Gln | Lys | Lys | Met | Gly Glu Val Glu Phe Ile |
| | | | | 740 | | | | 745 | | 750 |
| Lys | Val | Asn | Lys | Asp | Lys | His | Ser | Glu | Ser | Leu Leu Gly Ala Lys Phe |
| | | | 755 | | | | 760 | | | 765 |
| Gln | Leu | Gln | Ile | Glu | Lys | Asp | Phe | Ser | Gly | Tyr Lys Gln Phe Val Pro |
| | 770 | | | | | 775 | | | | 780 |
| Glu | Gly | Ser | Asp | Val | Thr | Thr | Lys | Asn | Asp | Gly Lys Ile Tyr Phe Lys |
| 785 | | | | 790 | | | | 795 | | 800 |
| Ala | Leu | Gln | Asp | Gly | Asn | Tyr | Lys | Leu | Tyr | Glu Ile Ser Ser Pro Asp |
| | | | | 805 | | | | 810 | | 815 |
| Gly | Tyr | Ile | Glu | Val | Lys | Thr | Lys | Pro | Val | Val Thr Phe Thr Ile Gln |
| | | | | 820 | | | | 825 | | 830 |
| Asn | Gly | Glu | Val | Thr | Asn | Leu | Lys | Ala | Asp | Pro Asn Ala Asn Lys Asn |
| | | | | 835 | | | | 840 | | 845 |
| Gln | Ile | Gly | Tyr | Leu | Glu | Gly | Asn | Gly | Lys | His Leu Ile Thr Asn Thr |
| | | | 850 | | | | 855 | | | 860 |
| Pro | Lys | Arg | Pro | Pro | Gly | Val | Phe | Pro | Lys | Thr Gly Gly Ile Gly Thr |
| 865 | | | | 870 | | | | 875 | | 880 |
| Ile | Val | Tyr | Ile | Leu | Val | Gly | Ser | Thr | Phe | Met Ile Leu Thr Ile Cys |
| | | | | 885 | | | | 890 | | 895 |
| Ser | Phe | Arg | Arg | Lys | Gln | Leu | | | | |
| | | | 900 | | | | | | | |

<210> SEQ ID NO 126
<211> LENGTH: 1251
<212> TYPE: DNA
<213> ORGANISM: Streptococcus agalactiae

<400> SEQUENCE: 126

| | |
|---|---|
| atgaatagaa aagttgagga aaaaatggct gggaatcgta ataacgatat gaatgtctat | 60 |
| tgttcatttt gtggcaaaag ccaagatgaa gtaaaaaaaa ttattgcagg taatggtgtt | 120 |
| ttcatttgta atgaatgtgt ggccttatca caagaaatta ttaaggaaga attagctgag | 180 |
| gaagtactgg ctcatttagc agaagtacca aaacctaagg aactattaga atattaaat | 240 |
| caatatgttg tagggcaaga tcgtgctaaa cgtgctttag cagttgctgt ctacaatcat | 300 |
| tacaagcgtg ttagttatac cgagagtagt gacgatgatg tagatttgca aaaatccaac | 360 |
| attttgatga ttggtccaac tggctcagga aaaaccttct tagcacaaac actggctaaa | 420 |
| agccttaatg taccgtttgc tattgcagat gcgacttcat tgaccgaagc aggatacgtt | 480 |
| ggagaagatg ttgagaatat tcttcttaaa ttgattcaag ctgctgatta taatgtcgaa | 540 |
| cgtgctgagc gtggtattat ctacgttgat gaaatagata aaattgctaa gaaaggcgaa | 600 |
| aatgtttcta tcacacgtga tgtgtctggt gaaggtgtac agcaagccct tcttaaaatt | 660 |
| attgagggta cggtagcaag tgttccccca cagggtgggc gtaaacatcc taaccaagaa | 720 |
| atgattcaaa ttaataccaa gaacatcctt tttattgtcg gtggtgcttt tgatggtatt | 780 |
| gaagaccttg tgaagcaacg tttaggcgaa aagttattg gttttggaca gacaagccgt | 840 |
| aaaattgatg acaacgcttc ttatatgcaa gagataattt ctgaggatat tcaaaagttt | 900 |

```
ggactgattc cagagtttat tggccgttta ccagtagttg cagcgttaga acttcttact    960
gcagaagatc tggttcgtat tctgacagaa ccacgcaatg ctttggttaa acaataccaa   1020
accttattat cttatgatgg tgtagaattg gaatttgacc aggatgctct attggctatc   1080
gctgataagg ctatcgagcg caagactggt gcacgtggtt tacgttctat tattgaagaa   1140
acgatgcttg atatcatgtt tgaaattcca agccaagaag atgtaacaaa agttcgtatc   1200
acaaaggctg ctgttgaggg tactgacaag cctgttttag agacggctta g            1251
```

<210> SEQ ID NO 127
<211> LENGTH: 416
<212> TYPE: PRT
<213> ORGANISM: Streptococcus agalactiae

<400> SEQUENCE: 127

```
Met Asn Arg Lys Val Glu Glu Lys Met Ala Gly Asn Arg Asn Asn Asp
1               5                   10                  15

Met Asn Val Tyr Cys Ser Phe Cys Gly Lys Ser Gln Asp Glu Val Lys
            20                  25                  30

Lys Ile Ile Ala Gly Asn Gly Val Phe Ile Cys Asn Glu Cys Val Ala
        35                  40                  45

Leu Ser Gln Glu Ile Ile Lys Glu Leu Ala Glu Glu Val Leu Ala
    50                  55                  60

His Leu Ala Glu Val Pro Lys Pro Lys Glu Leu Glu Ile Leu Asn
65                  70                  75                  80

Gln Tyr Val Val Gly Gln Asp Arg Ala Lys Arg Ala Leu Ala Val Ala
                85                  90                  95

Val Tyr Asn His Tyr Lys Arg Val Ser Tyr Thr Glu Ser Ser Asp Asp
            100                 105                 110

Asp Val Asp Leu Gln Lys Ser Asn Ile Leu Met Ile Gly Pro Thr Gly
        115                 120                 125

Ser Gly Lys Thr Phe Leu Ala Gln Thr Leu Ala Lys Ser Leu Asn Val
    130                 135                 140

Pro Phe Ala Ile Ala Asp Ala Thr Ser Leu Thr Glu Ala Gly Tyr Val
145                 150                 155                 160

Gly Glu Asp Val Glu Asn Ile Leu Leu Lys Leu Ile Gln Ala Ala Asp
                165                 170                 175

Tyr Asn Val Glu Arg Ala Glu Arg Gly Ile Ile Tyr Val Asp Glu Ile
            180                 185                 190

Asp Lys Ile Ala Lys Lys Gly Glu Asn Val Ser Ile Thr Arg Asp Val
        195                 200                 205

Ser Gly Glu Gly Val Gln Gln Ala Leu Leu Lys Ile Glu Gly Thr
    210                 215                 220

Val Ala Ser Val Pro Pro Gln Gly Gly Arg Lys His Pro Asn Gln Glu
225                 230                 235                 240

Met Ile Gln Ile Asn Thr Lys Asn Ile Leu Phe Ile Val Gly Gly Ala
                245                 250                 255

Phe Asp Gly Ile Glu Asp Leu Val Lys Gln Arg Leu Gly Glu Lys Val
            260                 265                 270

Ile Gly Phe Gly Gln Thr Ser Arg Lys Ile Asp Asp Asn Ala Ser Tyr
        275                 280                 285

Met Gln Glu Ile Ile Ser Glu Asp Ile Gln Lys Phe Gly Leu Ile Pro
    290                 295                 300

Glu Phe Ile Gly Arg Leu Pro Val Val Ala Ala Leu Glu Leu Leu Thr
305                 310                 315                 320
```

```
Ala Glu Asp Leu Val Arg Ile Leu Thr Glu Pro Arg Asn Ala Leu Val
            325                 330                 335

Lys Gln Tyr Gln Thr Leu Leu Ser Tyr Asp Gly Val Glu Leu Glu Phe
        340                 345                 350

Asp Gln Asp Ala Leu Leu Ala Ile Ala Asp Lys Ala Ile Glu Arg Lys
            355                 360                 365

Thr Gly Ala Arg Gly Leu Arg Ser Ile Ile Glu Thr Met Leu Asp
        370                 375                 380

Ile Met Phe Glu Ile Pro Ser Gln Glu Asp Val Thr Lys Val Arg Ile
385                 390                 395                 400

Thr Lys Ala Ala Val Glu Gly Thr Asp Lys Pro Val Leu Glu Thr Ala
            405                 410                 415

<210> SEQ ID NO 128
<211> LENGTH: 786
<212> TYPE: DNA
<213> ORGANISM: Streptococcus agalactiae

<400> SEQUENCE: 128
atgaaaagat tacataaact gtttataacc gtaattgcta cattaggtat gttgggggta      60
atgacctttg gtcttccaac gcagccgcaa aacgtaacgc cgatagtaca tgctgatgtc     120
aattcatctg ttgatacgag ccaggaattt caaaataatt taaaaaatgc tattggtaac     180
ctaccatttc aatatgttaa tggtatttat gaattaaata ataatcagac aaatttaaat     240
gctgatgtca atgttaaagc gtatgttcaa aatacaattg acaatcaaca aagactatca     300
actgctaatg caatgcttga tagaaccatt cgtcaatatc aaaatcgcag agataccact     360
cttcccgatg caaattggaa accattaggt tggcatcaag tagctactaa tgaccattat     420
gggcatgcag tcgacaaggg gcatttaatt gcctatgctt tagctggaaa tttcaaaggt     480
tgggatgctt ccgtgtcaaa tcctcaaaat gttgtcacac aaacagctca ttccaaccaa     540
tcaaatcaaa aaatcaatcg tggacaaaat tattatgaaa gcttagttcg taaggcggtt     600
gaccaaaaca aacgtgttcg ttaccgtgta actccattgt accgtaatga tactgattta     660
gttccatttg caatgcacct agaagctaaa tcacaagatg gcacattaga atttaatgtt     720
gctattccaa acacacaagc atcatacact atggattatg caacaggaga ataacacta     780 aattaa                                                                786

<210> SEQ ID NO 129
<211> LENGTH: 261
<212> TYPE: PRT
<213> ORGANISM: Streptococcus agalactiae

<400> SEQUENCE: 129

Met Lys Arg Leu His Lys Leu Phe Ile Thr Val Ile Ala Thr Leu Gly
1               5                   10                  15

Met Leu Gly Val Met Thr Phe Gly Leu Pro Thr Gln Pro Gln Asn Val
            20                  25                  30

Thr Pro Ile Val His Ala Asp Val Asn Ser Ser Val Asp Thr Ser Gln
        35                  40                  45

Glu Phe Gln Asn Asn Leu Lys Asn Ala Ile Gly Asn Leu Pro Phe Gln
    50                  55                  60

Tyr Val Asn Gly Ile Tyr Glu Leu Asn Asn Gln Thr Asn Leu Asn
65                  70                  75                  80

Ala Asp Val Asn Val Lys Ala Tyr Val Gln Asn Thr Ile Asp Asn Gln
```

|    |    |    |    | 85  |    |    |    |    | 90  |    |    |    |    | 95  |    |
|----|----|----|----|-----|----|----|----|----|-----|----|----|----|----|-----|----|

Gln Arg Leu Ser Thr Ala Asn Ala Met Leu Asp Arg Thr Ile Arg Gln
            100                    105                  110

Tyr Gln Asn Arg Arg Asp Thr Thr Leu Pro Asp Ala Asn Trp Lys Pro
     115                    120                  125

Leu Gly Trp His Gln Val Ala Thr Asn Asp His Tyr Gly His Ala Val
    130                    135                  140

Asp Lys Gly His Leu Ile Ala Tyr Ala Leu Ala Gly Asn Phe Lys Gly
145                    150                  155                160

Trp Asp Ala Ser Val Ser Asn Pro Gln Asn Val Thr Gln Thr Ala
            165                  170                175

His Ser Asn Gln Ser Asn Gln Lys Ile Asn Arg Gly Gln Asn Tyr Tyr
        180                  185                190

Glu Ser Leu Val Arg Lys Ala Val Asp Gln Asn Lys Arg Val Arg Tyr
    195                    200                  205

Arg Val Thr Pro Leu Tyr Arg Asn Asp Thr Asp Leu Val Pro Phe Ala
   210                    215                  220

Met His Leu Glu Ala Lys Ser Gln Asp Gly Thr Leu Glu Phe Asn Val
225                    230                  235                240

Ala Ile Pro Asn Thr Gln Ala Ser Tyr Thr Met Asp Tyr Ala Thr Gly
            245                  250                255

Glu Ile Thr Leu Asn
    260

```
<210> SEQ ID NO 130
<211> LENGTH: 621
<212> TYPE: DNA
<213> ORGANISM: Streptococcus agalactiae

<400> SEQUENCE: 130
atgaaaaact atcgaaaact tattgtacta ctacttctaa tctttttgc cattttatg      60 ggagcatatg cttacacgca tattgttgaa aaaagatccc taactagcaa tactattgaa    120
aaaactctac ctgtggtaaa tcagattaag cctcaaacca ttaaagaata ccaaaattac    180
ttaactaagg tagctaaacg taatgttctt cctgtagaca ttcctcaggc attaaataat    240
gaaaaggtag aaattactgc tactgatggc atgcaaacat tcacttggaa tgataaaaat    300
aatcctaagc aaaaggttat cttctatgtt catggaggat catatatcca tcaagcttcc    360
gaattacaat atattttgt caataaacta gctaaaaaat tagatgcaaa agttgtcttt    420
cctatttacc ctaaagctcc tacatataat tatagtgatg ctatccccaa aattaaaaaa    480
ttataccaaa atacattagc tagcgtcaca tctcacaaac agattatcct agtaggtgaa    540
agtgcaggcg gaggccttgc tttaggtatt gctgataacc ttgcacggag catatcaaac    600
aaccaaaaga aattatttta a                                              621

<210> SEQ ID NO 131
<211> LENGTH: 206
<212> TYPE: PRT
<213> ORGANISM: Streptococcus agalactiae

<400> SEQUENCE: 131
```

Met Lys Asn Tyr Arg Lys Leu Ile Val Leu Leu Leu Ile Phe Phe
1               5                  10                15

Ala Ile Phe Met Gly Ala Tyr Ala Tyr Thr His Ile Val Glu Lys Arg
        20                  25                30

```
Ser Leu Thr Ser Asn Thr Ile Glu Lys Thr Leu Pro Val Val Asn Gln
         35                  40                  45
Ile Lys Pro Gln Thr Ile Lys Glu Tyr Gln Asn Tyr Leu Thr Lys Val
 50                  55                  60
Ala Lys Arg Asn Val Leu Pro Val Asp Ile Pro Gln Ala Leu Asn Asn
 65                  70                  75                  80
Glu Lys Val Glu Ile Thr Ala Thr Asp Gly Met Gln Thr Phe Thr Trp
                 85                  90                  95
Asn Asp Lys Asn Asn Pro Lys Gln Lys Val Ile Phe Tyr Val His Gly
                100                 105                 110
Gly Ser Tyr Ile His Gln Ala Ser Glu Leu Gln Tyr Ile Phe Val Asn
            115                 120                 125
Lys Leu Ala Lys Lys Leu Asp Ala Lys Val Val Phe Pro Ile Tyr Pro
130                 135                 140
Lys Ala Pro Thr Tyr Asn Tyr Ser Asp Ala Ile Pro Lys Ile Lys Lys
145                 150                 155                 160
Leu Tyr Gln Asn Thr Leu Ala Ser Val Thr Ser His Lys Gln Ile Ile
                165                 170                 175
Leu Val Gly Glu Ser Ala Gly Gly Leu Ala Leu Gly Ile Ala Asp
            180                 185                 190
Asn Leu Ala Arg Ser Ile Ser Asn Asn Gln Lys Lys Leu Phe
195                 200                 205

<210> SEQ ID NO 132
<211> LENGTH: 885
<212> TYPE: DNA
<213> ORGANISM: Streptococcus agalactiae

<400> SEQUENCE: 132
ttgattctaa taacttccta tgggataata tctttatcac aaaaattgag ggaatttatt      60
atgaagttaa acatattgt cttaggatta gccttaacaa cacttttagg agtcacattt     120
agtaatcaag aagtttcagc aagctcaact tcaagtaaag ttgttaaagt tggtgttatg     180
acctttctg acactgaaaa agcacgttgg gataaaattg aaaagctagt aggtgataaa     240
gctaaaatca aatttacaga atttacagat tatacacaac caaatcaagc gacagccaat     300
aaggatgtgg atattaatgc ctttcaacat tacaattct tagaaaactg gaataaggaa     360
aataagaaaa acttaattcc acttgaaaag acttacttag ctccaattcg tatctattct     420
gagaaggtaa atctcttaa aaaattgaaa aaaggagcca ctattgcaat tccaaatgat     480
gcaacaaatg gtagccgtgc attgtatgtc cttcagtcag caggtttaat caaattgaat     540
gtttctggta agaaggttgc aacagttgct aatatcacat ctaataaaaa ggatattaat     600
attcaggagt tagatgcgag tcaaacacca cgtgcactca agatgtaga tgcagctatt     660
attaataata catacattga gcaagctaat ttaaaacctt cagatgctat ctttgttgag     720
aaatcagata aaaattcaaa acaatggatt aatatcattg cgggacgtaa aaattggaaa     780
aagcaaaaga acgctaaagc tatccaagct atcttggatg cttatcacac agatgaagtg     840
aaaaaagtta tcaaagatac ttcagctgat attccacaat ggtaa                     885

<210> SEQ ID NO 133
<211> LENGTH: 294
<212> TYPE: PRT
<213> ORGANISM: Streptococcus agalactiae

<400> SEQUENCE: 133
```

```
Met Ile Leu Ile Thr Ser Tyr Gly Ile Ser Leu Ser Gln Lys Leu
 1               5                  10                  15

Arg Glu Phe Ile Met Lys Leu Lys His Ile Val Leu Gly Leu Ala Leu
             20                  25                  30

Thr Thr Leu Leu Gly Val Thr Phe Ser Asn Gln Glu Val Ser Ala Ser
         35                  40                  45

Ser Thr Ser Ser Lys Val Val Lys Val Gly Val Met Thr Phe Ser Asp
     50                  55                  60

Thr Glu Lys Ala Arg Trp Asp Lys Ile Glu Lys Leu Val Gly Asp Lys
 65                  70                  75                  80

Ala Lys Ile Lys Phe Thr Glu Phe Thr Asp Tyr Thr Gln Pro Asn Gln
                 85                  90                  95

Ala Thr Ala Asn Lys Asp Val Asp Ile Asn Ala Phe Gln His Tyr Asn
             100                 105                 110

Phe Leu Glu Asn Trp Asn Lys Glu Asn Lys Lys Asn Leu Ile Pro Leu
         115                 120                 125

Glu Lys Thr Tyr Leu Ala Pro Ile Arg Ile Tyr Ser Glu Lys Val Lys
     130                 135                 140

Ser Leu Lys Lys Leu Lys Lys Gly Ala Thr Ile Ala Ile Pro Asn Asp
145                 150                 155                 160

Ala Thr Asn Gly Ser Arg Ala Leu Tyr Val Leu Gln Ser Ala Gly Leu
                 165                 170                 175

Ile Lys Leu Asn Val Ser Gly Lys Lys Val Ala Thr Val Ala Asn Ile
             180                 185                 190

Thr Ser Asn Lys Lys Asp Ile Asn Ile Gln Glu Leu Asp Ala Ser Gln
     195                 200                 205

Thr Pro Arg Ala Leu Lys Asp Val Asp Ala Ala Ile Ile Asn Asn Thr
210                 215                 220

Tyr Ile Glu Gln Ala Asn Leu Lys Pro Ser Asp Ala Ile Phe Val Glu
225                 230                 235                 240

Lys Ser Asp Lys Asn Ser Lys Gln Trp Ile Asn Ile Ile Ala Gly Arg
                 245                 250                 255

Lys Asn Trp Lys Lys Gln Lys Asn Lys Ala Ile Gln Ala Ile Leu
             260                 265                 270

Asp Ala Tyr His Thr Asp Glu Val Lys Lys Val Ile Lys Asp Thr Ser
     275                 280                 285

Ala Asp Ile Pro Gln Trp
    290
```

<210> SEQ ID NO 134
<211> LENGTH: 1350
<212> TYPE: DNA
<213> ORGANISM: Streptococcus agalactiae

<400> SEQUENCE: 134

| | | | | | | |
|---|---|---|---|---|---|---|
| atgtcaaatc | aaatatgatta | tatcgttatt | ggtggaggta | gtgcaggcag | tggtaccgct | 60 |
| aatagggcag | ccatgtatgg | agcaaaagtc | ctgttaattg | aaggtggaca | agtaggtgga | 120 |
| acttgtgtta | acttaggttg | tgtacctaag | aaaatcatgt | ggtatggtgc | acaagtttct | 180 |
| gagacactcc | ataagtatag | ttcaggttat | ggttttgaag | ccaataatct | tagttttgat | 240 |
| tttactactc | taaaagctaa | tcgcgatgct | tacgtgcagc | ggtctagaca | gtcgtatgcc | 300 |
| gctaattttg | agcgtaatgg | ggtcgaaaag | attgatggat | ttgctcgttt | tattgataac | 360 |
| catactattg | aagtgaatgg | tcagcaatat | aaagctcctc | acattactat | tgcaacaggt | 420 |

-continued

```
ggacaccctc tttaccctga tattattgga agtgaacttg gtgagacttc tgatgatttt    480
tttggatggg agaccttacc aaattctata ttgattgttg gggcgggcta tatcgcggca    540
gaacttgctg gagtggttaa tgaattaggc gttgaaaccc atcttgcatt tagaaaagac    600
catattctac gcggatttga tgacatggta acaagtgagg ttatggctga aatggagaaa    660 tcagtatct ctttacatgc taaccatgta cctaaatctc ttaaacgcga tgaaggtggc     720
aagttgattt tgaagctga aaatgggaaa acgcttgtcg ttgatcgtgt aatatgggct     780
atcggccgtg gaccaaatgt agacatggga cttgaaaata ccgatattgt tttaaatgat    840
aaagattata tcaaaacaga tgaatttgag aatacttctg tagatggcgt gtatgctatt    900
ggagatgtta atgggaaaat tgccttgaca ccggtagcaa ttgcagcagg tcgtcgctta    960
tcagaaagac tttttaatca taaagataac gaaaaattag attaccataa tgtaccttca   1020
gttattttta ctcaccctgt aattgggacg gtaggacttt cagaagcagc agctatcgag   1080
caatttggaa aagataatat caagtctat acatcaactt ttacctctat gtatacggct    1140
gttaccagta atcgccaagc agttaagatg aagctcataa ccctaggaaa agaggaaaaa   1200
gttattgggc ttcatggtgt tggttatggt attgatgaaa tgattcaagg tttttcagtt   1260
gctatcaaaa tgggggctac taaagcagac tttgatgata ctgttgctat tcacccaact   1320
ggatctgagg aatttgttac aatgcgctaa                                    1350
```

<210> SEQ ID NO 135
<211> LENGTH: 449
<212> TYPE: PRT
<213> ORGANISM: Streptococcus agalactiae

<400> SEQUENCE: 135

```
Met Ser Asn Gln Tyr Asp Tyr Ile Val Ile Gly Gly Ser Ala Gly
  1               5                  10                  15

Ser Gly Thr Ala Asn Arg Ala Ala Met Tyr Gly Ala Lys Val Leu Leu
                 20                  25                  30

Ile Glu Gly Gly Gln Val Gly Gly Thr Cys Val Asn Leu Gly Cys Val
             35                  40                  45

Pro Lys Lys Ile Met Trp Tyr Gly Ala Gln Val Ser Glu Thr Leu His
         50                  55                  60

Lys Tyr Ser Ser Gly Tyr Gly Phe Glu Ala Asn Asn Leu Ser Phe Asp
     65                  70                  75                  80

Phe Thr Thr Leu Lys Ala Asn Arg Asp Ala Tyr Val Gln Arg Ser Arg
                 85                  90                  95

Gln Ser Tyr Ala Ala Asn Phe Glu Arg Asn Gly Val Glu Lys Ile Asp
                100                 105                 110

Gly Phe Ala Arg Phe Ile Asp Asn His Thr Ile Glu Val Asn Gly Gln
            115                 120                 125

Gln Tyr Lys Ala Pro His Ile Thr Ile Ala Thr Gly His Pro Leu
        130                 135                 140

Tyr Pro Asp Ile Ile Gly Ser Glu Leu Gly Glu Thr Ser Asp Phe
145                 150                 155                 160

Phe Gly Trp Glu Thr Leu Pro Asn Ser Ile Leu Ile Val Gly Ala Gly
                165                 170                 175

Tyr Ile Ala Ala Glu Leu Ala Gly Val Val Asn Glu Leu Gly Val Glu
            180                 185                 190

Thr His Leu Ala Phe Arg Lys Asp His Ile Leu Arg Gly Phe Asp Asp
        195                 200                 205
```

```
Met Val Thr Ser Glu Val Met Ala Glu Met Glu Lys Ser Gly Ile Ser
    210                 215                 220
Leu His Ala Asn His Val Pro Lys Ser Leu Lys Arg Asp Glu Gly Gly
225                 230                 235                 240
Lys Leu Ile Phe Glu Ala Glu Asn Gly Lys Thr Leu Val Val Asp Arg
                245                 250                 255
Val Ile Trp Ala Ile Gly Arg Gly Pro Asn Val Asp Met Gly Leu Glu
            260                 265                 270
Asn Thr Asp Ile Val Leu Asn Asp Lys Asp Tyr Ile Lys Thr Asp Glu
        275                 280                 285
Phe Glu Asn Thr Ser Val Asp Gly Val Tyr Ala Ile Gly Asp Val Asn
    290                 295                 300
Gly Lys Ile Ala Leu Thr Pro Val Ala Ile Ala Gly Arg Arg Leu
305                 310                 315                 320
Ser Glu Arg Leu Phe Asn His Lys Asp Asn Glu Lys Leu Asp Tyr His
                325                 330                 335
Asn Val Pro Ser Val Ile Phe Thr His Pro Val Ile Gly Thr Val Gly
            340                 345                 350
Leu Ser Glu Ala Ala Ile Glu Gln Phe Gly Lys Asp Asn Ile Lys
        355                 360                 365
Val Tyr Thr Ser Thr Phe Thr Ser Met Tyr Thr Ala Val Thr Ser Asn
    370                 375                 380
Arg Gln Ala Val Lys Met Lys Leu Ile Thr Leu Gly Lys Glu Glu Lys
385                 390                 395                 400
Val Ile Gly Leu His Gly Val Gly Tyr Gly Ile Asp Glu Met Ile Gln
                405                 410                 415
Gly Phe Ser Val Ala Ile Lys Met Gly Ala Thr Lys Ala Asp Phe Asp
            420                 425                 430
Asp Thr Val Ala Ile His Pro Thr Gly Ser Glu Glu Phe Val Thr Met
        435                 440                 445
Arg

<210> SEQ ID NO 136
<211> LENGTH: 1317
<212> TYPE: DNA
<213> ORGANISM: Streptococcus agalactiae

<400> SEQUENCE: 136
atgagtatca aaaaagtgt gattggtttt tgcctcgaag ctgcagcatt atcaatgttt      60
gcttgtgtag acagtagtca atctgttatg ctgccgaga aggataaagt cgaaattacg     120
tggtgggctt ttccaacctt tactcaagaa aaggctaagg atggagtagg tacttatgag     180
aaaaaagtca tcaaggcttt tgaaaagaaa atcctaata taaagtaaa actagagaca     240
attgatttca catctggacc tgaaaaaatc actacagcaa ttgaagcagg acagcaccct     300
gatgtgcttt ttgatgcacc agggcgaatt attcaatatg gtaaaaatgg taaattagca     360
gatttgaatg atttatttac agaccaattt attaaggatg tcaataataa gaacatcatt     420
caagcttcta gtctggcga taaagcctac atgtatccaa taagttctgc cccatttat     480
atggcgttca ataaaaaaat gcttaaagat gcaggagttt tgaaacttgt aaaagaaggt     540
tggactacta gtgattttga aaagtacta aaagcactaa aaaataaagg ctatacacca     600
ggttcattct tgcaaacgg gcaaggagga gatcaaggac cacgtgcatt ttttgctaat     660
ctttatagtg ctccaataac agataaagaa gtaacaaaat ataccactga cactaaaaat     720
```

```
tctgtaaaat caatgaaaaa aatagttgaa tggattaaga aaggctactt gatgaatggg    780
tctcagtatg atggctcagc tgacattcaa aacttcgcca atggacaaac tgctttcact    840
atcctatggg ctccagctca accaaaaact caagcaaaat tattagagtc aagtaaagtg    900
gattaccttg aagtgccatt cccatcagaa gatggaaaac cagatttaga ataccttgtt    960
aatggttttg cggtctttaa taataaagat gaaaacaaag taaaagcctc taagaaattt   1020
atcactttta ttgctgatga taaaaaatgg ggaccaaaag atgttatacg tacaggtgct   1080
ttcccagtta gaacatcatt tggggatctt tataaaggtg ataaacgtat gatgaagatt   1140
tcaaaatgga ctcaatatta ttcaccatat tacaacacta tcgatggatt ttctgaaatg   1200
agaaccttat ggttcccaat ggttcaatct gtatccaatg gtgatgaaaa accagcagat   1260
gctttgaaag actttactca aaaagcaaat gataccatta aaaagcagc taaataa      1317
```

<210> SEQ ID NO 137
<211> LENGTH: 438
<212> TYPE: PRT
<213> ORGANISM: Streptococcus agalactiae

<400> SEQUENCE: 137

```
Met Ser Ile Lys Lys Ser Val Ile Gly Phe Cys Leu Glu Ala Ala Ala
 1               5                  10                  15

Leu Ser Met Phe Ala Cys Val Asp Ser Gln Ser Val Met Ala Ala
             20                  25                  30

Glu Lys Asp Lys Val Glu Ile Thr Trp Trp Ala Phe Pro Thr Phe Thr
         35                  40                  45

Gln Glu Lys Ala Lys Asp Gly Val Gly Thr Tyr Glu Lys Lys Val Ile
     50                  55                  60

Lys Ala Phe Glu Lys Lys Asn Pro Asn Ile Lys Val Lys Leu Glu Thr
 65                  70                  75                  80

Ile Asp Phe Thr Ser Gly Pro Glu Lys Ile Thr Thr Ala Ile Glu Ala
                 85                  90                  95

Gly Thr Ala Pro Asp Val Leu Phe Asp Ala Pro Gly Arg Ile Ile Gln
            100                 105                 110

Tyr Gly Lys Asn Gly Lys Leu Ala Asp Leu Asn Asp Leu Phe Thr Asp
        115                 120                 125

Gln Phe Ile Lys Asp Val Asn Asn Lys Asn Ile Ile Gln Ala Ser Lys
    130                 135                 140

Ser Gly Asp Lys Ala Tyr Met Tyr Pro Ile Ser Ser Ala Pro Phe Tyr
145                 150                 155                 160

Met Ala Phe Asn Lys Lys Met Leu Lys Asp Ala Gly Val Leu Lys Leu
                165                 170                 175

Val Lys Glu Gly Trp Thr Thr Ser Asp Phe Glu Lys Val Leu Lys Ala
            180                 185                 190

Leu Lys Asn Lys Gly Tyr Thr Pro Gly Ser Phe Phe Ala Asn Gly Gln
        195                 200                 205

Gly Gly Asp Gln Gly Pro Arg Ala Phe Phe Ala Asn Leu Tyr Ser Ala
    210                 215                 220

Pro Ile Thr Asp Lys Glu Val Thr Lys Tyr Thr Thr Asp Thr Lys Asn
225                 230                 235                 240

Ser Val Lys Ser Met Lys Lys Ile Val Glu Trp Ile Lys Lys Gly Tyr
                245                 250                 255

Leu Met Asn Gly Ser Gln Tyr Asp Gly Ser Ala Asp Ile Gln Asn Phe
            260                 265                 270
```

```
Ala Asn Gly Gln Thr Ala Phe Thr Ile Leu Trp Ala Pro Ala Gln Pro
        275                 280                 285

Lys Thr Gln Ala Lys Leu Leu Glu Ser Ser Lys Val Asp Tyr Leu Glu
    290                 295                 300

Val Pro Phe Pro Ser Glu Asp Gly Lys Pro Asp Leu Glu Tyr Leu Val
305                 310                 315                 320

Asn Gly Phe Ala Val Phe Asn Asn Lys Asp Glu Asn Lys Val Lys Ala
                325                 330                 335

Ser Lys Lys Phe Ile Thr Phe Ile Ala Asp Asp Lys Lys Trp Gly Pro
            340                 345                 350

Lys Asp Val Ile Arg Thr Gly Ala Phe Pro Val Arg Thr Ser Phe Gly
        355                 360                 365

Asp Leu Tyr Lys Gly Asp Lys Arg Met Met Lys Ile Ser Lys Trp Thr
    370                 375                 380

Gln Tyr Tyr Ser Pro Tyr Tyr Asn Thr Ile Asp Gly Phe Ser Glu Met
385                 390                 395                 400

Arg Thr Leu Trp Phe Pro Met Val Gln Ser Val Ser Asn Gly Asp Glu
                405                 410                 415

Lys Pro Ala Asp Ala Leu Lys Asp Phe Thr Gln Lys Ala Asn Asp Thr
            420                 425                 430

Ile Lys Lys Ala Ala Lys
        435

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 138
cgagatctga tatctcacaa acagataacg gcgtaaatag                          40

<210> SEQ ID NO 139
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 139
gaagatcttc cccgggatca caaacagata acggcgtaaa tag                      43

<210> SEQ ID NO 140
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 140
cgagatctga tatccatcac aaacagataa cggcgtaaat ag                       42

<210> SEQ ID NO 141
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 141
```

```
cgggatcctt atggacctga atcagcgttg tc                                    32
```

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 142

```
ggatgctttg tttcaggtgt atc                                              23
```

<210> SEQ ID NO 143
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 143

```
catgatatcg gtacctcaag ctcatatcat tgtccggcaa tggtgtgggc ttttttttgtt    60 ttagcggata acaatttcac ac                                              82
```

<210> SEQ ID NO 144
<211> LENGTH: 81
<212> TYPE: DNA
<213> ORGANISM: Artificial Sequence
<220> FEATURE:
<223> OTHER INFORMATION: Description of Artificial Sequence: Primer

<400> SEQUENCE: 144

```
gcggatcccc cgggcttaat taatgtttaa acactagtcg aagatctcgc gaattctcct     60
gtgtgaaatt gttatccgct a                                               81
```

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 145

```
cgccagggtt ttcccagtca cgac                                             24
```

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 146

```
tcaggggggc ggagcctatg                                                  20
```

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 147

```
tcgtatgttg tgtggaattg tg                                               22
```

<210> SEQ ID NO 148
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 148
tccggctcgt atgttgtgtg gaattg                                    26

<210> SEQ ID NO 149
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 149
aagtatcaga tctgatatct cacaaacaga taacggcgta aat                 43

<210> SEQ ID NO 150
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 150
aagtatcaga tcttccccgg gatcacaaac agataacggc gtaaat              46

<210> SEQ ID NO 151
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 151
aagtatcaga tctgatatcc atcacaaaca gataacggcg taaat               45

<210> SEQ ID NO 152
<211> LENGTH: 24
<212> TYPE: DNA
<213> ORGANISM: Staphylococcus aureus

<400> SEQUENCE: 152
tcacaaacag ataacggcgt aaat                                      24

<210> SEQ ID NO 153
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 153
cgggatccgc caccatgacc acttctcaag ctgttttagc                     40

<210> SEQ ID NO 154
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 154

```
ttgcggccgc acgattatca acaaagttct g                              31
```

<210> SEQ ID NO 155
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 155

```
cggatccgcc accatggcta ctcatattgg aagttaccag c                   41
```

<210> SEQ ID NO 156
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 156

```
ttgcggccgc agggtttatt tgttgaagtg tcttg                          35
```

<210> SEQ ID NO 157
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 157

```
cggatccgcc accatgtatc tatatcattt accaatgccc                     40
```

<210> SEQ ID NO 158
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 158

```
ttgcggccgc tttatgtata gaaacagcag tccc                           34
```

<210> SEQ ID NO 159
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 159

```
cggatccgcc accatgaaag gaagaacaac ctattcgttt ag                  42
```

<210> SEQ ID NO 160
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 160

```
ttgcggccgc aagagcaaat tttcgtatct cctc                           34
```

<210> SEQ ID NO 161
<211> LENGTH: 35
<212> TYPE: DNA
<213> ORGANISM: Artificial Sequence

```
<220> FEATURE:
<223> OTHER INFORMATION: Description of Artificial Sequence: Primer

<400> SEQUENCE: 161
cggatccgcc accatgattg ttggacacgg aattg                              35

<210> SEQ ID NO 162
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 162
ttgcggccgc tttttcttcc tccaaaataa cactagc                            37

<210> SEQ ID NO 163
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 163
cggatccgcc accatggcga ctaaagagtt aggtgttag                          39

<210> SEQ ID NO 164
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 164
ttgcggccgc tatagtttta gtttcaactt gtctagatg                          39

<210> SEQ ID NO 165
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 165
cgggatccac catgtatacg agtttacaac caaatcatg                          39

<210> SEQ ID NO 166
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 166
ttgcggccgc gtcagctcgt actgtttttt tagc                               34

<210> SEQ ID NO 167
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 167
cggatccgcc accatgtgtc aaatgaatag tgaacataaa ag                      42
```

<210> SEQ ID NO 168
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 168
ttgcggccgc ctcaaataat ttacctccaa ttcg                              34

<210> SEQ ID NO 169
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 169
cggatccgcc accatggctc cattcgaatt taaagattc                         39

<210> SEQ ID NO 170
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 170
ttgcggccgc tgatttacca gtttggaaga gttc                              34

<210> SEQ ID NO 171
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 171
cggatccgcc accatgaata ctatttataa tacattgaga acag                   44

<210> SEQ ID NO 172
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 172
ttgcggccgc ttctttgttc caactttctg g                                 31

<210> SEQ ID NO 173
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 173
cggatccgcc accatgatag agtggattca aacacattta c                      41

<210> SEQ ID NO 174
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 174
ttgcggccgc tttatgactc aagcgacgtg tta					33

<210> SEQ ID NO 175
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 175
cggatccgcc accatggagt tagtaattag agatattcgt aag					43

<210> SEQ ID NO 176
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 176
ttgcggccgc cttgtcatat tcatctccct tcaac					35

<210> SEQ ID NO 177
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 177
cggatccgcc accatggcta gttttgtcat gaatcataat gac					43

<210> SEQ ID NO 178
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 178
ttgcggccgc gttatttgct cgttgtttag ctaaatc					37

<210> SEQ ID NO 179
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 179
cggatccgcc accatggctc ttagtttttt tatggtttca gttcaagc					48

<210> SEQ ID NO 180
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 180
ttgcggccgc gaaggcaccg ccacctcc					28

<210> SEQ ID NO 181

```
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 181
cggatccgcc accatgggtg aaacccaaga taccaatcaa gc            42

<210> SEQ ID NO 182
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 182
ttgcggccgc aacacctggt gggcgtttgg                          30

<210> SEQ ID NO 183
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 183
cggatccgcc accatggctg ggaatcgtaa taacg                    35

<210> SEQ ID NO 184
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 184
ttgcggccgc agccgtctct aaaacaggct tg                       32

<210> SEQ ID NO 185
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 185
cggatccgcc accatgcttc caacgcagcc gcaaaac                  37

<210> SEQ ID NO 186
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 186
ttgcggccgc atttagtgtt atttctcctg ttgcataatc c             41

<210> SEQ ID NO 187
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 187
```

```
cgggatccac catgtacacg catattgttg aaaaaag                              37
```

<210> SEQ ID NO 188
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 188

```
ttgcggccgc aaataatttc ttttggttgt ttg                                  33
```

<210> SEQ ID NO 189
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 189

```
cggatccgcc accatgagta atcaagaagt ttcagcaagc                           40
```

<210> SEQ ID NO 190
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 190

```
ttgcggccgc ccattgtgga atatcagctg aag                                  33
```

<210> SEQ ID NO 191
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 191

```
cggatccgcc accatggtgc aggcagtggt accgct                               36
```

<210> SEQ ID NO 192
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 192

```
ttgcggccgc gcgcattgta acaaattcct cag                                  33
```

<210> SEQ ID NO 193
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 193

```
cgggatccac catggctgcc gagaaggata aag                                  33
```

<210> SEQ ID NO 194
<211> LENGTH: 34
<212> TYPE: DNA

```
<213> ORGANISM: Artificial Sequence
<220> FEATURE:
<223> OTHER INFORMATION: Description of Artificial Sequence: Primer

<400> SEQUENCE: 194
ttgcggccgc attatttagc tgcttttta atgg                              34

<210> SEQ ID NO 195
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 195
cgggatccac catgtgtcag gttgtttatg caagttttc                        39

<210> SEQ ID NO 196
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 196
ttgcggccgc tttactaatt gataaagagc aacttcg                          37

<210> SEQ ID NO 197
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 197
ggggtaccgg ccaccatggc tgaagtaatt tcaggaagt                        39

<210> SEQ ID NO 198
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 198
cggaattccg ttaatcctct tttttttctta gaaacagat                       39

<210> SEQ ID NO 199
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 199
cgggatccgc caccatg                                                17

<210> SEQ ID NO 200
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 200
ttgcggccgc                                                        10
```

<210> SEQ ID NO 201
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 201
atggaaaaaa atacttggaa aaaattac                                          28

<210> SEQ ID NO 202
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 202
ctattttgtt ttagcgatgt ctttatc                                           27

<210> SEQ ID NO 203
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 203
atgtcaaaac aaaaagtaac ggcaac                                            26

<210> SEQ ID NO 204
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 204
ttatttatgg ccaataccat aagttaattg                                        30

<210> SEQ ID NO 205
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 205
atgaaaaaag ttttttttct catggctatg                                        30

<210> SEQ ID NO 206
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 206
ttacttcaac tgttgataga gcacttcc                                          28

<210> SEQ ID NO 207
<211> LENGTH: 30
<212> TYPE: DNA
<213> ORGANISM: Artificial Sequence
<220> FEATURE:

<223> OTHER INFORMATION: Description of Artificial Sequence: Primer

<400> SEQUENCE: 207
ttgttcaatt ttataggttt tagaacttgg                30

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 208
ttaattttca ttgcgtctca aacc                24

<210> SEQ ID NO 209
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 209
atgacaaaaa aacttattat tgctatatta g                31

<210> SEQ ID NO 210
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 210
ttaacgatta tcaacaaagt tctgtac                27

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 211
atgatacgcc agttttttaag agaa                24

<210> SEQ ID NO 212
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 212
ttatttatgt atagaaacag cagtccc                27